United States Patent [19]
Lam et al.

[11] Patent Number: 5,994,072
[45] Date of Patent: Nov. 30, 1999

[54] **PROTEINS INVOLVED IN THE SYNTHESIS AND ASSEMBLY OF O-ANTIGEN IN *PSEUDOMONAS AERUGINOSA***

[75] Inventors: Joseph S. Lam; Lori Burrows; Deborah Charter; Teresa de Kievit, all of Guelph, Canada

[73] Assignee: University of Guelph, Guelph, Canada

[21] Appl. No.: 08/846,762

[22] Filed: Apr. 30, 1997

Related U.S. Application Data

[60] Provisional application No. 60/016,510, Apr. 30, 1996, and provisional application No. 60/039,473, Feb. 27, 1997.

[51] Int. Cl.$^6$ .............................. C12Q 1/68; C12N 1/21; C12N 15/31; C12N 15/70
[52] U.S. Cl. ...................... 435/6; 435/252.3; 435/320.1; 536/23.7
[58] Field of Search ...................... 435/6, 252.3, 252.34, 435/320.1, 91.2; 536/23.7, 24.32

[56] References Cited

PUBLICATIONS

Allen and Maskell, Mol Micriobiol 19: 37–52, 1996.
Burrows, L.L., et al., Mol. Microbiol. 22:481–495, 1996.
Coyne, M.J. and Goldberg, J.B., Gene, 167:82, 1995.
Coyne, M.J. et al., J. Bacteriol., 176: 3500–3507, 1994.
Dasgupta, T., and J.S. Lam. Infection and Immunity 63: 1674–1680, 1995.
Dasgupta, et al., *Program Abstr 93rd Gen Meet Amer Soc Microbiol* abstr. D–240, 1993.
de Kievit, T.R., et al., Mol. Microbiol. 16:565–574, 1995.
de Kievit, T. R., and Lam, J. S. *Program Abstr 94th Gen Meet Amer Soc Microbiol abstr.* D–192, 1994.
Delic–Attree, I., Gene 154:61–64, 1995.
Evans, D.J. et al., Mol. Microbiol., 13:427–434, 1994.
Goldberg, J.B., et al., Proc. Nat. Acad. Sci USA 89:10716–10720, 1992.
Goldberg J.B. et al., J. Bacteriol., 175:1303–1308, 1993.
Knirel, Y.A., and N.K. Kochetkov. Biochemistry (Moscow) 59:1325–1383, 1994.
Kuzio, J., and Kropinski A.M. *J Bacteriol* 155: 203–212, 1983.
Lam, J.S., et al., J. Bacteriol. 174:2178–2184, 1992.
Lam, J.S. et al., "Mol. Biol. Pseudo.", Chapt. 39, Nakazawa T. et al., Eds., ASM press, Washington, p. 454, Fig. 1, 1996.
Lightfoot, J.L., and J.S. Lam. J. Bacteriol. 173:5624–5630, 1991.
Lightfoot, J.L., and J.S. Lam. Mol. Microbiol. 8:771–782, 1993.
Liu, D., R.A. Cole, and P.R. Reeves, J. Bacteriol. 178:2102–2107, 1996.
Schnaitman, C.A., and J.D. Klena. Microbiol. Rev. 57:655–682, 1993.
Sokol, P.A., et al., *J Bacteriol* 176: 553–562, 1994.
Whitfield, C. Trends Microbiol. 3:178–185, 1995.
Whitfield, C., and M.A. Valvano, Adv. Microb. Physiol. 35:135–246, 1993.
Wozniak, D.J. J. Bacteriol. 176:5068–5076, 1994.
Wozniak, D.J., and D.E. Ohman J Bacteriol 175:4145–4153, 1993.
van den Berg et al. (1981) The structure and function of the regulatory elements of the *Escherichia coli* uvrB gene. Nucleic Acids Res. 9:5623–5643, Nov. 1981.
Delorme et al. (1992) Histidine biosynthesis genes in *Lactococcus lactis* subsp. lactis. J. Bacteriol. 174:6571–6579, Oct. 1992.
Schnier et al. (1982) Primary structure of *Escherichia coli* ribosomal protein S1 and of its gene rpsA. Proc. Natl. Acad. Sci. USA 79:1008–1011, Feb. 1982.

*Primary Examiner*—Nancy Degen
*Assistant Examiner*—Robert Schwartzman
*Attorney, Agent, or Firm*—Merchant & Gould P.C.

[57] ABSTRACT

Novel nucleic acid molecules encoding proteins involved in the synthesis and assembly of O-antigen in *P. aeruginosa*; and novel proteins encoded by the nucleic acid molecules are described. Methods are disclosed for detecting *P. aeruginosa* in a sample by determining the presence of the proteins or a nucleic acid molecule encoding the proteins in the sample.

14 Claims, 63 Drawing Sheets

The *Pseudomonas aeruginosa* O5 *wbp* gene cluster and flanking DNA

FIGURE 2A

```
BASE COUNT     4990 a    5938 c    7166 g    6323 t  ORIGIN
   1    ctcgagatat  tgagcagcgc  atacagaact  tgcggagaga  atgccaaggc  agacgtgaag
  61    atcgtattgt  tcagctcaag  gaggcgttga  aggtcgcagg  tgcgctgaaa  ttggaggagc
 121    ctccactgat  cagtgggcaa  tcctctgagg  agctctcggc  tatcatgaat  ggaagtctga
 181    tgtatatgcg  tggcagtaag  gcgattatgg  ccgagattca  gacattggag  gcgcgtagct
 241    ctgatgatcc  ttttattccg  gcgttgcgta  ctcttcagga  gcagcagtta  ttgctgagta
 301    gcttgcgtgt  taattcggag  cgggtttctg  tttttcgaca  agacggtccg  atagaaacgc
 361    cggactcacc  agttcgtcca  aggagagcga  tgattttgat  ttttggggttg  ataattggtg
 421    gtgtgcttgg  tggtttttctg gcgttgtgcc  ggattttttt  gaagaagtat  gctcgttagg
 481    aaagagctag  ttattgaagt  ggtgatgcgt  tgcacgtact  tggtcgagt   aattttgtgg
 541    agtaggtttt  cgttgggtgg  ctcgattgct  gagggggtgag aacgtttcca  tgcggtgttt
 601    cctcagctct  gtctcctgtg  ccttggctcc  ttgaacgcag  aggttaacag  ttgagctgtg
 661    gttgtgggta  tgtgacgtct  gttgcggtgg  tgtctggttc  ctggtgtcgg  gtgtgcgaga
 721    agatgccaag  ttgcctggca  ggtcgttacg  tgtcgtagcc  gtattcgaag  ctcggcaatc
 781    gcggggtgat  ttacaggact  gtgcttaata  cggcgcaggc  ttggtcaggg  tcgagtcggg
 841    tcttcgggtg  tcaactggat  cgtgcgaaaa  ccggtttcgt  ggatgctgat  aagctcggct
 901    tgactggcag  tccagggcgg  ttaccaggtc  tgtggaggcg  caaaatgtat  aggagcctgc
 961    gtgagctggg  caggctgaag  gcctgctcga  aagcgagtta  gcattgtggt  ccggaagggc
1021    atgggtggac  cagagtgccg  ttctgcacgg  caaaagccaa  cttgctcgga  ggttccctag
1081    cgcctatgat  tacgacgccc  ttcattttg   gccattgccg  ccaggtgctg  tggaaagcga
1141    cagtatccct  tctttatcga  tcttgtgaag  atgtcgagag  tggtcgcaga  aaggattcac
1201    tcgactgacg  aatgaatcgt  ggaagattta  agttcccgtt  gtgcggtcgc  aggcgcgggc
1261    aggtaaaatt  gaggtgagtt  ggaaaatgat  agatgttaac  acagtggtag  agaagttcaa
1321    aagccgacag  gccttgattg  gtatcgtggg  tctgggttat  gtcggtttac  cactgatgct
1381    gcgatacaac  gccattggtt  tcgatgtctt  gggtatcgat  atcgatgatg  tcaaggttga
1441    caagcttaat  gccgggcagt  gctatatcga  acatattccg  caagccaaaa  ttgctaaggc
1501    ccgtgcaagc  ggtttcgagg  ctacgaccga  tttcagccgt  gtcagtgaat  gtgatgccct
1561    gatcctttgt  gtgccgacgc  cgctgaacaa  gtatcgcgag  ccggatatga  gctttgtcat
1621    caataccacc  gacgcactaa  aaccgtatct  gcgcgtaggg  caggtggttt  cgctggaaag
1681    taccacctat  ccgggaacta  ccgaggaaga  gttgttgcca  cgcgtgcagg  agggtggcct
1741    cgtggttggc  cgggacatct  acctggtcta  ttctccggag  cgtgaagatc  cgggcaaccc
1801    gaacttcgag  actcgtacca  ttccgaaagt  gatcggtggt  cacactcctc  agtgtctgga
1861    agtcggcatt  gccctgtatg  aacaggccat  cgaccgggtc  gtgccggtca  gttccaccaa
1921    ggccgccgag  atgaccaagc  tgttggagaa  cattcatcgc  gcggtcaata  tcggtctggt
1981    caacgaaatg  aagatcgttg  ctgatcgcat  gggtatcgac  atctttgaag  tggttgatgc
2041    tgcggcgacc  aagccgttcg  gtttcactcc  ttactaccca  gggccgggac  tgggcgggca
2101    ctgtatcccg  atcgatccct  tctacctgac  ttggaaggct  cgcgaatacg  gactgcatac
2161    ccgcttcatc  gaactgtctg  gtgaggtcaa  ccaggccatg  ccggaatacg  tactgggcaa
2221    actcatggat  ggcctgaacg  aggcaggcag  ggccctcaag  ggcagtcgtg  tactggtatt
2281    gggtatcgct  tataagaaga  atgtcgacga  catgcgcgag  tcgccatccg  tggaaatcat
2341    ggagctgatc  gaagccaagg  gtgggatggt  cgcctatagc  gatccgcatg  tgccggtgtt
2401    cccgaagatg  cgtgaacacc  acttcgaact  gagcagtgag  ccgctgactg  ccgaaaacct
2461    ggctaggttc  gacgctgtag  tgcttgcgac  cgaccatgac  aagtttgact  atgagctgat
2521    caaggccgaa  gccaagctag  ttgttgacag  ccgtggcaag  taccgctccc  cggcggcaca
2581    catcatcaag  gcttgatcac  ccatcccagc  atgtccatcc  gctcgtgcca  gaaggccggg
2641    cggatccgct  catttccata  ggacgaacca  tgaaaaattt  cgctctcatc  ggtgctgccg
2701    gctacatcgc  tcctcgccat  atgcgcgcca  tcaaagacac  cggtaactgc  ctggtttcgg
2761    cctatgacat  caatgactcg  gtcggtatta  ttgatagcat  ctctccccag  agcgagtttt
2821    ttaccgagtt  cgagttcttt  cttgatcatg  cgagcaacct  caagcgcgac  tctgctaccg
2881    cgctggacta  cgtatcgatc  tgctcgccca  attcctgca   ctacccgcat  atcgctgcag
2941    gtctgcgctt  gggttgcgac  gtaatctgcg  aaaagccgct  tgttccaacc  ccagagatgc
```

FIGURE 2B

```
3001  tcgatcagtt ggctgttatc gagcgcgaaa ccgataagcg cctctacaac attctgcaac
3061  tgcgtcatca ccaggcgatc atcgcattga aggacaaggt cgcccgcgaa aaaagtccgc
3121  ataagtacga ggtcgatctg acttacatta cttcccgcgg caactggtat ctgaaaagct
3181  ggaagggaga tccacgtaag tcgttcggcg tggctaccaa catcggtgtg cacttctacg
3241  acatgctgca cttcatcttt ggcaagctgc agcgtaatgt tgtgcacttc acttccgagt
3301  acaagacagc tggttatctg gagtacgagc aggcccgtgt gcgttggttt ctgtccgtgg
3361  atgctaacga cctgccggag tcggtcaagg gcaaaaagcc gacctatcgt tcgattaccg
3421  tcaacggtga ggaaatggag ttctctgaag gctttaccga tctacataca accagctacg
3481  aagaaattct cgctggtcgt ggttatggca tcgatgacgc tcgtcattgt gtggaaactg
3541  tcaataccat tcgcagcgcc gtcatcgtac cggcctctga taacgaaggg catccgttcg
3601  tcgcggcgct tgcgcgttga ggtagaaaag gaggtggccg tcctcggtca cctgtttaca
3661  gcaggtttcc gcaggatcat tcatcagcat gtcatctagt agctctaaat tgctgaacgg
3721  tatggtcgcg gtaagttcag gcagaaacat tcggctggat gtccagggc  tgcgggctgt
3781  tgcagttctg gctgtgctag cttaccacgc caacagtgcc tggctcaggg ctgggtttgt
3841  cggcgttgac gtgttcttcg tcatttccgg gtttatcatt accgccttac tggtcgagcg
3901  cggtgtaaaa gttgatctgg tagagtttta cgcgggccgt atcaaacgta ttttccagc
3961  ctatttcgtc atgttggcga ttgtctgcat tgtctcgaca attctgtttc tgcctgatga
4021  ctatgttttt tttgaaaaaa gtctacagtc atctgtattt ttttccagta atcactattt
4081  cgctaatttt ggtagttact ttgctccgag agctgaagag ctgccgctgc tgcatacttg
4141  ttcaatagcc aacgagatgc agttttatct gttctaccct gtactgttca tgtgcctgcc
4201  atgtcgatgg cgcttccgg tgttcatcct attagctatt ttgctgttca tttggagtgg
4261  ctattgcgta ttcagcggca gccaagatgc tcagtacttc gccttgctag ctcgtgtacc
4321  tgagttcatg tcgggagctg ttgtcgcatt atcattacgt gatcgtgagc tacccgccag
4381  gcttgcgata cttgcggggt tattgggggc ggcgttgctg gtctgctcct tcattatcat
4441  cgacaagcag cactttcccg gattctggtc gctcctgcca tgcctgggag ccgctctgct
4501  cattgctgcc cgacgtggcc ctgccagcct gctgctggcc agcaggccca tggtctggat
4561  aggtggtatc tcctattcgt tgtatctgtg gcactggcca attctggcat tcatccgtta
4621  ctccaccggc caatacgaat tgagcttcgt ggcgctgttg gcatttctca caggttcgtt
4681  cctgctggcc tggttctcat accgctacat cgagacacct gccagaaagg ctgtgggtct
4741  gcgccagcag cgctgaagt ggatgttggc cgccagtgtg gtagctatag tggttacggg
4801  gggggcgcag ttcaatgtgt tggttgtggc gccggcgcca attcagttga cgcgctacgc
4861  tgtaccagag tcgatctgcc atggtgttca ggtaggggag tgcaagcgag cagcgtcaa
4921  tgccgtaccc cgtgtgctgg tgatcggtga tagccatgct gcgcagctta actacttctt
4981  cgacgtggtt ggcaacgagt caggtgtggc ttaccgagta ctcaccggaa gcagttgtgt
5041  gccaatacct gctttcgatc ttgaacgttt gccccgttgg gcgcggaaac cctgccaagc
5101  gcagattgat gcagttgccc aatcaatgtt gaactttgac aagatcattg tggcgggcat
5161  gtggcagtat cagatgcaga gtccggcatt tgcccaggct atgcgtgcct tccttgtcga
5221  taccagctat gccggcaagc aggtcgctct actcgggcag ataccgatgt tcgaatcaaa
5281  cgtgcagcgt gtgcgtcgtt tcagggagct gggtttgtca gctccgcttg ttagctccag
5341  ctggcaaggt gcgaaccagc tgttgcgtgc tctagccgag ggtattccaa acgtacggtt
5401  catggatttt tcttccagcg ccttcttcgc cgatgctcct tatcaggacg gagagcttat
5461  ttaccaggat agccatcacc ttaacgaggt ggggctcgc cgctatggat atttcgcgag
5521  ccgtcaattg cagcggctgt tgaacaacc acaatcgagt gtgagtctca agccatgagt
5581  tattatcagc accccagcgc gatcgtcgac gacggtgcgc agatcggtag cgactcccga
5641  gtttggcact tcgtgcacat ctgtgcaggt gcccggattg gcgcaggggt ttcgttgggt
5701  cagaacgtat tcgtcggcaa caaggtcgtt attggtgatc gctgcaagat ccagaacaac
5761  gtgtcggtat atgacaatgt cactctcgaa gagggcgtgt tctgcgggcc gagcatggta
5821  tttaccaacg tttacaaccc ccgctcgttg atcgagcgca aggatcagta ccgtaacacg
5881  ttggtaaaaa aaggtgccac gcttggtgcc aactgcacta tcgtctgtgg cgtgactatt
5941  ggtgaatatg ccttcctggg tgcgggtgcg gtcattaaca agaatgttcc atcttatgcc
6001  ctgatggtag gcgtgcccgc tcgacagatt ggttggatag cgaattcggt gagcagctgc
6061  agctgaacga gcagggcgaa gctgtctgct cacactccgg tgcgcgctat gtactcaatg
6121  gaaagatcct gagcaaggtg gacgtgtgac catgattgaa ttcatcgacc tgaagaacca
6181  gcaagcgcgt atcaaggaca agatcgatgc cggtatccag cgcgtgctga gacacgggca
6241  gtacattctt ggcccggaag tcactgagct tgaggatcgc ctcgccgatt tcgtcggcgc
```

FIGURE 2C

```
6301  taagtactgc atcagttgcg ccaacggtac tgacgctcta cagattgtgc agatggcctt
6361  gggtgttggc ccaggtgacg aagtaatcac ccctggtttt acttatgttg cgacagcgga
6421  gaccgtcgcg cttttgggag ccaagccggt ttacgtggat attgatccac gcacctacaa
6481  tcttgatccg cagttgctgg aggctgcgat cacaccgcgt acgaaggcta tcattcctgt
6541  ttcgctgtat ggccagtgtg cagacttcga tgcaatcaac gccattgcct ccaaatatgg
6601  tatccctgtc attgaggatg ctgcacagag cttcggtgct tcgtacaagg gtaagcgttc
6661  ttgtaatctg agtaccgttg cctgcaccag cttcttcccg agcaaaccgt tgggttgcta
6721  tggggatggt ggagcgatct tcactaacga cgatgaactg gctactgcta ttcgtcaaat
6781  tgcccggcat ggtcaggacc gccgctatca tcacattcgt gtggggggtga atagtcggtt
6841  ggacacattg caggctgcga ttcttctacc gaagcttgaa attttcgagg aggagattgc
6901  gttgcgccag aaggtagccg cggagtatga cctatcactg aaacaggtcg gtatcggcac
6961  gccgtttatt ggaagtggat aacatcagtg tttatgccca gtatacggtg cgtatggata
7021  atcgagagtc tgttcaggct tcttgaaag ctgccggggt tccaactgct gtgcattacc
7081  ctattccgct taataagcag cctgctgttg cggatgagaa agcgaaacta ccagtgggtg
7141  acaaggctgc tactcaagta atgagcctac ccatgcatcc ctatctggat acggcatcca
7201  tcaaaatcat ctgtgctgcg ttgacgaatt gacggatgta tacttgct cgagtcgaca
7261  ggtctattct gctgaacaca gtgttactgt ttgctttctt ttcagcgaca gtgtgggtga
7321  ataataatta tatctatcat ctctatgatt atatgggtc tgcgaaaaaa actgtcgact
7381  tcggcttgta tccgtacttg atggtcttgg cgctcatctg tgccctgttg tgtggagggg
7441  caattcgcag gccaggtgat ctgttagtta cattattagt tgtaatactt gttcctcatt
7501  cattggttct taatggagct aatcaatatt ctccggatgc gcaaccatgg gctggcgtgc
7561  ctctggcaat tgcttttggt attttgatca tcggcattgt caataagata agattccatc
7621  cgctaggtgc attgcagcga gaaaaccaag gaaggcgaat gttagtgcta ctgtcagtac
7681  tcaacatagt agtgcttgtg tttatttct ttaaaagcgc tggttatttt tcctttgact
7741  ttgctgggca gtatgctcgc cgtgcacttg ctcgtgaggt ttttgctgcg ggttctgcaa
7801  acggctactt gtcgtcaatc ggtacccagg cattcttcc tgtgttgttt gcctgggggg
7861  tctacagacg acaatggttc tacttggtcc tgggtattgt caatgcacta gtgctgtggg
7921  gagcgtttgg acagaagtat ccttttgtcg tgttgttct aatttatggc ctgatggttt
7981  attttcgacg attcggtcag gtcagagtgt cttgggttgt ctgcgcacta ttgatgcttt
8041  tgcttttagg ggcgttggaa catgaggtgt ttggctattc attcttgaat gattattttc
8101  tacgtcgtgc ttttattgtg ccttccaccc tgttgggggc agttgatcag tttgtgtctc
8161  agttcggatc caattattac agggataccc tgttgggcgc gctcttgggt cagggtagga
8221  ctgagccgtt gagctttcgt ctggggacgg aaattttcaa taatcccgat atgaatgcga
8281  atgtaaactt cttcgcgata gcctatatgc agtgggtta tgtgggggtt atggctgagt
8341  cgatgttggt gggcggtagt gtcgttctca tgaatttctt attttcgagg tatggtgcat
8401  tcatggccat tccggttgct ttgttattta ctacaaagat tcttgagcag cccctgctaa
8461  ctgtaatgct tggctctggt gttttcttga tactgctttt ccttgcgcta atttcttttc
8521  cactcaagat gtctttagga aaaactctat gagtgcggct tttatcaacc gtgtcgcacg
8581  agtattagta ggcaccttgg gagcacagct cataacgatt ggtgtcactc tgctactggt
8641  tcgtctgtat tctcctgctg aaatgggcgc tttcagtgtt tggctatcgt tcgctacgat
8701  ttttgcagtt gtagttactg ggcgctatga gttggctatt ttttcgactc gagaagaggg
8761  cgaactccag gcaatcgtca agctgatact tcagttgaca ctattgatttt tcgttgccgt
8821  ggcgattgct gttgttatag gtagacatct gattgagtcg atgccagttg tgatcggtga
8881  atactggttc gcattggcgg tggcttcgct ggggttgggg ataaataagc tagtcttgtc
8941  gttacttaca tttcaacaat cttttaatcg gttgggagtt gctcgtgtaa gcctggctgc
9001  atgtattgcc gttgcacaag tttcagctgc atatttactg gagggcgtat cagggctgat
9061  ctatggccag ctgtttggtg tcgtcgtagc cacggcgctt gcggcccttt gggtaggaaa
9121  gtcgctgatt taaattgta tcgagacacc gtggcgtatg gtacgacaag tagcggtaca
9181  gtacatcaat ttcccgaagt tttctctgcc tgcggatctg gtcaacacgg ttgccagtca
9241  ggtgcctgtg attttattgg cggcaaagtt tggtggagac agtgcaggct ggtttgccct
9301  gactctgaag ataatgggag ctcccatttc cttgttggct gcttcggtgc tcgatgtgtt
9361  caaagaacaa gccgctcgtg actaccgaga gtttggtaat tgccgaggta tcttcctcaa
9421  gactttcagg ttgcttgccg tcctcgcgct acctcctttt attatatttg gttcattggc
9481  gagtgggcct ttgggttagt cttttggcgaa gcgtgggctg agtcggggcg ttatgctgta
9541  ttgatggttc cgttgtttta tatgcgtttc gtggtgagtc cgctcagcta tacaatctat
```

FIGURE 2D

```
 9601  attgcccagc ggcagagtat ggatttgttg tggcagctag ccttgttgct cctgacgttt
 9661  atctgtttta ccttgcctga ctctgtcgac tcggtgttgt ggttttactc catagcatat
 9721  gctgttatgt attttgtcta tttctggatg tccttccagt gtgccaaggg agatgccaag
 9781  tgatcgttgt tattgattac ggtgtaggta acattgcttc agtcttgaac atgctgaagc
 9841  gagttggtgc caaagccaag gcatccgata gccgagagga tatcgagcag gcggagaaac
 9901  tgattttgcc tggtgtcggt gcttttgacg ccggaatgca aacactacgc aagagtgggc
 9961  tggtggatgt actgacagag caggtcatga tcaaacgaaa gccggtcatg ggggtgtgtc
10021  tcgggagtca gatgctgggg ctgcgatctg aggagggagc ggaaccgggg cttggatgga
10081  tcgatatgga tagcgtccgt ttcgaaaggc gtgacgaccg aaaggttcca catatgggct
10141  ggaatcaagt gtccccgcaa ttggagcatc ctatacttag cggtataaac gagcaaagcc
10201  gattctattt tgttcatagt tattatatgg ttccgaaaga cccagacgat atcctgttga
10261  gttgtaatta tggacaaaaa ttcactgcgg cggtggctcg ggataatgtt ttcggatttc
10321  agtttcatcc tgagaagagt cataaattcg gtatgcagtt attcaaaaac ttcgtggagc
10381  ttgtctgatg gtccggaggc gcgttatccc atgcttgctg ctcaaggatc gcggtctagt
10441  gaaaaccgtg aagttcaagg agcccaagta cgttggagac ccgatcaacg caatacgcat
10501  cttcaatgag aaagaagtcg acgaactgat tttgctggat atagatgctt ccaggctcaa
10561  tcaagagcct aactatgagt tgatcgcgga agtggctggt gagtgtttta tgcctatttg
10621  ctatggggc ggtatcaaga cattggagca tgcggaaaaa atcttttccc taggtgtcga
10681  aaaagtttcg ataaataccg ccgctcttat ggatctttcg ttgattcgaa gaattgccga
10741  taagtttggt tcgcaaagcg tagttggctc tatcgactgc cgcaagggtt tctggggagg
10801  acactccgtg ttctcagaga atgggacgcg cgacatgaaa cgctccccat tggagtgggc
10861  gcaagcgctc gaagaggctg gagtgggtga gattttttcta aattctattg atcgagatgg
10921  agtgcagaaa ggcttcgaca acgctctagt ggaaaatatc gcttctaacg tccatgtgcc
10981  agtgatcgcc tgtggtggag ctggctccat cgctgacctc atcgatcttt ttgagcgtac
11041  gtgtgtgtcg gcagtagcgg cgggaagcct attcgttttc catggcaagc atcgtgcggt
11101  actgattagt tatccggatg tcaacaagct cgacgtcggt tagagtgagc tgagttattt
11161  atggcaagga cgcttgttgg caacgctata tgcgcttcaa gattgtcgaa ctaaatttga
11221  gtttgtcagt ggggcgttcc attaggcagg ccgaggtgag tgcttcggga ggttgttgtg
11281  atgaagatct gttcgcgctg tgttatggat acatctgacg ctgaaatcgt atttgatgag
11341  gcgggagtct gtaatcactg ccataaattt gacaatgttc agtcccggca gctgttttcc
11401  gatgctagtg gtgagcagcg ccttcaaaag ataattgggc agatcaagaa ggacggttca
11461  ggtaaggatt atgactgcat cattggcctt agtggcggcg tagatagttc ctatcttgct
11521  gtaaaggtca aggatcttgg cttcgcccca ctggttgtgc atgtggacgc cggctggaat
11581  agcgaacttg cagtcagtaa tattgaaaag attgtaaaat attgcggttt tgatttacat
11641  actcatgtaa taaactggga ggaaattcgt gatcttcagt tggcttatat gaaagctgct
11701  gtcgccaatc aggatgtgcc tcaagatcat gccttcttcg ctagtatgta tcactttgct
11761  gtgaagaata atattaagta cattctgagt ggtggtaatt tggccactga ggcagtattc
11821  ccagatacat ggcacggcag cgctatggat gcaataaacc taaaggctat tcacaaaaaa
11881  tatggtgagc gtccgctaag ggactacaag actattagtt ttcttgagta ctatttctgg
11941  tatccctttg tcaaaggaat gagaacggtc cgtccgttga atttcatggc ctatgataag
12001  gccaaggctg aaaccttcct tcaagaaacg ataggctatc gttcttacgc gcgaaagcat
12061  ggagagtcga ttttcaccaa gcttttccag aactactatc taccgaccaa gtttggctat
12121  gataaacgca aactgcacta ctccagcatg attttgtctg ggcaaatgac gcgtgacgaa
12181  gctcaggcta aactggctga ccgctatat gatgcagatg aactgcagtt tgatatcgaa
12241  tatttctgca agaagatgcg aatcacccag gctcaatttg aagagttgat gaatgcacct
12301  gttcatgact attcggagtt tgccaactgg gattctcgac agaggattgc gaaaaaagtt
12361  caaatgattg tccagcgtgc gctgggtcgt cgcatcaatg tctactcgtg atgaccgggg
12421  ccgctcatga ctaaagttgc tcatttgaca tcggttcact cgcgttatga tattcgtata
12481  tttcgaaagc agtgtagaac actctctcaa tacggatacg atgtgtatct ggttgtcgca
12541  gatggtaagg gtgatgaagt caaggatggt gtaaggattg ttgatgtcgg agtactctca
12601  ggtcgcttga atcgtattct aaaaaccacc cgaaaaattt atgaacaggc tttggcgctt
12661  ggggctgatg tctatcattt tcatgatccc gaactgatac ctgttggtct tcgactgaaa
12721  aagcaaggta agcaggttat cttcgactcc catgaggatg tgccgaagca actgctgagt
12781  aaaccttaca tgcgaccgtt tttacgccgt gtagtggctg tgttattttc ctgctatgag
12841  aaatatgcat gccctaagct ggatgcagtc cttacggcaa cgccgcatat tcgtgaaaaa
```

FIGURE 2E

```
12901 tttaaaaata ttaatgggaa tgttctagat attaataact ttcccatgtt gggtgagttg
12961 gatgcgatgg ttccttgggc aagcaagaaa actgaagtct gctacgtcgg tggtatcact
13021 tccattcgtg gtgttcgtga agtcgttaag agtcttgagt gcttgaagtc ctcggcgcgc
13081 ttgaatttag tgggaaagtt ttcagagcca gagatagaaa aagaagtcag agcgctcaag
13141 ggatggaact ccgttaacga acatggtcag cttgatcgag aagatgttcg tcgtgtactc
13201 ggtgactctg ttgccgggtt ggtgacattt ctcccaatgc ctaatcatgt tgatgcacaa
13261 cctaataaga tgttcgagta tatgtcgtcg ggaatccctg tgatcgcttc caatttcct
13321 ctctggcggg aaattgttga aggtagcaat tgtggtatat gcgtagatcc tctaagtcct
13381 gctgccattg ctgaagcgat cgactatctg gtaagtaatc cgtgtgaggc ggcagcgctg
13441 ggacgtaatg gccagcgggc agtgaacgaa cgttataact gggatttgga agggcgcaaa
13501 ctagcgcggt tctattccga tctactgagt aagcgagatt ccatatgaaa attctgacca
13561 tcattggtgc gcgtccgcag tttattaaag cgagtgtggt ttcaaaggct atcattgagc
13621 agcagaccct ttcggaaatc atcgttcata ctggtcagca ttttgatgcc aatatgtctg
13681 aaatattttt cgaacagctg ggtattccaa agccggatta ccagttggat atccatggtg
13741 gtactcacgg ccaaatgacc gggcgtatgc taatggagat cgaggatgta attctcaagg
13801 agaaacctca tcgcgtattg gtatacggcg ataccaactc taccttggct ggagcgttgg
13861 ctgcctccaa gctgcatgtt cctatcgcac acatcgaagc cggcctgcga agtttcaata
13921 tgcggatgcc ggaggaaatt aaccgtattc ttactgatca ggttagtgat attctgtttt
13981 gccctactcg agttgcaatt gataatctca agaatgaagg tttcgaaaga aaggctgcga
14041 agatagtcaa cgtgggtgat gtgatgcagg atagcgctct attctttgcg cagcgtgcaa
14101 cctcgccaat tggacttgcg tcacaagatg ggtttattct cgcgaccctg catcgtgccg
14161 agaacaccga cgatccagtt cgcctgactt cgatagtcga ggctctgaat gaaatccaga
14221 ttaatgttgc acctgtggtg ctaccctgc atccacgtac ccgcggtgtc atcgagcgcc
14281 tagggctcaa gctggaagtg caggttatcg atcctgtcgg atatctggaa atgatctggc
14341 tgttgcaacg ctctggcctg gtgctcacgg acagcggcgg tgttcagaaa gaagcattct
14401 tcttcggcaa gccctgcgtg accatgcgtg accagaccga atgggtggag ctagtgacct
14461 gtggagccaa cgttcttgtg ggagcggccc gcgacatgat tgtcgaatct gcacggacta
14521 gcctgggaaa gaccattcaa gacgatggtc agctttacgg aggcggtcaa gcct?tctcg
14581 gattgctgaa tatcttgcca agctgtgatg ctttgcgtgt cgagtttaaa taaaggattt
14641 atttagttcc atgaacgtct ggtatgtgca tccctatgct ggcggccccg gagttggtcg
14701 ttattggcgg ccttattatt tctccaagtt ttggaatcag gctgggcatc ggtcggtcat
14761 aatctcggca ggctataccc atctgctgga accggatgaa aagcgttcgg gcgtcacctg
14821 tgtaaatgga gccgaatacg catatgtacc tactttgcgc tatttgggca atggcgtggg
14881 cagaatgcta tcgatgctca tatttaccat gatgttgctg ccattctgcc tgatcttggc
14941 cctgaagcgt ggaacgccgg atgcgattat ctactcatcg cctcaccgt ttggcgtcgt
15001 tagctgttgg ctggctgctc gcctgctagg tgcgaaattt gtatttgagg tgcgcgatat
15061 ctggcctttg agtctggtcg aactgggagg cttgaaagct gacaatcccc tggtgcgtgt
15121 taccggttgg atcgaaagat tctcctatgc gcgagctgat aagatcatca gtctgctgcc
15181 atgtgcggag ccgcacatgg ccgacaaagg acttcccgct ggaaagttcc tgtgggttcc
15241 gaatggcgtt gacagcagcg atatctctcc tgatagcgct gtgagttcaa gtgatttggt
15301 ccggcatgta caagttctca aggagcaggg tgttttcgtt gtgatctatg ctggagcgca
15361 cggcgaaccc aatgctctgg agggattggt tcgctctgcc ggactgctgc gcgagcgtgg
15421 tgcaagtatc agaatcattc tggtgggcaa gggagagtgc aaagagcaac tcaaggcgat
15481 tgccgcacag gatgccagcg ggctagtgga gttttcgat cagcagccca aagagactat
15541 catggctgtc ctgaagctgg cgtcggcggg ctacatctcg ctcaagtcag aaccgatctt
15601 ccgctttggc gtgagcccca acaagctatg ggattacatg ctggtgggt tgccagtcat
15661 tttcgcctgc aaggcaggga acgacccggt tagtgactac gattgcggtg tatctgccga
15721 cccagatgcc cctgaggata ttactgcagc catcttccgt ctgttgctgc tgagcgaaga
15781 cgagcgtcgc acaatgggc aaagagggcg tgatgcggtc ctggagcatt atacctacga
15841 gagtctggct cttcaggtgt tgaacgccct tgctgatggg cgcgcagcat gaaagctgtc
15901 atggtgaccg gtgcatcagg attcgtcgga tcggccttgt gctgtgagct tgctcggaca
15961 gggtatgcgg tgattgcggt ggtacggcgg gttgttgaaa gaataccttc tgtgacgtac
16021 atcgaagctg atctgaccga tccagccacg tttgccggcg agttcccgac ggtggattgc
16081 attattcatc tcgctggacg tgcccatata ctcactgaca aggttgcaga cccgctcgcc
16141 gcatttcgtg aagtcaaccg agatgcgact gtccggttgg ctacccgtgc gctcgaggct
```

FIGURE 2F

```
16201 ggggtgaagc gtttcgtgtt tgtcagttca attggcgtta acggtaacag cacccggcaa
16261 caggctttca acgaagattc tccagccggc ccacatgcgc cctatgccat ctccaaatac
16321 gaggctgagc aggagctggg gactttgctc cggggtaaag gtatggagtt ggtggttgtc
16381 cgaccgcctt tgatctatgc caatgatgcg ccaggtaact tcggccgttt gctcaagctc
16441 gtcgctagtg gtctgccgct tccgcttgac ggtgtccgta atgcgcgcag cctggtttct
16501 aggagaaaca tcgtgggttt cctgagtctt tgtgccgaac accccgatgc tgcgggcgaa
16561 ctgtttctgg tggcggatgg cgaggatgtt tccattgcgc aaatgatcga ggccctgagt
16621 cggggaatgg gcaggcgtcc agctcttttc acgtttccag cggtgctgct gaagcttgta
16681 atgtgcttgc tgggtaaggc ttccatgcat gaacagctct gtggctcgtt acaggtcgat
16741 gcttccaagg cccgccggct gctcggctgg gttcccgtcg agactattgg tgccggtctg
16801 caagcagcag gtcgagagta cattcttcgc cagagggagc gccgaaaatg acggacacat
16861 ccaaacccct ggtcggcaat tacgctgaac tttaataagt tctctttcca atgatgatct
16921 ggatgatcgc gtgtctagtt gtcttgctgt tttcatttgt cgctacctgg gggctgcgtc
16981 gctatgcatt agcgacgaaa ctgatggatg ttccgaatgc ccgtagctcc cacagtcaac
17041 cgacgcctag gggggaggt gttgcaatcg ttctggtctt ccttgcagcg ttggtgtgga
17101 tgctgagtgc aggcagtatc tccggcggct ggggggggc gatgctgggt gcaggttctg
17161 gcgtggcact gttagggttc ctggatgacc atgggcacat tgctgcgcgt tggcggctgc
17221 tcggccattt ctcagcagcg atatggatct tgctgtggac gggtggtttc ccgccgctgg
17281 atgtggttgg gcatgctgtc gacttaggat ggctgggcca cgtattggca gttttctatt
17341 tggtatgggt gctgaacctt tataacttca tggatggcat tgatggtatt gccagtgtcg
17401 aggccattgg tgtctgtgta ggaggggccc tgatctactg gcttacaggg catgtcgcga
17461 tggttggtat ccctctgttg ctggcgtgcg cggtcgccgg cttcctgatc tggaacttcc
17521 ctccagctcg aatcttcatg ggtgatgcgg ggagtggttt tcttggtatg gttattggtg
17581 cactagctat tcaggctgca tggaccgccc cctcgctgtt ctggtgctgg ttgatattgc
17641 tgggagtgtt catcgttgat gcaacctata ctctgatccg ccggatcgcc agaggggaga
17701 aattctatga ggcgcatcgc agccacgctt atcagtttgc ctcgcgtcgt tatgctagcc
17761 atctgcgggt taccttgggt gttctggcta tcaacactct ttggttgttg cgttggcact
17821 gatggttgca ttgggttgga tcagcggctt catcggtatc ctggttgctt atgctcctct
17881 ttgcctcttg gcggtaggat acaaggcggg ttccttggaa aaatcctaag ccgtggattg
17941 acctgctccc cgatttcagt accacgccga acttagtaga gtctgttttc cgagcaggag
18001 acggcagtga aaaagcgttt tactgaagaa cagattctag actttctgaa gcaggcagaa
18061 gccggtgtgc cggtgaagga gctgtgtcgc cgacacagct tcagtgatgc cacgttctac
18121 acctagcggg ccaagttcgt cggcatgacc gtgccggatg ccaagcgcct gaaggatctc
18181 gaactggaaa acagccggct gaagaagttg ctcgccgagt ccctcctcga catcggggcg
18241 ctgaaagtgg tcacccgggg aaaggggag cccggcagcg gggcggggg gcaggagatt
18301 caggcgcaaa ccgacatctc cgagcgtcgt gccctgtcag ttgttcaggc tgtcccgctc
18361 tgtgttgtgc caccagccgc gaactagtgt gcaaaacacc gagctgcaag cccaactggt
18421 ggaactggca agggcttcgg cactttggct atcaccgcct gcacattctg ctgcggcgtg
18481 ctggtgtgca gatcaactac aagcggactt accggctata ctgagccgtc ggcttgatgg
18541 tgaagcggcg gaggcgccgc cacaggggcg cggtggcgtg cgaatgcctg agcctgccga
18601 gcgcaccgaa ctaggtcttg tcgatggatt tcgtcttcga cgcgctcagc actgggcgac
18661 ggatcaaatg cctgacggtg gtcgatgact tcaccaagga gtcggttggc atcctggtgg
18721 agcacggtat cagcggtttt cgtgtcacac gggcgctgga cagatggcac ggttgcgcgg
18781 ttacccgaag gcgatccgca ccccgagtt caccggcaag gcgcttgatc agtgggccta
18841 tcggcgtgat attaagttga agctgactca gtccggcaag cccacgcaga acgccttcat
18901 cgtcattcca acggcaagtt ccgcaatgag cactgctgct cgctggtcga agccagaatc
18961 cgcatcgtgg cctggcggca cgattacaac gagcaccgac cgtccagcgc cattggcaat
19021 ctcacctcgc tagagtttgc tgcaagttgg cgaactcgcc agcagcaact gaagcaggaa
19081 aattgatgtc aaccccaggg cctactacct aggcagcgta ctaaaactgg ggcaggtca
19141 tctacgatcc ttgtgatagg tatcgacggt gctgtggcga tccgtgcatg tggaactgat
19201 ctgggatttt ccctgcgtgt gttttcaggg gcctggcagt gattttttga gcattgccat
19261 gggggggcgg ttttgcat cctgctcgga cgctggctga ttccactcg acgtgctcgt
19321 gttcgatgtc acttttactt tgctgctgca tcgtttgtta tgaggcgata aaattcggca
19381 gagctatcga gtcacgcatg atggcacgtt ggtgtcgtgc tgaagtggca tttgccggtt
19441 atcctttgtg gctgtgatca gtttcttctg gttattaccc tagcattgct ggtagtacta
```

FIGURE 2G

```
19501 agcattatcg acggagtact tgggggctta tcgcgtatgc tcctatggct tggatggcga
19561 cgagtcttgg gaggggatgt cctgagacgt agcgtgggcc ttgccatatt gttgccatgg
19621 ttatctgtct gatctgtctg gttggtatgg atgtattgaa cggggctgat aaataggatg
19681 ttggataatt tgaggataaa gctcctggga ttgccgcgcc gctataagcg aatgctgcaa
19741 gtcgctgccg atgtgactct tgtgtggcta tccctctggc tggctttctt ggtcaggttg
19801 ggcacagaag acatgatcag cccgtttagc ggccatgcct ggctgttcat cgccgccccg
19861 ttggtggcca ttcccctgtt catccgcttc ggcatgtacc gggcggtgat gcgctacctg
19921 ggcaacgacg cccttatcgc gatcgccaag gccgtcacca tttccgcgct ggtcctgtcg
19981 ttgctggtct actggtaccg ctccccgccg gcggtggtgc cgcgttccct ggtgttcaac
20041 tactggtggt tgagcatgct gctgatcggc ggcttgcgtc tggccatgcg ccagtatttc
20101 atgggagact ggtactctgc tgtgcagtcg gtaccatttc tcaaccgcca ggatggcctg
20161 cccagggtgg ctatctatgg cgcgggggcg gccgccaacc agttggttgc ggcattgcgt
20221 ctcggtcggg cgatgcgtcc ggtggcgttc atcgatgatg caagcagat cgccaaccgg
20281 gtcatcgccg gtctgcgggt ctataccgcc aagcatatcc gccagatgat cgacgagacg
20341 ggcgcgcagg aggttctcct ggcgattcct tccgccactc gggccggcg ccgagagatt
20401 ctcgagtccc tggagccgtt cccgctgcac gtgcgcagca tgcccggctt catggacctg
20461 accagcggcc gggtcaaggt ggacgacctg caggaggtgg acatcgctga cctgctgggg
20521 cgcgacagcg tcgcaccgcg caaggagctg ctggaacgtt gcatccgcgg tcaggtggtg
20581 atggtgaccg gggcgggcgg ctctatcggt tcggaactct gtcggcagat catgagttgt
20641 tcgcctagcg tgctgatcct gttcgagcac agcgaataca acctctatag catccatcag
20701 gaactggagc gtcggatcaa gcgcgagtcg ctttcggtga acctgttgcc gatcctcggt
20761 tcggtgcgca atcccgagcg cctggtggac gtgatgcgta cctggaaggt caataccgtc
20821 taccatgcgg cggcctacaa gcatgtgccg atcgtcgagc acaacatcgc cgagggcgtt
20881 ctcaacaacg tgataggcac cttgcatgcg gtgcaggccg cggtgcaggt cggcgtgcag
20941 aacttcgtgc tgatttccac cgacaaggcg gtgcgaccga ccaatgtgat gggcagcacc
21001 aagcgcctgg cggagatggt ccttcaggcg ctcagcaacg aatcggcacc gttgctgttc
21061 ggcgatcgga aggacgtgca tcacgtcaac aagacccgtt tcacaatggt ccgcttcggc
21121 aacgtcctcg gttcgtccgg ttcggtcatt ccgctgttcc gcgagcagat caagcgcggc
21181 ggcccggtga cggtcaccca cccgagcatc acccgttact tcatgaccat tcccgaggca
21241 gcgcagttgg tcatccaggc cggttcgatg gggcagggcg gagatgtatt cgtgctggac
21301 atggggccgc cggtgaagat cctggagctc gccgagaaga tgatccacct gtccggcctg
21361 agcgtgcgtt ccgagcgttc gccccatggt gacatcgcca tcgagttcag tggcctgcgt
21421 cctggcgaga agctctacga agagctgctg atcggtgaca acgtgaatcc caccgaccat
21481 ccgatgatca tgcgggccaa cgaggaacac ctgagctggg aggccttcaa ggtcgtgctg
21541 gagcagttgc tggccgccgt ggagaaggac gactactcgc gggttcgcca gttgctgcgg
21601 gaaaccgtca gcggctatgc gcctgacggt gaaatcgtcg actggatcta tcgccagagg
21661 cggcgagaac cctgagtcat cgttctccgg aaaaggccgc ctagcggcct ttttgttttt
21721 ctccgtacga tgtttccggt gccggaccag gaagcgactg ctttgctggg gctgtcgatc
21781 caggtgcgtt ccacggcgat aaggtggttt cgtggatggg catgaagccc tctacgtggt
21841 cattcatctc tgaaggagtg cacccatgca cctaatcaaa tccgctctgc ttctcatcct
21901 gttcgcctgt cttccgtttt cggcttccgc cgcaccggtc gccgtcgcca agaatccgct
21961 ggccgcaacg acacctgcga cgaccgtgtc gccggggag caggtcaata tcaatacggt
22021 cgacgaggcc gccctgatac gggggctcaa cggtgtcggc gaggccaagg ccagggcgat
22081 cctcgagtat cgtgcggccc atggtccgtt cgtctcggtg atcaactgc tggaagtgaa
22141 aggggtaggc ccggcgttgc tggagaagaa ccgggcgcgg atcgtcatcg agtgaggtgc
22201 gactgaaggg gcgaactttc gtcccgataa cgaaaaagcc cccggcatgt gccgagggct
22261 ttgaatttgg ctccgcgacc tggactcgaa ccagggaccc aatgattaac agtcatttgc
22321 tctaccgact gagctatcgc ggaacagcga ggcgtatgtt actgattaaa aaggggaagc
22381 ctctcccgat gacttcccca ttttccctac aggacctgga cgatggcctt ggtgatggtc
22441 tccaggttcg atttgttcag cgcggcgacg cagatacggc cggtgctgac ggcgtagata
22501 ccgaactcgg tcttcaggcg ctcgacctgg tcggcggtca ggccggaata ggagaacatg
22561 ccacgttggc gaccgacgaa actgaagtcg cgcttggcgc cgtgggctgc cagttgctcg
22621 accatcgcca ggcgcatgtc gcggatgcgg tcgcgcatct cgcccagttc ctgctcccag
22681 agggcccgca gttccgggct gttgagcacg gaggagacga cgctggcgcc gtgggtcggt
22741 gggttcgaat agttggtgcg gatcacccgc ttcacctggg acagcacgcg ggccgattca
```

FIGURE 2H

```
22801 tcgcggcttt cggtcacgat cgagagggcg ccgacgcgtt cgccatagag cgagaaggat
22861 ttggagaacg agctggaaac gaagaagctc aggcccgact gggcgaacag gcgcaccgcg
22921 gcggcgtctt cctcgatgcc gttgccgaag ccctggtagg cgatgtcgag gaacggcacg
22981 tggcccttgg ccttgagcac gtccagcacc tgtttccagt cgtccagctc gagatcgacg
23041 ccggtcggat tatggcagca ggcgtgcaga accacgatcg agcgggccgg cagggcattc
23101 aggtcttcca gcaggccggc gcggttcacg ccattgctgg cggcgtcgta atagcggtag
23161 ttctgcaccg ggaagccggc ggcttcgaac agtgcgcggt ggttttccca gctcgggtcg
23221 ctgatggcca cggtggcgtc gggcagcagg cgcttgagga agtcggcgcc gagcttgagc
23281 gcgccggtgc cgccgacggc ctgggtcgtg accacacggc cggcggccag cagctcggac
23341 tcgttaccga acagcagttt ctgtacgccc tggtcgtagg cggcgatccc ttcgatcggc
23401 aggtagccgc gcggcgcgtg ggcctcgatg cgggccttct cggcagcctg cacggcacgc
23461 aacagcggaa tgcgcccctc ctcgttgtag tacacgccca cgcccaggtt gatcttgccc
23521 ggacgggtat cggcgttgaa ggcttcgttc aggccaagga tgggatcacg cggtgccatt
23581 tcgacggcag aaaacagact cattttgcgg ctgctcggag tgtgaagaga ggagggcaac
23641 gcaaccgtt atgcggggc gcaaagggtt gcgcaaacgg ggggttatta tagacacccc
23701 ttgatgcatg cggcgacatt taggtgcatg ctttcagcta tttctgacgc cggattttcc
23761 ttggcgtcac agctccctgc gaggtttttc atggatacgt tccaactcga ctcgcgcttc
23821 aagcccgccg gcgaccagcc ggaagccatc cggcaaatgg tcgaggggct ggaggcgggg
23881 ctttcgcacc agaccctgct ggggtgacg ggctctggca agactttcag catcgccaac
23941 gtgattgccc aggtgcagcg cccgaccctg gtcctggcgc gaacaagac cctggcggcc
24001 cagctctacg gggagttcaa gacgttcttc ccgcacaatt ccgtggagta cttcgtttcc
24061 tactacgact actaccagcc ggaggcctac gtcccgtctt ccgataccta tatcgagaag
24121 gactcctcga tcaacgacca tatcgagcag atgcgcctgt cggcgaccaa ggcgctgctc
24181 gagcgtccgg atgcgatcat cgtcgccacc gtgtcgtcca tctacggcct cggtgatccc
24241 gcgtcctacc tgaagatggt cctgcacctg gaccgcggcg accgcatcga ccagcgcgaa
24301 ctgctgcggc gactgaccag cctgcagtac acccgcaacg acatggattt cgcccgtgcg
24361 actttccgtg tgcgtggcga tgtgatcgac atcttcccgg ccgaatccga tctcgag
//
```

FIGURE 3

CDS <1..479
/gene="wzz (rol)"
/codon_start=3
/product="Wzz (Rol)"
/db_xref="PID:g1545846"
/transl_table=11

/translation="RDIEQRIQNLRRECQGRREDRIVQLKEALKVAGALKLEEPPLIS

GQSSEELSAIMNGSLMYMRGSKAIMAEIQTLEARSSDDPFIPALRTLQEQQLLLSSLR

VNSERVSVFRQDGPIETPDSPVRPRRAMILIFGLIIGGVLGGFLALCRIFLKKYAR"

FIGURE 4

```
CDS             1286..2596
                /gene="wbpA"
                /codon_start=1
                /product="WbpA"
                /db_xref="PID:g1545847"
                /transl_table=11
```

/translation="MIDVNTVVEKFKSRQALIGIVGLGYVGLPLMLRYNAIGFDVLGI

DIDDVKVDKLNAGQCYIEHIPQAKIAKARASGFEATTDFSRVSECDALILCVPTPLNK

YREPDMSFVINTTDALKPYLRVGQVVSLESTTYPGTTEEELLPRVQEGGLVVGRDIYL

VYSPEREDPGNPNFETRTIPKVIGGHTPQCLEVGIALYEQAIDRVVPVSSTKAAEMTK

LLENIHRAVNIGLVNEMKIVADRMGIDIFEVVDAAATKPFGFTPYYPGPGLGGHCIPI

DPFYLTWKAREYGLHTRFIELSGEVNQAMPEYVLGKLMDGLNEAGRALKGSRVLVLGI

AYKKNVDDMRESPSVEIMELIEAKGGMVAYSDPHVPVFPKMREHHFELSSEPLTAENL

ARFDAVVLATDHDKFDYELIKAEAKLVVDSRGKYRSPAAHIIKA"

FIGURE 5

```
CDS             2670..3620
                /gene="wbpB"
                /codon_start=1
                /product="WbpB"
                /db_xref="PID:g1545848"
                /transl_table=11
```

/translation="MKNFALIGAAGYIAPRHMRAIKDTGNCLVSAYDINDSVGIIDSI

SPQSEFFTEFEFFLDHASNLKRDSATALDYVSICSPNYLHYPHIAAGLRLGCDVICEK

PLVPTPEMLDQLAVIERETDKRLYNILQLRHHQAIIALKDKVAREKSPHKYEVDLTYI

TSRGNWYLKSWKGDPRKSFGVATNIGVHFYDMLHFIFGKLQRNVVHFTSEYKTAGYLE

YEQARVRWFLSVDANDLPESVKGKKPTYRSITVNGEEMEFSEGFTDLHTTSYEEILAG

RGYGIDDARHCVETVNTIRSAVIVPASDNEGHPFVAALAR"

FIGURE 6

```
CDS             3689..5578
                /gene="wbpC"
                /codon_start=1
                /product="WbpC"
                /db_xref="PID:g1545849"
                /transl_table=11
```

/translation="MSSSSSKLLNGMVAVSSGRNIRLDVQGLRAVAVLAVLAYHANSA

WLRAGFVGVDVFFVISGFIITALLVERGVKVDLVEFYAGRIKRIFPAYFVMLAIVCIV

STILFLPDDYVFFEKSLQSSVFFSSNHYFANFGSYFAPRAEELPLLHTCSIANEMQFY

LFYPVLFMCLPCRWRLPVFILLAILLFIWSGYCVFSGSQDAQYFALLARVPEFMSGAV

VALSLRDRELPARLAILAGLLGAALLVCSFIIIDKQHFPGFWSLLPCLGAALLIAARR

GPASLLLASRPMVWIGGISYSLYLWHWPILAFIRYYTGQYELSFVALLAFLTGSFLLA

WFSYRYIETPARKAVGLRQQALKWMLAASVVAIVVTGGAQFNVLVVAPAPIQLTRYAV

PESICHGVQVGECKRGSVNAVPRVLVIGDSHAAQLNYFFDVVGNESGVAYRVLTGSSC

VPIPAFDLERLPRWARKPCQAQIDAVAQSMLNFDKIIVAGMWQYQMQSPAFAQAMRAF

LVDTSYAGKQVALLGQIPMFESNVQRVRRFRELGLSAPLVSSSWQGANQLLRALAEGI

PNVRFMDFSSSAFFADAPYQDGELIYQDSHHLNEVGARRYGYFASRQLQRLFEQPQSS

VSLKP"

FIGURE 7

```
CDS             5575..6066
                /gene="wbpD"
                /codon_start=1
                /product="WbpD"
                /db_xref="PID:g1545850"
                /transl_table=11
```

/translation="MSYYQHPSAIVDDGAQIGSDSRVWHFVHICAGARIGAGVSLGQN

VFVGNKVVIGDRCKIQNNVSVYDNVTLEEGVFCGPSMVFTNVYNPRSLIERKDQYRNT

LVKKGATLGANCTIVCGVTIGEYAFLGAGAVINKNVPSYALMVGVPARQIGWIANSVS

SCS"

FIGURE 8

```
CDS             6152..6982
                /gene="wbpE"
                /codon_start=1
                /product="WbpE"
                /db_xref="PID:g1545851"
                /transl_table=11
```

/translation="MIEFIDLKNQQARIKDKIDAGIQRVLRHGQYILGPEVTELEDRL

ADFVGAKYCISCANGTDALQIVQMALGVGPGDEVITPGFTYVATAETVALLGAKPVYV

DIDPRTYNLDPQLLEAAITPRTKAIIPVSLYGQCADFDAINAIASKYGIPVIEDAAQS

FGASYKGKRSCNLSTVACTSFFPSKPLGCYGDGGAIFTNDDELATAIRQIARHGQDRR

YHHIRVGVNSRLDTLQAAILLPKLEIFEEEIALRQKVAAEYDLSLKQVGIGTPFIGSG"

FIGURE 9

```
CDS             7236..8552
                /gene="wzy (rfc)"
                /codon_start=1
                /product="Wzy (Rfc)"
                /db_xref="PID:g1545852"
                /transl_table=11
```

/translation="MYILARVDRSILLNTVLLFAFFSATVWVNNNYIYHLYDYMGSAK

KTVDFGLYPYLMVLALICALLCGGAIRRPGDLLVTLLVVILVPHSLVLNGANQYSPDA

QPWAGVPLAIAFGILIIGIVNKIRFHPLGALQRENQGRRMLVLLSVLNIVVLVFIFFK

SAGYFSFDFAGQYARRALAREVFAAGSANGYLSSIGTQAFFPVLFAWGVYRRQWFYLV

LGIVNALVLWGAFGQKYPFVVLFLIYGLMVYFRRFGQVRVSWVVCALLMLLLLGALEH

EVFGYSFLNDYFLRRAFIVPSTLLGAVDQFVSQFGSNYYRDTLLGALLGQGRTEPLSF

RLGTEIFNNPDMNANVNFFAIAYMQLGYVGVMAESMLVGGSVVLMNFLFSRYGAFMAI

PVALLFTTKILEQPLLTVMLGSGVFLILLFLALISFPLKMSLGKTL"

FIGURE 10

```
CDS             8549..9499
                /gene="wbpF"
                /codon_start=1
                /product="WbpF"
                /db_xref="PID:g1545853"
                /transl_table=11
```

/translation="MSAAFINRVARVLVGTLGAQLITIGVTLLLVRLYSPAEMGAFSV

WLSFATIFAVVVTGRYELAIFSTREEGELQAIVKLILQLTLLIFVAVAIAVVIGRHLI

ESMPVVIGEYWFALAVASLGLGINKLVLSLLTFQQSFNRLGVARVSLAACIAVAQVSA

AYLLEGVSGLIYGQLFGVVVATALAALWVGKSLILNCIETPWRMVRQVAVQYINFPKF

SLPADLVNTVASQVPVILLAAKFGGDSAGWFALTLKIMGAPISLLAASVLDVFKEQAA

RDYREFGNCRGIFLKTFRLLAVLALPPFIIFGSLASGPLG"

FIGURE 11

```
CDS             9831..10388
                /gene="hisH"
                /codon_start=1
                /product="HisH"
                /db_xref="PID:g1545854"
                /transl_table=11
```

/translation="MLKRVGAKAKASDSREDIEQAEKLILPGVGAFDAGMQTLRKSGL

VDVLTEQVMIKRKPVMGVCLGSQMLGLRSEEGAEPGLGWIDMDSVRFERRDDRKVPHM

GWNQVSPQLEHPILSGINEQSRFYFVHSYYMVPKDPDDILLSCNYGQKFTAAVARDNV

FGFQFHPEKSHKFGMQLFKNFVELV"

FIGURE 12

```
CDS             10388..11143
                /gene="hisF"
                /codon_start=1
                /product="HisF"
                /db_xref="PID:g1545855"
                /transl_table=11
```

/translation="MVRRRVIPCLLLKDRGLVKTVKFKEPKYVGDPINAIRIFNEKEV

DELILLDIDASRLNQEPNYELIAEVAGECFMPICYGGGIKTLEHAEKIFSLGVEKVSI

NTAALMDLSLIRRIADKFGSQSVVGSIDCRKGFWGGHSVFSENGTRDMKRSPLEWAQA

LEEAGVGEIFLNSIDRDGVQKGFDNALVENIASNVHVPVIACGGAGSIADLIDLFERT

CVSAVAAGSLFVFHGKHRAVLISYPDVNKLDVG"

FIGURE 13

```
CDS             11281..12411
                /gene="wbpG"
                /codon_start=1
                /product="WbpG"
                /db_xref="PID:g1545856"
                /transl_table=11
```

/translation="MKICSRCVMDTSDAEIVFDEAGVCNHCHKFDNVQSRQLFSDASG

EQRLQKIIGQIKKDGSGKDYDCIIGLSGGVDSSYLAVKVKDLGLRPLVVHVDAGWNSE

LAVSNIEKIVKYCGFDLHTHVINWEEIRDLQLAYMKAAVANQDVPQDHAFFASMYHFA

VKNNIKYILSGGNLATEAVFPDTWHGSAMDAINLKAIHKKYGERPLRDYKTISFLEYY

FWYPFVKGMRTVRPLNFMAYDKAKAETFLQETIGYRSYARKHGESIFTKLFQNYYLPT

KFGYDKRKLHYSSMILSGQMTRDEAQAKLAEPLYDADELQFDIEYFCKKMRITQAQFE

ELMNAPVHDYSEFANWDSRQRIAKKVQMIVQRALGRRINVYS"

FIGURE 14

```
CDS             12427..13548
                /gene="wbpH"
                /codon_start=1
                /product="WbpH"
                /db_xref="PID:g1545857"
                /transl_table=11
```

/translation="MTKVAHLTSVHSRYDIRIFRKQCRTLSQYGYDVYLVVADGKGDE

VKDGVRIVDVGVLSGRLNRILKTTRKIYEQALALGADVYHFHDPELIPVGLRLKKQGK

QVIFDSHEDVPKQLLSKPYMRPFLRRVVAVLFSCYEKYACPKLDAVLTATPHIREKFK

NINGNVLDINNFPMLGELDAMVPWASKKTEVCYVGGITSIRGVREVVKSLECLKSSAR

LNLVGKFSEPEIEKEVRALKGWNSVNEHGQLDREDVRRVLGDSVAGLVTFLPMPNHVD

AQPNKMFEYMSSGIPVIASNFPLWREIVEGSNCGICVDPLSPAAIAEAIDYLVSNPCE

AAALGRNGQRAVNERYNWDLEGRKLARFYSDLLSKRDSI"

FIGURE 15

```
CDS             13545..14633
                /gene="wbpI"
                /codon_start=1
                /product="WbpI"
                /db_xref="PID:g1545858"
                /transl_table=11
```

/translation="MKILTIIGARPQFIKASVVSKAIIEQQTLSEIIVHTGQHFDANM
SEIFFEQLGIPKPDYQLDIHGGTHGQMTGRMLMEIEDVILKEKPHRVLVYGDTNSTLA
GALAASKLHVPIAHIEAGLRSFNMRMPEEINRILTDQVSDILFCPTRVAIDNLKNEGF
ERKAAKIVNVGDVMQDSALFFAQRATSPIGLASQDGFILATLHRAENTDDPVRLTSIV
EALNEIQINVAPVVLPLHPRTRGVIERLGLKLEVQVIDPVGYLEMIWLLQRSGLVLTD
SGGVQKEAFFFGKPCVTMRDQTEWVELVTCGANVLVGAARDMIVESARTSLGKTIQDD
GQLYGGGQASLGLLNILPSCDALRVEFK"

FIGURE 16

```
CDS            14651..15892
               /gene="wbpJ"
               /codon_start=1
               /product="WbpJ"
               /db_xref="PID:g1545859"
               /transl_table=11
```

/translation="MNVWYVHPYAGGPGVGRYWRPYYFSKFWNQAGHRSVIISAGYHH

LLEPDEKRSGVTCVNGAEYAYVPTLRYLGNGVGRMLSMLIFTMMLLPFCLILALKRGT

PDAIIYSSPHPFGVVSCWLAARLLGAKFVFEVRDIWPLSLVELGGLKADNPLVRVTGW

IERFSYARADKIISLLPCAEPHMADKGLPAGKFLWVPNGVDSSDISPDSAVSSSDLVR

HVQVLKEQGVFVVIYAGAHGEPNALEGLVRSAGLLRERGASIRIILVGKGECKEQLKA

IAAQDASGLVEFFDQQPKETIMAVLKLASAGYISLKSEPIFRFGVSPNKLWDYMLVGL

PVIFACKAGNDPVSDYDCGVSADPDAPEDITAAIFRLLLLSEDERRTMGQRGRDAVLE

HYTYESLALQVLNALADGRAA"

FIGURE 17

```
CDS             15889..16851
                /gene="wbpK"
                /codon_start=1
                /product="WbpK"
                /db_xref="PID:g1545860"
                /transl_table=11
```

/translation="MKAVMVTGASGFVGSALCCELARTGYAVIAVVRRVVERIPSVTY

IEADLTDPATFAGEFPTVDCIIHLAGRAHILTDKVADPLAAFREVNRDATVRLATRAL

EAGVKRFVFVSSIGVNGNSTRQQAFNEDSPAGPHAPYAISKYEAEQELGTLLRGKGME

LVVVRPPLIYANDAPGNFGRLLKLVASGLPLPLDGVRNARSLVSRRNIVGFLSLCAEH

PDAAGELFLVADGEDVSIAQMIEALSRGMGRRPALFTFPAVLLKLVMCLLGKASMHEQ

LCGSLQVDASKARRLLGWVPVETIGAGLQAAGREYILRQRERRK"

FIGURE 18

```
CDS             19678..21675
                /gene="wbpM"
                /codon_start=1
                /product="WbpM"
                /db_xref="PID:g1545862"
                /transl_table=11
```

/translation="MLDNLRIKLLGLPRRYKRMLQVAADVTLVWLSLWLAFLVRLGTE

DMISPFSGHAWLFIAAPLVAIPLFIRFGMYRAVMRYLGNDALIAIAKAVTISALVLSL

LVYWYRSPPAVVPRSLVFNYWWLSMLLIGGLRLAMRQYFMGDWYSAVQSVPFLNRQDG

LPRVAIYGAGAAANQLVAALRLGRAMRPVAFIDDDKQIANRVIAGLRVYTAKHIRQMI

DETGAQEVLLAIPSATRARRREILESLEPFPLHVRSMPGFMDLTSGRVKVDDLQEVDI

ADLLGRDSVAPRKELLERCIRGQVVMVTGAGGSIGSELCRQIMSCSPSVLILFEHSEY

NLYSIHQELERRIKRESLSVNLLPILGSVRNPERLVDVMRTWKVNTVYHAAAYKHVPI

VEHNIAEGVLNNVIGTLHAVQAAVQVGVQNFVLISTDKAVRPTNVMGSTKRLAEMVLQ

ALSNESAPLLFGDRKDVHHVNKTRFTMVRFGNVLGSSGSVIPLFREQIKRGGPVTVTH

PSITRYFMTIPEAAQLVIQAGSMGQGGDVFVLDMGPPVKILELAEKMIHLSGLSVRSE

RSPHGDIAIEFSGLRPGEKLYEELLIGDNVNPTDHPMIMRANEEHLSWEAFKVVLEQL

LAAVEKDDYSRVRQLLRETVSGYAPDGEIVDWIYRQRRREP"

FIGURE 19

```
CDS             22302..23693
                /gene="wbpN"
                /codon_start=1
                /product="WbpN"
                /db_xref="PID:g1545863"
                /transl_table=11
```

/translation="MINSHLLYRLSYRGTARRMLLIKKGKPLPMTSPFSLQDLDDGLG

DGLQVRFVQRGDADTAGADGVDTELGLQALDLVGGQAGIGEHATLATDETEVALGAVG

CQLLDHRQAHVADAVAHLAQFLLPEGPQFRAVEHGGDDAGAVGRWVRIVGADHPLHLG

QHAGRFIAAFGHDREGADAFAIEREGFGERAGNEEAQARLGEQAHRGGVFLDAVAEAL

VGDVEERHVALGLEHVQHLFPVVQLEIDAGRIMAAGVQNHDRAGRQGIQVFQQAGAVH

AIAGGVVIAVVLHREAGGFEQCAVVFPARVADGHGGVGQQALEEVGAELERAGAALGL

GRDHTAGGQQLGLVTEQQFLYALVVGGDPFDRQVAARRVGLDAGLLGSLHGTQQRNAP

LLVVVHAHAQVDLARTGIGVEGFVQAKDGITRCHFDGRKQTHFAAARSVKRGGQRNPL

CGGAKGCANGGLL"

FIGURE 20

```
CDS             23704..>24417
                /gene="uvrB"
                /codon_start=1
                /product="UvrB"
                /db_xref="PID:g1545864"
                /transl_table=11

/translation="MHAATFRCMLSAISDAGFSLASQLPARFFMDTFQLDSRFKPAGD

QPEAIRQMVEGLEAGLSHQTLLGVTGSGKTFSIANVIAQVQRPTLVLAPNKTLAAQLY

GEFKTFFPHNSVEYFVSYYDYYQPEAYVPSSDTYIEKDSSINDHIEQMRLSATKALLE

RPDAIIVATVSSIYGLGDPASYLKMVLHLDRGDRIDQRELLRRLTSLQYTRNDMDFAR

ATFRVRGDVIDIFPAESDLE"
```

FIGURE 21

```
CDS             16911..17822
                /gene="wbpL"
                /codon_start=1
                /product="WbpL"
                /db_xref="PID:g1545861"
                /transl_table=11

/translation="MMIWMIACLVVLLFSFVATWGLRRYALATKLMDVPNARSSHSQP

TPRGGGVAIVLVFLAALVWMLSAGSISGGWGGAMLGAGSGVALLGFLDDHGHIAARWR

LLGHFSAAIWILLWTGGFPPLDVVGHAVDLGWLGHVLAVFYLVWVLNLYNFMDGIDGI

ASVEAIGVCVGGALIYWLTGHVAMVGIPLLLACAVAGFLIWNFPPARIFMGDAGSGFL

GMVIGALAIQAAWTAPSLFWCWLILLGVFIVDATYTLIRRIARGEKFYEAHRSHAYQF

ASRRYASHLRVTLGVLAINTLWLLRWH"

source          17935..19144
                /organism="Pseudomonas aeruginosa"
                /insertion_seq="IS1209(PA)"
                /strain="PAO1"
                /serotype="O5"
misc_feature    18032..19141
                /note="IS407"
```

FIGURE 22
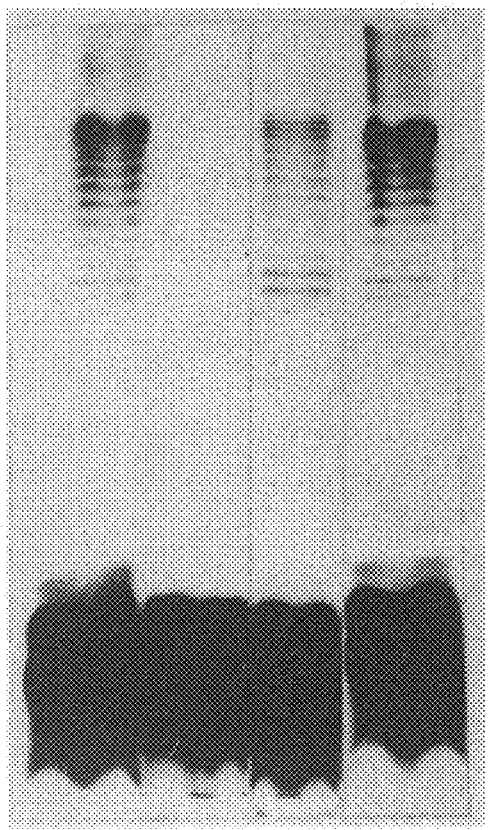
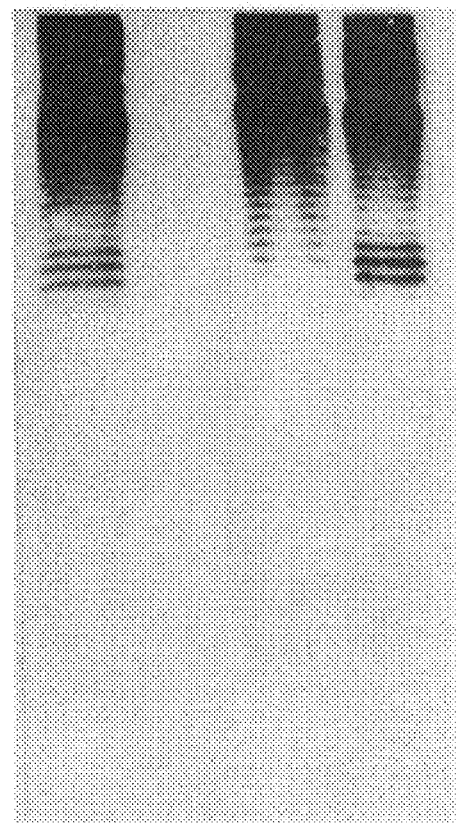

FIGURE 24
A 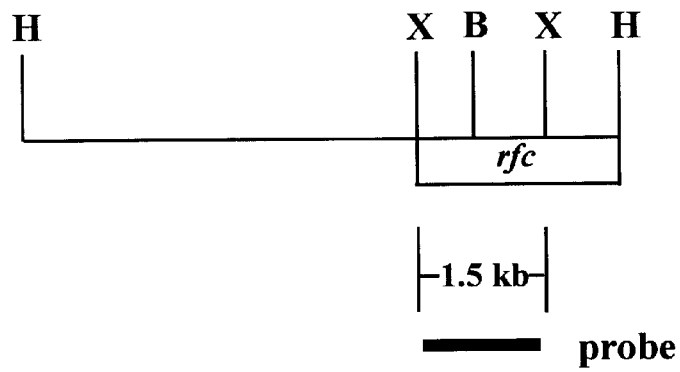
B 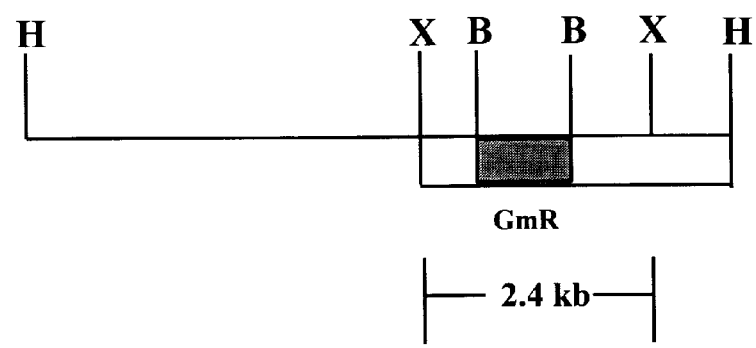
C
| kb | 1 | 2 | 3 | 4 |
|---|---|---|---|---|
| 2.4 — | | ● | ● | ● |
| 1.5 — | ● | | | |

FIGURE 26
pFV161 probe 
pFV161 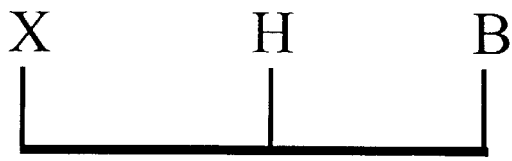
pFV401 
pFV402 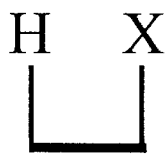
0.8 kb

FIGURE 30
Serotype O2.
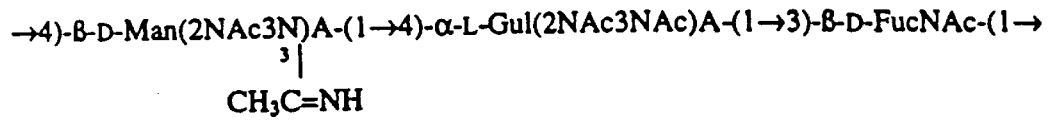
→4)-β-D-Man(2NAc3N)A-(1→4)-α-L-Gul(2NAc3NAc)A-(1→3)-β-D-FucNAc-(1→
         ³|
         CH₃C=NH
Serotype O5.
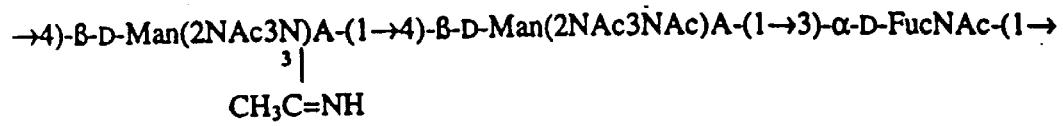
→4)-β-D-Man(2NAc3N)A-(1→4)-β-D-Man(2NAc3NAc)A-(1→3)-α-D-FucNAc-(1→
         ³|
         CH₃C=NH
Serotype O16.
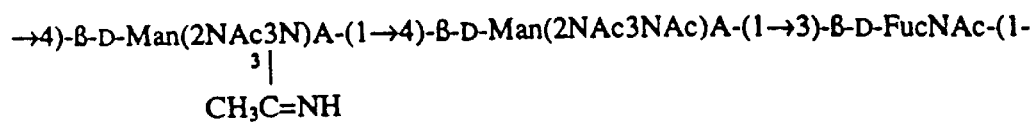
→4)-β-D-Man(2NAc3N)A-(1→4)-β-D-Man(2NAc3NAc)A-(1→3)-β-D-FucNAc-(1-
         ³|
         CH₃C=NH
Serotype O20.
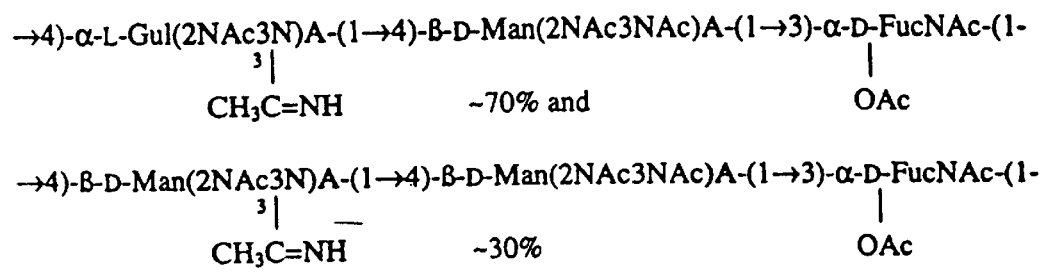
→4)-α-L-Gul(2NAc3N)A-(1→4)-β-D-Man(2NAc3NAc)A-(1→3)-α-D-FucNAc-(1-
         ³|                                                      |
         CH₃C=NH      ~70% and                                   OAc
→4)-β-D-Man(2NAc3N)A-(1→4)-β-D-Man(2NAc3NAc)A-(1→3)-α-D-FucNAc-(1-
         ³|                                                      |
         CH₃C=NH      ~30%                                       OAc

FIGURE 31

```
E. coli σ⁷⁰    c.a...t.....TTGACA..t   17bp   ggTATAATg psbA           c.t...t.....TTGtgA..a   18bp   cgcAgAAag
hisH           t.a...t.....TTGcCc..c   16bp   gcTtTgtTg
psbG           c.a...c.....TTGgCA..g   16bp   tcaAgAtTg
IS407-1        c.t...g.....TTGgCA..c   17bp   agTtTgcTg
IS407-2        g.t...t.....TTGgCg..c   17bp   acTAagcag
IS407-3        t.a...g.....TTGAtg..a   17bp   acTAcctag
psbN           t.g...c.....TTGctg..a   17bp   cggATcgTc
```

FIGURE 32

```
                        GTG
                        ATG
                AAA     AAA    TTAA
       21111111111             1111        Spaces between RBS
       09876543210987654321012345678901234  and first codon
```

| Gene | Sequence | Spaces |
|------|----------|--------|
| psbA | aaattGAGGTGAgttggAAAATGatagatgTTAA | 8 |
| psbB | tcatttccatAGGAcgaaccATGAAAaatttcgc | 6 |
| psbC | ctttggcAAGctgcagcgtaATGttgtgcacTTc | 10 |
| psbD | tcgagtgtGAGtctcaagccATGagttattaTcA | 9 |
| psbE | agcAAGGtGGacgtgtgaccATGattgaatTcAt | 10 |
| rfc | ctgcgttgacGAattgacggATGtatatatactt | 8 |
| psbF | atgtctttAGGAaaaactctATGagtgcggcTtt | 8 |
| hisH | tgtgccaagGGAGaTGccaaGTGatcgttgTTAt | 7 |
| hisF | aacttcgtGGAGcttgtctgATGgtccggaggcg | 8 |
| psbG | tgcttcgGGAGGTtgttGTGATGAAgatcTgtt | 4\7 |
| psbH | cgtgatgaccggggccgctcATGactAAAgTTgc | |
| psbI | ctgagtaagcGAGattccatATGAAAattcTgAc | 7 |
| psbJ | taaAGGAtttatttagttccATGaacgtctggtA | 13 |
| psbK | cttgctgatgGGcgcgcagcATGAAAgctgTcAt | 8 |
| psbM | gaacggggctGATaaataggATGttggataaTtt | 7 |
| psbN | ggactcgaaccAGGgacccaATGattaacagTcA | 6 |

FIGURE 33

| Protein | position | NAD-binding domains | Reference |
|---|---|---|---|
| PsbA | 17-45 | LIGIVGL-GYVGLPLMLRYNAI-----GGDVLGID | this study |
| PsbK | 5-32 | AVMVTGASGFVGSALCCELART-GYAVIAVRRVVE | this study |
| PsbM | 300-330 | VVMVTGAGGSIGSELCRQIMSC-----SPSVLILFE | this study |
|  | 524-553 | LVIQAGSMGQGGDVFVLDMGPP-------VKILELAE |  |
| AlgD | 2-30 | RISIFGL-GYVGAVCAGCLSAR-------GGEVIGVD | Deretic et al., 1987 |
| BplL | 287-317 | VVMVTGAGGSIGSELCRQILAL-----RPRKLVLFE | Allen and Maskell, 1996 |
|  | 495-524 | LVLQAGAMGESGSVFVLDMGEP-------VLIRELAE |  |
| CapD | 283-316 | TILVTGAGGSIGSEICRQVSKF--DPQKIILLGHGE | Lin et al., 1994 |
| CapI | 2-31 | KILITGTAGFIGSHLAKKLIKQ-------GGYVIGVD | Lin et al., 1994 |
| CapL | 4-32 | NIAVVGL-GYVGLPVAVTFGNK-------HKVIGFD | Lin et al., 1994 |
| CDH | 12-41 | CVLVTGGSGFVGANLVTELLDR-------GYAVRSFD |  |
| EpsD | 11-39 | TISVVGL-GYIGLPTATVLASR-------QRELIGVD | Huang and Schell, 1995 |
| ExoB | 5-34 | NILVVGGAGYIGSHTCLQLAAD-------GYQPVVYD | Buendia et al., 1991 |
| GalE | 2-31 | RVLVTGGSGVIGSKTCVQLLQN-------GHDVIILD | Busby and Dreyfus, 1983 |
| GraE | 2-37 | RLLVTGAAGFIGSHYVREILAGSYPESDDVHVTVVD | Bechtold et al., 1995 |
| o355 | 3-33 | KILITGGAGFIGSALVRYIINE-------TSDAVVVD | Daniels et al., 1992 |
| ORF1 | 9-36 | KIGIIGL-GYVGLPLAVEFGKK---------VTTIGFD | Sh. sonnei; acc.#U34305 |
| ORF7 | 8-35 | KIAIIGL-GYVGLPLAAEFGKI-------RQVVGFD | E. coli; acc.#221706 |
| ORF10 | 145-192 | VYLIYGA-GSAGRQLAIALRNSENYKEVIMGMQVHD | Comstock et al., 1996 |
| RfbB$_{Ec}$ | 2-32 | KILVTGGAGFIGSAVVRHIINN-------TQDSVVNVD | Marolda and Valvano, 1995 |
| RffD | 5-33 | TISVIGL-GYIGLPTAAAFASR-------QKQVIGVD | Meier-Dieter et al., 1992 |
| StrP | 2-31 | RILLTGHQGYLGTVMAPVLTAA-------GHQVTGLD | Str. glauciens; acc.#629223 |
| TrsG | 280-310 | VVMVTGAGGSIGSELCRQIVE------KPSLLILFD | Skurnik et al., 1995 |
|  | 490-516 | LVIQAGAMGQGODVFVLDMGDP---------VKIID |  |
| UGD | 2-30 | RVAIFGT-GYVGLVTGTCLAEV-------GHHVICVD | Lin et al., 1995 |
| VipA | 8-35 | KIAIIGL-GYVGLPLAVEFGKS-------RQVVGFD | Hashimoto et al., 1993 |
| VipB | 17-49 | RWLITGVAGFIGSGLLEELLFL-------NQTVIGLD | Hashimoto et al., 1993 |

GxxGxxG

FIGURE 34A

```
K-tuple value    : 1
Gap penalty      : 5
Window size      : 10
Filtering level  : 2.5
Open gap cost    : 10
Unit gap cost    : 10

Setting of other parameters
===========================

The alignment was done on 3 Protein sequences.
Character to show that a position in the alignment is perfectly conserved: '*'
Character to show that a position is well conserved: '.'

Alignment

PSBA       MIDVNTVVEKFKSRQALIGIVGLGYVGLPLMLRYNAIGFDVLGIDIDDVK       50
EC_RFFD    M--S------FAT----ISVIGLGYIGLPTAAAFASRQKQVIGVDINQHA       38
BS_EPSD    M--DRAIEIDFRT----ISVVGLGYIGLPTATVLASRQRELIGVDINQHA       44
           *         *  .   *...****.***      ....*.**..

PSBA       VDKLNAGQCYIEHIPQAKIAKARAS-GFEATTDFSRVSECDALILCVPTP       99
EC_RFFD    VDTINRGEIHIVEPDLASVVKTAVEGGFLRAS--TTPVEADAWLIAVPTP       86
BS_EPSD    VDTINQARIHIVEPDLDMLVRAAVSQGYLRAT--TEPEPADAFLIAVPTP       92
           **..*  . .*  .  ......  *  . ..   **  . ****

PSBA       LNKYREPDMSFVINTTDALKPYLRVGQVVSLESTTYPGTTEEELLPRVQE       149
EC_RFFD    FKGDHEPDMTYVESAARSIAPVLKKGALVILESTS-PVGSTEKMAEWLAE       135
BS_EPSD    FLEDKQPDLTYIEAAAKAIAPVLKRGDLVVLESTS-PVGATEQLSAWLSE       141
             .  .**....  ...  .. * *..*..**** .  ...*..   .  *

PSBA       --------GGLVVGRDIYLVYSPEREDPGNPNFETRTIPKVIGGHTPQCL       191
EC_RFFD    MRPDLTFPQQVGEQADVNIAYCPERVLPGQVMVELIKNDRVIGGMTPVCS       185
BS_EPSD    QRSDLSFPHQLGEESDIRVAHCPERVLPGHVLRELVENDRIIGGMTPRCS       191
                .  .....*** **. *   . ..*** **  *

PSBA       EVGIALYEQAIDRVVPVSSTKAAEMTKLLENIHRAVNIGLVNEMKIVADR       241
EC_RFFD    ARASELYKIFLEGECVVTNSRTAEMCKLTENSFRDVNIAFANELSLICAD       235
BS_EPSD    QAAQRLYELFVRGRCIVTDARTAEMCKLTENAFRDVNIAFANELSMICDE       241
            .   **.  .    *.....*** ** ** *.***...**.....

PSBA       MGIDIFEVVDAAATKPFGFTPYYPGPGLGGHCIPIDPFYLTWKAREYGLH       291
EC_RFFD    QGINVWELIRLANRHP-RVNILQPGPGVGGHCIAVDPWFIVAQNPQ---Q       281
BS_EPSD    IGVNVWELISVANRHP-RVNILQPGPGVGGHCIAVDPWFIVDAAPE---S       287
            *....*.. * .*.    ****.*****..**......

PSBA       TRFIELSGEVNQAMPEYVLGKLMDG----LNEAGRALKGSRVLVLGIAYK       337
EC_RFFD    ARLIRTAREVNDHKPFWVIDQVKAAVADCLAATDKRASELKIACFGLAFK       331
BS_EPSD    ARLIRTAREVNDAKPHYVLDRVKQAA--------RRFKEPVIACFGLSFK       329
           .*.*  . ***  .* .*........         ..  . .*...*
```

FIGURE 34B

```
PSBA     KNVDDMRESPSVEIMELIEA-KGGMVAYSDPHVPVFPKMREHHPELSSEP    386
EC_RFFD  PNIDDLRESPAMEIAELIAQWHSGETLVVEPNIHQLPKKLT---GLCTLA    378
BS_EPSD  ANIDDLRESPAIEIVRTMVQQQLGTVLVVEPHIKVLPASLE---GV-ELL    375
         *.**.****..**    ...*.  .*.. .*  .   .. .

PSBA     LTAENLARFDAVVLATDHDKFD-YELIKAEAKLVVDSRGKYRSPAAHIIK    435
EC_RFFD  QLDEALATADVLVMLVDHSQFKVINGDNVHQQYVVDAKGVWR--------    420
BS_EPSD  NAEPALSRADIVVLLVDHQKFRKLDTDRLQSRVVIDTRGMWS---AKRLA    422
         . .*.  * .*. .**.*     . ... *.*..* ..

PSBA     A   436
EC_RFFD  -   420
BS_EPSD  A   423
```

Consensus length: 451  
Identity  : 111 ( 24.6%)  
Similarity: 154 ( 34.1%)

Dictionary of the sequences used for the alignment
==================================================

[ 1] PSBA  
    Size: 436 residues.

[ 2] EC_RFFD  
    Size: 420 residues.

[ 3] BS_EPSD •  
    Size: 423 residues.

FIGURE 35

```
The two sequences to be aligned are:

PSBD.
Total number of residues: 163.

BP_BPLB.
Total number of residues: 191.

Comparison matrix : Structure-genetic matrix.
Open gap cost    : 5
Unit gap cost    : 1

The character to show that two aligned residues are identical is '|'
The character to show that two aligned residues are similar is '.'
Amino acids said to be 'similar' are: A,S,T; D,E; N,Q; R,K; I,L,M,V; F,Y,W PSBD    - MSYYQHPSAIVDDGAQIGSDSRVWHFVHICAGARIGAGVSLGQNVFVGNK -50
           |.|||||||.||||||.|||||||||||||||||||||||||||||
BP_BPLB - MTTI-HPTAIVDEGARIGANSRIWHWVHICGGAEIGAGCSLGQNVFVGNR -49

PSBD    - VVIGDRCKIQNNVSVYDNVTLEEGVFCGPSMVFTNVYNPRSLIERKDQYR -100
           ||||||.|||||||||||||||||.|||||||||||||||||.||.||
BP_BPLB - VRIGDRVKIQNNVSVYDNVFLEDDVFCGPSMVFTNVYNPRAAIERKNEYR -99

PSBD    - NTLVKKGATLGANCTIVCGVTIGEYAFLGAGAVINKNVPSYALMVGVPAR -150
           .||...||||||||||||||.|||.|||.|||||.|.|.|||||||||
BP_BPLB - DTLVRQGATLGANCTIVCGATVGRYAFVGAGAVVNKDVPDFALVVGVPAR -149

PSBD    - QIGW-------------------IANSVSSCS -163
           ||||                    |.|
BP_BPLB - QIGWMSRHGEQLDLPLAGNGQARCPHTGDLYILENGVCRLGE -191

Identity   : 120 ( 73.6%)
Similarity : 16  ( 9.8%)
Number of gaps inserted in PSBD: 1
Number of gaps inserted in BP_BPLB: 1
```

FIGURE 36A

```
Setting of computation parameters
=================================

K-tuple value    : 1
Gap penalty      : 5
Window size      : 10
Filtering level  : 2.5
Open gap cost    : 10
Unit gap cost    : 10

Setting of other parameters
===========================

The alignment was done on 6 Protein sequences.
Character to show that a position in the alignment is perfectly conserved: '*'
Character to show that a position is well conserved: '.'

Alignment

PSBE         M-IEFIDLKNQQARIKDKID-AGIQRVLRHGQYILGPEVTELEDRLADFV    48
BP_BPLC      M--QFIDLKTQYQALRDTIN-PRIQAVLDHGQFIMGPEVKELEAALCAYT    47
BS_DEGT      MNVPMLDLSEQYEQLKPEIM-RVLDEVMRSSRFILGDYVKKLEADIAAYS    49
S_ERYC1      MDVPFLDLQAAYLELRSDID-QACRRVLGSGWYLHGPENEAFEAEFAAYC    49
S_DNRJ       MSTYVWQYLNEYREERADIL-DAVETVFESGQLILGTSVRSFEEEFAAYH    49
BS_SPSC      MVQKRNHFLPYSLPLIGKEEIQEVTETLESGWLSKGPKVQQFEKEFAAFV    50
              *         .          ..  .    *     .*   . .,

PSBE         GAKYCISCANGTDALQIVQMALGVGPGDEVITPGFTYVATAETVALLGAK    98
BP_BPLC      GAKHCITVASGTEALLISLMALGVKAGDEVITTSFTFVATAEVIALLGAK    97
BS_DEGT      RAKHGIGCGNGSDAIHIALQAAGVGPGDEVITTAFTFFATAGSIARAGAK    99
S_ERYC1      ENAHCVTVGSGCDALELSLVALGVGQGDEVIVPSHTFIATWLGVP-VGAV    98
S_DNRJ       GLPYCTGVDNGTNALVLGLRALGIGPGDEVVTVSNTAAPTVVAIDAVGAT    99
BS_SPSC      GAKHAVAVNSCTAALFLALKAKGIGPGDEVITSPLTFSSTANTIIHTGAT   100
              . .. ..  .*. .   * *, .****..   *  .*   .  **

PSBE         PVYVDIDPRTYNLDPQLLEAAITPRTKAIIPVSLYGQCADFDAINAIASK   148
BP_BPLC      PVFVDVEPDTCNIKVSEIEAKITPRTKAIIPVSLYGQCGDMDEVNAVAAR   147
BS_DEGT      PVFVDIDPVTFNIDPAQVEAAVTEKTKAIIPVHLYGQMADMEAIAAIAKR   147
S_ERYC1      PVPVEPEGVSHTLDPALVEQAITPRTAAILPVHLYGHPADLDALRAIADR   149
S_DNRJ       PVFVDVHEENYLMDTGRLRSVIGPRTRCLLPVHLYGQSVDMTPVLELAAE   148
BS_SPSC      PVFADIDENTLNIDPVKLEAAVTPRTKAVVPVHFGGQSCDMDAILAVAQN   150
              ** ..  ..  ..      .  ..* ..**  .*.  *.   ..*

PSBE         YGIPVIEDAAQSFGASYKGKRSCNLSTVACTSFFPSKPLGCYGDGGAIFT   198
BP_BPLC      HGLPVIEDAAQSFGATYKGRKSCNLSTIGCTSFFPSKPLGCYGDGGALFT   197
BS_DEGT      HGLVVIEDAAQAIGAKYNGKCVGELGTAATYSFFPTKNLGAYGDGGMIIT   199
S_ERYC1      HGLALVEDVAQAVGARHRGHRVGAGSNAAAFSFYPGKNLGALGDGGAVVT   198
S_DNRJ       HDLKVLEDCAQAHGARRHGRLVGTQGHAAAFSFYPTKVLGAYGDGGAVVT   198
BS_SPSC      HGLFVLEDAAHAVYTTYKQRMIGSIGDATAFSFYATKNLAT-GEGGMLTT   199
              ...  .** *.. .     .   .   .   **...* *.  *.** . *
```

FIGURE 36B

```
PSBE      NDDELATAIRQIARHG----------QDRRYHHIRV-GVNSRLDTLQAA      236
BP_BPLC   NDDELAQAMREIRVHG----------QSGRYYHARI-GVGGRMDTLQCA      235
BS_DEGT   NDDELAEKCRVIRVHG----------SKPKYYH-HVLGYNSRLDEMQAA      237
S_ERYC1   TDPALAERIRLLRNYG----------SKQKYVH-EVRGTNARLDELQAA      236
S_DNRJ    PDAEVDRRLRRLRYYG----------MGERYYVVDTPGHNSRLDEVQAE      238
BS_SPSC   DDEELADKIRVLSLHGMSKAAWNRYSSNGSWYYEVESPGYKMNMFDLQAA      249
              *  ...    *  . *                *       *  ..  ...*  .

PSBE      ILLPKLEIFEEEIALRQKVAAEY-----DLS-------------------      262
BP_BPLC   VVLGKLERFDWEIAQRIKIGARYQQLLADLPGGACTVTVRPDR--DSVWA      283
BS_DEGT   ILSVKFPHLDRWTEQRRKHAATYTRLLEEAVGDLVVTPKEVDGRYH-VFH      286
S_ERYC1   VLRVKLRHLDDWNARRTTLAQHYQTELKDVPG---ITLPETHPWADSAWH      283
S_DNRJ    ILRRKLRRLDAYVEGRRAVARRYEEGLGDLDGLVLPTIAEGN---DHVYY      285
BS_SPSC   LGLHQLKRLDDMQKRREEIAGRYQTAFQQIPG-LITPFVHDDGR--HAWH      296
              .  ..  ..      *   .  *    .

PSBE      -----------------------LKQV-GIGTPFI---------------      273
BP_BPLC   QFTVMVPN------REAVIAQLKEA-GIPTAVHYPRPIHAQPAYE-QYAE      325
BS_DEGT   QYTIRAPK------RDELQAFLKEQ-GIATMVYYPLPLHLQPVFA-SLGY      328
S_ERYC1   LFVLRCEN------RDHLQRHLTDA-GVQTLIHYPTPVHLSPAYA-DLGL      325
S_DNRJ    VYVVRHPE------RDRILEALTAY-DIHLNISYPWPVHTMSGFA-HLGY      327
BS_SPSC   LYVLQVDEKKAGVTRSEMITALKDEYNIGTSVHF-IPVHIHPYYQKQFGY      345
                             *..  ..

PSBE      GSG-----------------------------------------      276
BP_BPLC   GAGATPVSDDLAARVMSLPMHPDLDEATQDKIVAALRQALN---      366
BS_DEGT   KEGQLPEAEKAAKEALSLPMFPELKEEQQQYVVEKIAEFYRHFA      372
S_ERYC1   PPGSFPVAESLAGEVLSLPIGPHLSREAADHVIATL----KAGA      365
S_DNRJ    GPGDLPVTERLAGEIFSLPMYPSLRPDAQEKVIDAVREVV-GSL      370
BS_SPSC   KEADFPNAMNYYKRTLSLPLYPSMSDDDVDDVIEAVRDIVKGAD      389
               .
```

Consensus length: 394
Identity   :  42 ( 10.7%)
Similarity:  83 ( 21.1%)

Dictionary of the sequences used for the alignment
==================================================

[ 1] PSBE
    Size: 276 residues.

[ 2] BP_BPLC
    Size: 366 residues.

[ 3] BS_DEGT
    Size: 372 residues.

[ 4] S_ERYC1
    Size: 365 residues.

[ 5] S_DNRJ
    Size: 370 residues.

[ 6] BS_SPSC
    Size: 389 residues.

Program SOAP.

Hydropathy index computation for sequence PSBF.

Total number of amino acids is: 316.

Hydropathic index of PSBF from amino acid 1 to amino acid 316.

Computed using an interval of 5 amino acids.    (GRAVY = 10.14)

FIGURE 38A

```
Setting of computation parameters
=================================

K-tuple value   : 1
Gap penalty     : 5
Window size     : 10
Filtering level: 2.5
Open gap cost   : 10
Unit gap cost   : 10

Setting of other parameters
===========================

The alignment was done on 5 Protein sequences.
Character to show that a position in the alignment is perfectly conserved: '*'
Character to show that a position is well conserved: '.'

Alignment

PA_PSBI    M---KILTIIGARPQFIKASVVSKAIIEQQTLSEIIVHTGQHFDANMSEI    47
BP_BPLD    MPK-KILTVLGARPQFIKASVVSAAIAQHPELTEVVVHTGQHFDANMSDV    49
EC_NFRC    MK---VLTVFGTRPEAIKMAPLVHALAKDPFFEAKVCVTAQHRE--MLDQ    45
BS_ORFX    MKKLKVMTVFGTRPEAIKMAPLVLELKKYPEIDSYVTVTAQHRQ--MLDQ    48
SB_RFBC    MSK--VLFVGTRPEAIKMAPLVIEFKNNPAIEVKVCVTGQHRE--MLDQ     46
            *    .. ..*.**. **  .  ..  . .     . *.** . *  .

PA_PSBI    FFEQLGIPKPDYQLDI--HGGTHGQMTGRMLMEIEDVILKEKPHRVLVYG    95
BP_BPLD    FFDELGMQTPAHQLDI--HGGGHGDMTGRMLVALEQVMQAEKPDVVLVYG    97
EC_NFRC    VLKLFSI-VPDYDLNIMQPGQGLTEITCRILEGLKPILAEFKPDVVLVHG    94
BS_ORFX    VLDAFHI-KPDFDLNIMKERQTLAEITSNALVRLDELFKDIKPDIVLVHG    97
SB_RFBC    VLDFFEI-EPDYDLNIMKQKQSLGSITCSILTRLDEILASFMPAHIFVHG    95
            ..  .    *. .*.*       ..*. *    .   .*  ..*.*

PA_PSBI    DTNSTLAGALAASKLHVPIAHIEAGLRSFNM--RMPEEINRILTDQVSDI   143
BP_BPLD    DTNSTLAGALAAVKLHIPVAHVEAGLRSFNL--RMPEEVNRILTDRISRW   145
EC_NFRC    DTTTTLATSLAAFYQRIPVGHVEAGLRTGDLYSPWPEEANRTLTGHLAMY   144
BS_ORFX    DTTTTFAGSLAAFYHQIAVGHVEAGLRTGNKYSPFPEELNRQMTGAIADL   147
SB_RFBC    DTTTTFAASLAAFYQNIKVWHIEAGLRTWNMNSPFPEEGNRQLTSKLAFF   145
           **..*.*..***     ... *.*****. .    *** **  .*. ..

PA_PSBI    LFCPTRVAIDNLKNEGFERKAAKIVNVGDVMQDSALFFAQRATSP-IGLA   192
BP_BPLD    LFTPTDSATRHLAAEG--QSGEKVVQVGDVMYDVALHHGARVTAEGRALA   193
EC_NFRC    HFSPTETSRQNLLRE--NVADSRIFITGNTVIDALLWVRDQVMSSDKLRS   192
BS_ORFX    HFAPTGQAKDNLLKE--NKKADSIFVTGNTAIDAL---------NTTVRD   186
SB_RFBC    HAAPTLQAKDNLLRE--SVKEKNIIVTGNTVIDALLIGIKKITGSTGDVR   193
           ..  *     . .*  *     ... .*.. *

PA_PSBI    S-----QD----G---FILATLHRAENTDDPVRLTSIVEALNEIQINVA-   229
```

FIGURE 38B

```
BP_BPLD     A-----HGLKPGG---YVLATIHRAENTDDAQRLTTIVRALQALAAERQ-       234
EC_NFRC     ELAANYPFIDP--DKKMILVTGHRRESFGRG--FEEICHALADIATTHQD          238
BS_ORFX     GY--SHPVLDQVGEDKMILLTAHRRENLGEP--MENMFKAIRRIVGEFED          232
SB_RFBC     EIISLKNKLNL--DKKIILVTLHRRENQGEL--LRTICDDIKQLALEHDD          239
                       .*  *  **  *.          .   ..    .  .

PA_PSBI     -PVVLPLH--PRTRGVIERLGLKLE----VQVIDPVGYLEMIWLLQRSGL          272
BP_BPLD     --VVWPLH--PRTWGILARLGLLDELASTVTLLEPVGYLDMVQLEKYAAL          280
EC_NFRC     IQIVYPVHLNPNVREPVNR---ILGHVKNVILIDPQEYLPFVWLMNHAWL          285
BS_ORFX     VQVVYPVHLNPVVREAAHK---HFGDSDRVHLIEPLEVIDFHNFAAKSHF          279
SB_RFBC     IEIVFPVHMSPRIREVVNE---KLSGVVNIKLVEPLAYPGFIWLMNNAHF          286
              .*  *.*   *  ...        . ...*   .      .  .  .

PA_PSBI     VLTDSGGVQKEAFFFGKPCVTMRDQTEWVELVTCGANVLVGAARDMIVES          322
BP_BPLD     IATDSGGVQKEAFFHRIPCVTLRDETEWTELVDAGWNRLAPPVSSAVVAQ          330
EC_NFRC     ILTDSGGIQEEAPSLGKPVLVMRDTTERPEAVTAGTVRLVGTD-KQRIVE          334
BS_ORFX     ILTDSGGVQEEAPSLGKPVLVLRDTTERPEGVEAGTLKLAGTD-EENIYQ          328
SB_RFBC     ILSDSGGVQEEAPSLQKPVLVARDTTERPEVIENGAAMLVDPRIPNNIYS          336
             . .****.*.**       *  .. ** **. *  .. *   *.  .

PA_PSBI     ARTSLGKTIQ------DDGQLYGGGQASLGLLNIL------PSCDALRVE         360
BP_BPLD     AVQDALREQP------RDVQPYGDGQAARRIVDAL------AA-------         361
EC_NFRC     EVTRLLKDENEYQAMSRAHNPYGDGQACSRILEAL------KNNRISL-         376
BS_ORFX     LAKQLLTDPDEYKKMSQASNPYGDGEASRRIVEELLFHYGYRKEQPDSFT         378
SB_RFBC     SCKKLLSDERLYEKMSQAGNPFGDGKASKKILD-----Y-FVSLEDI---         377
                        .      ...*.*.*    ...

PA_PSBI     FK    362
BP_BPLD     -H    362
EC_NFRC     --    376
BS_ORFX     GK    380
SB_RFBC     -K    378
```

Consensus length: 402
Identity    : 71  ( 17.7%)
Similarity: 109 ( 27.1%)

Dictionary of the sequences used for the alignment
==================================================

[ 1]  PA_PSBI
      Size: 362 residues.

[ 2]  BP_BPLD
      Size: 362 residues.

[ 3]  EC_NFRC
      Size: 376 residues.

[ 4]  BS_ORFX
      Size: 380 residues.

[ 5]  SB_RFBC

FIGURE 39A

```
Setting of computation parameters
================================

K-tuple value   : 1
Gap penalty     : 5
Window size     : 10
Filtering level: 2.5
Open gap cost   : 10
Unit gap cost   : 10

Setting of other parameters
===========================

The alignment was done on 3 Protein sequences.
Character to show that a position in the alignment is perfectly conserved:
Character to show that a position is well conserved: '.'

Alignment

PA_PSBJ      MNVWYVHPYAGGPGVGRYWRPYYFSKFWNQAGHRSVIISAGYHHLLEPDE      50
BP_BPLE      ME---------------FRPYYFGREWIGHGHQVKVAASTISHIRARAP      34
YE_TRSE      M---Y----------------------EAGHNVMIISLTGETLVRPND       23
             *                          **.  . . . .  . ..

PA_PSBJ      KRSGVTC---VNGAEYAYVPTLRYLGNGVGRMLSMLIFTMMLLPFCLILA      97
BP_BPLE      QAGGRLTRENVDGIEYLWYATLPYQGNGARRLLNMLQFSARL--YGLRRD      82
YE_TRSE      --GIQLNELKLDKAPFSLFKGL-------------------FEVKKI        49
              .  ..  .    .*              ..

PA_PSBJ      LKRGTPDAIIYSSPHPFGVVSCWLAARLLGAKFVFEVRDIWPLSLVELGG      147
BP_BPLE      LGGWRPDIVIASSTHPYDVLPAARLARQTGARLVFEVHDLWPLTPRLLGG      132
YE_TRSE      IKKFKPDIV---HSHMFHA-------NLFARILRVFTKIPALICTAHNT       88
             .  **. .*..       *...   ..*     ..

PA_PSBJ      LKADNPLVRVTGWIERFSYARADKIISLLPCAEPHMADKGLPAGKFLWVP      197
BP_BPLE      FKAWHPMIASMQYAEDYAYRHADLTVSMLPCALPYMRERGLDPRRYAHVP      182
YE_TRSE      NEGSSLRMLAYKYTDKLASLSTNVSQDAV---DSFIHKGASSTGRMIAVS      135
             ..  .   .   .   ..  . ..  . . . .     *.

PA_PSBJ      NGVDSSDISPDSAVSSSDLVR---HVQVLKEQGVFVVIYAGAHGEPNALE      244
BP_BPLE      NGVPVTEYSS-PDFDNPDYLRVRAQIRQLREQCDFVLAYAGTHGHANALD      231
YE_TRSE      NGIDASQF----DFSMDERKVKRSELGIFNDTPIILSV--GRLTEAKDYP      179
             **. ..   .  ..   ..  ...   ..   *  .....

PA_PSBJ      GLVRSAGLLRERGASIR---IILVGKGECKEQLKAIAAQDAS-GLVEFFD      290
BP_BPLE      MLLQAMARLRDQ--PIG---LLLLGDGPDKPELKRLAGQLGL-RHIAFAD      275
YE_TRSE      NLLTAFSLLIKDNSLQSFPQLFIVGTGHLDGYLKNMSKEFGIDKYVTLFG      229
             *. . .* .       ....*.*  .  **  ..    ... .
```

FIGURE 39B

```
PA_PSBJ    QQPKETIMAVLKLASAGYISLKSEPIFRFGVSPNKLWDYMLVGLPVIFAC    340
BP_BPLE    PVPRPAVQAVMADIDAAYIGLRRSPLFQFGVSPNKLFDYMLSACPVVQSI    325
YE_TRSE    Q--RDDILQLMCAADI-FVLSSEWEGPPLVITEA------MACKKIIVAT    270
                       .  . ..   ..   *..  ..           . ..  .

PA_PSBJ    KAGNDPVSDYDCGVSADPDAPEDITAAIFRLLLLLSEDERRTMGQRGRDAV    390
BP_BPLE    ESGNDIVADARCGLSVPAEDPAALAAALHGLRTLPAAERQAMGRRGRDYV    375
YE_TRSE    DAGGITEALGDCGSIVPIKDPNSLSQAINKMIKLSDNEKEILGNKARERI    320
           ..*.   .  **    . ..*.....*.  . *...*. .*...*. .

PA_PSBJ    LEHYTYESLALQVLNALADG---RAA--    413
BP_BPLE    LARHDYPVLAQQFLDAVQSVTPRRAASR    403
YE_TRSE    IQTNSIEKIIE--LGCLFILNLKNNC--    344
            ..  .     .     *..      ..
```

Consensus length: 428
Identity   : 30 ( 7%)
Similarity: 132 ( 30.8%)

Dictionary of the sequences used for the alignment
==================================================

[ 1] PA_PSBJ
     Size: 413 residues.

[ 2] BP_BPLE
     Size: 403 residues.

[ 3] YE_TRSE
     Size: 344 residues.

FIGURE 40A

```
Setting of computation parameters
=================================

K-tuple value   : 1
Gap penalty     : 5
Window size     : 10
Filtering level : 2.5
Open gap cost   : 10
Unit gap cost   : 10

Setting of other parameters
===========================

The alignment was done on 3 Protein sequences.
Character to show that a position in the alignment is perfectly conserved: '*'
Character to show that a position is well conserved: '.'

Alignment

PA_PSBL    MMIWMIACLVVLLFSFVATWGLRRYALATKLMDVPNARSSHSQPTPRGGG    50
YE_TRSF    MPTFFFLLTIFFLLSVGLTYLLRLYALKNNIIDTPNSRSSHVTPTPRGGG    50
HI_RFE     MLSIF----VTFLGAFLTLIVMRPLANWIGLVDKPNYRKRHQGTIPLIGG    46
              *     .  .*.       .* *    ..* ** *..*   ..*   **

PA_PSBL    VAIVLVFLAALVWMLSAGSISGGWGGAMLGAGSGVALLGFLDDHGHIAAR   100
YE_TRSF    VAIVISFLIGIILFYFLGYLPILSVVGLIVSGGVIALVGFWDDHGHIAAR   100
HI_RFE     ASLFVGNLCYYLMEWDQLRLPYLYLFSIFV----LLAIGILDDRFDISPF    92
           ...  .  *  .         ..   ...    .  .*. **. .*..

PA_PSBL    WRLLGHFSAAIWILLWTGGFPPLDVVG-----HAVDLGWLGHVLAVFYLV   145
YE_TRSF    WRLLAHFSAAAFLLFCFGGFPVLNVSG-----FIIELGIFGSLFGLLFLV   145
HI_RFE     LR--AGIQAILAILMIDLGNIYLDHLGQILGPFQLTLGSIGLIITVFATI   140
             *  .*  .*. * *. *       ..** .*  .....    .

PA_PSBL    WVLNLYNFMDGIDGI-ASVEAIGVCVGGALIYWLTG-HVAMVGIPLL--L   191
YE_TRSF    WMLNLYNFMDGIDGL-ASAEAVTACIGMIAIYYISGDHIELNSFLVLWLL   194
HI_RFE     AIINAFNMIDGIDGLLGGLSCVSFAAIGILMY--RDGQMDMAHWSFA--L   186
           ..* .*..******.  ..    . ..   .*    .....      *

PA_PSBL    ACAVAGFLIWNF-----PPARIFMGDAGSGFLG------MVIGALAIQAA   230
YE_TRSF    ACTVLGFLLWNF-----PPAKIFMGDAGSGFLG------LMIGSLAISAG   233
HI_RFE     IVSILPYLMLNLGIPFGPKYKVFMGDAGSTLIGFTIIWILLLSTQGKGHP   236
              . .*. *.    *  ..*******...*        ......

PA_PSBL    WTAPSLFWCWLILLGVFIVDATYTLIRRIARGEKFYEAHRSHAYQFASRR   280
YE_TRSF    WIDTRFFFCWLILLGLFIVDATWTLVRRVLGGFKVYEAHRSHGYQIASRR   283
HI_RFE     MNPVTALW----IIAIPLIDMVAIIYRRVRKGKSPFRPDRLHVHHLMVR-   281
            ..        .... ..*. . ..**.  *  . . ..*.*  .   *
```

FIGURE 40B

```
PA_PSBL     YASHLRVTLGVLAINTLWLL--R------------------------     301
YE_TRSF     FKRHLPVTLSAIAINIIWLF--PIALLAGLNIVNPIIALIISYIPLLYI-   330
HI_RFE      --AGLTSRQAFLLITFVSAVCATIGILGEVYYVNEW-AMFVGFFILFFLY   328
                 *       . . *. .

PA_PSBL     ------------------------WH     303
YE_TRSF     DYKLNAG---------------VNND     341
HI_RFE      VYSITHAWRITRWVRRMKRRAKRLKKA    355
```

Consensus length: 377
Identity   : 55 ( 14.6%)
Similarity: 98 ( 26%)

Dictionary of the sequences used for the alignment
==================================================

[ 1] PA_PSBL
    Size: 303 residues.

[ 2] YE_TRSF
    Size: 341 residues.

[ 3] HI_RFE
    Size: 355 residues.

FIGURE 41A

```
Setting of computation parameters
==================================

K-tuple value    : 1
Gap penalty      : 5
Window size      : 10
Filtering level  : 2.5
Open gap cost    : 10
Unit gap cost    : 10

Setting of other parameters
===========================

The alignment was done on 4 Protein sequences.
Character to show that a position in the alignment is perfectly conserved: *
Character to show that a position is well conserved: '.'

Alignment

PSBM       MLDNLRIK--LLGLPRRYKRMLQVAADVTLVWLSLWLAFLVRLGTEDMIS      48
TRSG       MFLVF-----LLSLPRPVKRTIMLLLDTILIALAYWGAFWVRL---DVDS      42
BP_BPLL    MTLPYAIRRLFVDLPRPFKQMLAIVLDAVILLGAFHLALWLRFEL-----      45
SA_CAPD    MT---------SISAKLRFLILIIDSFIVTFSVFLGYAI---LEPYFK       37
                        *    . . .         *      .

PSBM       PFSG-HAWLFIAAPLVAIPLF--IRFGMYRAVMRYLGNDALIAIAKAVTI      95
TRSG       PFTSIEQWVALAA-IIPPTLFAYIKLGLYRTVLRYVSAKIVSIVLVGVVL      91
BP_BPLL    -FFLTDQYLFLSLLACAGGIAALAAFGVYLYILRYMSERVLAAILGGIVV      94
SA_CAPD    GYSIDLLVLSSVILLVSHHIFAYV-FNLYHRAWEYASVSELMSVLKAVTS      86
                .          .      ...*     *    .     . ...

PSBM       SALVLSLLVYWYRSPPAVVPRSLVFNYWWLSMLLIGGLRLAMRQYFMGDW     145
TRSG       SSGLLVLGSYFL---GVYLPRTVSVMFFIFSLVLICGSRLFFRMLLN---     135
BP_BPLL    SVMVVTAGNTFLQLAT--ISRGVLVLYAALALVGLIGVRLIARKLL----     138
SA_CAPD    SIVVTLLLVSLLISESPFLR--LYFITWMMHLLLIGGSRLFWRVY---RR     131
             *  .           ..   .    . ...  * ** *

PSBM       YSAVQSVPFLNRQDGLPRVAIYGAGAAANQLVAALRLGRAMR--PVAFID     193
TRSG       YGVRGQIP----------VVIYGAGASGRQLLPALMQASEYF--PIAFVD     173
BP_BPLL    FPADHHMA-----DPRTPVLIYGAGGAGSQLAMALRTGPHYR--PVAMLD     181
SA_CAPD    Y-------FIDNAVEKKATLVVGAGQGGSVLIREMLRSQDMRMQPVLAVD     174
                       . .  *** ...  *   ..      *.   *

PSBM       DDKQIANRVIAG---LRVYTAKHIRQMIDETGAQEVLLAIPSATRARRRE     240
TRSG       DNPKLHKAVIHG---VTVYPSEKLEYLIGRYGIKKVLLAMPSVSQSQRRA     220
BP_BPLL    DDKRKHRLVVNG---LRVYPPEQLPKLIDRHNIRQLLIAMPSAPPKQIRS     228
SA_CAPD    DDKNKQKMTITERVKVQGYV-EDIPELVKKFRIKKIIIAIPTLSQKRLNE     223
           *.   ..  .     .  *  ...   ..     ..... *.*.  ..

PSBM       ILESLEPFPLHVRSMPGFMDLTSGRVKVDDLQEVDIADLLGRDSVAPRKE     290
TRSG       VVNKLENLSCEVLSIPGMSDLVEGRAQISSLKKVSIEELLGRDPVVPDEK     270
BP_BPLL    IVEAAEPYRLRIRLVPSMRELIDPTNGVR-LRDVQVEDLLGRDPVAPIDT     277
SA_CAPD    INKICNIEGVELFKMPNIEDVLSGELEVNNLKKVEVEDLLGRDPVELDMA     273
            .  .  .    .*. . ..          *..* ...*****.*
```

FIGURE 41B

```
PSBM      LLERCIRGQVVMVTGAGGSIGSELCRQIMSCSPSVLILFEHSEYNLYSIH    340
TRSG      LLAKNITGKVVMVTGAGGSIGSELCRQIIVEKPSLLILFDISEFSLYSIE    320
BP_BPLL   LLGRCVTDRVVMVTGAGGSIGSELCRQILALRPRKLVLFEIAEPALYAIE    327
SA_CAPD   LISRELTNKTILVTGAGGSIGSEICRQVSKFDPQKIILLGHGENSIYSIH    323
          *... . ....**********.***.    *   ..*..  .* ..*..*.

PSBM      QELERRIKRESLSVNLLPILGSVRNPERLVDVMRTWKVNTVYHAAAYKHV    390
TRSG      NEMAAICKKNKIETEFVALLGSVQSEKRLVQIMSNFHVNTVYHAAAYKHV    370
BP_BPLL   QDLRQRIGERNIEIA--GVLGSVRDAAHCLAQLQEHGVQTIYHAAAYKHV    375
SA_CAPD   QELSKTYGNR---IEFVPVIADVQNKTRILEVMNEFKPYAVYHAAAHKHV    370
          ...          ..  .....*..  .....  .  ..*****.***

PSBM      PIVEHNIAEGVLNNVIGTLHAVQAAVQVGVQNEVLISTDKAVRPTNVMGS    440
TRSG      PLVENNVIEGVRNNIFGTLYCAKAAIKSGVEKFVLISTDKAVRPTNTMGA    420
BP_BPLL   PIVEHNVSEGIRTNAFGTLNMAETAIQAGVLDFVLISTDKAVRPTNVMGA    425
SA_CAPD   PLMEYNPHEAIRNNILGTKNVAESAKEGEVSKFVMISTDKAVNPSNVMGA    420
          *..* *  *...* **   ...*..  .*  .**.*******.*.*.**.

PSBM      TKRLAEMVLQALSNESAPLLFGDRKDVHHVNKTRFTMVRFGNVLGSSGSV    490
TRSG      TKRMAELVLQALSTEQ--------------NKTKFCMVRFGNVLGSSGSV    456
BP_BPLL   SKRLAELILQA-------------HAQIQDKTRFSMVRFGNVLGSSGSV    461
SA_CAPD   TKRIAEMVIQSLNEDNS-------------KTSFVAVRFGNVLGSRGSV    456
          .**.**...*.                   **.*  *********.***

PSBM      IPLFREQIKRGGPVTVTHPSITRYFMTIPEAAQLVIQAGSMGQGGDVFVL    540
TRSG      VPLFKKQIAEGGPITLTHKDIIRYFMTIPEAAQLVIQAGAMGQGGDVFVL    506
BP_BPLL   VPLFRRQILEGGPITLTHPEITRYFMTIPEAAQLVLQAGAMGESGSVFVL    511
SA_CAPD   IPLFKNQIESGGPVTVTHPEMTRYFMTIPEASRLVLQAGALAQGGEVFVL    506
          .***. **  ***.*.**  .*********..**.***. .**.****

PSBM      DMGPPVKILELAEKMIHLSGLSVRSERSPHGDIAIEFSGLRPGEKLYEEL    590
TRSG      DMGDPVKIIDLAKRMINLSGLSIKSEENLDGDIAIEISGLRPGEKLYEEL    556
BP_BPLL   DMGEPVLIRELAERMVRLYGLTVKNSDQPDGDIEIRITGLRPGEKLYEEL    561
SA_CAPD   DMGKPVKIVDLAKNLIRLSG-------KKEEDIGIEFSGIRPGEKLYEEL    549
          ***  ** *  .**.....*  *      ..**.* ...*.*********

PSBM      LIGDNVPTDHPMIMRANEEHLSWEAFKVVLEQLLAAVEKDDYSRVRQLL    640
TRSG      LIGDSVQHTYHPRIMTATEIMLEWDDLNILLNKIETACNDFNYECIRSLL    606
BP_BPLL   LIGEDSRETLHPRIMRATEYSLPYETLMGQLRMLDRSLQMCSPRQAAELL    611
SA_CAPD   LNKNEIHPQ----------------QVYEKIYRGKVDHYIKTEVDLIV    581
          *   ...                         .            ..

PSBM      RETVSGYAPDGEIVDWIYRQRRRE------P    665
TRSG      LEAPTGFQPTDGICDVVWQKTHSENAKNVIVH    638
BP_BPLL   GQIVREYAS-------------------VTYA    624
SA_CAPD   EDLINNFS-------------KEKLLKIANR    599
                .    ..
```

Consensus length: 682
Identity    : 154 ( 22.6%)
Similarity: 185 ( 27.1%)

Dictionary of the sequences used for the alignment
══════════════════════════════════════════════════

[ 1] PSBM
    Size: 665 residues.

[ 3] BP_BPLL
    Size: 624 residues.

[ 2] TRSG
    Size: 638 residues.

[ 4] SA_CAPD
    Size: 599 residues.

FIGURE 42

Entire sequence of *rol* gene:

ATGACTGACGAAATACAAAAGCACGGCGGTGTAGCTGGCGATATCGATCTGGTTGAGCTGGTTCGAGGA
TTATGGGAGGAGAAGTGGATAGTTCTTATATTTTCTTTGCTAGGTATTTTGTTTGCAGCTATCTACGCT
TTTCTCAGTACTCCTGTCTATGAGGCCCGCATAGCGATTTTGCCTCCGTCGTTGAGTGATGTGGCAGGT
TTCAATCAGGGACGTACCAGGGAAACCGGGCTTGGTCCCTTCAAGGTCCAGGATGTGTACTCTGTTTTT
GTTCGCAACCTGCAGGCTGATGGAACTCGTCATCGTTTTTTCAATGAGACCTATTTGCCTTCTTTGGAT
GAAGAGCTTCGTTCGGTTTCGCGTGATGCGCTCTATAAAAGGTTCACTGATCAGATAAGTATTAGTTTG
CCGGGGAAAGACTTTCCGGGTCGTTATCTTGTTGCGATTGAACAGGAGGATCCGGAGCGTGCGGCGAGT
TGGGTTCGTCGGTATATAGCTGATGCGGCCGAGATTTCTATTCAGGAAATGTTGAACAATGCGCATCGC
GAGATTGAGGTCAAGGCTCGAGATATTGAGCAGCGCATACAGAACTTGCGGAGAGAATGCCAAGGCAGA
CGTGAAGATCGTATTGTTCAGCTCAAGGAGGCGTTGAAGGTCGCAGGTGCGCTGAAATTGGAGGAGCCT
CCACTGATCAGTGGGCAATCCTCTGAGGAGCTCTCGGCTATCATGAATGGAAGTCTGATGTATATGCGT
GGCAGTAAGGCGATTATGGCCGAGATTCAGACATTGGAGGCGCGTAGCTCTGATGATCCTTTTATTCCG
GCGTTGCGTACTCTTCAGGAGCAGCAGTTATTGCTGAGTAGCTTGCGTGTTAATTCGGAGCGGGTTTCT
GTTTTTCGACAAGACGGTCCGATAGAAACGCCGGACTCACCAGTTCGTCCAAGGAGAGCGATGATTTTG
ATTTTTGGGTTGATAATTGGTGGTGTGCTTGGTGGTTTTCTGGCGTTGTGCCGGATTTTTTTGAAGAAG
TATGCTCGTTAG

FIGURE 48
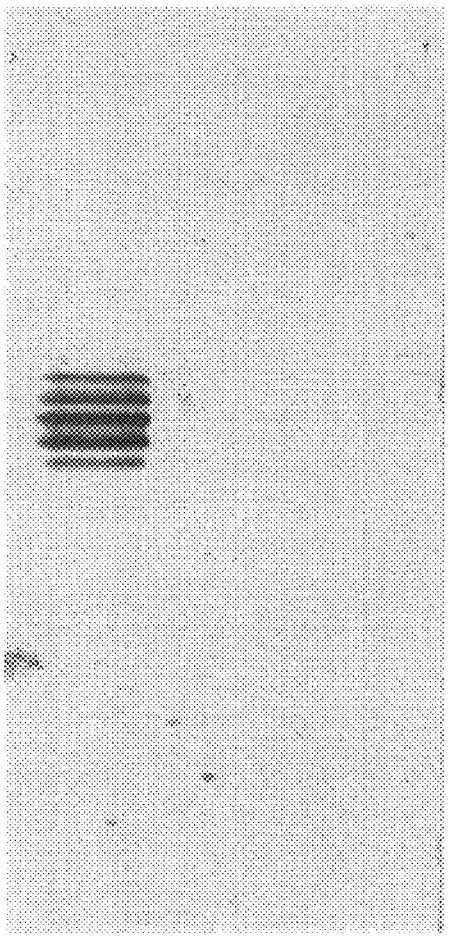
mAb N1F10
A-band LPS
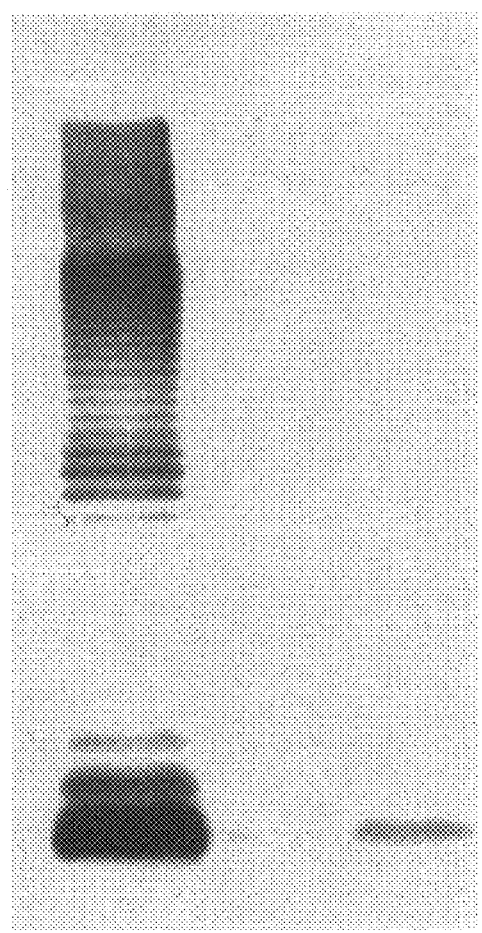
mAb 18-19
B-band LPS

FIGURE 49

GAGCTCGAGTTCAAGGTCATCAAGCTCGACCAGAAGGCGCAACAAGTTGTCGTTCCCGCCGCAGGTCC
GGAAGCCGAGAACAGCCGCGAGCCGAGCCGTGAAGCTCTGCTGAATCGCTGCAGGAAGCCCAGCAGTCAAAGT
TCGTCAAGAACCTCACGGACTACGGGGCCATTCGTGGACCTGGGCGGTAGACGCCTAGAGCCTGCTACACATCAC
GACATGGCCTGGAAGGCCATCAAGCATCCGAGATCCGTCAACGTTGGCGAGAGATGCGAGATGAGTCAAGG
CCTGAAGTTCGACCGCGAGCGCAACCGTGTATCCCTGGGCTGAAGCAACTGGGCGAAGACCCGTGGGTT
CCATCAAGGCGCGTTACCCGGAAGTACCGGTCATGGCCGTCACCAACCTCACCGACTACGGCTGCTT
GCCGAACTGGAAGAGGCGTGGAAGCTGGTACACGTGGTAAATGGACTGGACCAACAAGAACATCCATC
GTCGAAAGTCGTCCAGGTTGGCGATGAAGTGAAGTTCAGTTCTGGACATCGACGAAGAGGGTCGTCGT
TCTCCCTGGTATCAAGCAGTGCAAATCCAACCCGTGGAAGACTTCTCCAGCCAGTTCAACAAGGGTGA
CGTATCTCCGGTACCATCAAGTCGATCACCGACTTCGGTATCTTCATGGTCTTGACGGGGCCATCGACG
CCTGGTCCACCTGTCCGACATCTCCTGGAAGAAGTGCGCGAAGAAGCCGAGGCCATCTCCCTGGCATCAAGCT
ACGAGCTGGAAACCGTCAAACGTCATCATCCTGTCGGTGATCCGGTTCCGCACGAGAAAGCAGCAGCTT
GAAGACGATCCGTTCTCCAACTACGGCGTCCTGCACGAGAAATCGTCCGGTACCGTGAAGGAA
TCAACGCCCA

FIGURE 50

```
AAAAATCGAAGTATCCTGAAGGCTTCCGAAATCAGCCCGTGACCGCGTCGAAGACGGGCGCAAGTCCTGAA
GAAGGGAGGAAGTCGAAGCCAAGATTATCAGCATCGACCCGCAAGAGCGGGTCATCAGCTTTCCGTCAA
TCCAAGGACGTCGACGACGAAGGACGCAATGAAAGAACTGCGTAAGCAGGAAGTAGAAAGCCGTGGTC
GACCACCATCGGTGATCTGATCCGTGCTCAGATGGAGAATCAGGGCTAAGTCTCGATCCATCATGAAAA
GGGCGGCCTAGGCCGCCCTTTTCGTTTCCCCTTGGACCTGTTCAAGACTGATCAGCATGCTAAA
GAGACCTGAGCTGATCTAGCCGCTTGAAAAGAAGGAAAACCATGACCAAGTCGGAGTTGATGAACGG
TCGTTACCCATCAGGGCGCAACTGTCCGCGAAGGATGTCGAGATCCGTGGCTTCGGCTTCAAGACCATGCTGGAGCAAAT
TCCCAGGCCTGGCGACCGGACCCCAAGACCGGGAGTCGAGATCCGTGGCTTCGGCTTCGACGCCAGTTCGGCCACTTCA
CGCGCGTCGTTGCCAACCCCAAGAACCGGGATCGGGTCAACGAGCCGAGTGATTTCTGCCTTGCTCAGAGTTCGTTGGAGTT
GCCGGGCAAGGAGTTGCGGGATCGGTCAACGCGTAATGGCGGTGGGCGTCGTTAGTGCCAAGCCGAGTGGCCCTTTTCATGATTGTGGT
CCATGCTTTGGCTCAAGCCGTCAAGCGCAAGCCGTCAGCTTGCATTTATTGCTGGCGGTATGGCGGCGATCTGAACTCTGGAAGCTTTATGCAGGTGTATACCTGTGGTCC
GCTTTGGAGAACCGGCAGCATTATTGCTGGCGGTATCTGCAAGATCTGATCGTTCGTACTCGAAAAGAACTCGAGTCGATCAGTCCAGTATCCAGT
TTATGTGCGTTAGCATTTATTGCTGGCGGTATCTGCAAGATCTGATCGTTCGTACTCGAAAAGAACTCGAGTCGATCAGT
CCAAGTGCGTCAGATCTGATGATCCGAGTCTGCTCAGTCCCTGTCCTTTGTGGGCTCGAGTGCTGAGTTACCATGT
ACCGCCCTGCGGTGAGGTCTTGAAGGTCTTGGAAGGTCGGGATGCGGGTGCCTGTTAGAGGGGTTGCTGAGTTACCATGT
TGACACAAATGCTTGGAAGGTCTTGGAAGGTCGGGATGCGGGTGCCTGTTAGAGGGGTTGCTGAGTTACCATGTC
TACTGGTTTGGCTGGCCAAGGTCAAGCTT
GGTTGGGTCTTCGCCAAAGGTCAAGCTT
```

PROTEINS INVOLVED IN THE SYNTHESIS AND ASSEMBLY OF O-ANTIGEN IN *PSEUDOMONAS AERUGINOSA*

This application claims benefit from U.S. Provisional Application Ser. No. 60/016,510 filed on Apr. 30, 1996 and U.S. Provisional Application Ser. No. 60/039,473 filed on Feb. 27, 1997.

FIELD OF THE INVENTION

The invention relates to novel nucleic acid molecules encoding proteins involved in the synthesis and assembly of O-antigen in *P. aeruginosa*; the novel proteins encoded by the nucleic acid molecules; and, uses of the proteins and nucleic acid molecules.

BACKGROUND OF THE INVENTION

The opportunistic pathogen *P. aeruginosa* remains a problem in the nosicomial infection of immunocompromised individuals. *P. aeruginosa* infections are particularly a problem in burn patients, people receiving medical implants, and in individuals suffering from cystic fibrosis (Fick, R. B. Jr., 1993). The organism is intrinsically resistant to many antibiotics and capable of forming biofilms which are recalcitrant to treatment. Several virulence factors have been identified in the pathogenesis of *P. aeruginosa* infections, including proteins such as exotoxin A, proteases, and exopolysaccharides including alginate and lipopolysaccharide (LPS). The LPS of *P. aeruginosa* is typical of Gram-negative bacteria, composed of lipid A-core oligosaccharide-O antigen repeating units.

*P. aeruginosa* is capable of coexpressing two distinct forms of LPS, designated A-band and B-band LPS, respectively. A-band LPS is a shorter, common form expressed by the majority of *P. aeruginosa* serotypes, and has a trisaccharide repeating unit of α-D-rhamnose linked 1→3, 1→3, 1→2. B-band LPS is the serotype-specific, O-antigen-containing form, and is a heteropolymer composed of di- to pentasaccharide repeats containing a wide variety of acyl sugars, amino sugars, and uronic acids. Both the A- and B-band repeating units are attached to lipid A-core, but there appear to be differences between them regarding point of attachment to and composition of the outer core region (Rivera et al., 1992).

The gene clusters for biosynthesis of core oligosaccharides/O-antigens rfb have been cloned and characterized from several bacterial species, including some from non-enteric genera such as Bordetella (Allen and Maskell, 1996), Haemophilus (Jarosik and Hansen, 1994), Neisseria (Gotschlich, 1994), Vibrio (Stroeher et al., 1992; Amor and Mutharia, 1995; Comstock et al., 1996), and Xanthamonas (Kingsley et al., 1993).

rfb clusters appear to be composed of mosaics of biosynthetic genes acquired horizontally from different sources (Reeves, 1993). Biochemical characterization of O-antigens from various species has shown that conservation of structure does not necessarily mirror conservation at the genetic level. Strains with identical O-antigens can differ significantly in their rfb clusters, while unique O-antigens can be encoded by only slightly variant rfb genes in other strains (Whitfield and Valvano, 1993).

Lightfoot and Lam were the first to report the cloning of genes involved in the expression of A-band (Lightfoot and Lam, 1991) and B-band (Lightfoot and Lam, 1993) LPS of *P. aeruginosa*. A recombinant cosmid clone pFV3 complemented A-band LPS synthesis in an A-band-deficient mutant, rd7513. pFV3 also mediated A-band LPS synthesis in five of the six *P. aeruginosa* O serotypes which lack A-band LPS. Another cosmid clone, pFV100, complemented B-band LPS synthesis in mutant ge6, which lacks B-band LPS. Physical mapping of the genes involved in A-band and B-band LPS synthesis indicated that the two gene clusters are physically distinct and are separated by more than 1.9 Mbp on the *P. aeruginosa* PAO1 genome. A-band LPS genes mapped between 5.75 and 5.89 Mbp (10.5 to 13.3 min), and B-band LPS genes mapped at 1.9 Mbp (near 37 min) on the 5.9-Mbp chromosome.

The structure of the *P. aeruginosa* O5 O-antigen has been elucidated (Knirel et al., 1988). O5 has a trisaccharide repeating unit of 2-acetamido-3-acetamidino-2,3-dideoxy-D-mannuronic acid, 2,3-diacetamido-D-mannuronic acid, and N-acetyl-D-fucosamine (FIG. 30). Serotypes O2, O16, O18, and O20 of *P. aeruginosa* have similar O-antigens to serotype O5, varying only in one linkage or one epimer from O5 (Knirel et al., 1988) (FIG. 30). Immunochemical cross reactions have also been demonstrated among LPS of serotypes O2, O5 and O16 by the use of monoclonal antibodies (Lam et al., 1992). The rfbA (herein also referred to as "psbL" and "wbp1") from the O5 gene cluster has been characterized (Dasgupta and Lam, 1995). This O5 O-antigen biosynthetic gene has been shown to hybridize only with chromosomal DNA from the group of five serotypes with similar O-antigens, and not with the remaining fifteen serotypes.

There are currently three pathways proposed for biosynthesis and assembly of LPS, the Rfc-dependent and Rfcindependent pathways. Rfc is the O-antigen polymerase, and appears to be required for assembly of heteropolymeric O-antigens (Mäkelä and Stocker, 1984). In contrast, homopolymeric O-antigens appear to be assembled without an O-antigen polymerase (Whitfield, 1995). Rfc-dependent (or Wzy) LPS synthesis has been shown to involve at least two other gene products which act in concert with Rfc; RfbX (or Wzx), the putative flippase which translocates individual O-antigen units across the cytoplasmic membrane where they are polymerized by Rfc (or Wzy), and Rol (or Wzz), the regulator of O-antigen chain length, which determines the preferred O-antigen chain length characteristic of the individual strain or serotype (Batchelor et al., 1993; Bastin et al., 1993; Morona et al., 1994b; Dodgson et al., 1996).

SUMMARY OF THE INVENTION

The present inventors have characterized a *P. aeruginosa* B-band (psb) gene cluster involved in the synthesis and assembly of B-band lipopolysaccharide i.e. O-antigen. The gene cluster is also known as and referred to herein as the wbp gene cluster.

The cluster contains two groups of genes, one of which is found in *P. aeruginosa* serotypes O2, O5, O16, O18, and O20, and the other is found in serotypes O1 to O20. The genes found in serotypes O2, O5, O16, O18, and O20 include the psbL gene also known as wbpL and rFA (Dasgupta and Lam, 1995), and the novel genes designated rol, psbA, psbB, psbC psbD, psbE, rfc, psbF, psbG, psbH, psbI, psbJ, and psbK ("Group I genes"), also known as and referred to herein as wzz, wbpA, wbpB, wbpC, wbpD, wbpE, wzy, wbpF, wbpG, wbpH, wbpI, wbpJ, and wbpK respectively. The genes found in serotypes O1 to O20 include the novel genes psbM and psbN which are also known as and referred to herein as wbpM and wbpN respectively ("Group II genes"). The psb gene cluster also contains genes which are not involved in LPS synthesis including the genes rpsA and himD and the novel genes designated uvrB, insertion element IS407, hisH and hisF. The arrangement of the genes in the wbp gene cluster is shown in FIG. 1.

The identification and sequencing of the genes and proteins in the wbp gene cluster permits the identification of substances which affect O-antigen synthesis or assembly in *P. aeruiginosa*. These substances may be useful in inhibiting O-antigen synthesis or assembly thereby rendering the microorganisms more susceptible to attack by host defence mechanisms.

Broadly stated the present invention relates to an isolated *P. aeruginosa* B-band gene cluster containing the following genes:rol (wzz), psbA (wbpA), psbB (wbpB), psbC (wbpC), psbD (wbpD), psbE (wbpE), rfc (wzy), psbF (wbpF), psbG (wbpG), psbH (wbpH), psbI (wbpI), psbJ (wbpJ), psbK (wbpK), psbL (wbpL), psbM (wbpM), and psbN (wbpN) involved in the synthesis, and assembly of lipopolysaccharide in *P. aeruginosa*. The terms in parenthesis correspond to other designations that have been given to these genes. The gene cluster may also contain the non-LPS gene uvrB, the insertion element IS407 (IS1209), the genes hisH and hisF involved in histidine synthesis, the gene rpsA which encodes a 30 S ribosomal subunit protein S1 and the gene himD which encodes an integration host factor.

The present invention also relates to nucleic acid molecules encoding the following proteins: (1) (a) Rol (also known as Wzz); (b) PsbA (also known as WbpA); (c) PsbB (also known as WbpB); (d) PsbC (also known as WbpC); (e) PsbD (also known as WbpD); (f) PsbE (also known as WbpE); (g) Rfc (also known as Wzy); (h) PsbF (also known as wbpF); (i) PsbG (also known as WbpG); (j) PsbI (also known as WbpI); (k) PsbJ (also known as WbpJ); (l) PsbK (also known as WbpK); (m) PsbM (also known as WbpM); (n) PsbH (also known as wbpH) or (o) PsbN (also known as WbpN), involved in *P. aeruginosa* O-antigen synthesis and assembly; (2) UvrB involved in ultraviolet repair; (3) HisH or HisF involved in histidine synthesis, or (4) RpsA a 30 S ribosomal subunit protein S1. In addition, nucleic acid molecules are provided which contain sequences encoding two or more of the following proteins (1) (a) Rol (also known as Wzz); (b) PsbA (also known as WbpA); (c) PsbB (also known as WbpB); (d) PsbC (also known as WbpC); (e) PsbD (also known as WbpD); (f) PsbE (also known as WbpE); (g) Rfc (also known as Wzy); (h) PsbF (also known as WbpF); (i) HisH; (j) HisF; (k) PsbG (also known as WbpG); (l) PsbI (also known as WbpI); (m) PsbJ (also known as WbpJ); (n) PsbK (also known as WbpK); (o) PsbM (also known as WbpM); (p) PsbN (also known as WbpN); (q) PsbH (also known as WbpH); (r) PsbL (also known as WbpL); and (s) RpsA.

The invention also contemplates a nucleic acid molecule comprising a sequence encoding a truncation of a protein of the invention, an analog, or a homolog of a protein of the invention, or a truncation thereof.

The nucleic acid molecules of the invention may be inserted into an appropriate expression vector, i.e. a vector which contains the necessary elements for the transcription and translation of the inserted coding sequence. Accordingly, recombinant expression vectors adapted for transformation of a host cell may be constructed which comprise a nucleic acid molecule of the invention and one or more transcription and translation elements operatively linked to the nucleic acid molecule.

The recombinant expression vector may be used to prepare transformed host cells expressing a protein of the invention. Therefore, the invention further provides host cells containing a recombinant molecule of the invention.

The invention further provides a method for preparing a protein of the invention utilizing the purified and isolated nucleic acid molecules of the invention. In an embodiment a method for preparing a protein of the invention is provided comprising (a) transferring a recombinant expression vector of the invention into a host cell; (b) selecting transformed host cells from untransformed host cells; (c) culturing a selected transformed host cell under conditions which allow expression of the protein; and (d) isolating the protein.

The invention further broadly contemplates an isolated protein characterized in that it has part or all of the primary structural conformation (ie. continuous sequence of amino acid residues) of a novel protein encoded by a gene of the wbp gene cluster of the invention. In an embodiment of the invention, a purified protein is provided which has the amino acid sequence as shown in FIG. 3 or SEQ ID NO:2;, FIG. 4 or SEQ ID NO:3; FIG. 5 or SEQ ID NO:4; FIG. 6 or SEQ ID NO:5; FIG. 7 or SEQ ID NO:6; FIG. 8 or SEQ ID NO:7; FIG. 9 or SEQ ID NO:8; FIG. 10 or SEQ ID NO:9; FIG. 11 or SEQ ID NO:10; FIG. 12 or SEQ ID NO:11; FIG. 13 or SEQ ID NO:12; FIG. 14 or SEQ ID NO:13; FIG. 15 or SEQ ID NO:14; FIG. 16 or SEQ ID NO:15; FIG. 17 or SEQ ID NO:16; or, FIG. 18 or SEQ ID NO:17; FIG. 19 or SEQ.ID. No.: 18; or, FIG. 20 or SEQ.ID. No.: 19. The invention also includes truncations of the protein and analogs, homologs, and isoforms of the protein and truncations thereof.

The proteins of the invention may be conjugated with other molecules, such as proteins, to prepare fusion proteins. This may be accomplished, for example, by the synthesis of N-terminal or C-terminal fusion proteins.

The nucleic acid molecules of the invention allow those skilled in the art to construct nucleotide probes for use in the detection of nucleotide sequences in samples such as biological (e.g clinical specimens), food, or environmental samples. The nucleotide probes may also be used to detect nucleotide sequences that encode proteins related to or analogous to the proteins of the invention.

Accordingly, the invention provides a method for detecting the presence of a nucleic acid molecule having a sequence encoding a protein of the invention, comprising contacting the sample with a nucleotide probe which hybridizes with the nucleic acid molecule, to form a hybridization product under conditions which permit the formation of the hybridization product, and assaying for the hybridization product.

The invention further provides a kit for detecting the presence of a nucleic acid molecule having a sequence encoding a protein of the invention, comprising a nucleotide probe which hybridizes with the nucleic acid molecule, reagents required for hybridization of the nucleotide probe with the nucleic acid molecule, and directions for its use.

The nucleic acid molecules of the invention also permit the identification and isolation, or synthesis, of nucleotide sequences which may be used as primers to amplify a nucleic acid molecule of the invention, for example in the polymerase chain reaction (PCR).

Accordingly, the invention relates to a method of determining the presence of a nucleic acid molecule having a sequence encoding a protein of the invention in a sample, comprising treating the sample with primers which are capable of amplifying the nucleic acid molecule in an amplification reaction, preferably in a polymerase chain reaction, to form amplified sequences, under conditions which permit the formation of amplified sequences, and, assaying for amplified sequences.

The invention further relates to a kit for determining the presence of a nucleic acid molecule having a sequence encoding a protein of the invention in a sample, comprising primers which are capable of amplifying the nucleic acid molecule in an amplification reaction, preferably a polymerase chain reaction, to form amplified sequences, reagents required for amplifying the nucleic acid molecule thereof in the amplification reaction, means for assaying the amplified sequences, and directions for its use.

The invention also relates to an antibody specific for an epitope of a protein of the invention, and methods for preparing the antibodies. Antibodies specific for a protein encoded by a Group I gene can be used to detect P. aeruginosa serotypes O2, O5, O16, O18, and O20 in a sample, and antibodies specific for a protein encoded by a Group II gene can be used to detect P. aeruginosa serotypes O1 to O20 in a sample.

Therefore, the invention also relates to a method for detecting P. aeruginosa serotypes O2, O5, O16, O18, and O20 in a sample comprising contacting a sample with an antibody specific for an epitope of a protein encoded by a Group I gene which antibody is capable of being detected after it becomes bound to a protein in the sample, and assaying for antibody bound to protein in the sample, or unreacted antibody. A method is also provided for detecting P. aeruginosa serotypes O1 to O20 in a sample comprising contacting a sample with an antibody specific for an epitope of a protein encoded by a Group II gene which antibody is capable of being detected after it becomes bound to a protein in the sample, and assaying for antibody bound to protein in the sample, or unreacted antibody.

A kit for detecting P. aerutginosa serotypes in a sample comprising an antibody of the invention, preferably a monoclonal antibody and directions for its use is also provided. The kit may also contain reagents which are required for binding of the antibody to the protein in the sample.

As discussed above, the identification and sequencing of genes in the wbp gene cluster in P. aeruginosa permits the identification of substances which affect the activity of the proteins encoded by the genes in the cluster, or the expression of the proteins, thereby affecting O-antigen synthesis or assembly. These substances may be useful in rendering the microorganisms more susceptible to attack by host defence mechanisms. Accordingly, the invention provides a method for assaying for a substance that affects one or both of P. aeruginosa O-antigen synthesis or assembly comprising mixing a protein or nucleic acid molecule of the invention with a test substance which is suspected of affecting P. aeruginosa O-antigen synthesis or assembly, and determining the effect of the substance by comparing to a control.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF DRAWINGS

The invention will now be described in relation to the drawings:

FIGS. 2A–2H shows the nucleic acid sequence of the P. aeruginosa PAO1 gene cluster (SEQ. ID. NO. 1);

FIG. 3 shows the amino acid sequence of the Rol protein of the invention (SEQ. ID NO. 2);

FIG. 4 shows the amino acid sequence of the PsbA (WbpA) protein of the invention (SEQ. ID NO. 3);

FIG. 5 shows the amino acid sequence of the PsbB (WbpB) protein of the invention (SEQ. ID NO. 4);

FIG. 6 shows the amino acid sequence of the PsbC (WbpC) protein of the invention (SEQ. ID NO. 5);

FIG. 7 shows the amino acid sequence of the PsbD (WbpD) protein of the invention (SEQ. ID NO. 6);

FIG. 8 shows the amino acid sequence of the PsbE (WbpE) protein of the invention (SEQ. ID NO. 7);

FIG. 9 shows the amino acid sequence of the Rfc (Wzy) protein of the invention (SEQ. ID NO. 8);

FIG. 10 shows the amino acid sequence of the PsbF (WbpF) protein of the invention (SEQ. ID NO. 9);

FIG. 11 shows the amino acid sequence of the HisH protein of the invention (SEQ. ID NO. 10);

FIG. 12 shows the amino acid sequence of the HisF protein of the invention (SEQ. ID NO. 11);

FIG. 13 shows the amino acid sequence of the PsbG (WbpG) protein of the invention (SEQ. ID NO. 12);

FIG. 14 shows the amino acid sequence of the PsbH (WbpH) protein of the invention (SEQ. ID NO. 13);

FIG. 15 shows the amino acid sequence of the PsbI (WbpI) protein of the invention (SEQ. ID NO. 14);

FIG. 16 shows the amino acid sequence of the PsbJ (WbpJ) protein of the invention (SEQ. ID NO. 15);

FIG. 17 shows the amino acid sequence of the PsbK (WbpK) protein of the invention (SEQ. ID NO. 16);

FIG. 18 shows the amino acid sequence of the PsbM (WbpM) protein of the invention (SEQ. ID NO. 17);

FIG. 19 shows the amino acid sequence of the PsbN (WbpN) protein of the invention (SEQ. ID NO. 18);

FIG. 20 shows the amino acid sequence of the UvrB protein of the invention (SEQ. ID NO. 19);

FIG. 21 shows the amino acid sequence of PsbL (SEQ. ID NO. 20) (WbpL);

FIG. 22A shows a silver-stained SDS-PAGE gel of LPS from PAO1, AK14O1, AK14O1(pFV100), and AK14O1 (pFV.TK8) [(Panel A) and Western immunoblots of this LPS reacted with O5-specific MAb MF15-4 (Panel B)];

FIG. 22B shows a Western immunoblots of this LPS reacted with O5-specific MAb MF15-4;

FIG. 24A shows a restriction map of the PAO1 wild-type rfc (wzy) coding region [are shown];

FIG. 24B shows a restriction map of the PAO1 mutant rfc (wzy) coding regions;

FIG. 24C shows a Southern analysis of the three rfc (wzy) chromosomal mutants, OP5.2, OP5.3 and OP5.5, showing the insertion of an 875 bp $Gm^R$ cassette into the rfc (wzy) gene;

FIG. 26 shows the restriction maps of recombinant plasmids pFV161, pFV401, and pFV402;

FIG. 30 is a diagram showing the structures of the O-antigens of P. aeruginosa serotypes related to O5;

FIG. 31 shows E. coli $\sigma^{70}$ (SEQ ID NO: 21) and similar regions in psbA (wpbA) (SEQ ID NO: 22), hisH (SEQ ID NO: 23), psbG (wpbG) (SEQ ID NO: 24), IS407 (SEQ ID NO: 25–27) and psbN (wpbN) (SEQ ID NO: 28);

FIG. 32 shows features of the psb genes (SEQ ID NO: 29–44) of the psb gene cluster identifying the presumed start codon and spaces between RBS (ribosome binding sequence) and the first codon;

FIG. 33 shows the sequences of the NAD-binding domains of PsbA (SEQ ID NO: 45), PsbK (SEQ ID NO: 46), and PsbM (SEQ ID NO: 47) aligned with those of other bacterial proteins involved in polysaccharide biosynthesis (SEQ ID NO: 48–71);

FIG. 34 shows a sequence alignment for PsbA (WpbA) (SEQ ID NO: 72), E. coli RffD (SEQ ID NO: 73), and B. solanaceraeum EpsD (SEQ ID NO: 74);

FIG. 35 shows a sequence alignment for PsbD (WpbD) (SEQ ID NO: 75) and Bordetella pertussis BplB (SEQ ID NO: 76), CysE of a number of bacteria;

FIGS. 36A and 36B shows a sequence alignment for PsbE (WpbE) (SEQ ID NO: 77) and BP-BplC (SEQ ID NO: 78), BS-DegT (SEQ ID NO: 79), S-EryC1 (SEQ ID NO: 80), S-DnrJ (SEQ ID NO: 81), and BS-SpsC (SEQ ID NO: 82);

FIG. 38 shows a sequence alignment for PA-PsbI (SEQ ID NO: 83), BP-BplD (SEQ ID NO: 84), EC-NfrC (SEQ ID NO: 85), BS-OrfX (SEQ ID NO: 86), and SB-RfbC (SEQ ID NO: 87);

FIGS. 39A and 39B shows a sequence alignment for PA-PsbJ (SEQ ID NO: 88), BP-BplE (SEQ ID NO: 89), and YE-TrsE (SEQ ID NO: 90);

FIGS. 40A and 40B shows a sequence alignment for PA-PsbL (SEQ ID NO: 91), YE-TrsF (SEQ ID NO: 92) and HI-Rfe (SEQ ID NO: 93);

FIGS. 41A and 41B shows a sequence alignment for PsbM (SEQ ID NO: 94), TrsG (SEQ ID NO: 95), BP-BplL (SEQ ID NO: 96), and SA-CapD (SEQ ID NO: 97);

FIG. 42 shows the nucleotide sequence of the rol (wzz) gene (SEQ ID NO: 98);

FIG. 48 shows an SDS-PAGE gel from WbpF knockout mutants;

FIG. 49 shows the amino acid and nucleotide sequence encoding Rps A (SEQ ID NO: 99); and FIG. 50 shows the amino acid and nucleotide sequence encoding Him D (SEQ ID NO: 100).

DETAILED DESCRIPTION OF THE INVENTION

The following standard abbreviations for the amino acid residues are used throughout the specification: A, Ala—alanine; C, Cys—cysteine; D, Asp- aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp-tryptophan; Y, Tyr—tyrosine; and p.Y., P.Tyr—phosphotyrosine.

I. Nucleic Acid Molecules of the Invention

As hereinbefore mentioned, the present invention relates to an isolated P. aeruginosa B-band gene cluster containing genes involved in the synthesis and assembly of O-antigen in P. aeruginosa. The present invention also relates to the isolated genes which comprise the cluster.

The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

The *P. aeruginosa* B-band gene cluster comprises the following genes: rol (wzz), psbA (wbpA), psbB (wbpB), psbC (wbpC), psbD (wbpD), psbE (wbpE), rfc (wzy), psbF (wbpF), psbG (wbpG), psbH (wbpH), psbI (wbpI), psbJ (wbpJ), psbK (wbpK), psbL (wbpL), psbM (wbpM), and psbN (wbpN) involved in the synthesis, and assembly of lipopolysaccharide in *P. aeruginosa*. The gene cluster may also contain the non-LPS genes hisH, hisF, himD, rspa, uvrB, and the insertion element IS407 (IS1209).

Figure 1:
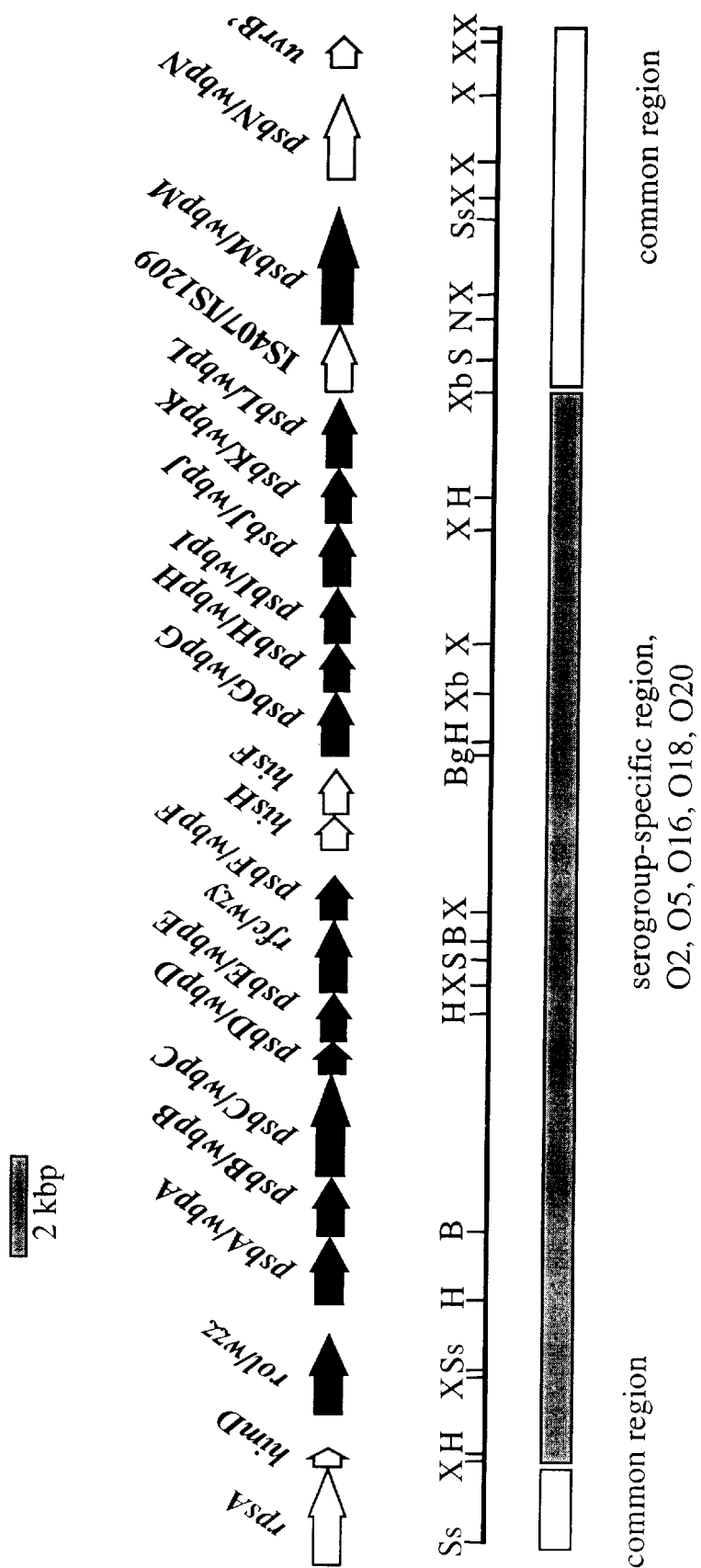
FIG. 1 shows the organization of the P. aeruginosa PAO1 psb (wbp) gene cluster.

The genes preferably have the organization as shown in FIG. 1 (SEQ. ID. NO. 1). In FIG. 1, the genes necessary for sugar biosynthesis (Man(2NAc3N)A and Man(2NAc3NAc) biosynthesis) are scattered throughout the gene cluster (wpbI (psbI), wpbE (psbE), wpbD (psbD), wpbB (psbB), wpbC (psbC). The genes encoding transferases are interspersed throughout the wpb (psb) cluster (wpbH (psbH), wpbJ (psbJ), wpbL, (wpbL)), and are separated from one another by one gene each. The gene encoding the putative first transferase (Wpb (PsbL)), thought to initiate O-antigen assembly by attachment of an FucNAc residue to undecaprenol, is the most distal.

The invention provides nucleic acid molecules encoding the following proteins: (1) (a) Rol (Wzz); (b) PsbA (WbpA); (c) PsbB (WbpB); (d) PsbC (WbpC); (e) PsbD (WbpD); (f) PsbE (WbpE); (g) Rfc (Wzy); (h) PsbF (WbpF); (i) PsbG (WbpG); (j) PsbI (WbpI); (k) PsbJ (WbpJ); (l) PsbK (WbpK); (m) PsbM (WbpM); (n) PsbH (WbpH); and (o) PsbN (WbpN) involved in *P. aeruginosa* O-antigen synthesis and assembly; (2) UvrB involved in ultraviolet repair; (3) HisH or HisF involved in histidine synthesis or (4) himD involved in host factor integration and (5) RpsA a 30S ribosomal subunit protein S1. In addition, nucleic acid molecules are provided which contain sequences encoding two or more of the following proteins (1) (a) Rol (wzz); (b) PsbA (WbpA); (c) PsbB (WbpB); (d) PsbC (WbpC); (e) PsbD (WbpD); (f) PsbE (WbpE); (g) Rfc (Wzy); (h) PsbF (WbpF); (i) HisH; (j) HisF; (k) PsbG (WbpG); (l) PsbI (WbpI); (m) PsbJ (WbpJ); (n) PsbK (WbpK); (o) PsbM (WbpM); (p) PsbN (WbpN); (q) PsbH (WbpH); (r) PsbL (WbpL); (s) RpsA or (t) HimD.

In an embodiment of the invention, an isolated nucleic acid molecule is provided having a sequence which encodes a protein having an amino acid sequence as shown in FIG. 3 or SEQ.ID. No.: 2; FIG. 4 or SEQ.ID. No.: 3; FIG. 5 or SEQ.ID. No.: 4; FIG. 6 or SEQ.ID. No.: 5; FIG. 7 or SEQ.ID. No.: 6; FIG. 8 or SEQ.ID. No.: 7; FIG. 9 or SEQ.ID. No.: 8; FIG. 10 or SEQ.ID. No.: 9; FIG. 11 or SEQ.ID. No.: 10; FIG. 12 or SEQ.ID. No.: 11; FIG. 13 or SEQ.ID. No.: 12; FIG. 14 or SEQ.ID. No.: 13; FIG. 15 or SEQ.ID. No.: 14; FIG. 16 or SEQ.ID. No.: 15; FIG. 17 or SEQ.ID. No.: 16.; FIG. 18 or SEQ.ID. No.: 17; FIG. 19 or SEQ.ID. No.: 18; and FIG. 20 or SEQ.ID. No.: 19.

Preferably, the purified and isolated nucleic acid molecule comprises (a) a nucleic acid sequence containing nucleotides 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 1, wherein T can also be U;

(b) a nucleic acid sequence containing two or more of nucleotides 1–479; 1286–2596; 2670–3620; 3689–5578; 5575–6066; 6152–6982; 7236–8552; 8549–9499; 9830–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 1, wherein T can also be U;

(c) nucleic acid sequences complementary to (a) or (b);

(d) nucleic acid sequences which are homologous to (a) or (b);

(e) a fragment of (a) to (d) that is at least 15 bases, preferably 20 to 30 bases, and which will hybridize to (a) to (d) under stringent hybridization conditions; or (f) a nucleic acid molecule differing from any of the nucleic acids of (a) to (c) in codon sequences due to the degeneracy of the genetic code.

Specific embodiments of the nucleic acid molecule of the invention include the following:

1. An isolated nucleic acid molecule characterized by having a sequence encoding a Rol (Wzz) protein of *P. aeruginosa* which regulates O-antigen linking. The nucleic acid molecule preferably encodes Rol having the amino acid sequence as shown in FIG. 3 or SEQ.ID. No.: 2, and most preferably comprises nucleotides 1–479 as shown in FIG. 2 or SEQ.ID. No.: 1, or a nucleotide sequence as shown in FIG. 42, which shows the full length nucleotide sequence of the rol gene.

2. An isolated nucleic acid molecule characterized by having a sequence encoding a PsbA (WbpA) protein of *P. aeruginosa* which has dehydrogenase activity. The nucleic acid molecule preferably encodes PsbA having the amino acid sequence as shown in FIG. 4 or SEQ.ID. No.: 3, and most preferably comprises nucleotides 1286–2596 as shown in FIG. 2 or SEQ.ID. No.: 1.

3. An isolated nucleic acid molecule characterized by having a sequence encoding a PsbB (WbpB) protein of *P. aeruginosa*. The nucleic acid molecule preferably encodes PsbB having the amino acid sequence as shown in FIG. 5 or SEQ.ID. No.: 4, and most preferably comprises nucleotides 2670–3620 as shown in FIG. 2 or SEQ.ID. No.: 1.

4. An isolated nucleic acid molecule characterized by having a sequence encoding a PsbC (WbpC) protein of *P. aeruginosa* which has acetyltransferase activity. The nucleic acid molecule preferably encodes PsbC having the amino acid sequence as shown in FIG. 6 or SEQ.ID. No.: 5, and most preferably comprises nucleotides 3689–5578 as shown in FIG. 2 or SEQ.ID. No.: 1.

5. An isolated nucleic acid molecule characterized by having a sequence encoding a PsbD (WbpD) protein of *P. aeruginosa* which has acetyltransferase activity. The nucleic acid molecule preferably encodes PsbD having the amino acid sequence as shown in FIG. 7 or SEQ.ID. No.: 6, and most preferably comprises nucleotides 5575–6066 as shown in FIG. 2 or SEQ.ID. No.: 1.

6. An isolated nucleic acid molecule characterized by having a sequence encoding a PsbE (WbpE) protein of *P. aeruginosa*. The nucleic acid molecule preferably encodes PsbE having the amino acid sequence as shown in FIG. 8 or SEQ.ID. No.: 7, and most preferably comprises nucleotides 6152–6982 as shown in FIG. 2 or SEQ.ID. No.: 1.

7. An isolated nucleic acid molecule characterized by having a sequence encoding a Rfc (Wzy) protein of *P. aeruginosa* which has O-polymerase activity. The nucleic acid molecule preferably encodes Rfc having the amino acid sequence as shown in FIG. 9 or SEQ.ID.

No.: 8, and most preferably comprises nucleotides 7236–8552 as shown in FIG. 2 or SEQ.ID. No.: 1. The nucleic acid molecule may comprise nucleotides 7236 to 8552 where base 8059 is "G". The Rfc coding region has a lower mol. % G+C than the *P. aeruginosa* chromosomal average and it has similar amino acid composition and codon usage to that reported for other Rfc proteins. Using a novel gene-replacement vector, the present inventors were able to generate PAO1 chromosomal rfc mutants. These knockout mutants express LPS containing complete core plus one O-repeat unit, indicating that they are no longer producing a functional O-polymerase enzyme.

8. An isolated nucleic acid molecule characterized by having a sequence encoding a PsbF (WbpF) protein of *P. aeruginosa*. The nucleic acid molecule preferably encodes PsbF having the amino acid sequence as shown in FIG. 10 or SEQ.ID. No.: 9, and most preferably comprises nucleotides 8549–9499 as shown in FIG. 2 or SEQ.ID. No.: 1.

9. An isolated nucleic acid molecule characterized by having a sequence encoding a PsbG (WbpG) protein of *P. aeruginosa*. The nucleic acid molecule preferably encodes PsbG having the amino acid sequence as shown in FIG. 13 or SEQ.ID. No.: 12, and most preferably comprises nucleotides 11281–12411 as shown in FIG. 2 or SEQ.ID. No.: 1.

The present inventors have inserted a gentamicin cassette into psbG which resulted in B-band deficient mutants of PAO1.

10. An isolated nucleic acid molecule characterized by having a sequence encoding a PsbH (WbpH) protein of *P. aeruginosa* which has ManA transferase activity. The nucleic acid molecule preferably encodes PsbH having the amino acid sequence as shown in FIG. 14 or SEQ.ID. No.: 13, and most preferably comprises nucleotides 12427–13548 as shown in FIG. 2 or SEQ.ID. No.: 1. The present inventors have produced a psbH knockout mutant of PAO1 which is B-band deficient.

11. An isolated nucleic acid molecule characterized by having a sequence encoding a PsbI (WbpI) protein of *P. aeruginosa* which converts UDP-N-acetylglucosamine to UDP-N-acetylmannosamine. The nucleic acid molecule preferably encodes PsbI having the amino acid sequence as shown in FIG. 15 or SEQ.ID. No.: 14, and most preferably comprises nucleotides 13545–14633 as shown in FIG. 2 or SEQ.ID. No.: 1.

12. An isolated nucleic acid molecule characterized by having a sequence encoding a PsbJ (WbpJ) protein of *P. aeruginosa* which has ManA transferase activity. The nucleic acid molecule preferably encodes PsbJ having the amino acid sequence as shown in FIG. 16 or SEQ.ID. No.: 15, and most preferably comprises nucleotides 14651–15892 as shown in FIG. 2 or SEQ.ID. No.: 1.

13. An isolated nucleic acid molecule characterized by having a sequence encoding a PsbK (WbpK) protein of *P. aeruginosa* which has dehydratase activity. The nucleic acid molecule preferably encodes PsbK having the amino acid sequence as shown in FIG. 17 or SEQ.ID. No.: 16, and most preferably comprises nucleotides 15889–16851 as shown in FIG. 2 or SEQ.ID. No.: 1.

14. An isolated nucleic acid molecule characterized by having a sequence encoding a PsbM (WbpM) protein of *P. aeruginosa* and having dehydrogenase activity. The nucleic acid molecule preferably encodes PsbM having the amino acid sequence as shown in FIG. 18 or SEQ.ID. No.: 17, and most preferably comprises nucleotides 19678–21675 as shown in FIG. 2 or SEQ.ID. No.: 1. PsbM knockout mutants do not produce LPS.

15. An isolated nucleic acid molecule characterized by having a sequence encoding a PsbN (WbpN) protein of *P. aeruginosa*. The nucleic acid molecule preferably encodes PsbN having the amino acid sequence as shown in FIG. 19 or SEQ.ID. No.: 18, and most preferably comprises nucleotides 22302–23693 as shown in FIG. 2 or SEQ.ID. No.: 1.

16. An isolated nucleic acid molecule characterized by having a sequence encoding a UvrB protein of *P. aeruginosa* which is involved in ultraviolet repair. The nucleic acid molecule preferably encodes UvrB having the amino acid sequence as shown in FIG. 20 or SEQ.ID. No.: 19, and most preferably comprises nucleotides 23704–24417 as shown in FIG. 2 or SEQ.ID. No.: 1.

17. An isolated nucleic acid molecule characterized by having a sequence encoding a RpsA protein for a 30S ribosomal subunit. The nucleic acid molecule preferably encodes RpsA having the amino acid sequence as shown in FIG. 49.

18. An isolated nucleic acid molecule characterized by having a sequence encoding a HimD protein for a host integration factor. The nucleic acid molecule preferably encodes HimD having the amino acid sequence as shown in FIG. 50.

In an embodiment of the invention, the nucleic acid molecule contains two genes from the gene cluster of the invention, preferably two genes which are adjacent in the gene cluster. For example, the present inventors have found that rfc (wzy) and psbf (wbpF) are cotranscribed and they are both required for B-band synthesis. If psbF (wbpF) is absent, both A and B synthesis are knocked out indicating that its gene product is required for expresser of A and B-band LPS onto the core oligosaccharide. Accordingly, the invention provides a nucleic acid molecule encoding a PsbF (WpbF) protein and an Rfc (Wzy) protein. Preferably a nucleic acid molecule comprising nucleotides 7239 to 9499 as shown in FIG. 2 or SEQ.ID. No.: 1.

It will be appreciated that the invention includes nucleic acid molecules encoding truncations of the proteins of the invention, and analogs and homologs of the proteins of the invention and truncations thereof, as described below. It will further be appreciated that variant forms of the nucleic acid molecules of the invention which arise by alternative splicing of an mRNA corresponding to a cDNA of the invention are encompassed by the invention.

Further, it will be appreciated that the invention includes nucleic acid molecules comprising nucleic acid sequences having substantial sequence homology with the nucleic acid sequences containing nucleotides 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 2 and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Nucleic acid sequences having substantial homology include nucleic acid sequences having at least 80–90%, preferably 90% identity with the nucleic acid sequence 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 2. By way of example, it is expected that a sequence having 80% sequence homology with the DNA sequence encoding PsbM of the invention will provide a functional PsbM protein.

Another aspect of the invention provides a nucleic acid molecule, and fragments thereof having at least 15 bases, which hybridizes to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 6.0×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Isolated and purified nucleic acid molecules having sequences which differ from the nucleic acid sequence shown in SEQ ID NO:1 or FIG. 2, and the nucleic acid sequences 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 1, due to degeneracy in the genetic code are also within the scope of the invention. Such nucleic acids encode functionally equivalent proteins (e.g., a PsbM (WpbM) protein having dehydrogenase activity) but differ in sequence from the above mentioned sequences due to degeneracy in the genetic code.

An isolated nucleic acid molecule of the invention which comprises DNA can be isolated by preparing a labelled nucleic acid probe based on all or part of the nucleic acid sequences containing nucleotides 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 2, and using this labelled nucleic acid probe to screen an appropriate DNA library (e.g. a cDNA or genomic DNA library). For example, a whole genomic library isolated from a microorganism, such as a serotype of P. aerugitiosa, can be used to isolate a DNA encoding a novel protein of the invention by screening the library with the labelled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a novel protein of the invention using the polymerase chain reaction (PCR) methods and cDNA or genomic DNA. It is possible to design synthetic oligonucleotide primers from the nucleic acid molecules containing the nucleotides 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417, as shown in FIG. 2 or SEQ. ID. NO.: 2, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes a novel protein of the invention. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel protein of the invention may be accomplished by expressing the cDNA in an appropriate host cell by standard techniques, and testing the activity of the protein using the methods as described herein. For example, the activity of a putative PsbM protein may be tested by mixing with an appropriate substrate and assaying for dehydrogenase activity. A cDNA having the activity of a novel protein of the invention so isolated can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of the nucleic acid molecules of the invention may be determined using currently available computer software designed for the purpose, such as PC/Gene (IntelliGenetics Inc., California). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably one or more of the nucleic acid sequences shown in the Sequence Listing as SEQ. ID. NO. 1 and in FIG. 2 (i.e. a nucleic acid molecule containing nucleotides 1–479; 1286–2596; 2670–3620; 3689–5578; 5575–6066; 6152–6982; 7236–8552; 8549–9499; 9831–10388; 10388–11143; 11281–12411; 12427–13548; 13545–14633; 14651–15892; 15889–16851; 17935–19144; 19678–21675; 22302–23693; or 23704–24417) may be inverted relative to their normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further broadly contemplates an isolated protein characterized in that it has part or all of the primary structural conformation (ie. continuous sequence of amino acid residues) of a novel protein encoded by a gene of the psb gene cluster of the invention. In an embodiment of the invention, an isolated protein is provided which has the amino acid sequence as shown in FIG. 3 or SEQ ID NO:2; (Rol or Wzz), FIG. 4 or SEQ ID NO:3 (PsbA or WbpA) FIG. 5 or SEQ ID NO:4 (PsbB or WbpB); FIG. 6 or SEQ ID NO:5 (PsbC or WbpC); FIG. 7 or SEQ ID NO:6 (PsbD or WbpD); FIG. 8 or SEQ ID NO:7 (PsbE or wbpE); FIG. 9 or SEQ ID NO:8 (Rfc or Wzy); FIG. 10 or SEQ ID NO:9 (PsbF or WbpF); FIG. 11 or SEQ ID NO:10 (HisH); FIG. 12 or SEQ ID NO:11 (HisF); FIG. 13 or SEQ ID NO:12 (PsbG or WbpG); FIG. 14 or SEQ ID NO:13 (PsbH or WbpH); FIG. 15 or SEQ ID NO:14 (PsbI or WbpI); FIG. 16 or SEQ ID NO:15 (PsbJ or WbpJ); FIG. 17 or SEQ ID NO:16 (PsbK or WbpK); FIG. 18 or SEQ ID NO:17 (PsbM or WbpM); FIG. 19 or SEQ ID NO:18 (PsbN or WbpN); or FIG. 20 or SEQ ID NO:19 (UvrB).

The gene products of rol, psbA, psbB, psbC, psbD, psbE, rfc, psbF, hisH, hisF, psbG, psbH, psbI, psbJ, psbL, and psbK (also known as wzz, wbpA, wbpB, wbpC, zwbpD, wbpE, wzy, wbpF, hisH, hisF, wbpG, wbpH, wpbI, wbpj respectively) are expected to be found in serotypes O2, O5, O16, O18, and O20, and the gene products of psbM and psbN (also known as wbpM and wbpN, respectively) are expected to be found in serotypes O1 to O20. The gene products of hisF and hisH are not found in serotype O6.

Specific embodiments of the invention include the following:

1. An isolated Rol (Wzz) protein of P. aeruginosa which regulates O-antigen linking, having the amino acid sequence as shown in FIG. 3 or SEQ.ID. No.: 2. The function of Rol may be associated with the Rfc protein.
2. An isolated PsbA (WbpA) protein of P. aeruginosa which has dehydrogenase activity, and the amino acid sequence as shown in FIG. 4 or SEQ.ID. No.: 3. PsbA may be involved in the biosynthesis of mannuronic acid residues.
3. An isolated PsbB (WbpB) protein of P. aeruginosa having the amino acid sequence as shown in FIG. 5 or SEQ.ID. No.: 4. PsbB may be involved in Fuc2NAc biosynthesis.
4. An isolated PsbC (WbpC) protein of P. aeruginosa which has acetyltransferase activity and the amino acid sequence as shown in FIG. 6 or SEQ.ID. No.: 5. PsbC may be involved in the acetylation of mannuronic acid residues in the O-antigen.
5. An isolated PsbD (WbpD) protein of P. aeruginosa which has acetyltransferase activity and the amino acid sequence as shown in FIG. 7 or SEQ.ID. No.: 6. PsbD may be involved in the acetylation of mannuronic acid residues in the O-antigen.
6. An isolated PsbE (WbpE) protein of P. aeruginosa. having the amino acid sequence as shown in FIG. 8 or SEQ.ID. No.: 7. PsbE may be involved in the biosynthesis of 2,3-, 2,4-, and 2,6-dideoxy sugars such as 2,3-dideoxy mannuronic acid produced by P. aeruginosa O5.
7. An isolated Rfc (Wzy) protein of P. aeruginosa which has O-polymerase activity and the amino acid sequence as shown in FIG. 9 or SEQ.ID. No.: 8. The Rfc protein is characterized as very hydrophobic, and it is an integral membrane protein with 11 putative membrane spanning domains.
8. An isolated PsbF (WbpF) protein of P. aeruginosa. having the amino acid sequence as shown in FIG. 10 or SEQ.ID. No.: 9. PsbF is translationally coupled with rfc and it is a putative flippase.
9. An isolated PsbG (WbpG) protein of P. aeruginosa which has the amino acid sequence as shown in FIG. 13 or SEQ.ID. No.: 12.
10. An isolated PsbH (WbpH) protein of P. aeruginosa which has ManA transferase activity and the amino acid sequence as shown in FIG. 14 or SEQ.ID. No.: 13. PsbH may be involved in the addition of ManA (i.e. Man(2NAc3N)A) to the O-antigen unit.
11. An isolated PsbI (WbpI) protein of P. aeruginosa which converts UDP-N-acetylglucosamine to UDP-N-acetylmannosamine, and has the amino acid sequence as shown in FIG. 15 or SEQ.ID. No.: 14.
12. An isolated PsbJ (WbpJ) protein of P. aeruginosa which has ManA transferase activity, and the amino acid sequence as shown in FIG. 16 or SEQ.ID. No.: 15. Based on their gene order and their relative hydropathic indices, the psbj and psbH gene products are thought to transfer Man(NAc)2A and Man(2Nac3N)A, respectively.
13. An isolated PsbK (WbpK) protein of P. aeruginosa which has dehydratase activity, and the amino acid sequence as shown in FIG. 17 or SEQ.ID. No.: 16.
14. An isolated PsbM (WbpM) protein of P. aeruginosa having dehydrogenase activity, and the amino acid sequence as shown in FIG. 18 or SEQ.ID. No.: 17. PsbM is involved in the biosynthesis of N-acetylfucosamine residues of the O-antigen. PsbM contains 2 NAD binding domains.
15. An isolated PsbN (WbpN) protein of P. aeruginosa. having the amino acid sequence as shown in FIG. 19 or SEQ.ID. No.: 18.
16. An UvrB protein of P. aeruginosa which is involved in ultraviolet repair and has the amino acid sequence as shown in FIG. 20 or SEQ.ID. No.: 19.

The molecular weights, isoelectric points, and hydropathic indices of the Rol (Wzz), PsbA (WbpA), PsbB (WbpB), PsbC (WbpC), PsbD (WbpD), PsbE (WbpE), Rfc (Wzy), PsbF (WbpF), PsbG (WbpG), PsbH (WbpH), PsbI (WbpI), PsbJ (WbpJ), PsbK (WbpK), PsbM (WbpM) and PsbN (WbpN) proteins are shown in Table 1.

Within the context of the present invention, a protein of the invention may include various structural forms of the primary protein which retain biological activity. For example, a protein of the invention may be in the form of acidic or basic salts or in neutral form. In addition, individual amino acid residues may be modified by oxidation or reduction.

In addition to the full length amino acid sequences (FIGS. 3 to 20 or SEQ. ID.NOS:2 to 19), the proteins of the present invention may also include truncations of the proteins, and analogs, and homologs of the proteins and truncations thereof as described herein. Truncated proteins may comprise peptides of at least fifteen amino acid residues.

The proteins of the invention may also include analogs of the proteins having the amino acid sequences shown in FIGS. 3 to 20, or SEQ.ID. NOS: 2 to 19 and/or truncations thereof as described herein, which may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characterisitics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences shown in FIGS. 3 to 20, or SEQ.ID. NOS:2 to 19. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequences shown in FIGS. 3 to 20 or SEQ.ID. NOS:2 to 19. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequences shown in FIGS. 3 to 20, or SEQ.ID. NOS:2 to 19 and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Homologs of a protein of the invention will have the same regions which are characteristic of the protein.

Amino acid homologies for WbpA, WbpD, WbpE, HisH, HisF, WbpI, WbpJ, wbpK, WbpM and Wzz proteins are shown in Table 2 to 4. It will be appreciated that the invention includes WbpA, WbpD, WbpE, HisH, HisF, WbpI, WbpJ, WbpK, WbpM and Wzz proteins having at least 51%, 84%, 76%, 57%, 54%, 70%, 53%, 54%, 61% and 51% homology, respectively.

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising 1–479; 1293–2596; 2670–3620; 3277–5577; 5574–6065; 6151–6981; 7235–8551; 8548–9498; 9830–10388; 10388–11143; 11281–12411; 12427–13548; 13545–14633; 14651–15892; 15889–16851; 18032–19141; 19678–21675; 22302–23693; or 23704–24417, as shown in FIG. 2 or SEQ. ID. NO.: 2. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-tranferase (GST), maltose E binding protein, or protein A, respectively, to the recombinant protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include E. coli, as well as many other bacterial species well known to one of ordinary skill in the art. Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20: 231, 1982). Representative selectable markers include various antibiotic resistance markers such as the kanamycin or ampicillin resistance genes. Suitable expression vectors include but are not limited to bacteriophages such as lambda derivatives or plasmids such as pBR322 (see Bolivar et al., Gene 2:9S, 1977), the pUC plasmids pUC18, pUC19, pUC118, pUC119 (see Messing, Meth in Enzymology 101:20–77, 1983 and Vieira and Messing, Gene 19:259–268, 1982), and pNH8A, pNH16a, pNH18a, and Bluescript M13 (Stratagene, La Jolla, Calif.).

Yeast and fungi host cells suitable for carrying out the present invention include, but are not limited to Saccharomyces cerevisae, the genera Pichia or Kluyveromyces and various species of the genus Aspergillus. Examples of vectors for expression in yeast S. cerivisae include pYepSec1 (Baldari. et al., (1987) Embo J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.). Protocols for the transformation of yeast and fungi are well known to those of ordinary skill in the art.(see Hinnen et al., PNAS USA 75:1929, 1978; Itoh et al., J. Bacteriology 153:163, 1983, and Cullen et al. (Bio/Technology 5:369, 1987).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

III. Applications

Detection of Nucleic Acid Molecules, Antibodies, and Diagnostic Applications

The nucleic acid molecules of the invention, allow those skilled in the art to construct nucleotide probes for use in the detection of nucleotide sequences in a sample. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

The nucleotide probes may be used to detect genes that encode proteins related to or analogous to proteins of the invention.

Accordingly, the present invention also relates to a method of detecting the presence of nucleic acid molecules encoding a protein of the invention in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

In an embodiment of the invention a method for detecting *P. aeruginosa* serotypes O1 to O20 in a sample comprising contacting the sample with a nucleotide sequence encoding PsbM, or PsbN, or a fragment thereof, under conditions which permit the nucleic acid molecule to hybridize with a complementary sequence in the sample to form a hybridization product, and assaying for the hybridization product.

In another embodiment of the invention a method for detecting *P. aeruginosa* serotypes O2, O5, O16, O18, O20 in a sample comprising contacting the sample with a nucleotide sequence encoding one or more of Rol, PsbB, PsbC, PsbD, PsbE, rfc, PsbF, PsbG, PsbH, PsbI, PsbJ, PsbK (also known as Wzz, WbpB, WbpC, WbpD, WbpE, Wzy, WbpF, WbpG, WbpH, WbpI, WbpJ, WbpK, respectively), HisH, or HisF or a fragment thereof, under conditions which permit the nucleic acid molecule to hybridize with complementary sequences in the sample to form hybridization products, and assaying for the hybridization products.

Hybridization conditions which may be used in the methods of the invention are known in the art and are described for example in Sambrook J, Fritch EF, Maniatis T. In: Molecular Cloning, A Laboratory Manual,1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

The nucleic acid molecule of the invention also permits the identification and isolation, or synthesis of nucleotide sequences which may be used as primers to amplify a nucleic acid molecule of the invention, for example in the polymerase chain reaction (PCR) which is discussed in more detail below. The primers may be used to amplify the genomic DNA of other bacterial species known to have LPS. The PCR amplified sequences can be examined to determine the relationship between the various LPS genes.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length.

Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15:15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule having a sequence encoding a protein of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

In a preferred embodiment of the invention, a method for detecting *P. aeruginosa* serotypes O1 to O20 in a sample is provided comprising treating the sample with a primer which is capable of amplifying nucleic acid molecules comprising nucleotide sequences encoding PsbM (WbpM), or PsbN (WbpN), or a predetermined oligonucleotide fragment thereof, in a polymerase chain reaction to form amplified sequences, under conditions which permit the formation of amplified sequences and, assaying for amplified sequences.

In another preferred embodiment of the invention, a method for detecting *P. aeruginosa* serotypes O2, O5, O16, O18, O20 in a sample is provided comprising treating the sample with a primer which is capable of amplifying nucleic acid molecules comprising nucleotide sequences encoding Rol, PsbA, PsbB, PsbC, PsbD, PsbE, Rfc, PsbF, PsbG, PsbH, PsbI, PsbJ, PsbK, (also known as Wzz, WbpA, WbpB, wbpC, WbpD, WbpE, Wzy, WbpF, WbpG, WbpH, WbpI, WbpJ, WbpK respectively) HisH or HisF, or a predetermined oligonucleotide fragment thereof, in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis el al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp3–12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UW) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3–12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol.1(1), page 5, and European Published Application No. 0320308, published Jun. 14, 1989, and U.S. Pat. No. 5,130,238 to Malek).

A protein of the invention can be used to prepare antibodies specific for the protein. Antibodies can be prepared which bind a distinct epitope in an unconserved region of the protein. An unconserved region of the protein is one which does not have substantial sequence homology to other proteins. Alternatively, a region from a well-characterized domain can be used to prepare an antibody to a conserved region of a protein of the invention. Antibodies having specificity for a protein of the invention may also be raised from fusion proteins.

Conventional methods can be used to prepare the antibodies. For example, by using a peptide of a protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein, of the invention, or peptide thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of the genes of the psb cluster of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16

(1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against proteins of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)). In an embodiment of the invention, antibodies that bind to an epitope of a protein of the invention are engineered using the procedures described in N. Tout and J. Lam (Clinc. Diagn. Lab. Immunol. Vol. 4(2):147–155, 1997).

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labeled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immunoprecipitation, latex agglutination, hemagglutination, and histochemical tests. Thus, the antibodies may be used to identify or quantify the amount of a protein of the invention in a sample in order to diagnose P. aeruginosa infections.

A sample may be tested for the presence or absence of P. aeruginosa serotypes O1 to O20 by contacting the sample with an antibody specific for an epitope of PsbM (WbpM) or PsbN (WbpN) which antibody is capable of being detected after it becomes bound to PsbM (WbpM) or PsbN (WbpN) in the sample, and assaying for antibody bound to PsbM (WbpM) or PsbN (WbpN) in the sample, or unreacted antibody. A sample may also be tested for the presence or absence of P. aeruginosa serotypes O2, O5, O16, O18, and O20 by contacting the sample with an antibody specific for an epitope of a Rol, PsbA, PsbB, PsbC, PsbD, PsbE, Rfc, PsbF, PsbG, PsbH, PsbI, PsbJ, PsbK (also known as Wzz, WbpA, WbpB, WbpC, WbpD, WbpE, Wzy, WbpF, WbpG, WbpH, WbpI, WbpJ, WbpK respectively), HisH or HisF, protein which antibody is capable of being detected after it becomes bound to the protein in the sample, and assaying for antibody bound to protein in the sample, or unreacted antibody.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of a P. aeruginosa serotype can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of a P. aeruginosa serotype can be determined by measuring the amount of antibody bound to the P. aeruginosa serotype using substances that interact specifically with the antibody to cause agglutination or precipitation. In particular, labelled antibody against an antibody specific for a protein of the invention, can be added to the reaction mixture. The presence of a P. aeruginosa serotype can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

The reagents suitable for applying the methods of the invention may be packaged into convenient kits providing the necessary materials, packaged into suitable containers. Such kits may include all the reagents required to detect a P. aeruginosa serotype in a sample by means of the methods described herein, and optionally suitable supports useful in performing the methods of the invention.

In one embodiment of the invention the kit contains a nucleotide probe which hybridizes with a nucleic acid molecule of the invention, reagents required for hybridization of the nucleotide probe with the nucleic acid molecule, and directions for its use. In another embodiment of the invention the kit includes antibodies of the invention and reagents required for binding of the antibody to a protein specific for a P. aeruginosa serotype in a sample. In still another embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences.

The methods and kits of the present invention have many practical applications. For example, the methods and kits of the present invention may be used to detect a P. aeruginosa serotype in any medical or veterinary sample suspected of containing P. aeruginosa. Samples which may be tested include bodily materials such as blood, urine, tissues and the like. Typically the sample is a clinical specimen from wound, burn and urinary tract infections. In addition to human samples, samples may be taken from mammals such as non-human primates, etc. Further, water and food samples and other environmental samples and industrial wastes may be tested.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

Substances that Affect O-antigen Synthesis and Assembly

A protein of the invention may also be used to assay for a substance which affects O-antigen synthesis or assembly in P. aeruginosa Accordingly, the invention provides a method for assaying for a substance that affects O-antigen synthesis or assembly in P. aeruginosa comprising mixing a protein of the invention with a test substance which is suspected of affecting the expression or activity of the protein, and determining the effect of the substance by comparing to a control.

In an embodiment of the invention the protein is an enzyme, and a method is provided for assaying for a substance that affects O-antigen synthesis and assembly in P. aeruginosa comprising incubating a protein of the invention with a substrate of the protein, and a test substance which is suspected of affecting the activity of the protein, and determining the effect of the substance by comparing to a control.

In a preferred embodiment the protein is PsbM which has dehydrogenase activity. Representative substrates which may be used with PsbM in the assay are precursor sugars such as glucose. Dehydrogenase activity may be assayed using conventional methods.

Compositions and Methods of Treatment

The substances identified by the methods described herein, antisense nucleic acid molecules, and antibodies, may be used for modulating one or both of O-antigen synthesis and assembly in P. aeruginosa and accordingly may be used in the treatment of infections caused by P. aeruginosa. O-antigen is a virulence factor of P. aeruginosa and it is responsible for serum resistance. Therefore, substances which can target LPS biosynthesis in P. aeruginosa to change the organism into making "rough" LPS devoid of the long chain O-antigen (B-band) polymers will be useful in rendering the bacterium susceptible to attack by host defense mechanisms. The substances identified by the methods described herein, antisense nucelic acid molecules, and antibodies are preferably used to treat infections caused by P. aeruginosa serotypes O2, O5, 16, 18 and 20. The substances etc. are also preferably used to treat infections caused by P. aeruginosa serotypes O3 or O6 which are predominant clinical isolates. It will be appreciated that the substances may also be useful to treat infections caused by other members of the family Pseudomonadaceae (eg. P. cepacia and P. pseudomallei), and to treat other bacteria which produce O-antigen, (e.g. other gram negative bacteria such as E. coli, S. enterica, Vibrio cholera, Yersinia entercolitica and Shigella flexneri).

The substances identified using the methods described herein may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The reagents suitable for applying the methods of the invention to identify substances that affect O-antigen synthesis and assembly in P. aeruginosa may be packaged into convenient kits providing the necessary materials packaged into suitable containers. The kits may also include suitable supports useful in performing the methods of the invention.

The utility of the substances, antibodies, and compositions of the invention may be confirmed in experimental model systems.

The invention will be more fully understood by reference to the following examples. However, the examples are merely intended to illustrate embodiments of the invention and are not to be construed to limit the scope of the invention.

EXAMPLES

Materials and methods used in Examples 1 to 3 described herein include the following:

Bacterial Strains and Culture Conditions

The bacterial strains used in this study are listed in Table 6. All bacterial strains were maintained on Tryptic Soy Agar (Difco Laboratories, Detroit, Mich). P. Isolation Agar (PIA; Difco) was used for selection of transconjugants following mating experiments. Antibiotics used in selection media include: ampicillin at 100 μg/ml for E. coli and carbenicillin at 450 μg/ml for P. aeruginosa, tetracycline at 15 μg/ml for E. coli and 90 μg/ml for P. aeruginosa (250 μg/ml in PIA), gentamicin at 10 μg/ml for E. coli and 300 μg/ml for P. aeruginosa.

DNA Procedures

Small-scale preparation of plasmid DNA was done utilizing the alkaline lysis method of Birnboim and Doly (1979). Large-scale preparations of plasmid DNA were obtained using the Qiagen midi plasmid kit (Qiagen Inc., Chatsworth, Calif.), according to procedures specified by the manufacturer. Whole genomic DNA was isolated from P. aeruginosa following the method of Goldberg and Ohman (1984). Restriction enzymes were purchased from GIBCO/BRL and Boehringer-Mannheim (Mannheim, Germany). T4 DNA ligase, T4 DNA polymerase and alkaline phosphatase were purchased from Boehringer-Mannheim. All enzymes were used following suppliers' recommendations. DNA was transformed into E. coli and P. aeruginosa by electroporation using a Bio-Rad electroporation unit (Bio-Rad Laboratories, Richmond, Calif.) and according to the protocols supplied by the manufacturer. Electrocompetent cells of E. coli and P. aeruginosa were prepared according to the methods of Binotto et al. (1991) and Farinha and Kropinski (1990), respectively. Recombinant plasmids were mobilized from E. coli DH5α to P. aeruginosa through triparental matings as described by Ruvkun and Ausubel (1981). Plasmids were also mobilized from E. coli SM10 to P. aeruginosa using the method of Simon et al. (1983). Genomic DNA was transferred to Zetaprobe membrane (Bio-Rad) by capillary transfer following the manufacturer's instructions. Southern hybridizations were done at 42° C. for 18–24 h with DNA previously labelled with dUTP conjugated to digoxigenin (DIG) (Boehringer-Mannheim). Labelling of DNA was done according to the manufacturer's recommendations. Hybridized DNA was detected using an anti-DIG polyclonal antibody conjugated to alkaline phosphatase and AMPPD (0.235 mM 3-(2'-Spiroadamantane)-4-methoxy-4 (3"-phosphoryloxy)-phenyl-1,2-dioxetane) (Boehringer-Mannheim), followed by exposure to X-ray film (E. I. Du Pont de Nemours & Co., Wilmington, Del.).

Tn10000 Mutagenesis of pFV.TK6

Tn1000 mutagenesis of pFV.TK6 was performed as described previously (Lightfoot and Lam, 1993) using the method of de Lencastre et al. (1983).

DNA Sequencing

DNA sequence analysis of the 1.9 kb insert of pFV.TK8 was performed by the MOBIX facility (McMaster University, Hamilton ON). The 1.9 kb XhoI-HindIII insert of pFV.TK8 was cloned into the sequencing vector pBluescript II KS and double-strand sequenced using a model 373A DNA sequencing unit (Applied Biosystems, Foster City, Calif.). Oligodeoxynucleotide primers for sequencing were synthesized on an Applied Biosystems model 391 DNA synthesizer and purified according to the manufacturers' instructions. The Taq DyeDeoxy™ Terminator Cycle Sequencing Kit (Applied Biosystems) was used for cycle sequencing reactions which were carried out in an Ericomp (San Diego, Calif.) model TCX15 thermal cycler.

Sequence Analysis

The computer software programs Gene Runner for Windows (Hastings Software, New York, N.Y.) and PCGENE (IntelliGenetics, Mountain View, Calif.) were used for nucleic acid sequence analysis, amino acid sequence analysis, and characterization of the predicted protein. DNA and protein database searches were performed using the NCBI BLAST network server (Altschul et al., 1990; Gish and States, 1993).

Mutagenesis of the rfc Gene of P. aeruginosa PAO1

In order to construct P. aeruginosa rfc chromosomal mutants a novel gene replacement vector, pEX100T (Schweizer and Hoang, 1995) was used. This vector, called pEX100T, contains the sacB gene of B. subtilis which imparts sucrose sensitivity on gram-negative organisms and allows for positive selection of true mutants from the more frequently occurring merodiploids. In the first step of this experiment, the 5.6 kb HindIII fragment of pFV.TK6 was blunt-ended using T4 DNA polymerase and subcloned into the SmaI site of pEX100T. An 875 bp $Gm^R$ cassette from pUCGM (Schweizer, 1993) was then cloned into the single BamHi site of the insert DNA. The resulting plasmid, pFV.TK9, was transformed into the mobilizer strain E. coli SM10 and then conjugally transferred into PAO1 (Simon et al., 1983). After mating, cells were plated on PIA containing 300 μg/ml of Gm. Colonies that grew on the Gm-containing medium were picked and streaked on PIA containing 300 μg/ml Gm and 5% sucrose to identify isolates that had lost the vector-associated sacB gene, and thus had become resistant to sucrose. Southern blot analysis was performed to verify that gene replacement had occurred (FIG. 24).

Preparation of LPS

LPS used in sodium dodecyl sulfate-polyacrylamide gel electrophoresis (SDS-PAGE) and Western immunoblotting experiments was prepared according to the proteinase K digest method of Hitchcock and Brown (1983).

SDS-PAGE

The discontinuous SDS-PAGE procedure of Hancock and Carey (1979) utilizing 15% running gels was used. LPS separated by SDS-PAGE was visualized by silver-staining according to the method of Dubray and Bezard (1982).

Immunoblotting

The Western immunoblotting procedure of Burnette (1981) was used with the following modifications. Nitrocellulose blots were blocked with 3% (w/v) skim milk followed by incubation with hybridoma culture supernatant containing either MAb MF15-4, specific for O5 LPS, or MAb N1F10, specific for A-band LPS. The blots were developed at room temperature, using goat anti-mouse F(ab')$_2$ fragment conjugated antibody (Jackson Immunoresearch Laboratories, West Grove, Pa.) and a substrate consisting of 30 mg of Nitro Blue Tetrazolium and 15 mg of 5-bromo-4-chloro-3-indolyl phosphate toluidine (Sigma, St. Louis, Mo.) in 100 ml of 0.1 M bicarbonate buffer (pH 9.8).

Example 1

Analysis of the LPS from mutants AK14O1 and rd7513. Strain AK14O1 has been previously shown to contain A-band LPS; its B-band LPS consists of complete core plus one O-repeat unit (SR phenotype) (Berry and Kropinski, 1986; Lam et al., 1992). Strain rd7513 is a mutant of AK14O1 that has the SR phenotype but is no longer producing A-band LPS, due to a mutation in an A-band biosynthetic gene (Lightfoot and Lam, 1991). Strain rd7513 was used in this study described in the examples, in addition to AK1401; but the majority of this investigation will focus on AK1401.

Complementation of O-antigen Expression in *P. aeruginosa* AK1401. Mobilization of pFV100, which contains the O5 rfb gene cluster, into SR mutant AK1401 resulted in production of O5 B-band LPS. These results suggest that an O-polymerase gene might be localized on the cloned DNA. Analysis of LPS isolated from PAO1 and AK1401(pFV100) in both silver-stained SDS-PAGE gels and Western immunoblots, reacted with O5-specific MAb MF15-4, revealed that the two strains expressed similar high molecular weight LPS profiles (FIG. 22 *a, b*). In order to localize the putative rfc gene on the 26 kb insert of pFV100, various subclones were made (FIG. 23) and used in complementation studies with AK1401. Plasmid pFV.TK2, which contains a 16.5 kb XbaI fragment from pFV100 was able to complement O5 O-antigen production after mobilization into AK1401 (data not shown). Plasmids pFV.TK3, pFV.TK4, and pFV.TK5 were generated and mobilized into AK1401, however none of the three plasmids was able to complement B-band synthesis in this mutant. Subsequently, pFV.TK6 which contains a 5.6 kb HindIII insert was made and was able to complement the SR phenotype of AK1401 (data not shown).

Figure 23:
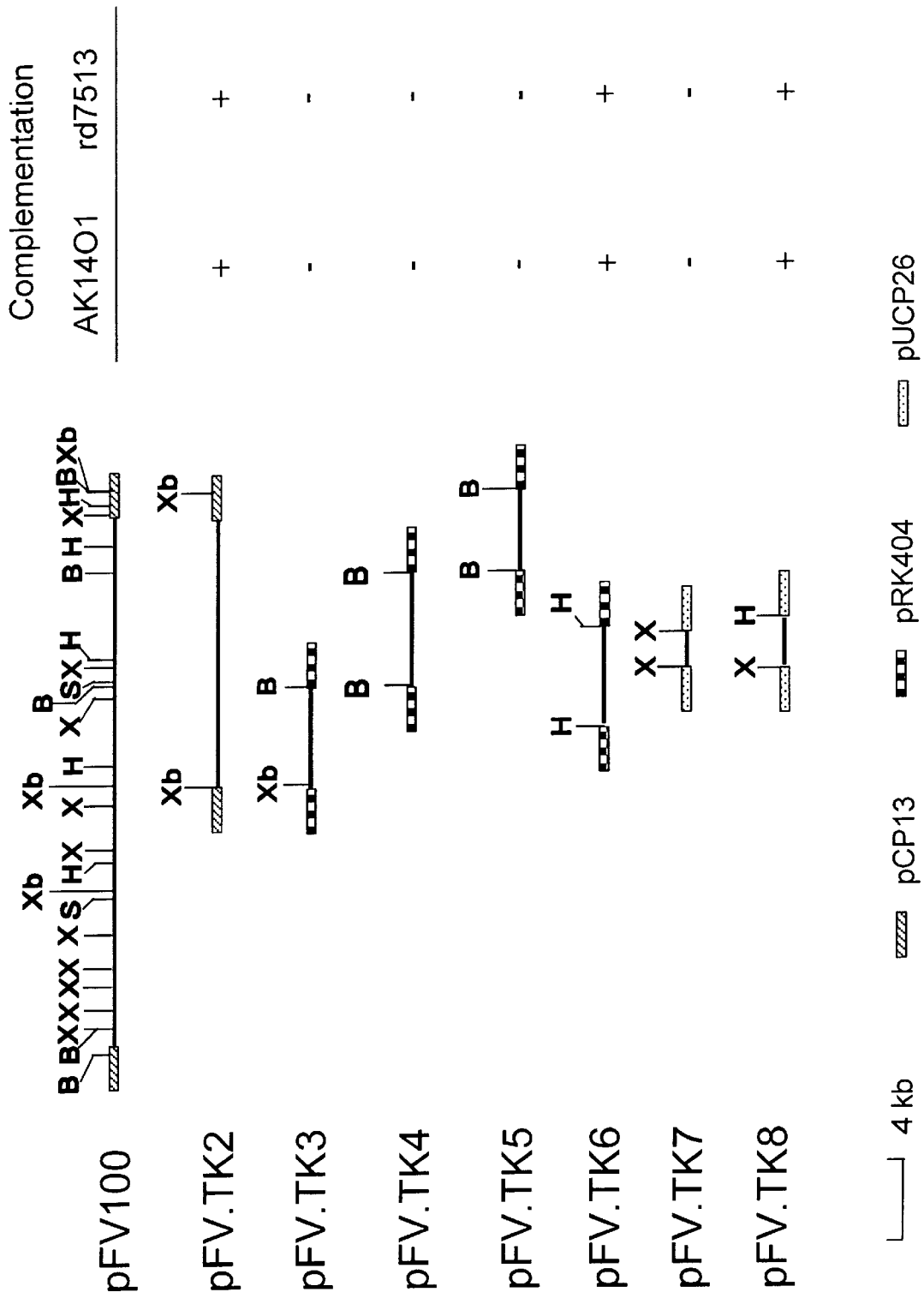
FIG. 23 shows restriction maps of the chromosomal inserts from pFV100 and several pFV subclones, and the results of complementation studies of the SR mutants AK14O1 and rd7513 with the pFV subclones are also shown.

Transposon Tn1000 mutagenesis of pFV.TK6. Transposon mutagenesis using Tn1000 was performed in order to more precisely define the region of insert DNA in pFV.TK6 responsible for complementation of O-antigen expression in AK1401. pFV.TK6::Tn1000 recombinants were mobilized into AK1401 and then screened for the lack of expression of O-antigen using O5-specific MAb MF15-4. Plasmid DNA was isolated from colonies that did not react with MAb MF15-4, and subjected to restriction enzyme analysis to determine the location of the Tn1000 insertion in pFV.TK6. Three Tn1000 insertions in a 1.5 kb XhoI fragment were found to interrupt O-antigen expression in AK1401 (FIG. 23). This 1.5 kb XhoI fragment was cloned into vector pUCP26 (pFV.TK7) and mobilized into AK1401. In Western immunoblots of LPS from AK1401(pFV.TK7) with MAb MF15-4 no reaction of this antibody with high molecular weight B-band LPS could be detected (data not shown). Therefore, the 1.5 kb XhoI insert in pFV.TK7 was unable to restore the O-polymerase function in AK1401. A 1.9 kb XhoI-HindIII fragment was then subcloned into pUCP26 and the resulting plasmid was designated pFV.TK8 (FIG. 23). Mobilization of this recombinant plasmid into both SR mutants, AK1401 and rd7513, resulted in restoration of O-antigen expression. Silver-stained SDS-PAGE gels and Western blots reacted with MAb MF15-4, showed that the AK1401(pFV.TK8) transconjugants expressed levels of O5 B-band LPS comparable to that produced by the wild-type PAO1 (FIG. 22).

Southern analysis using a 1.5 kb XhoI probe. The 1.5 kb XhoI insert of pFV.TK7, internal to the rfc coding region, was labelled with dUTP conjugated to digoxigenin and used to probe XhoI-digested chromosomal DNA from the twenty *P. aeruginosa* serotypes. The probe hybridized to a 1.5 kb fragment in serotypes O2, O5, O16, O18 and O20 (data not shown), suggesting that these serotypes may share a similar O-polymerase gene. These hybridization results are not surprising in that serotypes O2, O5, O16, and O20 share a similar O-repeat backbone structure (Knirel, 1990). Although the O-antigen structure of serotype O18 has not yet been determined, it exhibits cross-reactivity with polyclonal antisera raised against serotype O5 (data not shown), suggesting that it has an O-repeat unit structure similar to that of O5. In a recent study, Collins and Hackett (1991) found that a probe generated from the rfc gene of *S. enterica* (*typhimurium*) cross-hybridized to chromosomal DNA of Salmonella groups A, B, and D1 strains but not with strains of groups D2 or E2, suggesting that the former may share a common rfc gene. In addition, studies done by Nurminen and coworkers (1971) have shown that the O-polymerase enzymes of Salmonella groups B and D1 strains are able to polymerize O-repeat units of either serotype.

Generation of *P. aeruginosa* chromosomal rfc-mutants. In order to confirm that the insert DNA of pFV.TK8 codes for an O-polymerase gene, insertional mutagenesis was performed and the resulting plasmid used for homologous recombination with the PAO1 chromosome. In the first step, the 5.6 kb insert of plasmid pFV.TK6 was cloned into a novel gene replacement vector, pEX100T, (Schweizer and Hoang, 1995). pEX100T is a pUC19-based plasmid that does not replicate in *P. aeruginosa*; therefore, maintenance of plasmid DNA can only occur after homologous recombination into the chromosome. The 5.6 kb insert of pFV.TK6 was used for gene replacement instead of the 1.9 kb insert of pFV.TK8 to ensure that there was sufficient DNA for homologous recombination. The next step involved insertion of an 875 bp $Gm^R$ cassette into a unique BamHI site in the insert DNA (FIG. 24*b*). This step generated a mutation in the rfc gene and provided a means of later selecting for colonies that had undergone homologous recombination. Because the vector, pEX100T, contains the sacB gene of *Bacillus subtilis* it renders Gram-negative organisms sensitive to sucrose. Streaking $Gm^R$ recombinants on media containing 5% sucrose allowed separation of true recombinants from merodiploids, since merodiploids exhibit sucrose-sensitivity because of the presence of the vector-associated sacB gene. Of the eighty $Gm^R$ colonies that were isolated, twenty-four were found to be sucrose-resistant. Three of the twenty-four isolates were randomly chosen for further characterization and were designated OP5.2, OP5.3, and OP5.5. Southern blot analysis of chromosomal DNA from these three putative mutants was performed in order to confirm that gene replacement had occurred. The 1.5 kb XhoI fragment of pFV.TK8 was used to probe XhoI-digested chromosomal DNA isolated from the PAO1 wild-type strain as well as OP5.2. OP5.3, and OP5.5. In strains that had undergone gene replacement, XhoI digestion should yield a probe-hybridizable fragment of 2.4 kb instead of 1.5 kb because of the insertion of the 875 bp $Gm^R$ cassette (FIG. 24 *a, b*). Southern blot analysis of the three $Gm^R$, sucrose-resistant isolates revealed a probe-reactive fragment of 2.4 kb (FIG. 24*c*, lanes 2–4); whereas, the probe reacted with a 1.5 kb fragment of the PAO1 control DNA (FIG. 24*c*, lane 1), demonstrating that gene replacement had occurred in OP5.2, OP5.3, and OP5.5. Analysis of LPS from these three strains in silver-stained gels and Western immunoblots with O5-specific MAb MF15-4 demonstrated that they were not capable of producing long chain B-band O-antigen (FIG. 25*a, b*). Immunoblots reacted with A-band specific MAb N1F10 revealed that, like the SR mutant AK1401, these three mutants were still producing A-band LPS (FIG. 25*c*). Biosynthesis of A-band LPS therefore, appears to be unaffected by this chromosomal mutation. The relative mobility of the core-lipid A bands was also similar to that of the SR mutant AK1401 (FIG. 25*a*); therefore the LPS phenotype of the three rfc knockout mutants was identical to that of AK1401. Mobilization of pFV.TK8 into OP5.2, OP5.3 and OP5.5 restored O-antigen expression in the three mutants (data not shown), indicating that the PAO1 chromosomal modification was the result of a direct mutation of the rfc gene and not caused by a secondary mutation.

Nucleotide sequence determination and analysis of rfc. The 1.9 kb XhoI-HindIII insert of pFV.TK8, containing the rfc coding region, was cloned into pBluescript and subjected to double-strand nucleotide sequence analysis. Examination of the nucleotide sequence (FIG. 9; GenBank accession number U17294) revealed one open reading frame (ORF) that coded for a protein of 438 amino acids, with a predicted mass of 48.9 kDal. This ORF was designated ORF48.9.

Analysis of the *P. aeruginosa* rfc mol. % G+C content (44.8%; Table 6) revealed that it is significantly lower than that of the rest of the genome (67.2%; Palleroni, 1984). A low G+C content is a common feature of reported rfc genes (Collins and Hackett, 1991; Brown et al., 1992; Klena and Schnaitman, 1993; Morona et al., 1994) and has also been observed in all of the rfb clusters so far analyzed. The finding that the gene coding for the O-polymerase enzyme and the genes encoding the O-antigen repeat units have a compatible G+C content is not surprising since the specificity of the enzyme must relate to the structure of it substrate.

Homology searches of both the nucleotide and the amino acid sequences of the *P. aeruginosa* rfc gene were performed using EMBL/GenBank/PDB and Swiss-PROT (release 28.0) databases (Altschul et al., 1990; Gish and States, 1993). Comparison of the *P. aeruginosa* rfc sequences with sequences reported for other prokaryotic genes revealed no significant homology, including with those reported for other rfc genes. Previous studies on the structure of *P. aeruginosa* O-antigens have revealed that their sugar compositions differ significantly from most other enterobacterial O-antigens (Knirel et al., 1988). Neutral sugars, which are commonly found in enteric O-antigens, are only rarely found in O-antigens of *P. aeruginosa*. In addition, *P. aeruginosa* O-antigens are rich in amino sugars, many of which are substituted with acyl groups, a phenomenon rarely found in natural carbohydrates. Given the unique sugar composition of *P. aerutginosa* O-antigens, and the finding by Morona et al. (1994) that the *S. flexneri* Rfc protein showed no homology with other enteric Rfc proteins, it is not surprising that the *P. aeruginosa* Rfc protein exhibited no sequence homology with those of other enteric organisms.

The *P. aeruginosa* rfc gene product does, however, have several features in common with other reported Rfc proteins, including the fact that it is very hydrophobic. The mean hydropathic index of the *P. aeruginosa* Rfc is 0.8 while those of other enteric organisms have been reported to range from 0.65–1.08 (Table 7). Examination of the hydropathy profile of this protein and analysis of the amino acid sequence, using the software program PCGENE, revealed that it is an integral membrane protein with 11 putative membrane-spanning domains (Klein et al., 1985). The Rfc proteins of *S. enterica* (*typhimurium*) and *S. enterica* (*mitenchen*) are reported to have 11 membrane-spanning domains, while that of *S. flexneri* is reported to have 13 (Morona et al., 1994); therefore, structural similarities appear to exist among the Rfc proteins of these four organisms.

Codon usage and amino acid composition analysis. When the codon usage and amino acid composition of the *P. aeruginosa* Rfc protein was compared with that reported for *S. enterica* (*typhimurium*), *S. enterica* (*muenchen*), and *Shigella flexneri* Rfc proteins (Collins and Hackett, 1991; Brown et al., 1992; Morona et al., 1994), significant similarities were found between them (data not shown). Rfc proteins have been reported to contain a high content of three amino acids, namely, leucine, isoleucine, and phenylalanine (Morona et al., 1994). These three amino acids account for 27, 30, and 37% of the total amino acids of the Rfc proteins of *S. enterica* (*typhimrtrium*), *S. enterica* (*muenchen*), and *Shigella flexneri*, respectively (Morona et al., 1994). In the Rfc protein of *P. aeruginosa*, these amino acids represent 30% of the total amino acid composition.

In summary, the present inventors have isolated an rfc gene in *P. aeruginosa* O5 encoding an O-polymerase enzyme. Using a gene-replacement system, *P. aeruginosa* rfc-chromosomal mutants were generated which expressed the typical sr lps phenotype. The *P. aeruginosa* Rfc is similar to other reported Rfc proteins in that it is very hydrophobic, containing 11 membrane-spanning domains; the Rfc coding region has a lower mol. % G+C than the *P. aeruginosa* chromosomal average; and it has a similar amino acid composition and codon usage to that reported for other Rfc proteins.

Example 2

Isolation of a rol Gene in *P. aeruginosa* O5 (PAO1) Encoding a Protein Which Regulates O-antigen Chain Length The *P. aeruginosa* serotype O5 (PAO1) rol gene (regulator of O-chain length) was cloned from a genomic DNA cosmid library. An open reading frame (ORF) of 1046 bp, encoding a 39.3 kDa protein, was identified. The characterization of the function of Rol was facilitated by the generation of knockout mutants.

The DNA sequence of a subclone of pFV100, pFV161 (FIG. 26), was found to have homology to the rol genes from a number of members of the family Enterobacteriaceae. However, only the 3' end of the putative rol gene was present on pFV161. A cosmid library of *P. aeruginosa* (PAO1) genomic DNA was screened using a digoxigenin-labeled probe from pFV161 to identify an overlapping cosmid (pFV400) containing the complete rol gene. Southern blot analysis of DNA from pFV400, digested with a number of different restriction enzymes, was performed. The pFV161 probe hybridized to an approximately 2.3 kb HindIII fragment of pFV400. Assuming the rol gene of *P. aeruginosa* serotype O5 (PAO1) was similar in size (approx. 1 kb) to members of the family Enterobacteriaceae (Morona et al., 1995), this fragment would be sufficient to contain the entire putative rol gene. This 2.3 kb HindIII fragment was subcloned into the vector pBluescript II SK (PDI Biosciences, Aurora, Ontario, Canada) and named pFV401 (FIG. 26).

Nucleotide sequencing of the 2.3 kb HindIII insert was performed using dye terminator cycle sequencing (GenAlyTiC sequencing facility, University of Guelph), and an open reading frame (ORF) that coded for a protein of 348 amino acids, with a predicted mass of 39.3 kDA, was identified (GenBank accession #U50397). Homology searches using the GenBank database through the NCBI Blast network server were performed (Altschul et al., 1990; Gish and States, 1993). Both the nucleotide and the deduced amino acid sequences of the putative *P. aeruginosa* rol gene showed approximately 33–35% amino acid homology between the putative Rol protein and the Rol proteins of *Salmonella enterica* serovar typhimurium, *Escherichia coli*, and *Shigella flexneri* (Morona et al., 1995) (Table 5).

Figure 27:
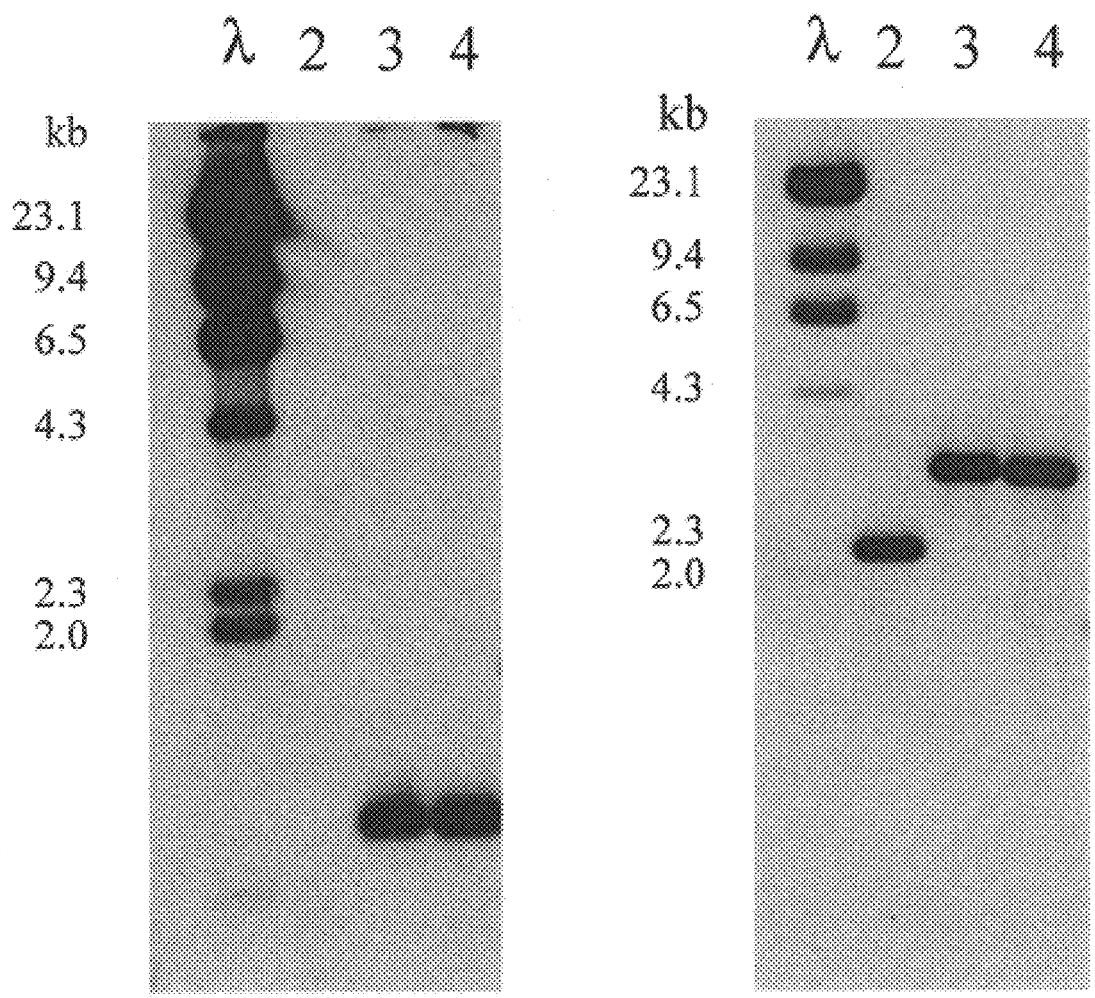
FIG. 27A shows a blot of a Southern hybridization of chromosomal DNA from PAO1 (lane 2) and rol (wzz) mutants (lanes 3 and 4) where the chromosomal DNA was digested with PstI and SstI.
FIG. 27B shows a blot of a Southern hybridization of chromosomal DNA from PAO1 (lane 2) and rol (wzz) mutants (lanes 3 and 4) where the chromosomal DNA was digested HindIII.

To confirm that the insert DNA of pFV401 codes for a Rol protein, insertional mutagenesis was performed and the resulting plasmid construct used for homologous recombination with the PAO1 chromosome. Briefly, the 2.3 kb insert of pFV401 was cloned into a novel gene-replacement vector, pEX100T (Schweizer and Hoang, 1995), that does not replicate in *P. aeruginosa*. pEX100T also contains the sacB gene of *B. subtills* which imparts sucrose sensitivity on Gram-negative organisms and allows for positive selection of true mutants from the more frequently occurring merodiploids. Next, an 875 bp gentamicin-resistance ($GM^R$) cassette from pUCGM (Schweizer, 1993) was inserted into a unique XhoI site in the insert DNA. The resulting plasmid (pFV401TG) was transformed into the mobilizer strain *E. coli* SM10 and then conjugally transferred into PAO1 (Simon et al., 1983). After mating, cells were plated on P. isolation agar (PIA; Difco Laboratories, Detroit, Mich.) containing 300 μg ml$^{-1}$ gentamicin (Sigma Chemical Co., St. Louis, Mo.) and 5% sucrose. This selective medium allows the identification of isolates that have undergone homologous recombination and lost the vector-associated sacB gene thus, becoming resistant to sucrose. Southern blot analysis with both wild-type rol gene and Gm$^R$ cassette probes was used to confirm the insertional mutation. The wild-type control and the mutants showed probe reactive fragments of 2.3 kb and 3.1 kb respectively (FIG. 27).

Figure 28:
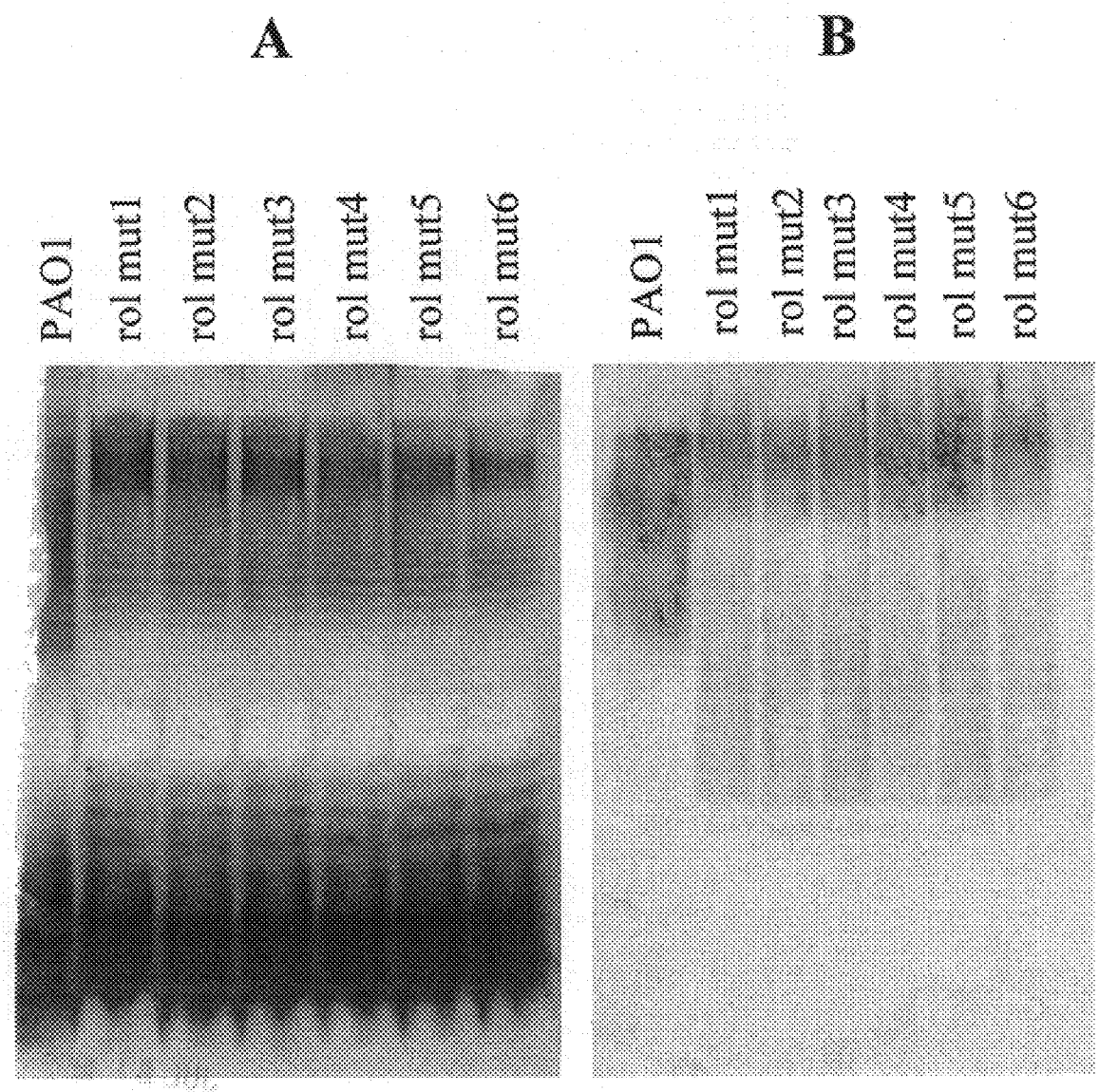
FIG. 28A shows a Western immunoblot[s] which illustrates a characterization of LPS from PAO1 and PAO1 rol (wzz) chromosomal mutant where the blot is silver-stained SDS-PAGE gel.
FIG. 28B shows a Western immunoblot which illustrates a characterization of LPS from PAO1 and PAO1 rol (wzz) chromosomal mutant where the immunoblot was reacted with an O5 (B-band)-specific mAb MF15-4.

The LPS of the mutants was prepared according to the proteinase K digest method of Hitchcock and Brown (1983). The LPS was analyzed using sodium dodecyl sulfate polyacrylamide gel electrophoresis (SDS-PAGE) and Western immunoblots according to the methods described previously (de Kievit et al., 1995). When compared with the wild-type strain, the mutant LPS showed a marked alteration in the O-antigen ladder-like banding pattern, in which there was a decrease in high molecular weight bands and an increase in visible low molecular weight bands. This change corresponds to a loss of bimodal distribution in O-antigen length (FIG. 28).

Figure 29:
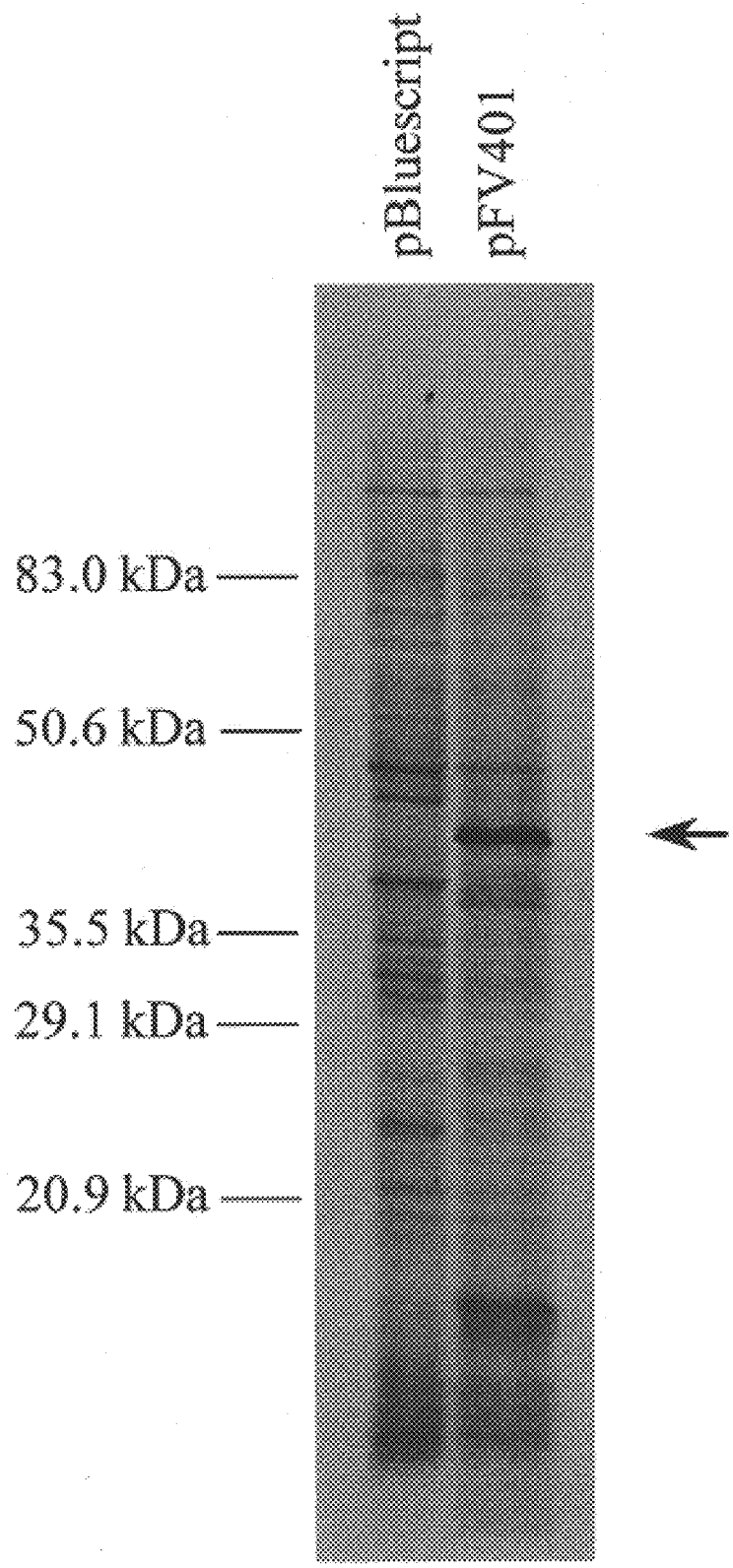
FIG. 29 is an autoradiogram showing $^{35}$S-labeled proteins expressed by pFV401, which contains the rol (wzz) gene and corresponding control plasmid vector pBluescript II SK in E. coli JM 109DE3 by use of the T7 expression system.

A T7 expression system (Tabor and Richardson, 1985) was used for expression of the Rol protein. A unique protein band with an apparent molecular mass of 39 kDa was observed. This expressed polypeptide corresponded well to the predicted mass of 39.3 kDa. This band was not observed in the vector-only control (FIG. 29).

In conclusion, a rol gene was isolated in *P. aeruginosa* O5 (PAO1) encoding a protein which regulates O-antigen chain length. Using a gene-replacement system, *P. aeruginosa* rol::Gm$^R$ knockout mutants were generated which express LPS with unregulated O-antigen chain length. Thus, the *P. aeruginosa* O5 (PAO1) Rol protein has both sequence and functional homology to other reported Rol proteins. This also confirms that the pathway for *P. aeruginosa* B-band LPS biosynthesis is Rfc-dependent. The function of Rol is often associated with the Rfc protein, an O-polymerase (Whitfield, 1995, Kievit et al., 1995).

Example 3
Sequencing of the psb Gene Cluster.

The isolation of a cosmid clone, pFV100, containing the psb gene cluster of *P. aeruginosa* O5 identified in accordance with the present invention, was previously described (Lightfoot and Lam, 1993). Several subclones of pFV100 containing the psb genes were constructed. The sequencing and characterization of two of these clones (pFV111 and pFV110), containing the rfc and psbL (rfbA) genes respectively, has previously been described (de Kievit et al., 1995; Dasgupta and Lam, 1995). Sequencing of the remainder of the pFV100 insert was undertaken in order to identify all the genes required for synthesis of the O5 O-antigen.

Sequencing of the entire insert of pFV100, a total of 24416 bp, revealed a large number of open reading frames (ORFs) on both strands. ORFs which were reading in the same direction as rfc and psbL and which had homology either to any previously identified polysaccharide or antibiotic biosynthetic genes or to highly conserved bacterial genes were characterized further. A total of 21 ORFs which could be involved in synthesis of the O5 O-antigen were identified (Table 1). These genes were designated psbA through psbN in the 5' to 3' direction, with the exceptions of rol and rfc, which were named according to convention. A further 4 ORFs with high homology to other bacterial genes or insertion sequences but which are not thought to be involved with LPS synthesis were identified (hisH, hisF, uvrB, IS407; Table 1).

Distribution of the psb Genes among the 20 serotypes of *P. aeruginosa* and Localization of the O5-Specific Region.

Southern blot analysis of the 20 serotypes of *P. aeruginosa* using various psb genes as probes revealed an interesting dichotomy. All of the probes tested which were 5' to the IS407 element hybridized only with chromosomal DNA from serotypes O2, O5, O16, O18 and O20 (Table 1). As stated above, these five serotypes have biochemically and structurally similar O-antigens (FIG. 1). Although the O-antigens of serotypes O2, O5, O16, O18, and O20 are serologically distinct and have been shown to have clear biochemical differences, none of the psb genes tested hybridized only to serotype O5 chromosomal DNA at high stringency.

In contrast with these findings, probes for DNA sequences 3' to the IS407 element, and the IS407 element itself, hybridized with the chromosomal DNA from all 20 serotypes of *P. aeruginosa* (Table 1). These results show that the insertion sequence is the junction between the portion of the psb cluster specific for O5 and related serotypes (hereinafter referred to as the O5-specific region, or sometimes as the Group I genes) and the non-specific chromosomal DNA. Therefore, psbL appears to be the last gene of the O5-specific region. Despite the fact that the DNA 3' of the insertion element is not O5-specific, this region is thought to contain at least two ORFs (psbM and psbN or sometimes referred to as the Group II genes) which may be involved in O5 LPS biosynthesis (see below).

A 1.2 kb probe from the extreme 5' end of the insert of pFV100 hybridized only to the five related serotypes, indicating that the 5' end of the O5-specific region had not been cloned. This probe was used to isolate an overlapping cosmid, pFV400. Various subclones of pFV400 were constructed to localize the 5' end of the O5-specific region to within a 1.3 kb SstI-XhoI fragment located 1.7 kb upstream of the 5' end of pFV100. Preliminary sequence analysis of this upstream region revealed no additional ORFs thought to be involved with LPS synthesis. Also, no insertion sequences could be found in this region of DNA. Localization of the 5' end of the O5-specific region to the 1.3 kb SstI-XhoI fragment means the total amount of DNA which is specific to O5 and related serotypes is approximately 20 kb.

The Composition and Chromosomal Milieu of the O5 psb Cluster.

The %G+C of the *P. aeruginosa* chromosome has been determined by various methods to be approximately 65–67% (Palleroni, 1984; West and Iglewski, 19XX). The %G+C content of the *P. aeruginosa* O5 psb cluster within the O5-specific region averages 51.1% overall, with individual genes ranging from a low of 44.5% (psbG) to a high of 56.8% (psbK) (Table 1). These results are consistent with those seen for other rfb genes, averaging at least 10% below the chromosomal background, and this is thought to be reflective either of origin in a low %G+C background (Reeves, 1993) or of possible regulatory constraints (Collins and Hackett, 1991; Morona et al., 1994a). The %G+C content of the psbM and psbN genes, which fall outside the O5-specific region, averages 62.6%.

Sequence analysis of pFV100/pFV400 revealed no homology to gnd (encoding 6-phosphogluconate dehydrogenase) in the regions flanking the LPS genes.

However, *P. aeruginosa* has been shown to convert glucose-6-phosphate to 6-phosphogluconate as part of the Entner-Douderoff pathway, suggesting a homologue of the gnd gene is located elsewhere on the chromosome. The location of the *P. aeruginosa his* operon is not known, but the few his auxotrophic lesions that have been mapped on the chromosome of serotype O5 (strain PAO1) are several minutes from the A- and B-band LFS clusters (Lightfoot and Lam, 1993; Hollaway et al., 1994). Interestingly, two his genes (hisH and hisF) were found in the middle of the psb cluster, within the O5-specific region (see below). Because these genes fail to hybridize with all twenty serotypes of *P. aeruginosa* at high stringency, it is likely they are not native *P. his* genes, but were acquired along with the psb genes in a horizontal transfer event.

Homology searches of the Genbank databases with each of the ORFs in the psb cluster were performed. Assignment of putative function for the products of the ORFs was made based on homology of the encoded proteins to those previously described. Because the O-antigen of *P. aeruginosa* O5 contains two similar 2,3-diacetaminido-mannuronic acid residues, it is anticipated that both residues share a common biosynthetic pathway.

The 5' End of the pFV100 Insert Contains a Partial rol Gene.

The partial open reading frame at the 5' end of the insert of pFV100 was found to have low homology at the amino acid level (34–37%) with the Rol proteins of *Escherichia coli* (Batchelor et al., 1992; Bastin et al., 1993), *Salmonella enterica* sv Typhimurium (Batchelor et al., 1992; Bastin et al., 1993), and *Shigella flexneri* (Morona et al., 1994b). Only 479 bp of rol-homologous DNA (encoding 159 amino acids) were present from the XhoI cloning site of pFV100. This sequence represented approximately the 3' half of the putative rol gene, based on the sizes of previously described rol genes. Using the partial gene as a probe, the entire rol gene has been cloned from an overlapping cosmid, pFV400, and its function confirmed by mutational analysis (Example 2). In other Rfc-dependent LPS gene clusters, the rol gene is positioned near or at the end of the cluster. These results, along with the large number of ORFs already identified on pFV100 suggested that most, if not all, of the genes required for O5 O-antigen biosynthesis are present on this cosmid.

psbA.

There is a distance of 807 bases between the rol gene and the first adjacent gene, psbA. Although *P. aeruginosa* promoters are not well defined, there are similarities with *E. coli* promoters (Harley and Reynolds, 1987; Deretic et al., 1989). There is a possible $\sigma^{70}$-like promoter sequence and a putative ribosomal binding site (RBS) located 93 bp and 7 bp, respectively, upstream of the start of psbA (FIG. 31). PsbA has homology (summarized in Table 2) to EpsD, thought to be a dehydrogenase required for synthesis of exopolysaccharide in *Burkholderia solanaceraecum* (Huang and Schell, 1995); to VipA, involved in synthesis of the Vi antigen in *S. enterica* sv Typhi (Hashimoto et al., 1993); and to RffD, a UDP-N-acetyl-D-mannosaminuronic acid dehydrogenase involved in synthesis of Enterobacterial Common Antigen (ECA) in *E. coli* (Meier-Dieter et al., 1992). ECA is an exopolysaccharide common to most enterics that can be linked to lipid A-core in rough strains. It is composed of N-acetyl-D-glucosamine (GlcNAc), N-acetyl-D-mannosaminuronic acid (ManNAcA), and 4-acetamido-4,6-dideoxy-D-galactose (Fuc4NAc).

PsbA also has homology with CapL, involved in type 1 capsular polysaccharide production in *Staphylococcus aureus* (Lin et al., 1994). The type 1 capsule is composed of taurine, 2-acetamido-2-deoxyfucose (Fuc2NAc) and 2-acetamido-2-D-galacturonic acid (Gal2NAcA). The sugar composition of both ECA and type 1 capsule are similar to the *P. aeruginosa* O5 O-antigen. PsbA also has a low level of homology with ORF7 of the Vi antigen region of *E. coli/Citrobacter freundii* (accession #Z21706), and several GDP-mannose and UDP-glucose dehydrogenases, including AlgD of *P. aeruginosa* (Deretic et al., 1987). AlgD is a GDP-mannose dehydrogenase required for alginate synthesis. These homologies suggest that PsbA functions as a dehydrogenase involved in the biosynthesis of the mannuronic acid residues, possibly converting UDP-N -a cetyl-D -mannosamine into UDP-N-acetyl-D-mannosaminuronic acid. A large number of dehydrogenases including PsbA (as well as PsbK and PsbM, below) contain a consensus nicotinamide adenosine dinucleotide (NAD)-binding domain, thought to be important for activity (FIG. 33). An alignment of the amino acid sequences of some PsbA-like proteins is shown in FIG. 34.

psbB.

The psbB gene start is 74 bases from the termination codon of psbA, but no separate promoter sequence for psbB could be detected. A putative RBS is located 6 bp from the initiation codon for psbB and the second codon is AAA, the preferred second codon in *E. coli* (Gold and Stormo, 1987; FIG. 32). The psbB gene product is possibly an oxidoreductase, dehydratase, or dehydrogenase. It is 28.2% homologous to the LmbZ protein of *Streptomyces lincolnesis* required for lincomycin production (Peschke et al., 1995), and also has homology with the pur10 gene product of *Streptoinyces alboniger* required for puromycin production (Tercero et al., 1996). PsbB has 17% homology to the BplA protein from *B. perttussis* required for LPS production (Allen and Maskell, 1996) and even weaker homology to ORF334 and MocA from *Rhizobium meliloti* found in the operon for rhizopine catabolism (Rossbach et al., 1994). In *B. pertussis*, the BplA protein is thought to catalyze the final step in the biosynthesis of UDP-diNAcManA from UDP-diNAcMan (Allen and Maskell, 1996).

Several of the psb genes were found to have high homology with bpl genes, suggesting a common ancestry. *B. pertussis* has semi-rough LPS, with only one O-antigen unit attached to the core oligosaccharide. The composition of the *B. pertussis* O-antigen unit is N-acetylglucosamine (GlcNAc), 2,3-dideoxy-2,3-N-acetylmannosaminuronic acid (2,3-diNAcManA), and N-acetyl-N-methyl fucosamine (FucNAcMe) (Allen and Maskell, 1996). These sugars are similar to those comprising ECA, *S. aureus* type 1 capsule, and the *P. aeruginosa* O5 O-antigen. The amino acid homology between PsbB and BplA as well as the similarities in O-antigen unit composition suggest that PsbB could have a homologous function to that of BplA. Unlike the other putative dehydrogenases encoded in the psb cluster, PsbB does not contain a consensus NAD-binding domain.

psbC.

The start of psbC overlaps significantly (343 bases) with the stop of psbB, and psbC could encode a large protein of 85.3 kDa (766 amino acids). Careful scrutiny of the DNA sequencing results confirmed no sequencing errors were present. Protein expression will determine whether this entire large ORF is translated. The large size of this protein may indicate it resulted from a fusion event. There is a weak potential RBS upstream of the AUG codon of psbC (FIG. 32).

The carboxy-terminal portion of PsbC has homology with a hypothetical protein (HI0392) derived from the *Haemophilus influenzae* genome sequence (Fleischmann et al., 1995). HI0392 is a 245 amino acid protein of unknown function, with several hydrophobic domains, and is thought to be an integral membrane protein. There is homology between PsbC and the macrolide 3-O-acyltransferase acyA gene from the *Streptomyces thermotolerans* carbomycin biosynthetic cluster (Arisawa et al., 1995). PsbC also has weak homology with ExoZ of *R. meliloti*, involved in succinoglycan production (Buendia et al., 1991), and with NodX of *R. legitininosarum*, involved in nodulation (Davis et al., 1988). ExoZ is a 317 amino acid protein, also with multiple hydrophobic domains, while NodX is a 367 amino acid protein thought to be located in the cytoplasmic membrane. ExoZ and NodX genes are both putative 3-O-acyltransferases. A summary of the homologies between the above proteins is shown in Table 2. The similarities indicate PsbC, particularly the carboxy terminal portion, may have 3-O-acyltransferase activity, and could be involved in acetylation of the mannuronic acid residues in the O5 O-antigen.
psbD.

The psbD gene appears to be translationally coupled with the psbC gene, since its start codon overlaps the stop codon of psbC. A potential RBS is located 9 bp upstream of the psbD AUG codon (FIG. 32). The product of the psbD gene is most homologous with the product of the bplB gene in the *B. pertussis* LPS biosynthetic cluster (Allen and Maskell, 1996). PsbD and BplB appear to be O-acetyl transferases, and have some homology to serine O-acetyl transferases (CysE) from a variety of bacteria, including *Buchnera aphidicola* (Lai and Baumann, 1992), *Bacillus stearothermophilus* (Gagnon et al., 1994), *B. subtilis* (Ogasawata et al., 1994), *E. coli* (Denk and Bock, 1987), *S. enterica* sv Typhimurium (accession #P29847), *H. influenzae* (Fleischmann et al., 1995), and the plant *Arabidopsis thaliana* (Bogdanova et al., 1995) (Table 2, FIG. 35). As with PsbC, PsbD is probably involved in the acetylation of the mannuronic acid residues comprising two-thirds of the O5 repeat unit. While bplA and bplB are contiguous on the *B. pertussis* chromosome, the psb homologues, psbB and psbD respectively, are separated by the large psbC gene.
psbE.

psbE has high homology with a *B. pertussis* LPS biosynthetic gene, bplC. psbD and psbE are adjacent to one another in the psb cluster, as are bplB and bplC in the bpl cluster (Allen and Maskell, 1996). However, they do not appear to be translationally coupled, since there are 86 bases between the end of psbD and the start of psbE. While there is a potential RBS 9 bp before the psbE start (FIG. 32), it is not known whether this gene can be transcribed from a promoter internal to the psbD gene. There are some sequences with weak homology to the *E. coli* consensus promoter sequence in that area.

Also homologous to PsbE are DegT, from *B. subtilis* (Takagi et al., 1990), *Saccharopolyspora erythraea* ErbS (ERYC1) involved in erythromycin synthesis (Dhillon et al., 1989), DnrJ from *Streptomyces peucetius* required for daunorubicin biosynthesis (Stutzman et al., 1992) and SpsC from *B. subtilis* involved in spore coat polysaccharide biosynthesis (Glaser et al., 1993) (summarized in Table 2). There is also weak homology between PsbE and both MosB for rhizopine synthesis in *R. meliloti* (Murphy et al., 1993) and YifI, a hypothetical protein in the rffE/rffT intragenic region of *E. coli* (Daniels et al., 1992). The proteins DegT/DnrJ/ERYC1/SpsC form a family of proteins formerly thought to form the DNA-binding component of sensory-transduction two-component regulatory systems. More recently, however, their function is suggested to be in the biosynthesis of 2,3-, 2,4-, and 2,6-dideoxy sugars such as the 2,3-dideoxy mannuronic acid produced by *P. aeruginosa* O5 (Thorsen et al., 1993). An alignment of the amino acid sequences of the PsbE-like proteins is shown in FIG. 36.
The O-antigen polymerase, rfc.

The rfc gene starts 254 bases downstream of the end of the psbE gene. This gene was cloned, sequenced and characterized as described in Example 1. Knockout mutations generated by insertion of a gentamicin cassette into rfc were used to confirm this gene encoded the O-antigen polymerase. Gentamicin-resistant mutants were shown to have the semi-rough phenotype (See Example 1) characteristic of an rfc mutant (Mäkelä and Stocker, 1984).
psbF.

Figure 37:
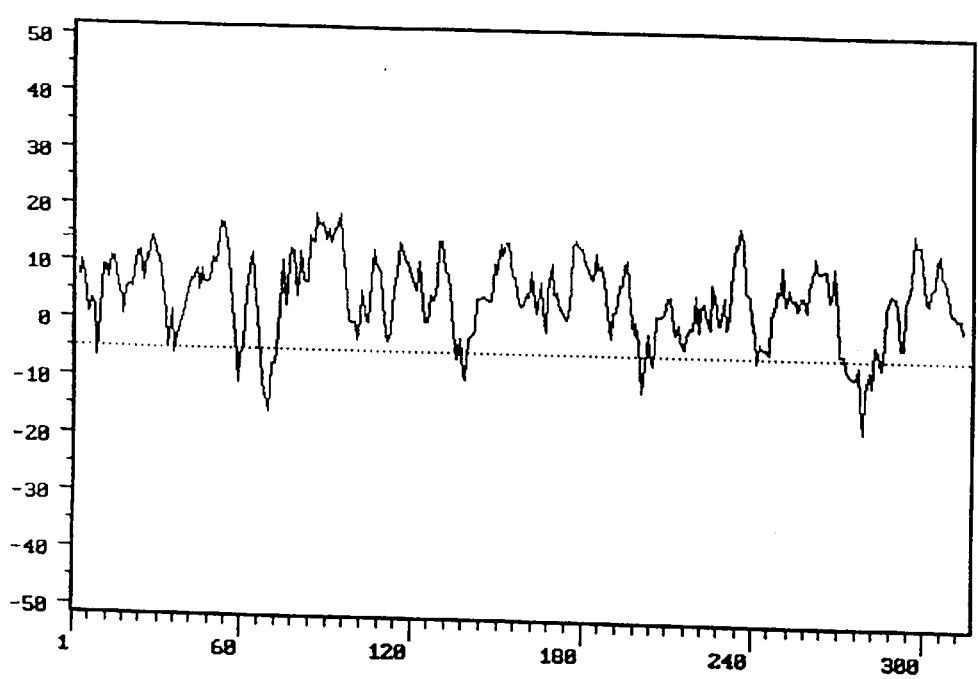
FIG. 37 shows a hydropathy index computation for sequence PsbF.

The psbF gene appears to be translationally coupled with the rfc gene since they have an overlapping stop and start. There is a RBS sequence 8 bp upstream of the initiation codon of psbF. It is most homologous to the ExoT protein of *R. meliloti* (Glucksmann et al., 1993), which is thought to be involved in succinoglycan transport. There is also a small amount of homology to FeuC of *B. subtilis*, part of its iron uptake system (Quirk et al., 1994). PsbF is the most hydrophobic protein encoded by the psb cluster (Table 1) and has 9–10 membrane-spanning domains. This secondary structure is remniscent of that of RfbX, the putative flippase found in Rfc-dependent O-antigen clusters (FIG. 37) (Schnaitman and Klena, 1993). Mutations in RfbX have been found to be unstable and deleterious to the host strain (Schnaitman and Klena, 1993). Recently Liu et al. (1996) confirmed that RfbX (Wzx) mutants accumulate one O-antigen unit on undecaprenol on the inside of the cytoplasmic membrane. PsbF knockout mutants generated by insertion of a gentamicin resistance cassette into psbF are both A and B-band minus (FIG. 48). PsbF may be the *P. aeruginosa* O5 equivalent of RfbX.
The hisH and hisF genes.

The histidine operon, containing genes required for the biosynthesis of the amino acid histidine, has previously been shown to lie adjacent to the rfb clusters of several enteric species (reviewed in Schnaitman and Klena, 1993). Comparison of the chromosomal map locations of the *P. aeruginosa* O5 A- and B-band LPS clusters with those of known PAO1 his mutations showed there were no his genes located adjacent to either the psa (11–13 min) or psb (37 min) clusters (Lightfoot and Lam, 1993; Holloway et al., 1994). Therefore, the identification of two genes with high homology to the genes hisF and hisH of various bacterial species in the middle of the psb cluster was unexpected. The hisH and hisF genes are located between the psbF and psbG genes (FIG. 1), and transcribed in the same direction. The direction of transcription of the his genes in previously characterized rjb clusters is opposite to that of the rfb genes (Ames and Hartman, 1974; Macpherson et al., 1994).

While the deduced amino acid sequence of hisF appears to give a complete open reading frame (from bases 10387 to 11142), the sequence of hisH appears to be lacking an AUG initiation codon at the location predicted for the start of the protein based on amino acid homology. However, there are potential starts at three GUG codons located 51, 72, and 132 bp upstream of the first AUG, located at base 9830. The size of the protein corresponding to the product of hisH is approximately 21 kDa, indicating it is probably translated from either of these putative starts. Only the GUG codon at 9777 is preceded by a good RBS (FIG. 32); none of the other potential start codons have consensus RBS sites. N-terminal analysis of the HisH product will confirm the translational start.

Protein expression analysis of this region shows the products of these genes are expressed in vitro in both orientations, indicating there is a promoter region preceding the his genes that can be recognized by *E. coli*. Analysis of the sequence upstream of the putative start sites of hisH shows there is a potential promoter sequence with partial homology to the *E. coli* consensus −35 and −10 regions (FIG. 31). This homology is within the range seen in previously reported *P. aeruginosa* promoter sequences that can function in *E. coli* (Deretic et al., 1989; Ronald et al., 1992).

In *K. pnellinoniae*, the products of the hisH and hisF genes have been shown to form a heterodimeric enzyme complex required for the conversion of N'-[(5'phosphoribulosyl)-formimino]-5-aminoimidazole-4-carboxamide-ribonucleotide (5'-PRFAR) to imidazole glycerol-phosphate (IGP) and 5'-phosphoribosyl-4-carboxamide-5-aminoimidazole (ZMP) (Rieder et al., 1994). Although the products of the hisH and hisf genes have been shown to function together, the hisH and hisF genes themselves are separated by a third gene, hisA (Alifano et al., 1996). The hisA and hisH genes are highly related and are thought to have arisen through gene duplication. The gene order of hisHAF has been found in all bacterial species characterized to date (Alifano et al., 1996).

Comparison of the amino acid sequence homologies of various HisF and HisH proteins (Tables 3 and 4) showed that the *P. aeruginosa* psb HisF and HisH proteins are not closely related to any of the HisF/HisH proteins characterized thus far. Comparisons of *P. aeruginosa* psb HisF with the other HisF proteins shown in Table 6 shows that it is the most distantly related protein of the group analyzed, at approximately 50% homology.

psbG.

There is a distance of 138 bp between hisF and psbG, and a putative promoter is identified in this region (FIG. 31). A RBS is identified 4 bp from a putative GUG start and 7 bp from the adjacent AUG start codon (FIG. 32). The optimum spacing of a RBS from the initiation site is 8 ±2 bp, suggesting the AUG codon is likely to be the start. PsbG has limited homology to ORF2 (11.2%) of *Vibrio cholerae* O-antigen (Comstock et al., 1996), and less homology with NfrB of *H. influenzae*, a formate-dependent nitrate reductase (Fleischmann et al., 1993), and Pfk, a phosphofructokinase of the Gram positive bacterium, *Lactococcus lactis* (Xiao and Moore, 1993). Interestingly, the homology is associated with NfrB centres around the metal binding recognition site CXXCH, of which there are five in NfrB and one in PsbG (amino acids 24–28).

Insertion of a gentamicin cassette into psbG results in B-band deficient mutants of PAO1, suggesting a role for it in O-antigen biosynthesis.

psbH.

There are 15 bp between psbG and psbH, however, no RBS can be detected upstream of the psbH start codon. The third codon is AAA (FIG. 32). PsbH demonstrates low homology with CapM (14.2%) of *S. aureus* (Lin et al., 1994), involved in the synthesis of N-acetogalactosamino uronic acid. PsbH also has homology with a number of glycosyl transferases, including IcsA (17.1%) (accession #U39810) and RfaK (13%) (accession #U35713) of *Neisseria meningitidis*, RfbF (11.3%) of *Klebsiella pnetimoniae* (Keenleyside and Whitfield, 1994). There is also a low level of homology with RfpB of *Shigella dysenteriae* (Göhmann et al., 1994), and BplH and BplE of *B. pertussis* (Allen and Maskell, 1996). These enzymes are likely to belong to a family of transferases involved in the addition of a similar sugar to the growing O-antigen unit.

RfpB, RfaK, and RfbF are glucosyl- or galactosyl transferases and it is likely that CapM is the transferase involved in the addition of N-acetogalactosaminouronic acid. This suggests that PsbH is one of the two ManA transferases.

PsbH also has very limited homology to the DnaK proteins of *R. meliloti* (Falah and Gupta, 1994) and *Agrobacterium tumefaciens* (Segal and Ron, 1995). However, the homology is concentrated around the central region of PsbH. DnaK is a chaperonin, and is thought to have a role in gene regulation. Homology around the functional domain of DnaK may suggest a role for psbH/PsbH in regulation of the psb cluster.

psbI.

The start codon of psbI overlaps the stop codon of psbH. A putative RBS is situated 6 bp upstream of the AUG start and the second codon is AAA (FIG. 32). PsbI demonstrates strong homology with BplD of *B. pertussis* (Allen and Maskell, 1996) (Table 2). BplD is purported to initiate the first step in the biosynthesis of 2,3-diNAcManA. PsbI also demonstrates moderate homology to NfrC and ORF o389 (RffD) of *E. coli* (Daniels et al., 1992), EpsC of *Burkholderia solanacearum* (Huang and Schell, 1995), YvyH of *B. subtilis* (Soldo et al., 1993) and RfbC of *S. enterica* sv Borreze (Keenleyside and Whitfield, 1995). EpsC is thought to be involved in the biosynthesis of N-acetylgalactosaminuronic acid, and RfbC is thought to be UDP-N-acetylglucosamine 2-epimerase. Alignment of PsbI and related proteins is shown in FIG. 10. Based on these homologies, it is likely that PsbI converts UDP-N-acetylglucosamine to UDP-N-acetylmannosamine as the first step in the biosynthesis of mannuronic acid. Interestingly, the genes encoding the remaining enzymes in this pathway are located upstream and somewhat removed from the psbi gene (psbABDE).

psbJ.

The distance between psbI and psbJ is 17 bp. A putative RBS is present immediately following the stop codon of psbI, 13 bp from the AUG start codon of psbj (FIG. 4). PsbJ demonstrates reasonable homology to BplE (52.6%) of *B. pertussis*, a glycosyl transferase thought to attach either 2,3-diNAcManA or FucNAcMe to the O-unit (Allen and Maskell, 1996) (Table 2). TrsE of *Yersinia enterocolitica* also has homology to PsbJ (Skurnik et al., 1995), and is thought to be one of the galactosyl- or mannosyl transferases. An alignment of PsbJ and PsbJ-like proteins is shown in FIG. 39. As BplE also has limited homology with PsbH, it is likely that both PsbH and PsbJ are the transferases involved in the addition of the two mannuronic acid residues to the B-band O-antigen unit. PsbJ has two putative membrane-spanning domains at the N-terminus, and may be anchored in the cytoplasmic membrane.

psbK.

The start codon of psbK overlaps the stop codon of psbJ, and the second codon is AAA (FIG. 32). PsbK demonstrates homology to a series of glucose dehydratases, including StrP of *Streptomyces glauciens* involved in streptomycin biosynthesis (accession number 629223), ExoB of *R. meliloti* (Buendia et al., 1991), ORF o355 (incorrectly assigned RffE) of *E. coli* (Daniels et al, 1992, Macpherson et al., 1994), GraE of *Streptomyces violaceoritben* (Bechtold et al., 1995) and RfbB of a number of organisms including *N. meningitidis* (Hamerschmidt et al., 1994) and *E. coli* (Marolda and Valvano, 1995). Alignment of these proteins show the presence of an NAD-binding domain (GXXGXXG) near the N-terminal end (FIG. 5; Macpherson et al., 1994). RfbB and o355 are known to be involved in the biosynthesis of FucNAc (Meier-Dieter et al., 1992). Based on these homologies, PsbK is thought to be dTDP-D-glucose 4,6-dehydratase, required as the second step in the biosynthesis of FucNAc.

psbL.

There are 59 bp between the end of psbK and the start of psbL but no RBS could be detected in the region preceding the double start codons (FIG. 32. Identification of the psbL(rfbA) gene has previously been reported (Dasgupta and Lam, 1995). Further characterization of PsbL suggests it functions as a transferase, and is thought to initiate O-antigen unit biosynthesis with the addition of FucNAc to undecaprenol, based on its homology to Rfe. The alignment of PsbL with TrsF from *Y. enterocolitica* (Skurnik et al., 1995) and Rfe from *E. coli* (Daniels et al., 1992) is shown in FIG. 40. Rfe is the initial transferase involved in the biosynthesis of ECA and some O-antigens (Schnaitman and Klena, 1993; Macpherson et al., 1994), transferring GlcNAc to undecaprenol (Meier-Dieter et al., 1992). Because the first transferase in the biosynthesis of O-antigen interacts with undecaprenol, it would be expected to be a hydrophobic protein. PsbL is the most hydrophobic (hydropathy index of 0.84, Table 1) of the three putative transferases encoded in the psb cluster (PsbH, PsbJ, PsbL).

IS407$_{Pa}$.

Following the psbL gene is an insertion sequence with 61.5% nucleotide identity with the previously characterized IS407 element of *B. cepacia* (Wood et al., 1991). This homology prompted the designation IS407$_{Pa}$, with the subscript $_{Pa}$ to indicate it is the *P. aeruginosa* version. Both elements are similar in size (1243 bp for IS407$_{Bc}$ and 1211 for IS407$_{Pa}$) and have very similar imperfect inverted repeats (IR) of 12 and 11 bp respectively. The IS407 elements are similar to IS sequences from other soil-, water- and plant-associated bacteria, including ISRI from *R. meliloti* (Priefer et al., 1989), IS511 from *Catilobacter crescentens*, IS1222 from *Enterobacter agglomerans*, IS476 from *Xanthamonas campestris* (Kearney and Staskawicz, 1990), and IS911 from *S. dysenteriae* (Prère et al., 1990). There have been previous reports of IS elements in *P. aeruginosa* (Pritchard and Vasil, 1990; Sokol et al., 1994) but none of these have homology to the above group; therefore this is the first report of IS407 in *P. aeruginosa*. Southern blot analysis using the IS407$_{Pa}$ as a probe showed it is present in all 20 serotypes of *P. aeruginosa* (Table 2), and most serotypes appear to have only a single copy of the element.

psbM.

The psbM gene follows the IS407$_{Pa}$ element and may be transcribed from one of three potential promoters present in the right IR (FIG. 31). A gene-activating promoter was previously shown to be present in the right IR of IS407$_{Bc}$ (Wood et al., 1991). psbM is unusual because in contrast to other psb genes described above, it hybridizes to chromosomal DNA from all 20 serotypes (Table 1). PsbM mutants, generated by insertion of a gentamicin cassette into a unique NruI site within psbM, exhibit B-band LPS-minus phenotype. This confirms the involvement of the psbM product in LPS biosynthesis, despite the fact it lies outside of the O5-specific region (FIG. 41). PsbM has homology to a range of proteins involved in exopolysaccharide synthesis, including BplL from the *B. pertussis* LPS cluster (Allen and Maskell, 1996), TrsG from the core biosynthetic cluster of *Y. enferocolitica* O3 (Skurnik et al., 1995), and CapD from the *S. aureius* capsular gene cluster (Lin et al., 1994). These homologies are summarized in Table 2.

As shown previously for BplL, only the carboxy half of the PsbM protein has homology to GalE from several bacterial species, suggesting it may have originated as a fusion protein. In support of this hypothesis, PsbM also has homology to two adjacent ORFs (ORF10 and ORF11) in the LPS cluster of *V. cholerae* O139 (Comstock et al., 1996). The homology to ORF10 and ORF11 lies in the amino-terminal and carboxy-terminal half of PsbM, respectively (Table 2), suggesting that two similar ORFs were fused during the evolution of PsbM and the BpIL/TrsG/CapD group.

Based on these homologies, PsbM is thought to be involved in the biosynthesis of the N-acetylfucosamine residue of the O5 O-antigen. As mentioned above, the O-antigen of *B. pertussis* and the type 1 capsule of *S. aureus* and the outer core of *Y. enterocolitica* O3 all contain N-acetylfucosamine. PsbM could function as a dehydrogenase, and it contains two putative NAD-binding domains (FIG. 33), as do BplL and TrsG. Again, these duplications may have arisen from an ancestral fusion of two NAD-binding domain-containing proteins and may be bifunctional.

psbN.

The psbN gene has some homology to eryA, a gene involved in erythromycin biosynthesis in *Sacchropolyspora erythrae*. Generation of knockout mutations in psbN will demonstrate its function in biosynthesis of the O5 O-antigen.

uvrB.

The last partial open reading frame present on pFV100 has high homology to the highly conserved uvrB gene from several bacterial species, including *E. coli, S. enterica* sv Typhimurium, and Micrococcus luteus. UvrB is a subunit of the UvrABC DNA excision repair complex involved in removal of thymidine dimers induced by irradiation with ultraviolet light. The presence of uvrB adjacent to psbN confirms that psbN is the last gene in the psb cluster that could be involved in O-antigen biosynthesis.

Organization of the psb Gene Cluster in *P. aeruginosa* O5.

Several entire rfb clusters, particularly from enteric bacteria, have been characterized to date (reviewed in Whitfield and Valvano, 1993; and Schnaitman and Klena, 1993). In general, rfb clusters are located on the chromosome adjacent to the his operon and the gnd gene. Amongst the enterics, it has previously been shown that the rfb clusters are organized in a specific fashion (Reeves, 1993; Schnaitman and Klena, 1993). Genes necessary for sugar biosynthesis are arranged in discrete blocks located 5' to the transferases and other assembly genes (rfbX, rfc and rol). The psb cluster, however, appears to be almost randomly organised, with genes thought to be involved in the biosynthesis of Man(2NAc3N)A and Man(2NAc3NAc)A scattered throughout the gene cluster (psbI, psbE, psbD, psbB and psbC). The genes thought to encode for the biosynthesis of FucNAc are also scattered throughout the cluster (psbK, psbM, psbG, psbN). Further, the genes encoding transferases are interspersed throughout the psb cluster (psbH, psbJ, psbL), and are separated from one another by one gene each. However, the transferase genes do appear to be organized such that the gene encoding the putative first transferase (PsbL), thought to initiate O-antigen assembly on undecaprenol, is the most distal. Recent results from detailed spectroscopic analysis, using high resolution NMR and Mass Spectroscopy of an rfc mutant of PAO1, strain AK14O1, show that FucNAc is the first sugar of the O-antigen unit, attached to the core oligosaccharide. PsbL's homology to Rfe, and its hydropathicity support the interpretation that it is the first transferase, and is responsible for attachment of the FucNAc residue to undecaprenol. Therefore, based on their gene order and their relative hydropathic indices (−0.21 and 0.10), the psbJ and psbH gene products are thought to transfer Man(NAc)$_2$A and Man(2NAc3N)A, respectively.

The O-antigen of *P. aeruginosa* O5 is an Rfc-dependent Heteropolymer.

The psb cluster was shown to contain an rfc gene, (See Example 1) the interruption of which (by knockout mutation and gene replacement) resulted in a SR phenotype (de Kievit et al., 1995). At least two other gene products, Rol and RfbX, are thought to be involved in Rfc-dependent synthesis of heteropolymeric O-antigens (Whitfield, 1994). Here a rol gene has been identified in the psb cluster. However, in the analysis of the psb genes, no rfbX-like gene was identified. The psbF gene product appeared to be the most likely candidate, based on its hydropathy profile (FIG. 9), but insertional mutants of psbF do not have the phenotype expected of rfbX mutants.

Identification of his Genes Within the psb Gene Cluster.

The identification of the hisH and hisF genes in the middle of the psb cluster raises some interesting evolutionary questions. It appears that these two his genes are not native to *P. aeruginosa*, because they have a lower %G+C content than background (50% vs. 67%) and they hybridize only to a limited number of serotypes with related O-antigens instead of all 20 serotypes. It is not uncommon for his operons to be located adjacent to rfb clusters, and it is likely that the his genes were acquired simultaneously with some or all of the psb genes. The lack of significant homology with any of the HisF and HisH proteins characterized to date, and particularly with those of other Gram-negative bacteria precludes the use of these genes as evolutionary "luggage tags". The lack of homology with other Gram-negative HisH/F proteins suggests either they came from an as-yet uncharacterized source or that they have been resident in *P. aeruginosa* for a long time. The latter possibility is bolstered by the divergence over time of the O-antigen structures/genes from the ancestral psb cluster in the five O5-related serotypes in which these hisH and hisF genes are found.

The location of HisH and HisF adjacent to one another is unique in bacteria. The similarity between hisH and hisA genes, and the usual location of hisA, rather than hisH, adjacent to hisF, raises the possibility that the *P. aeruginosa* psb hisH gene was originally a hisA gene that has diverged so as to be more similar to hisH than to hisA. However, there is precedent for the juxtaposition of hisH and hisF; in the yeast *Sacchromyces cerevisiae*, the homologues of the hisH and hisF genes are adjacent, and are fused into one translational unit called HIS7 (Kuenzler et al., 1993). Alternatively, the hisHF arrangement may be ancestral to the duplication event which resulted in the hisHAF gene order. Another possibility is that the hisA gene may have been lost, leaving hisH and hisT adjacent.

psb Gene Dissemination Amongst the 20 Serotypes of *P. aeruginosa*.

The observation that no genes were found in the O5 cluster which hybridize only to chromosomal DNA from serotype O5 and not to the other related serotypes was intriguing. The differences among these five serotypes is confined to changes in the type of linkage between sugars or to the epimer present in the O-antigen, either mannuronic or guluronic acid (FIG. 30). These differences could result from variation in transferase activity or in epimerization activity, respectively. Further analysis of the putative transferase activities will be necessary to determine whether there are differences in activity among serotypes despite the obvious homology at the genetic level. It will be interesting to determine whether the introduction of multicopy plasmids containing the O5 transferase genes into the related serotypes will result in an alteration in O-antigen structure that could be detectable with serotype-specific monoclonal antibodies. There is precedence for this, as a *P. aeruginosa* strain PAO1 (serotype O5) phage induced mutant, strain AK1380, was isolated which was identified as serotype O16 (see Lam et al., 1992, FIG. 30; and Kuzio and Kropinski, 1993).

The genetic differences among the five serotypes with related O-antigens are obviously quite minor. Comparison of the DNA sequences of the O2 rfc and the O5 rfc genes revealed they are very homologous at the nucleotide level).

Example 4

Further Characterization of Rol (Wzz) Gene and Region Upstream

In this example the rol gene is generally referred to as the wzz gene.

The materials and methods used in Example 4 are as follows:

Bacterial Strains and Plasmids.

The bacterial strains and plasmids used in this study are listed in Table 8. *P. aeruginosa* strains were cultured either on Luria broth or plates or on Pseudoiioiias Isolation Agar (PIA: Difco, Detroit, Mich.). *E. coli* strains were cultured on Luria broth or plates. Media were supplemented with antibiotics ampicillin, carbenicillin, tetracycline, or gentamicin (all from Sigma, St. Louis, Mo.) as required, using the concentrations outlined in de Kievit et al., 1995.

DNA Methods

Chromosomal DNA was isolated from *P. aeruginosa* using the method of Goldberg and Ohman, 1984. Plasmid and cosmid DNA was isolated using the Qiagen midi-prep kit (Qiagen Inc., Chatsworth, Calif.) as directed by the manufacturer. Restriction and modification enzymes were supplied by Gibco/BRL (Gaithersburg, Md.), Boehringer Mannheim (Laval, PQ), and/or New England Biolabs (Beverly, Mass.) and were used as directed by the manufacturers.

Plasmids were introduced into *E. coli* by $CaCl_2$ transformation (Huff et al., 1990) and into *P. aeruginosa* by electroporation using a BioRad (Richmond, Calif.) Gene Pulser apparatus following manufacturers protocols. *P. aeruginosa* electrocompetent cells were prepared by washing early log phase cells twice for 5 min each in sterile 15% room-temperature glycerol followed by immediate resuspension in the same solution. Cells were either used immediately or frozen at −80° C. for future use. Alternatively, plasmids were mobilized into *P. aeruginosa* through biparental mating with *E. coli* SM10 carrying plasmids of interest (Simon et al., 1983).

Construction of Plasmids

Figure 43:
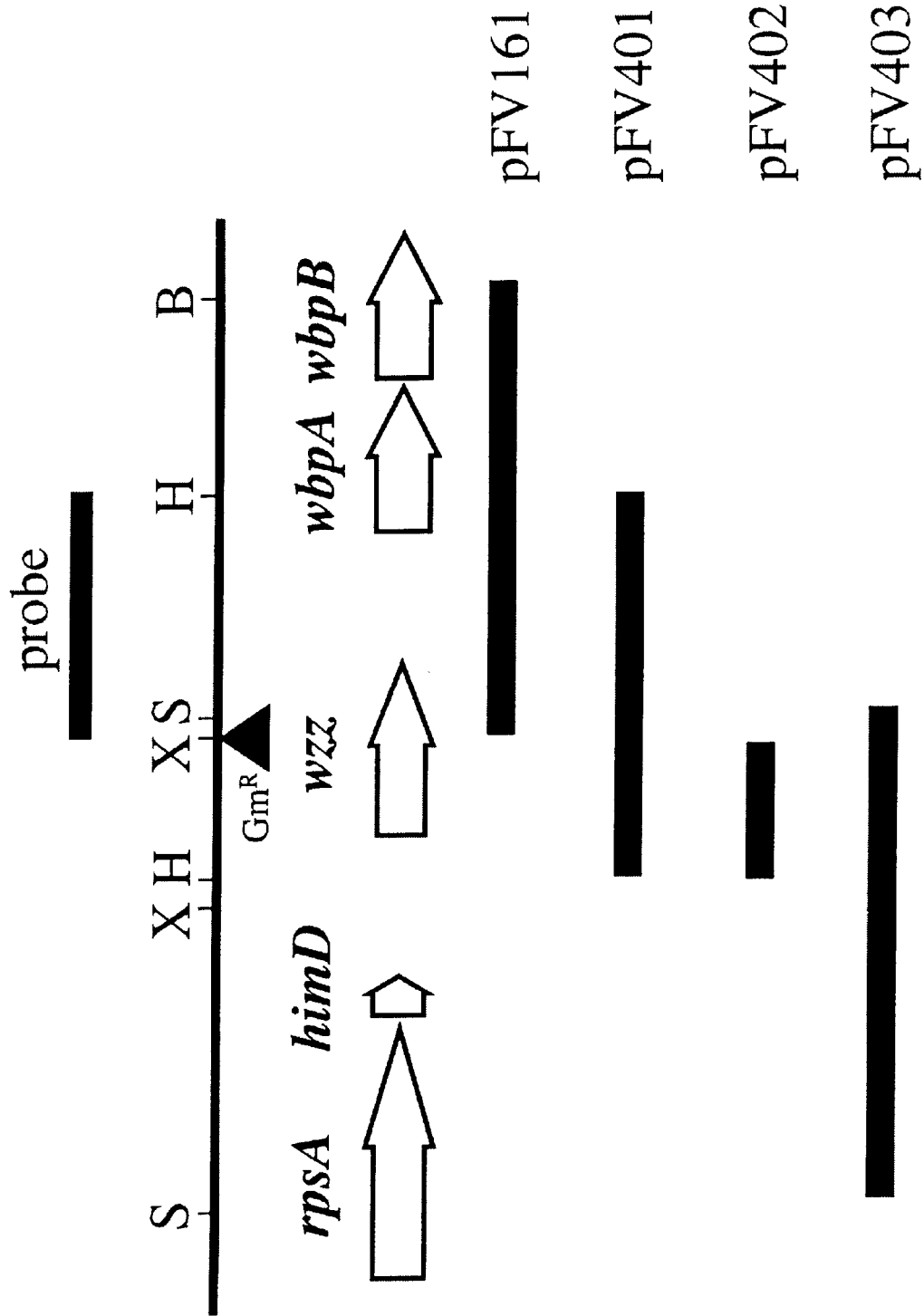
FIG. 43 is a physical map of the 5' end of the wbp cluster.

The cosmid pFV100, containing the *P. aeruginosa* wbp cluster, was used as a source of DNA for the construction of pFV161 (FIG. 43). An overlapping cosmid, pFV400, was the source of a 2.3-kb HindIII fragment cloned into pBluescript II SK (pFV401). For DNA sequencing, a 0.8 kb HindIII-XhoI fragment from pFV401 was subcloned into pBluescript II SK (pFV402). A 3.0 kb SstI fragment containing the 5 portion of wzz and upstream sequences was cloned from pFV400 into pBluescript II SK (pFV403). For complementation experiments, the 2.3 kb insert of pFV401 was cloned into the *Pseudomonas-E. coli* shuttle vector pUCP26 (Table 14), downstream of the vectors lacZ promoter (pFV401–26).

DNA Sequencing and Analysis

Using the above plasmids, the DNA sequences of both strands of the pFV401 insert were determined by the GenAlyTiC facility (University of Guelph, Guelph, ON) employing the Taq DyeDeoxy Terminator Cycle Sequencing Kit (Applied Biosystems, Mississauga, ON) and an Ericomp Model TCX15 Thermal cycler. Oligonucleotide primers were synthesized on an Applied Biosystems model 391 DNA synthesizer and purified as directed by the manufacturer.

DNA sequences were collated and analyzed using GENE RUNNER for Windows (Hastings Software, Newark, N.J.), DNAsis for Windows (Hitachi Software, Helixx, Scarborough, ON), and PC/GENE (IntelliGenetics Inc., Mountain View, Calif.). DNA and protein database searches were performed using the NCBI BLAST network server (Altschul et al., 1990; Gish and States, 1993).

Expression of the Wzz Protein

An *E. coli* S30 extract in vitro protein expression kit (Promega, Madison, Wis.) was used to examine the product encoded by the O5 wzz gene. Column-purified (Qiagen) plasmid DNA of pBluescript II SK, pFV401a (containing the O5 wzz gene cloned downstream of the lacZ promoter of pBluescript II SK) and pFV401b (containing the same DNA cloned in the opposite orientation) were used as templates in the coupled transcription/translation reaction in the presence of $^{35}$S-labelled methionine (Trans35-Label, ICN, Costa Mesa, Calif.). The labelled proteins were precipitated with acetone, separated on standard discontinuous 12.5% SDS-PAGE along with unstained BioRad low-molecular-weight markers and visualized by autoradiography using $^{35}$S-sensitive film (BioMax, Kodak, Toronto, ON).

Preparation and Visualization of LPS.

LPS from *P. aeruginosa* was prepared by the method of Hitchcock and Brown, 1983. The LPS preparations were separated on standard discontinuous 12.5% SDS-PAGE gels and visualized by silver staining using the method of Dubray and Bezard, 1982. Alternatively, LPS separated on SDS-PAGE gels was transferred to nitrocellulose and visualized by immunoblotting (Burnete, 1981). Nitrocellulose blots were blocked with 3% skim milk followed by overnight incubation with hybridoma culture supernatants containing MAb MF15-4 (specific for O5 B-band LPS), MAb 18–19 (cross-reactive for O2, O5, and O16 B-band LPS core-plus-one O-antigen unit; 28) or MAb N1F10 (specific for A-band LPS; 30). The second antibody was a goat anti-mouse F(ab)$_2$-alkaline phosphatase conjugate (Jackson Laboratories, Bio/Can Scientific, Mississauga, ON). The blots were developed using a substrate containing 0.3 mg/ml NBT (Nitro Blue Tetrazolium) and 0.15 mg/ml BCIP (5-bromo-4-chloro-3-indolyl phosphate toluidine) (Sigma) in 0.1 M bicarbonate buffer (pH 9.8).

Creation of wzz Knockout Mutants through Gene Replacement

The gene replacement strategy of Schweitzer and Hoang, 1985 was used for generation of knockout mutations in wzz. The 2.3 kb HindIII insert of pFV401 was cloned into pEX100T, a pUC19-based vector containing the sacB gene as a selectable marker (pFV401T). An 875 bp gentamicin resistance cassette from the plasmid pUCGM was then cloned into the unique XhoI site within the insert (pFV401TGm). Constructs containing the interrupted wzz gene were mobilized into *P. aeruginosa* O5 by biparental mating with *E. coli* SM10. Since pEX100T does not replicate in *P. aeruginosa*, selection for gentamicin resistance allows detection of chromosomally-integrated copies of the mutated gene.

Determination of sucrose and carbenicillin (Cb) sensitivities distinguishes between merodiploids (sucrose$^S$, Cb$^R$) and true recombinants (sucrose$^R$, Cb$^S$). The presence of the gentamicin cassette in the chromosomal DNA of *P. aeruginosa* O5 and O16 wzz mutants was confirmed by Southern blot analysis (not shown).

RESULTS

Cloning and Sequencing of the *P. aeruginosa* O5 wzz Gene.

Nucleotide sequences with homology to wzz from *E. coli*, *Salmonella enterica* sv Typhimurium and *Shigella flexneri* (Bastin et al., 1993; Batchelor et al., 1992; Morona et al., 1995) were identified ending approximately 800 bp upstream of the first gene of the *P. aeruginosa* O5 wbp gene cluster, wbpA (FIG. 43). The amount of DNA with homology to wzz was 479 bp, starting at the XhoI cloning site of the insert of pFV100 and ending with a stop codon. Based on the average size (1 kb) of previously characterized wzz genes (Bastin et al., 1993; Batchelor et al., 1992; Morona et al., 1995), this sequence represented approximately half of the putative *P. aeruginosa* wzz gene.

A 1.5 kb XhoI-HindIII fragment from pFV161 containing the 3 end of the putative wzz gene (FIG. 43) was used as a probe to screen a *P. aeruginosa* O5 cosmid library. One cosmid (pFV400) which hybridized with the probe was isolated. A probe-reactive 2.3 kb HindIII fragment from pFV400 was subcloned into pBluescript II SK to form pFV401 (FIG. 43).

DNA sequence analysis revealed an open reading frame (ORF) of 1046 base pairs (bp), sufficient to encode a protein of 348 amino acids with a molecular mass of 39.3 kilodaltons (kDa), and an isoelectric point of 6.26. Comparison of the deduced amino acid sequence of the *P. aeruginosa* O5 protein with those in GenBank revealed from 11.5 to 20.0% amino acid identity with Wzz-like proteins of other species (Table 15). *P. aeruginosa* Wzz also has similarity with proteins thought to be involved in polymerization or export of exopolysaccharide capsules in *E. coli* O8/O9 (13, 15; accession #U39306), *Vibrio cholerae* O139 (4; OtnB, X90547), *Klebsiella pneumoniae* (ORF6, 747665), and *Rhizobium meliloti* (ExoP, Z22636). *P. aeruginosa* Wzz also has similarity with FepE from *E. coli*, thought to be a component of the ferric enterobactin permease (Ozenburger et al., 1987; X74129).

Figure 44:
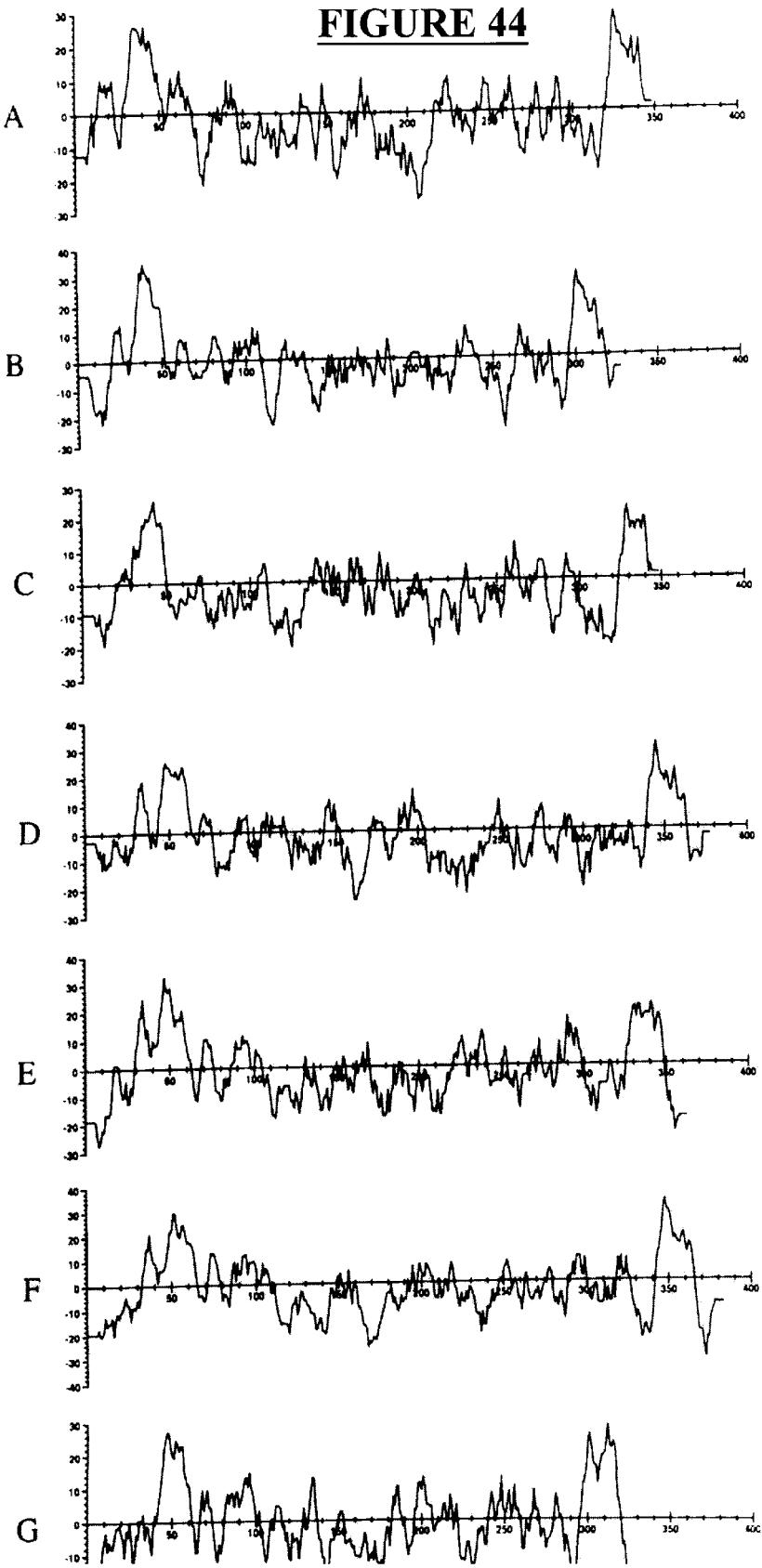
FIG. 44A is a hydropathy plot of a selected Wzz-like protein which represents P. aeruginosa O5 Wzz.
FIG. 44B is a hydropathy plot of a selected Wzz-like protein which represents E. coli O111 Wzz,Z17241.
FIG. 44C is a hydropathy plot of a selected Wzz-like protein which represents E. coli O349, M87049.
FIG. 44D is a hydropathy plot of a selected Wzz-like protein which represents E. coli FepE, P262661.
FIG. 44E is a hydropathy plot of a selected Wzz-like protein which represents Y. enterocolitica O8 Wzz, U43708.
FIG. 44F is a hydropathy plot of a selected Wzz-like protein which represents Y. pseudotuberculosis Wzz.
FIG. 44G is a hydropathy plot of a selected Wzz-like protein which represents V. cholerae O139 OtnB, X90547.

While there is poor primary sequence homology between the Wzz protein of *P. neruginosa* O5 and related proteins, their predicted secondary structures are similar (FIG. 44). There are conserved hydrophobic regions at both the amino and carboxy termini, and hydrophilic regions in the central portion of the protein. The predicted transmembrane helices in *P. aeruginosa* O5 Wzz are between amino acids 29–49 and 319–339. These hydrophobic regions contain the amino acid residues which are most highly conserved among Wzz-like proteins.

Analysis of the Region Upstream of wzz.

The wzz gene is upstream of the wbp cluster of *P. aeruginosa* O5. As described in Example 3, most of the genes in this cluster, including wzz, are serogroup-specific, and are found only in serotypes O2, O5, O16, O18, and O20. These serotypes have chemically- and structurally-related O antigens (Knirel and Koch et Kov., 1994). Based on Southern blot hybridization results, the 5 end of the serogroup-specific region was previously localized to a 1.9-kb SstI- XhoI fragment located 1.1 kb upstream of the 5 end of pFV100. DNA sequence analysis of this fragment revealed a gene with 85% nucleotide identity with the *E. coli* gene rpsA, encoding 30S ribosomal protein S1 (Schnier et al., 1982), and a second gene which has 98% identity with *P. aeruginosa* himD, encoding the β subunit of integration host factor (IHF) (Delic-Atree et al., 1995). The rpsA and himD genes are transcribed in the same direction as wzz. These data locate rpsA and himD adjacent to the wbp cluster at 37 minutes on the chromosomal map of *P. aeruginosa* O5 strain PAO1 (Holloway et al., 1994; Lightfoot and Lam, 1993).

Expression of the Putative Wzz Protein.

Figure 45:
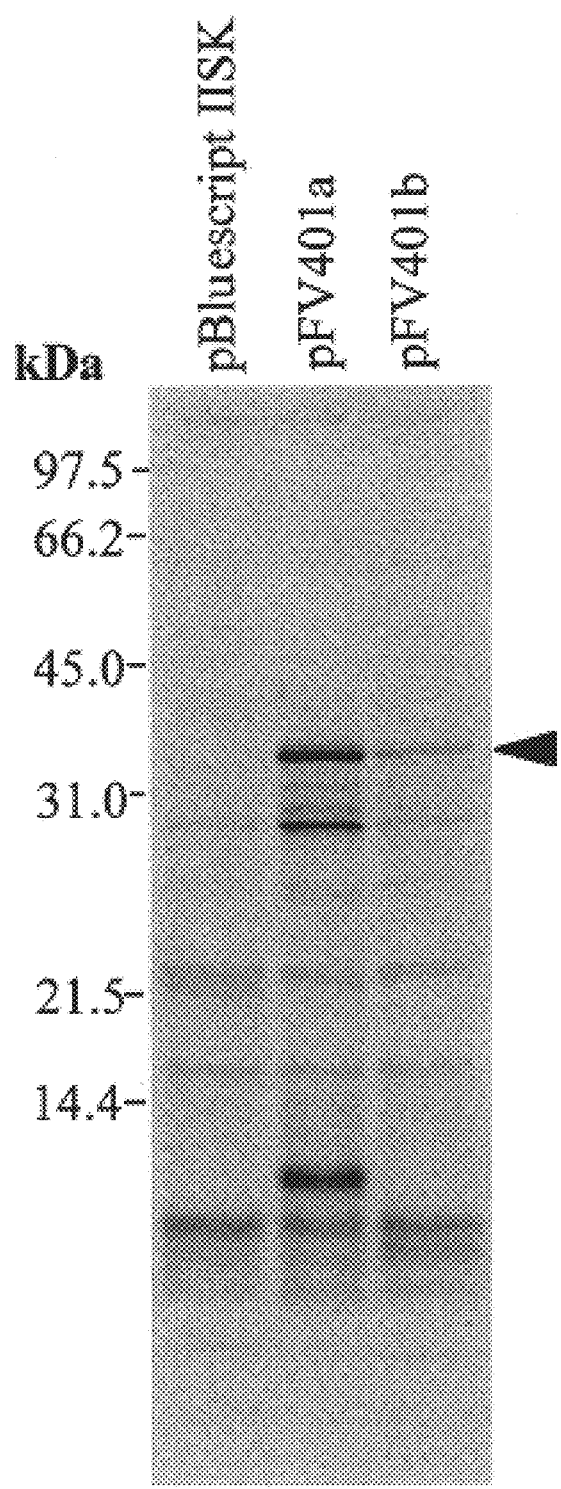
FIG. 45 shows the expression of P. aeruginosa Wzz in vitro.

Using an *E. coli* S30 extract expression system, the putative wzz gene was shown to encode a protein with an apparent molecular weight of 40 kDa which was not present in samples containing only the vector, pBluescript II SK (FIG. 45). The estimated size of 40 kDa is in good agreement with that predicted from the DNA sequence (39.3 kDa). A reduced amount of the same protein was detected in the sample in which the insert DNA was cloned in the opposite orientation (pFV401b), indicating that there is a native promoter present upstream of the wzz gene which functions weakly in *E. coli*. Examination of the DNA sequence upstream of wzz revealed at least three potential promoter sequences with partial homology to the *E. Coli* $\delta^{70}$ consensus. The −10 regions of these putative promoters are located approximately 60, 140, or 155 bp upstream of the wzz initiation codon.

Analysis of the Putative Wzz Protein Function using Chromosomal Knockout Mutants.

Figure 46:
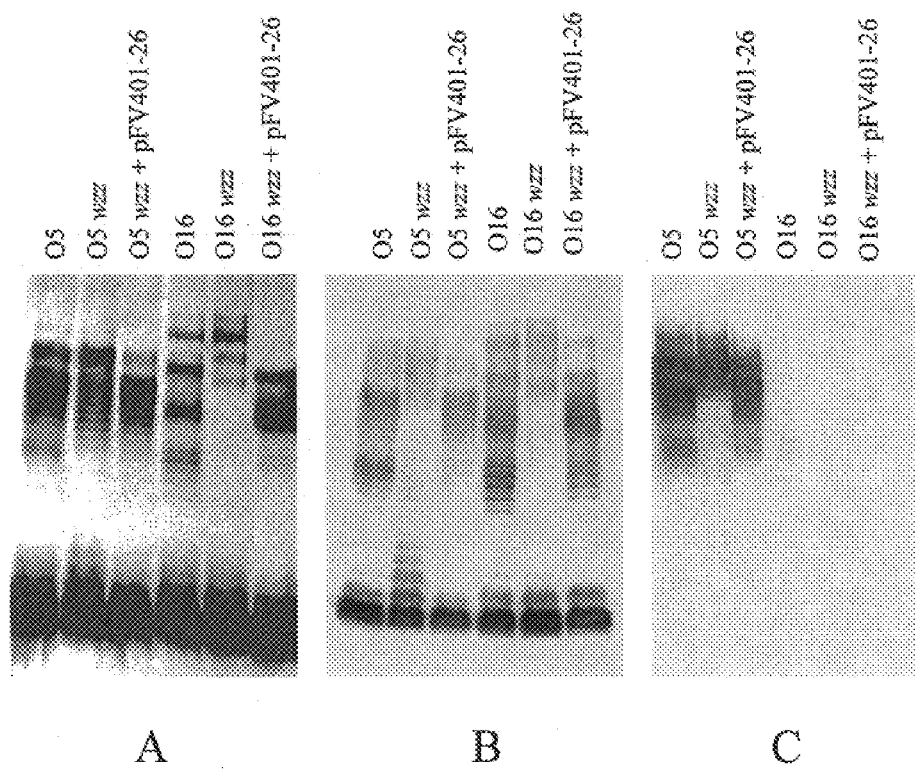
FIG. 46A shows an SDS-PAGE gel of LPS from Wzz knockout mutants.
FIG. 46B shows a western immunoblot using Mab 18–19.
FIG. 46C shows a western immunoblot using Mab MF15-4.

A gentamicin-resistance ($Gm^R$) cassette was inserted into the putative wzz gene of *P. aeruginosa* O5, and the interrupted gene was reintroduced into the O5 chromosome by homologous recombination. Comparison of LPS from the wild-type strain and the $Gm^R$ mutant on silver-stained SDS-PAGE gels and Western immunoblots using B-band-specific MAbs MF15-4 and 18–19 showed that the mutant had an altered LPS banding pattern. When MAb 18–19 was used, the LPS from the wzz mutant showed an increase in both shorter and longer B-band LPS O chains and a decrease in B-band O chains whose length corresponded to that preferred in the O5 parent strain (FIG. 46). On the immunoblot using MAb MF15-4, which is specific for high-molecular-weight LPS (Lam et al., 1992), there is also an increase in both shorter and longer B-band O chains. Similar Western immunoblots using the A-band LPS-specific MAb N1F10 showed the modality of A-band was unaffected by the wzz mutation (not shown). Although the B-band LPS pattern of the wzz mutant is significantly different from the parent strain, it does not show the linear distribution of O-antigen chain lengths seen in enteric zvzz mutants (FIG. 47A). Reintroduction of the O5 wzz gene on pFV401-26 restored the mutant to a phenotype similar to that of the parent but missing both the shortest and longest groups of chain lengths (FIG. 46).

Comparison of the Function of wzz in Two Related Serotypes of *P. aeruginosa*.

A DNA probe containing the O5 wzz gene hybridized with chromosomal DNA only from serotypes O2, O5, O16, O18, and O20 of *P. aeruginosa*, all of which have chemically- and structurally-related O antigens (Example 3). The O antigens of both O5 and O16 are composed of two mannuronic acid and one N-acetyl fucosamine residues, but differ in one glycosidic linkage. In O5, the linkage is (1(3)-(-D-Fuc2NAc, while in O16, the linkage is (1(3)-(-D-Fuc2NAc. This change results in a discernible difference in the LPS patterns of O5 and O16 (FIG. 46).

Taking advantage of the similarity between the O-antigen gene clusters of O5 and O16, a wzz knockout mutation was introduced into O16, using the O5 wzz knockout construct. As an additional benefit, O16 does not express A-band LPS (Lam et al., 1989), thus any changes in B-band LPS patterns on silver-stained gels were more easily visualized. The structural difference between O5 and O16 LPS is detected by MAb MF15-4, which recognizes only O5 and not O16 LPS. To examine LPS from both O5 and O16 simultaneously on Western immunoblots, MAb 18–19, which cross-reacts with all five serotypes in the O5 serogroup (Lam et al., 1992), was used. Comparison of LPS from the wild-type O16 parent and the O16 wzz knockout mutant showed the mutant displayed a loss of modality corresponding to the preferred chain lengths of the parent, and an increase in higher-molecular-weight LPS (FIG. 46). Interestingly, there still appeared to be chain length modulation in the O16 wzz mutant that was different from that of the parent, with a decrease in short O chains in comparison to the O5 wvzz mutant. Bastin and coworkers (1996) showed that the modality of chain length distribution was dependent on the source of the wzz gene. However, the pattern of LPS chain length distribution of O16 zVzz mutants carrying the O5 wzz gene on pFV401-26 resembled that of the O16 parent strain, rather than the O5 strain (FIG. 46).

Ability of the *P. aeruginosa* O5 wzz Gene to Function in *E. coli*.

In order to determine whether wzz from *P. aeruginosa* O5 could complement an enteric wzz mutation, *E. coli* strain CLM4, which is deleted for O-antigen genes including wzz (Marolda and Valvano, 1993), was used. CLM4 was transformed with either pSS37 (containing the O-antigen biosynthetic genes from *S. dysenteriae* type I without a wzz gene alone, or with both pSS37 and pFV401, containing *P. aeruginosa* O5 wzz. While LPS from *E. coli* CLM4/pSS37 showed an unregulated distribution of chain lengths, LPS from *E. coli* CLM4/pSS37/pFV401 showed a restoration to modality, with a decrease in short and very long O chains, and an increase in chains with approximately 10–20 repeats (FIG. 47A).

The core oligosaccharide of the *E. coli* K-12 hybrid strain HB101, but not K-12 itself, can act as an acceptor for *P. aeruginosa* O antigens (Goldberg et al., 1992; Lightfoot and Lam, 1993). The structure of the HB101 core has not been elucidated. Although *E. coli* HB101 carrying pFV100 had previously been shown to express LPS which could be recognized by B-band-specific MAb MF15-4, its chain-length regulation had not been examined. pFV100 is now known to contain a truncated wzz gene. The expression of LPS from *E. coli* HB101 carrying both pFV100 and the complete O5 zvzz gene on pFV401 was examined. *E. coli* HB101 carrying pFV100 alone expressed an O5 O antigen with modulated, short-chain O-antigen molecules (FIG. 47B). When both pFV100 and pFV401 were present in *E. coli* HB101, a dual LPS banding pattern was visible on Western immunoblots (FIG. 47B). The coexpression of both *E. coli* and *P. aeruginosa* Wzz proteins resulted in a major group of short O chains attributable to HB101 Wzz, and a minor group with longer chains attributable to the *P. aeruginosa* O5 Wzz protein.

The identification of the rpsA and himD genes upstream of wzz completes the delineation of the region of serogroup-specific DNA responsible for encoding the B-band LPS O antigen of *P. aeruginosa* O5 and related serotypes. The entire O5 wbp cluster is thus bounded by himD on the 5 end and utvrB on the 3 end and is approximately 24.3 kb from the start of wzz to the end of wbpN. The serogroup-specific portion is approximately 18.4 kb from the start of wzz to the end of wbpL. Unlike enteric O-antigen (rfb) clusters, the wbp cluster is not flanked by his and gnd, although there are two his genes, hisH and hisf, located in the center of the cluster. The location of wzz upstream of the wbp cluster in *P. aeruginosa* is opposite to that in many enteric bacteria, where wzz is located downstream of the O-antigen cluster (Batchelor et al., 1992; Morona et al., 1995). The presence of the rpsA and himD genes, which are highly conserved among bacterial species, at the junction between the serogroup-specific and common regions suggests they may have been the site of a past recombination event. himD encodes the β-subunit of IHF which has previously been shown to be involved in regulation of biosynthesis of the exopolysaccharide alginate (Wozniak and Ohman, 1993; Wozniak, 1994).

The presence of a functional wzz gene in *P. aeruginosa* O5 confirms that both the O-antigen polymerase, Wzy, and Wzz are required for expression of the heteropolymeric B-band O antigen, as predicted by current models. Growing evidence suggests that Wzz proteins may also play a role in the modulation of the length of capsular exopolysaccharide polymers (Bik et al., 1996; Dodgson et al., 1996; Franco et al., 1996). A possible homologue of the third component of Wzy-dependent systems, Wzx, is present in the wbp cluster (Burrows et al., 1996).

The LPS banding pattern of enteric wzz mutants consists mainly of short O chains with steadily decreasing amounts of longer chains (FIG. 47A). In contrast, neither the O5 nor the O16 wzz mutants display this typical wzz phenotype, and the O16 mutant in particular continues to display some chain length regulation. It is possible that chain length regulation in *P. aeruginosa* is not simply dependent on wzz. In the case of O16, there may be a second wzz gene present in the O16 chromosome whose activity is normally masked by the wzz of the O5 serogroup. Complementation of the O5 and O16 mutants by wzz on a multicopy plasmid gave rise to strains whose LPS appeared even more tightly regulated for size than that of the parent strains, since the complemented wzz mutants lacked both short- and very long-chain modal groups, and had an increase in medium-length groups. One possible interpretation of these results is that the regulation of chain length by wzz in *P. aeruginosa* is normally imprecise, giving rise to groups with multiples of the preferred chain length instead of a single group. This interpretation fits the model of Bastin et al., 1993 who suggested that multimodal distributions of chain lengths could result from reinitiation of polymerization without an intervening ligation step.

Complementation of the O16 mutants by the O5 wzz gene restored them to a phenotype resembling the O16 parent. Contrary to the findings of Bastin and colleagues, 1993, these results show that in these closely-related serotypes, the structure of the O antigen, or possibly difference in the O5 vs O16 genetic background, determines the preferred O-antigen chain length. While the O16 wzz and wzy genes have not been isolated, they are probably highly similar to those of O5 based on the results of high-stringency Southern blot analysis. The analysis of wzy from the related serotypes O2 and O5 demonstrated that the genes are essentially identical.

The *P. aeruginosa* O5 Wzz protein can modulate expression of both homologous (*P. aeruginosa* O5) and heterologous (*S. dysenteriae*) O antigens in *E. coli* although it has only 20% identity with the Wzz protein of *E. coli*. The ablility of *P. aeruginosa* Wzz to modulate a heterologous O antigen is consistent with previous work showing Wzz is not specific for O-antigen type. When *E. coli* and *P. aeruginosa* Wzz proteins are coexpressed in *E. coli*, the modulating effect of the native protein predominates although the *P. aeruginosa* wzz is present in multicopy. This difference can be seen in the increased proportion of short O chains versus longer O chains which are expressed. Despite variations in efficacy, it appears that the Wzz proteins from different Gram-negative families function in an analogous manner and can act as interchangeable components of the O-antigen assembly complex.

The ability of Wzz, Wzy and WaaL proteins with divergent primary sequences to act reciprocally suggests that they are interacting through recognition of common, conserved structural features. Although the amino acid similarities between the Wzz proteins are low, their secondary structures are alike (FIG. 44). Similarly, although the primary sequence similarities of the Wzy proteins from a number of bacteria are poor, all have highly similar secondary structures containing multiple membrane-spanning domains (Cryz et al., 1984). Comparison of the WaaL proteins from *E. coli* and *S. enterica* sv Typhimurium, the only O-antigen ligases characterized to date, show that they too have conserved secondary structures, but less than 20% primary sequence homology (Liu and Wang, 1990). In light of this information, it is now possible to target conserved structural features of these proteins for modification in order to further define the areas critical for putative protein interactions.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

Below full citations are set out for the references referred to in the specification and detailed legends for the figures are provided.

The application contains sequence listings which form part of the application.

TABLE 1

*Pseudomonas aeruginosa* serotype O5 wbp gene cluster.

| locus | base positions | % G + C | MW encoded | AAs[d] | pI[e] | H.I.[f] | distribution[g] |
|---|---|---|---|---|---|---|---|
| wzz[a] | 1–479 | 49.5 | 38.6 kDa | 158 | nd | nd | 2, 5, 16, 18, 20 |
| wbpA | 1286–2596 | 54.5 | 48.2 kDa | 436 | 5.36 | −0.08 | 2, 5, 16, 18, 20 |
| wbpB | 2670–3620 | 52.8 | 35.8 kDa | 316 | 6.40 | −0.27 | 2, 5, 16, 18, 20 |
| wbpC | 3689–5578 | 53.1 | 69.9 kDa | 629 | 9.06 | 0.48 | 2, 5, 16, 18, 20 |
| wbpD | 5575–6066 | 53.9 | 17.4 kDa | 163 | 8.25 | 0.19 | 2, 5, 16, 18, 20 |
| wbpE | 6152–6982 | 52.8 | 29.9 kDa | 276 | 5.26 | −0.01 | 2, 5, 16, 18, 20 |
| wzy[b] | 7236–8552 | 44.6 | 48.9 kDa | 438 | 9.63 | 0.80 | 2, 5, 16, 18, 20 |
| wbpF | 8549–9499 | 49.0 | 33.8 kDa | 316 | 9.49 | 0.99 | 2, 5, 16, 18, 20 |

TABLE 1-continued

Pseudomonas aeruginosa serotype O5 wbp gene cluster.

| locus | base positions | % G + C | MW encoded | AAs[d] | pI[e] | H.I.[f] | distribution[g] |
|---|---|---|---|---|---|---|---|
| hisH | 9831–10388 | 49.3 | 20.9 kDa | 185 | nd | nd | 2, 5, 16, 18, 20 |
| hisF | 10388–11143 | 50.0 | 27.5 kDa | 251 | nd | nd | 2, 5, 16, 18, 20 |
| wbpG | 11281–12411 | 44.5 | 43.4 kDa | 375 | 8.15 | −0.38 | 2, 5, 16, 18, 20 |
| wbpH | 12427–13548 | 45.6 | 42.0 kDa | 373 | 8.79 | −0.21 | 2, 5, 16, 18, 20 |
| wbpI | 13545–14633 | 50.2 | 39.7 kDa | 362 | 5.40 | 0.06 | 2, 5, 16, 18, 20 |
| wbpJ | 14651–15892 | 54.5 | 45.3 kDa | 413 | 6.54 | 0.10 | 2, 5, 16, 18, 20 |
| wbpK | 15889–16851 | 56.8 | 34.4 kDa | 320 | 9.03 | 0.14 | 2, 5, 16, 18, 20 |
| wbpL[c] | 16911–17822 | 55.5 | 32.9 kDa | 303 | 9.08 | 0.84 | 2, 5, 16, 18, 20 |
| IS1209 | 17935–19144 | 59.3 | nd | n/a | n/a | n/a | 1 to 11, 13 to 20 |
| wbpM | 19678–21675 | 61.9 | 74.5 kDa | 665 | 9.33 | 0.09 | 1 to 20 |
| wbpN | 22302–23693 | 63.6 | 48.5 kDa | 463 | 6.12 | −0.09 | 1 to 20 |
| uvrB[a] | 23704–24417 | 61.2 | 26.7 kDa | 238 | nd | nd | 1 to 20 |

[a]truncated ORF
[b]de Kievit et al. (1995)
[c]wbpL was originally named rfbA; Dasgupta and Lam (1995)
[d]number of amino acids
[e]isoelectric point of the protein, calculated using GeneRunner for Windows (Hastings Software).
[f]hydropathic index of the protein, calculated using DNAsis for Windows (Hitachi Software). Positive values indicate the protein is hydrophobic, while negative values indicate the protein is hydrophilic.
[g]distribution of this gene among the 20 serotypes of P. aeruginosa, based on positive hybridization in high-stringency Southern blot analysis.

TABLE 2

Similarities of P. aeruginosa O5 Wbp proteins to those in the databases.

| P. aeruginosa protein | Similar proteins | Putative function | % identity (% similarity)* | Database accession number |
|---|---|---|---|---|
| WbpA | EpsD-Burkholderia solanacearum | dehydrogenase | 33.1 (50.6) | U17898 |
|  | CapL-Staphylococcus aureus | capsule sythesis | 31.6 (45.3) | U10927 |
|  | VipA-Salmonella enterica vs Typhi | Vi antigen synthesis | 30.8 (44.9) | D14156 |
|  | RffD (O379)-Escherichia coli | UDP-ManNAc dehydrogenase | 30.2 (42.8) | M87049 |
| WbpB | LmbZ-Streptomyces lincolnesis | oxidoreductase | 19.3 (28.2) | X79146 |
|  | BplA-Bordetella pertussis | dehydrogenase | 12.4 (17.0) | X90711 |
|  | Pur10-Str. alboniger | oxidoreductase | 5.7 (12.0) | X92429 |
| WbpC | HI0392-Haemophilus influenzae | unknown | 24.9 (37.2) | U00073 |
|  | ExoZ-Rhizobium meliloti | O-acylase | 27.4 (40.3) | U50300 |
|  | AcyA-Str. thermotolerans | O-acylase | 24.9 (37.2) | X58126 |
|  | unknown-Caenorhabditis elegans | unknown | 18.0 (26.7) | D30759 |
|  | NodX-R. leguminosarum | O-acylase | 16.3 (23.1) | X07990 |
| WbpD | BplB-B. pertussis | acetylase | 73.6 (83.4) | X90711 |
|  | CysE-Buchnera aphidicola | serine O-acetylase | 28.2 (45.4) | M90644 |
|  | CysE-Arabidopsis thalnia | serine O-acetylase | 30.7 (42.4) | L42212 |
|  | CysE-H. influenzae | serine O-acetylase | 28.2 (39.9) | U32689 |
|  | CysE-E. coli | serine O-acetylase | 28.8 (38.6) | M15745 |
| WbpE | BplC-B. pertussis | aminase | 64.1 (75.7) | X90711 |
|  | DegT-Bacillus subtilis | dideoxy sugar biosynthesis | 51.2 (62.4) | M29002 |
|  | ERYC1-Saccharopolyspora erythrae | dideoxy sugar biosynthesis | 37.3 (48.2) | P14290 |
|  | SpsC-Ba. subtilis | dideoxy sugar biosynthesis | 37.4 (53.3) | P39623 |
|  | Dnrj-Str. peucetius | dideoxy sugar bioxynthesis | 34.1 (50.4) | P25048 |
| WbpF | ExoT-R. meliloti | succinoglycan export | 20.3 (32.3) | Z22646 |
|  | FeuC-B. subtilis | iron uptake | 17.1 (28.8) | L19954 |
| WbpG | ORF2-Vibrio choleae O139 | unknown | 19.0 (23.7) | U47057 |
|  | Pfk-Lactococcus lactis | phosphofructokinase | 9.7 (14.4) | L07920 |
|  | NrfB-H. influenzae | formyl-dependent nitrate reductase | 5.8 (9.3) | U32733 |
| WbpH | RfaK-Neisseria meningitidis | glycosyl transferase | 20.1 (28.9) | U35713 |
|  | CapM-S. aureus | GalNAcA transferase | 17.4 (29.7) | U10927 |
|  | IcsA-N. meningitidis | glycosyl transferase | 17.1 (27.0) | U39810 |
|  | BplH-B. pertussis | glycosyl transferase | 16.6 (23.0) | X90711 |
|  | BplE-B. pertussis | glycosyl transferase | 15.8 (24.6) | X90711 |
| WbpI | DplD-B. pertussis | GlcNAc to ManNAc epimerase | 56.6 (69.3) | X90711 |
|  | EpsC-B. solanacearum | GalNAcA biosynthesis | 29.3 (42.3) | U17898 |
|  | RffE(o389)-E. coli | UDP-GlcNAc-2-epimerase | 12.9 (18.8) | M87049 |
|  | YvyH-Ba. subtilis | unknown | 12.3 (18.5) | P39131 |
|  | RfbC-S. enterica sv Borreze | UDP-GlyNAc-2-epimerase | 11.8 (18.2) | L39794 |
| WbpJ | BplE-B. pertussis | glycosyl transferese | 39.5 (52.2) | X90711 |
|  | TrsE-Yersinia enterocolitica 0:3 | galactosyl transferese | 15.7 (26.7) | Z47767 |
| WbpK | ORF6-V. cholerae O139 | UDP-galactose-4-epimerase | 37.2 (53.8) | U47057 |
|  | ExoB-R. meliloti | UDP-galactose-4-epimerase | 22.8 (32.8) | X58126 |
|  | StrP-Str. glaucescens | dehydratase or epimerase | 22.5 (34.7) | X78974 |

TABLE 2-continued

Similarities of *P. aeruginosa* O5 Wbp proteins to those in the databases.

| P. aeruginosa protein | Similar proteins | Putative function | % identity (% similarity)* | Database accession number |
|---|---|---|---|---|
| | RffG(o355)-*E. coli* | TDP-glucose-dehydratase | 25.5 (38.1) | M87049 |
| | GraE-*Str. violaceoruben* | unknown | 21.3 (29.7) | L37334 |
| | RfbB-*N. meningitidus* | TDP-glucose dehydratase | 21.9 (31.6) | L09189 |
| | RfbB-*E. coli* | TDP-glucose dehydratase | 18.8 (28.5) | U23775 |
| WbpL | TrsF-*Y. enterocolitica* O3 | UDP-GalNAc transferase | 54.5 (67.7) | Z47767 |
| | Rfe-*Mycobacterium leprae* | UDP-GlcNAc transferase | 28.7 (46.5) | U15186 |
| | Rfe-*M. tuberculosis* | UDP-GlcNAc transferase | 28.5 (46.6) | Z73419 |
| | Rfe-*E. coli* | UDP-GlcNAc transferase | 19.8 (30.3) | M76129 |
| | Rfe-*H. influenzae* | UDP-GlcNAc transferase | 19.1 (29.7) | U32791 |
| WbpM | BplL-*B. pertussis* | dehydratase | 48.4 (59.6) | X90711 |
| | TrsG-*Y. enterocolitica* O3 | UDP-GalNAc biosynthesis | 48.1 (60.0) | Z47767 |
| | CapD-*S. aureus* | unknown | 39.2 (53.9) | U10927 |
| | ORF10-*V. cholerae* O139 | unknown | 32.5 (52.4)[a] | U47057 |
| | ORF11-*V. cholerase* O139 | unknown | 52.7 (61.0)[b] | U47057 |
| WbpN | NifV-*Rhodobacter sphaeroides* | homocitrate synthase | 19.2 (27.1) | Q01181 |

TABLE 3

Amino acid homologies of HisH proteins

| | PA | AB | EC | HI | LL | SC | ST |
|---|---|---|---|---|---|---|---|
| PA | 100.0 | — | — | — | — | — | — |
| AB | 53.6 | 100.0 | — | — | — | — | — |
| EC | 56.1 | 47.4 | 100.0 | — | — | — | — |
| HI | 51.8 | 47.9 | 63.3 | 100.0 | — | — | — |
| LL | 51.0 | 52.6 | 50.0 | 52.3 | 100.0 | — | — |
| SC | 54.9 | 47.9 | 55.1 | 45.2 | 48.0 | 100.0 | — |
| ST | 54.7 | 43.2 | 92.2 | 60.9 | 45.4 | 49.5 | 100.0 |

Amino acid homologies of HisH proteins from various bacterial species. The amino acid sequences of various HisH proteins were aligned pairwise using the PC/GENE PALIGN program with the following parameters: K-tuple value = 1; gap penalty = 5; window size = 10; open gap cost = 10; unit gap cost = 10; filtering level = 2.5. The numbers showns are a summation of identical and conserved amino acid residues. KEY: PA, *Pseudomonas aeruginosa* O5 psb cluster HisH; AB, *Azospirilum brazilense* HisH; EC, *Escherichia coli* HisH; HI, *Haemophilus influenzae* HisH; LL, *Lactobacillus lactis* HisH; RS, *Rhodobacter sphaeroides* HisH; and ST, *Salmonella enterica* typhimurium HisH.

TABLE 4

Amino acid homologies of HisF proteins.

| | Pa | Ab | Ec | Hi | Kp | Ll | Rs | St |
|---|---|---|---|---|---|---|---|---|
| Pa | 100.0 | — | — | — | — | — | — | — |
| Ab | 51.4 | 100.0 | — | — | — | — | — | — |
| Ec | 48.2 | 56.2 | 100.0 | — | — | — | — | — |
| Hi | 50.6 | 52.3 | 87.2 | 100.0 | — | — | — | — |
| Kp | 49.8 | 55.5 | 97.7 | 86.4 | 100.0 | — | — | — |
| Ll | 53.7 | 70.1 | 58.6 | 57.0 | 58.6 | 100.0 | — | — |
| Rs | 44.6 | 81.3 | 54.8 | 46.8 | 54.0 | 63.2 | 100.0 | — |
| St | 49.4 | 56.5 | 97.3 | 87.6 | 96.5 | 58.6 | 55.2 | 100.0 |

Amino acid homologies of HisF proteins from various bacterial species. The amino acid sequences of various HisF proteins were aligned pairwise using the PC/GENE PALIGN program with the following parameters: K-tuple value = 1; gap penalty = 5; window size = 10; open gap cost = 10; unit gap cost = 10; filtering level = 2.5. The numbers showns are a summation of identical and conserved amino acid residues. Key: Pa, *Pseudomonas aeruginosa* O5 psb cluster HisF; Ab, *Azospirilum brazilense* HisF; Ec, *Escherichia coli* HisF; Hi, *Haemophilus influenzae* HisF; Ll, *Lactobacillus lactis* HisF; Rs, *Rhodobacter sphaeroides* HisF; and St, *Salmonella enterica* typhimurium HisF.

TABLE 5

Pairwise comparison of Rol amino acid homologies[1,2]

| | PA | EC1 | EC2 | SF | ST |
|---|---|---|---|---|---|
| PA | 100.0 | 34.4 | 35.1 | 35.4 | |
| EC1 | | 100.0 | 79.3 | 79.0 | 78.6 |
| EC2 | | | 100.0 | 98.1 | 81.5 |
| SF | | | | 100.0 | 81.2 |
| ST | | | | | 100.0 |

[1]Analyses were done using PCGENE PALIGN program.
[2]PA, *Pseudomonas aeruginosa* O5 Rol; EC1, *E. coli* O75 Rol; EC2, *E. coli* O111 CLD; SF, *Shigella flexneri* Rol; ST, *Salmonella enterica* serovar typhimurium strain LT2 CLD. Note that CLD (chain length determinant) is another nomenclature used by some researchers (Bastin et al., 1993) to describe the same class of Rol proteins.

TABLE 6

Bacterial strains and plasmids

| Strain or plasmid | Genotype or relevant characteristics | Reference or source |
|---|---|---|
| *P. aeruginos* | | |
| PAO1 | sertype O5, A+, B+ | Hancock and Carey (1979) |
| AK14O1 | mutant of OT684[a], A+, B-band contains core + one O-repeat unit (SR) | Berry and Kropinski (1986) |
| rd7513 | mutant of AK14O1, A−, B-band contains core + one O-repeat unit (SR) | Lightfoot and Lam (1991) |
| OP5.2 | mutant of PAO1, A+, B-band contains core + one O-repeat unit (SR) | This study |
| OP5.3 | mutant of PAO1, A+, B-band contains core + one O-repeat unit (SR) | This study |
| OP5.5 | mutant of PAO1, A+, B-band contains core + one O-repeat unit (SR) | This study |
| *E. coli* | | |
| DH5n | supE44 hsdR17 recA1 endA1 gyrA96 thi-I relA1 | GIBCO/Bethesda Research Laboratories |
| HB101 | subE44 hsdS20($r^-_B m^-_B$) recA13 ara-14 proA2 lacY1 galK2 rspL20 xyl-5 mtl-1 F− Str$^R$ | Boyer and Roulland-Dussoix (1969) |
| SM10 | thi-1 thr leu tonA lacY supE recA RP4-2-Tc::Mu Km$^R$ | Simon et al. (1983) |
| Plasmids | | |
| pFV100 | pCP13 derivative containing cloned PAO1 O-antigen biosynthetic genes on a 26 kb insert | Lightfoot and Lam (1993) |
| pCP13 | RK2 derivative cos+, Mob+, Tra−, Tc$^R$ Km$^R$ | Darzins and Chakrabarty (1984) |
| pRK404 | RK2 derivative Mob+, Tra−, Tc$^R$ | Ditta et al. (1985) |
| pUCP26 | pUC18-derived broad-host-range vector, Tc$^R$ | West et al. (1994) |
| pEX100T | gene-replacement vector, oriT+, SacB+, Ap$^R$ | Schweizer and Hoang (submitted) |
| pUCPGM | source of Gm$^R$ cassette; Ap$^R$ Gm$^R$ | Schweizer (1993) |
| pBluescript KS (+/−) | Ap$^R$ | PDI Biosciences, Aurora, ON |

[a]OT684 is the immediate progenitor strain of AK14O1 and is a restrictionless mutant of PAO1 (Potter and Loutit, 1982).

TABLE 7

Rfc proteins of *P. aeruginosa* and other gram-negative organisms

| Rfc protein | Total # amino acids | Mol. weight (kD)[a] | Hydropathy index[b] | % G + C[c] | Reference |
|---|---|---|---|---|---|
| *P. aeruginosa* | 438 | 48.9 | 0.8 | 44.8 | This study |
| *S. enterica* (*typhimurium*) | 407 | 47.5 | 0.65 | 33.5 | Collins and Hackett (1991) |
| *S. enterica* (*muenchen*) | 399 | 44.8 | 0.77 | 33.8 | Brown et al. (1992) |
| *Shigella dysenteriae* | 380 | 43.7 | 0.84 | 30.9 | Klena and Schaitman (1993) |
| *Shigella flexneri* | 382 | 43.7 | 1.08 | 27.3 | Morona et al. (1994) |

[a]Molecular weight based on nucleotide sequence.
[b]Hydropathy index deduced from hydrophobicity analysis (Kyte and Doolittle, 1982).
[c]Percentage of the bases G and C in the coding sequence.

TABLE 8

Bacterial strains and plasmids used in this study.

| Strain or plasmid | Genotype, phenotype or properties | Reference/source |
|---|---|---|
| *P. aeruginosa* | | |
| O5 | strain PAO1, wild type A+ B+ | 20 |
| O5 wzz | PAO1, azz insertion mutation at XhoI; A+ B+ | this study |
| IATS O16 | Sertype O16 wild type A− B+ | 33 |
| O16 wzz | Serotype O16 wzz insertion mutation at XhoI; A− B+ | this study |
| *E. coli* | | |
| JM109 | recA1 supE44 endA1 hsdR17 gyrA95 relA1 thi (lac-proAB | 53 |

TABLE 8-continued

Bacterial strains and plasmids used in this study.

| Strain or plasmid | Genotype, phenotype or properties | Reference/source |
|---|---|---|
| SM10 | F'[tra D36, proAb$^+$, lacI$^q$, lacZ(M15)] thi-1 thr leu tonA lacY supE recA RP4-2-Tc::Mu, Km$^R$ | 45 |
| HB101 | F-thi-1 hsdS20 serA ara14 proA2 lacY1 galK2 rpsL20 xyl mtl-1 supE44 recA13 leuB6 Str$^R$ | 27 |
| CLM4 | lacZ2286 trp-49 ((sbcB-rfb)86 upp-12 relA1 rps1150 (-recA | 35 |
| Plasmids | | |
| pFV100 | 24.4 kb XhoI fragment in cosmid pCP13; contains the wbp cluster | 8, 31 |
| pFV400 | 25.0 kb Sau3A1 fragment in pCP13; overlaps pFV100 | this study |
| pFV401 | 2.3 kb HindIII fragment in pBluescript II SK; contains the P. aeruginosa O5 wzz gene | this study |
| PFV401-26 | same insert in pUCP26 | this study |
| pFV401TGm | same insert in pEX100T, with Gm$^R$ cassette inserted at unique XhoI site within wzz | this study |
| pFV403 | 3.0 kg SstI fragment in pBluescript II SK; contains 5 portion of wzz and upstream sequences | this study |
| pBluescript II SK | 2.9 kb cloning vector containing T7 promoter; Ap$^R$ | Stratagene |
| pUCP26 | 4.9 kg pUC18-based broad-host-range vector; Tc$^R$ | 48 |
| pEX100T | gene-replacement vector; oriT$^+$, secB$^+$, Ap$^R$ | 44 |
| pUCPGM | source of gentamicin resistance cassette; Ap$^R$, Gm$^R$ | 44 |

TABLE 9

Amino acid identities/similarities of various wzz-like proteins.

|  | Ec Wzz | Ec o349 | Sf Wzz | Ec O8 St Wzz | Wzz | Ye Wzz | Yp Wzz | Ec FepE | Vc OtnB |
|---|---|---|---|---|---|---|---|---|---|
| Pa Wzz | 19.9 (33.4) | 15.5 (26.5) | 20.0 (35.4) | 19.6 (32.8) | 19.3 (32.9) | 11.5 (19.0) | 13.2 (23.3) | 17.0 (27.3) | 18.8 (30.4) |
| Ec Wzz | 100.0 | 25.1 (35.8) | 65.5 (79.0) | 64.8 (78.6) | 65.2 (80.4) | 19.3 (27.3) | 22.6 (35.4) | 26.9 (39.4) | 18.7 (28.4) |
| Ex 0349 | — | 100.0 | 20.3 (32.0) | 24.8 (37.6) | 21.2 (33.9) | 14.7 (22.7) | 20.7 (31.9) | 19.5 (31.3) | 18.5 (26.3) |
| Sf Wzz | — | — | 100.0 | 72.0 (81.2) | 88.9 (93.6) | 15.7 (25.9) | 20.9 (33.5) | 24.6 (36.6) | 18.8 (25.0) |
| St Wzz | — | — | — | 100.0 | 71.2 (82.6) | 15.6 (23.6) | 22.6 (33.3) | 26.6 (41.9) | 22.6 (32.7) |
| Ec O8 Wzz | — | — | — | — | 100.0 | 15.2 (26.0) | 15.5 (26.9) | 24.7 (36.1) | 15.2 (26.3) |
| Ye Wzz | — | — | — | — | — | 100.0 | 37.3 (56.9) | 25.1 (38.4) | 10.4 (19.7) |
| Yp Wzz | — | — | — | — | — | — | 100.0 | 36.1 (51.8) | 18.2 (29.2) |
| Ec FepE | — | — | — | — | — | — | — | 100.0 | 14.0 (24.2) |

Numbers shown are percent identity, with percent similarity in brackets.
Pa, p. aeruginosa O5, accession U50397; Ex Wzz, E. coli O111, Z17241; Ec o349, E. coli, M87049; Sf Wzz, Shigella flexneri, X71970; St, S. enterica sv Typhimurium LT2, M89933; Ex O8 Wzz, E. coli O8, U39306; Ye Wzz, Yersinia enterocolitica O:8, U43708; Yp Wz pseudotuberculosis, U13685; Ex FepE, E. coli, P26266; Vc OtnB, Vibrio cholerae O139, X90547.

REFERENCES

Alifano, P., Fani, R., Liò, P., Lazcano A., Bazzicalpo, M., Stella Carlomagno, M., and Bruni, C. B. (1996) Histidine biosynthetic pathway and genes: structure, regulation, and evolution. Microbiol Rev 60: 44–69. Allen and Maskell, (1996) The identification, cloning and mutagenesis of genetic loxus required for lipoplysaccharide biosynthesis in Bordetella pertussis. Mol Microbiol 19: 37–52.

Altschul, S. E., G. Warren, W. Miller, E. U. Myers, and D. J. Lipman. 1990. Basic local alignment search tool. J. Mol. Biol. 215:403–410.

Amor, P., and L. Mutharia. (1995) Cloning and expression of rfb genes from Vibrio angulillarum serotype O2 in Escherichia coli: evidence for cross-reactive epitopes. Infect Immun 63: 3537–3542

Ariswa, A., Tsunekawa, H., Okamura, K. and Okamoto, R. (1995) Nucleotide sequence analysis of the carbomycin bisynthetic genes including the 3-O-acyltransferase gene from Streptomyces thermotolerans. Biosci Biotechnol Biochem 59: 582–588.

Arsenault, T. L., Hughes, D. W., MacLean, D. B., Szarek, W. A., Kropinski, A. M. B. and Lam, J. S. 1991. Structural studies on the polysaccharide protion of "A-band" lipolysaccharide from a mutant (AK14O1) of P. aeruginosa strain PAO1. Can J Chem 69: 1273–1280.

Bastin, D. A. G. Stevenson, P. K. Brown, A. Haase, and P. R. Reeves. 1993. Repeat unit polysaccharides of bacteria: a model for polymerization resembling that of ribosomes and fatty acid synthetase, with a novel mechanism for determining chain length. Mol. Microbiol. 7:752–734.

Batchelor, R. A., P. Alifano, E. Biffali, S. I. Hull, and R. A. Hull. 1992. Nucleotide sequences of the genes regulating O-polysaccharide antigen chain length (rol) from *Escherichia coli* and *Salmonella typhimurium*: Protein homology and functional complementation. J. Bacteriol. 174:5228–5236

Bechthold, A., Sohng, J. K., Smith, T. M. Chu, X. and Floss, H. G. (1995) Identification of *Streptomyces violaceoruber* Tu22 genes involved in the biosynthesis of granaticin. *Mol Gen Genet* 248:610–620.

Berry, D., and Kropinski, A. M. 1986. Effect of lipopolysaccharide mutations and temperature on plasmid transformation efficiency in *P. aeruginosa*. *Can J Microbiol* 32:436–438.

Bik, E. M., A. E. Bunschoten, R. J. L. Willems, A. C. Y. Chang, and F. R. Mooi. 1996. Genetic organization and functional analysis of the otn DNA essential for cell-wall polysaccharide synthesis in Vibrio cholerae O139. Mol. Microbiol. 20:799–811.

Binotto, J., MacLachlan, R., and Sanderson, K. E. 1991. Electrotransformation in *Salmonella typhimurium* LT2. *Can J Microbiol* 37:474–477.

Birnboim, H. C., and Doly, J. 1979. A rapid extraction procedure for screening recombinant plasmid. *Nucleic Acids Res.* 7:1513–1523.

Bogdanova, N., Bork, C., and Hell, R. (1995) Cysteine biosynthesis in plants: isolation and functional identification of a cDNA encoding a serine acetyltransferase from *Arabidopsis thaliana. FEBS Lett* 358: 43–47.

Boyer, H. W., and Rotulland-Dussoix, D. 1969. A complementation analysis of the restriction and modification of DNA in *Escherichia coli. J Mol Biol* 41:459–496.

Brown, P. K., Romana, L. K., and Reeves, P. R. 1992. Molecular analysis of the rfb gene cluster of Sali0ionella serovar muenchen (strain M67), the genetic basis of the polymorphism between groups C2 and B. *Mol Microbiol* 6:1385–1394.

Buendia, A. M., Enenkel, B., Koplin, R., Niehaus, K., Arnold W., and Piihler, A. (1991) The *Rhizobium meliloti* exoZ/exoB fragment of megaplasmid 2: ExoB functions as a UDP-glucose-4-epimerase and ExoZ shows homology to NodX of *Rhizobium leguminosarum* biovar viciae strain TOM. *Mol Microbiol* 5: 1519–1530.

Burnette, W. N. 1981. Western blotting: electrophoretic transfer of proteins from sodium dodecyl sulphate-polyacrylamide gels to unmodified nitrocellulose and radiographic detection with antibody and radioiodinated protein A. Anal. Biochem. 112:195–203.

Burrows, L. L., D. Chow, and J. S. Lam. 1997. *Pseudomonas aeruginosa* B-band O antigen chain len,th is modulated by Wzz (Rol). J. Bacteriol. 179: in press.

Burrows, L. L., D. F. Charter, and J. S. Lam. 1996. Molecular characterization of the *Pseudomonas aeruginosa* serotype O5 B-band lipopolysaccharide gene cluster. Mol. Microbiol. 22:481–495.

Collins, L. V., and Hackett, J. 1991. Molecular cloning, characterization, and nucleotide sequence of the rfc gene, which encodes an O-antigen polymerase of *Salmonella typhimurium. J Bacteriol* 173:2521–2529.

Comstock, L. E., Johnson, J. A., Michalski, J. M., Morris, J. G., Jr., and Kaper, J. P. (1996) Cloning and sequence of a region encoding a surface polysaccharide of *Vibrio cholerae* O139 and characterization of the insertion site in the chromosome of *Vibrio cholerae* O1. *Mol Microbiol* 19: 815–826.

Cryz, S. J. Jr., T. L. Pitt, E. Furer, and R. Germanier. 1984. Role of lipopolysaccharide in virulence of *Pseudomonas aeruginosa*. Infect. Immun. 44:508–513.

Daniels, D. L., Plunkett, G., Burland, V., and Blattner, F. R. (1992) Analysis of the *Escherichia coli* genome: DNA sequence of the region from 84.5 to 86.5 minutes. *Science* 257: 771–778.

Darzins, A., and Chakrabarty, A. M. 1984. Cloning of genes controlling alginate biosynthesis froni a mucoid cystic fibrosis isolate of *P. aeruginosa. J Bacteriol* 159:9–18.

Dasgupta, T., and Lam, J. S. Identification of putative rfb genes involved in B-band lipopolysaccharide biosynthesis in *P. aeruginosa* serotype O5. Submitted for publication.

Dasgupta, T., and J. S. Lam. (1995) Identification of rfbA, involved in B-band lipopolysaccharide biosynthesis in *Pseudomonas aeruginosa* serotype O5. Infection and Iiiimunity 63: 1674–1680.

Dasgupta, T., Malburg, S., and Lam, J. S. 1993. *Program Abstr 93rd Gen Meet Amer Soc Microbiol* abstr. D-240.

Davis, E. O., Evans, I. J. and Johnston, A. W. (1988) Identification of nodX, a gene that allows *Rhizobium leguminosarum* biovar viciae strain TOM to nodulate Afghanistan peas. *Mol Gen Genet* 212: 531–535.

Denk, D. and Bock, A. (1987) L-cysteine biosynthesis in *Escherichia coli*: nucleotide sequence and expression of the serine acetyltransferase (cysE) gene from the wildtype, anid a cysteine-excreting mutant. *J Gen Microbiol* 133: 515–525.

de Kievit, T. R., T. Dasgupta, H. Schweitzer, and J. S. Lam. 1995. Molecular cloning and chalacterization of the rfc gene of *Pseudomonas aeruginosa* (serotype O5). Mol. Microbiol. 16:565–574.

de Kievit, T. R., and J. S. Lam. 1997. *Pseudomonas aeruginosa* rfc genes of serotypes O2 and O5 could complement O-polymerase deficienct SR mutants of either serotype. FEMS Microbiol. Letters, in press.

de Kievit, T. R., and Lam, J. S. 1994. *Program Abstr 94th Gen Meet Amer Soc Microbiol abstr.* D-192.

de Kievit, T. R., Dasgupta, T., Schweizer, H., and Lam, J. S. (1995) Molecular cloning and characterization of the rfc gene of *Pseudomonas aeruginosa* (serotype O5). *Mol Microbiol* 16: 565–574.

de Lencastre, H., Chak, K.-F., and Piggot, P. J. 1983. Use of *Escherichia coli* transposon Tn1000 (γδ) to generate mutations in *Bacillus subtilis* DNA. *J Gen Microbiol* 129:3202–3210.

Delic-Attree, I., B. Toussaint, and P. M. Vignais. 1995. Cloning and sequence analyses of the genes coding for the integration host factor (IHF) and HU proteins of *Pseudomonas aeruginosa*. Gene 154:61–64.

Deretic, V., Gill, J. F., and Chakrabarty, A. M. (1987) Gene algD coding for GDPmannose dehydrogeinase is transcriptionally activated in mucoid *Pseudomonas aeruginosa. J bacteriol* 169: 351–358.

Dhillon, N., Hale, R. S., Cortes, J., and Leadlay, P. F. (1989) Molecular characterization of a gene from *Saccharopolyspora erythraea* (*Streptomyces erythraeus*) which is involved in erythromycin biosynthesis. *Mol Microbiol* 3: 1404–1414.

Ditta, G., Schmidhauser, T., Yakobson, E., Su, P., Liang, X.-W., Finlay, D. R., Guiney, D., and Helinski, D. R. 1985. Plasmids related to the broad host range vector, pRK290, useful for gene cloning and for monitoring gene expression. *Plasmid* 13:149–153.

Dodgson, C., P. Amor, and C. Whitfield. 1996. Distribution of the rol gene encoding the regulator of lipopolysaccharide O-chain length in *Escherichia coli* and its influence on the expression of group I capsular K antigens. J. Bacteriol. 178:1895–1902.

Dodgson, C., P. Amor, and C. Whitfield. 1996. Distribution of the rol gene encoding the regulator of lipopolysaccharide O-chain length in *Escherichia coli* and its itlfLuclce on the expression of group I capsular K antigens. J. Bacteriol. 178:1895–1902.

Dubray, G., and G. Bezard. 1982. A highly sensitive periodic acid-silver stain for 1,2-diol grotipos of glycoproteins and polysaccharides in polyacrylamide gels. Anal Biochem 119:325–329.

Falah, M. and R. S. Gupta. 1994. Cloning of the hsp70 (dnaK) genes from *Rhizobium meliloti* and *Pseudomonas cepacia*: phylogenetic analyses of mitochondrial origin baiscd on a highly conserved protein sequence. J Bacteriol 176: 7748–7753.

Farinha, M. A., and Kropinski, A. M. 1990. High efficiency electroporation of *P. aeruginos* using frozen cell suspensions. *FEMS Microbiol Lett* 70:221–226.

Fleischmann, R. D., Adams, M. D., White, O., Clayton, R. A., Kirkness, E. F., Kerlavage, A. R., Bult, C. J., Tomb, J. -F., Dougherty, B. A., Merrick, J. M., McKenney, K., Sutton, G., FitzHugh, W., Fields, C. A., Gocayne, J. D., Scott, J. D., Shirley, R., Liu, I. -I., Glodek, A., Kelley, J. M., Weidman, J. F., Phillips, C. A., Spriggs, T., fledblom, E., Cotton, M. D., Utterback, T. R., Hanna, M. C., Nguyen, D. T., Saudek, D. M., Brandon, R. C., Fine, L. D., Fritchman, J. L., Fuhrmann, J. L., Geoghagen, N. S. M., Gnehm, C. L., McDonald, L. A., Small, K. V., Fraser, C. M., Smith, H. O. and Venter, J. C. (1995) Whole-genome random sequencing and assembly of *Haemophilus influenzae* Rd. *Science* 269: 496–512.

Franco, A. V., D. Liu, and P. R. Reeves. 1996. A Wzz (Cld) protein determines the chain length of K lipopolysaccharide in *Escherichia coli* O8 and O9 strains. J. Bacteriol. 178:1903–1907. Gagnon, Y., Breton, R., Putzer, H., Pelchat, M., Grunberg-Manago, M., and Lapointe, J. (1994) Clustering and co-transcription of the *Bacillus subtilis* genes encoding the aminoacyl-tRNA synthetases specific for glutamate and for cysteile and the first enzyme for cysteine biosynthesis. *J Biol Chem* 269: 7473–7482.

Gish, W., and D. J. States. 1993. Identification of protein coding regions by database similarity search. Nature Genet. 3:266–272.

Glaser, P., Kunst, F., Arnaud, M., Coudart, M. -P., Gonzales, W., Hullo, M. -F., Ionescu, M., Lubochinsky, B., Marcelino, L., Moszer, I., Presecan, E., Santana, M., Schneider, E., Schweizer, J., Vertes, A., Rapoport, G., and Danchin, A. (1993) Baillzvs subtilis genome project: cloning and sequencing of the 97 kb region from 325° to 333°. *Mol Microbiol* 10: 371–384.

Glucksmann, M. A., Reuber, T. L., Walker, G. C. (1993) Genes needed for the modification, polymerization, export, and processing of succinoglycan by *Rhizobium meliloti*: a model for succinoglycan biosynthesis. *J Bacteriol* 175: 7045–7055.

Göhmann, S., Manning, P. A., Alpert, C. A., Walker, M. J., and Timmis, K. N. (1994) Lipopolysaccharide O-antigen biosynthesis in *Shigella dysenteriae* serotype 1: analysis of the plasmid-carried rfp determinant. *Microb Pathog* 16: 53–64

Gold, L., and Stormo, G., (1987) Transcriptional initiation. In *Escherichia coli* and *Salmonella typhimurium*: Cellular and *Molecular Biology*. Vol. 2. Neidhardt, F. C. (ed). Washington, D.C. American Society for Microbiology, pp.807–876.

Goldberg, J. B., K. Hatano, G. Small Meluleni, and G. B. Pier. 1992. Cloning and surface expression of *Pseudomonas aeruginosa* O antigen in *Escherichia coli*. Proc. Nat. Acad. Sci USA 89:10716–10720.

Goldberg, J. B., and D. E. Ohman. 1984. Cloning and expression in *Pseudomonas aeruginosa* of a gene involved with the production of alginate. J. Bacteriol. 158:1115–1121.

Goldberg, J. B., K. Hatano, G. Small Meluleni, and G. B. Pier. 1992. Cloning and surface expression of *Pseudomonas aeruginosa* O antigen in *Escherichia coli*. Proc. Nat. Acad. Sci USA 89:10716–10720.

Goldman, R. C., and L. Leive. 1980. Heterogeneity of antigenic-side-chain length in lipopolysaccharide from *Escherichia coli* O111 and *Salmonella typhimurium* LT2. Eur. J. Biochem. 107:145–153. Gotschlich, 1994.

Hammerschmidt, S., Birklholz, C., Zahringer, U., Robertson, B. D., van Putten, J., Ebelling, O., and Frosch, M., (1994) Contribution of genes from the capsule gene complex (cps) to lipooligosaccharide biosynthesis and serum resistance in *Neisseria meningitidis*. *Mol Microbiol* 11: 885–896.

Hancock, R. E. W., and A. M. Carey. 1979. Outer membrane of *Pseudomonas aeruginosa*: heat- and 2-mercaptoethanol-modifiable proteins. J. Bacteriol. 158: 1115–1121.

Harley, C. B. and R. P. Reynolds (1987) Analysis of *E. coli* promoter sequences. Nucleic Acids Res 15: 2343–2361.

Hashimoto, Y., Li, N., Yokoyama, H. and Ezaki, T. (1993) Complete nucleotide sequence and molecular characterization of ViaB region encoding Vi antigen in *Salmonella typhi*. *J Bacteriol* 175: 4456–4465.

Hitchcock, P. J., and T. M. Brown. 1983. Morphological heterogeneity among *Salmonella* lipopolysaccharide chemotypes in silver-stained polyacrylamide gels. J. Bacteriol. 154:269–277.

Holloway, B. W., Römling, U., Tümmler, B. (1994) Genomic mapping of *Pseudomonas aeruginosa* PAO. Microbiology 140: 2907–2929.

Holloway, B. W., U. Rmling, and B. Tmmler. 1994. Genomic mapping of *Pseudomonas aeruginosa* PAO. Microbiology 140:2907–2929.

Huang, J., and Schell, M. (1995). Molecular characterization of the eps gene cluster of *Pseudomonas solanacearum* and its transcriptional regulation at a single promoter. *Mol Microbiol* 16: 977–989.

Huff, J. P., B. J. Grant, C. A. Penning, and K. F. Sullivan. 1990. Optimization of routine transformation of *Escherichia coli* with plasmid DNA. Biotechniques 9:570–577.

Jarosik, G. P. and E. J. Hansen. 1994. Identification of a new locus involved in expression of *Haemophilus influenzae* type b lipooligosaccharide. Infect Immun 62: 4861–4867.

X. M. Jiang, B. Neal, F. Santiago, S. J. Lee, L. K. Romana & P. R. Reeves (1991). Structure and sequence of the rfb (O antigen) gene cluster of Salmonella serovar typhiiili-rilii (strain LT2).Mol Microbiol 5: 695–713.

Kao, C. C. and L. Sequeira. 1991. A gene cluster required for coordinated biosynthesis of lipopolysaccharide and extracellular polysaccharide also affects virulence of *Pseudomonas solanacearum*. J Bacteriol 173: 7841–7847.

Kearney, B., and Staskawicz, B. J. (1990) Characterization of IS476 and its role in bacterial spot disease of tomato and pepper. *J Bacteriol* 172: 143–148.

Keenleyside W. J., M. Perry, L. Maclean, C. Poppe and C. Whitfield. 1994. A plasmid-encodecl rfb O:54 gene cluster is required for biosynthesis of the O:54 antigen in *Salmonalla enterica* serovar Borreze. Mol Microbiol 11: 437–448.

Keenleyside, W. J., and Whitfield, C. (1995) Lateral transfer of rfb genes: a mobilizable ColE1-type plasmid carries the rfb O:54 (O:54 antigen biosynthesis) gene cluster from *Salmonella enterica* serovar Borreze. *J Bacteriol* 177: 5247–5253.

Keenleyside, W. J., and C. Whitfield. 1996. A novel pathway for O-polysaccharide biosynthesis in *Salmonella enterica* serovar Borreze. J. Biol. Chem. 271:28581–28592.

Kingsley, M. T., D. W. Gabriel, G. C. Marlow & P. D. Roberts. 1993. The opsX locus of *Xanthomonas campestris* affects host range and biosynthesis of lipopolysaccliaride and extracellular polysaccharide. J Bacteriol 175: 5839–50.

Klein, P., Kanehisa, M., and DeLisi, C. 1985. Description of one of the methods used in SOAP. *Biochimica et Biophysica Acta* 815:468–476.

Klena, J. D., and Schnaitman, C. A. 1993. Function of the rfb gene cluster and the rfe gene in the syinthesis of O-antigen by *Shigella dysenteriae* 1. *Mol Microbiol* 9:393–402.

Knirel, Y. A. 1990. Polysaccharide antigens of *P. aeruginosa*. Crit Rev Microbiol 17:273–304.

Knirel, Y. A., and N. K. Kochetkov. 1994. The structure of lipopolysaccharides of Gram-negative bacteria. III. The structure of O-antigens: a review. Biochemistry (Moscow) 59:1325–1383.

Knirel, Y. A., E. V. Vinogradov, N. A. Kocharova, N. A. Paramonov, N. K. Kochetkov, B. A. Dmitriev, E. S. Stanislavsky, and B. Lanyi. 1988. The structure of O-specific polysaccharides and the serological classification of *Pseudomonas aeruginosa*. Acta Microbiol. Hung. 35:3–24.

Kuenzler, M., Balmelli, T., Egli, C. M., Paravicini, G., and Braus, G. H. (1993) Cloning, primary structure, and regulation of the HIS7 gene encoding a bifunctional (lutamine amidotransferase: cyclase from *Saccharomyces cerevisiae*. J bacteriol 175: 5548–5558.

Kuzio, J., and Kropinski A. M. (1983) O-antigen conversion in *Pseudomonas aeruginosa* PAO1 by bacteriophage D3. *J Bacteriol* 155: 203–212

Lacks, S., and J. R. Greenberg. 1977. Complementary specificity of restriction endonucleases of *Diplococcus pneumoniae* with respect to DNA methylation. J. Mol. Biol. 114: 153–168.

Lam, M. Y. C., E. J. McGroarty, A. M. Kropinski, L. A. MacDonald, S. S. Pedersen, N. Hiby, and J. S. Lam. 1989. Occurrence of a common lipopolysaccharide antig,en in standard and clinical strains of *Pseudomonas aeruginosa*. J. Clin. Microbiol. 27:962–967.

Lam, J. S., M. Y. C. Handelsiian., T. R. Chivers, and L. A. MacDonald. 1992. Monoclonal antibodies as probes to examine serotype-specific and cross-reactive epitopes of lipopolysaccharides from serotypes O2, O5, and O16 of *Pseudomionas aeruginosa*. J. Bacteriol. 174:2178–2184.

Lai, C. -Y. and Baumann, P. (1992) Sequence analysis of a DNA fragment from *Buchnera aphidicola* (an endosymbiont of aphids) containing genes homologous to dnaG, rpoD, cysE, and secB. *Gene* 119: 113–118.

Lightfoot, J. L., and J. S. Lam. 1991. Molecular cloning of genes involved with expression of A-band lipopolysaccharide, an antigenically conserved form, in *Pseudomonas aeruginosa*. J. Bacteriol. 173:5624–5630.

Lightfoot, J. L., and J. S. Lam. 1993. Chromosomal mapping, expression and synthesis of lipopolysaccharide in *Pseudomonas aeruginosa*: a role for guanosine diphospho ((JDP)-D-mannose. Mol. Microbiol. 8:771–782.

Liu, D., R. A. Cole, and P. R. Reeves. 1996. An O-antigen processing function for Wzx (RfbX): a promising candidate for O-unit flippase. J. Bacteriol. 178:2102–2107.

Liu, P. V. and S. Wang. 1990. Three new major somatic antigens of *Pseudomonas aeruginosa*. J. Clin. Microbiol. 28:922–925.

Lin, W. S., Cunneen, T. and Lee, C. Y. (1994) Sequence analysis and molecular characterization of genes required for the biosynthesis of type 1 capsular polysaccharide in *Staphylococcus aureus*. J Bacteriol 176: 7005–7016.

Liu, P. V., Matsumoto, H., Ktisama, H., and Bergan, T. 1983. Survey of heat-stable major somatic antigens of *P. aeruginosa*. Int J Syst Bacteriol 33:256–264.

Macpherson, D. F., Mannling, P. A., and Morona, R. (1994) Characterization of the dTDP rhamnose biosynthethic genes encoded in the rfb locus of *Shigella flexneri*. Mol Microbiol 11: 281–292.

MacLachian, P. R., S. K. Kadam, and K. E. Sanderson. 1991. Cloning, characterization, and DNA sequence of the rfaLK region for lipopolysaccharide synthcsis in *Salmonella typhimurium* LT2. J. Bacteriol. 173:7151–7163.

Mäkelä, P. H., and Stocker, B. A. D. 1984. Genetics of lipopolysaccharide, p. 59–137. In E. T. Rietschel (ed.), Handbook of endotoxin, vol. 1. Elsevier Science Publishing, Amsterdam.

Marolda, C. L., and M. A. Valvano. 1993. Identification, expression, and DNA sequence of the GDP-manose biosynthesis genes encoded by the O7 rfb cluster of strain VW187 (*Escherichia coli* O7:K1). J. Bacteriol. 175:148–158.

Marolda, C. L., and Valvano, M. A. (1995) Genetic analysis of the dTDP-rhamnose biosynthcsis region of the *Escherichia coli* VW187 (O7:K1) rfb gene cluster: identification of functional homologs of rfbB and rfbA in the rff cluster and coiri ect location of the rffE gene. *J Bacteriol* 177: 5539–5546.

May, T. B., D. Shinabarger, R. Maharaj, J. Kato, L. Chu, J. D. DeVault, S. Roychoudhury, N. A. Zielinski, A. Berry, R. K. Rothmel, T. K. Misra, and A. M. Chakrabarty. 1991. Alginate synthesis by *Pseudomonas aeruginosa*: a key pathogenic factor in chrixonic pulmonary infections of cystic fibrosis patients. Clin. Microbiol. Rev. 4:191–206.

Meier-Dieter, U., Barr, K., Starman, R., Hatch, L. and Rick, P. D. (1992) Nucleotide sequence of tie *Escherichia coli* rfe gene involved in the synthesis of enterobacteri() common antigen: Molecular cloning of the rfe-rff gene cluster. *J Biol Chem* 267: 746–753.

Morona, R., Mavris, M., Fallarino, A., and Manning, P. A. 1994. Characterization of the rfc region of *Shigella flexneri*. *J Bacteriol* 176: 733–747.

Morona, R., L. van den Bosch, and P. A. Manning. 1995. Molecular, genetic, and topological chateracterization of O-antigen chain length regulation in *Shigella flexneri*. J Bacteriol 177:1059–1068.

Nurminen, M., Hellerqvist, C. E., Valtonen, V. V., and Mäkelä, P. H. 1971. The smooth lipopolysaccharide character of 1, 4, (5), 12 and 1, 9, 12 transductants formed as hybrids between groups B and D of Salmonella. Eur J Biochein 22: 500–505.

Ogasawara, N., Nakai, S. and Yoshikawa, H. (1994) Systematic sequencing of the 180 kilobase region of the *Bacillus subtilis* chromosome containing the replication origin. DNA Res 1: 1–14.

Ozenberger, B. A., M. Schrodt Nahlik, and M. A. McIntosh. 1987. Genetic organization of multiple fep genes encoding ferric enterobactin transport functions in *Escherichia coli*. J. Bacteriol. 169:3638–3646.

Palleroni, N. J. 1984. Genus I. P. p. 141–199. In N. R. Krieg and J. C. Holt. (ed.), Bergey's Manual of Systematic Bacteriology, Vol. 1, Williams and Wilkins, Baltimore.

Peschke, U., Schmidt, H., Zhang, H. Z. and Piepersberg, W. (1995) Molecular characterization ol- the lincomycin-production gene cluster of *Streptomyces lincolnensis* 78–11. *Mol Microbiol* 16: 1137–1156.

Potter, A. A. and Loutit, J. S. 1982. Exonuclease activity from *P. aeruginosa* which is missing in phenotypically restrictionless mutants. *J Bacteriol* 151: 1204–1209.

Prère, M. F., Chandler, M., and Fayet, O. (1990) Transposition in *Shigella dysenteriae*: isolation and analysis of IS911, a new member of the IS3 group of insertion sequences. *J Bacteriol* 172: 4090–4099.

Priefer, U. B., Kalinowski, J., Ruger, B., Heumann, W., and Puhler, A. (1989) ISR1, a transposable DNA sequence resident in Rhizobium class IV strains, shows structural characteristics of classical insertion elements. *Plasmid* 21: 120–128.

Pritchard, A. E., and Vasil, M. L. (1990) Possible insertion sequences in a mosaic genome organization upstream of the exotoxin A gene in *Pseudomonas aeruginosa*. *J bacteriol* 172: 2020–2028.

Quirk, P. G., Guffanti, A. A., Clejan, S., Cheng, J., and Krulwich, T. A. (1994) Isolation of Tn917 insertional mutants of *Bacillus subtilis* that are resistant to the protonophore carbonyl cyanide m-chlorophenylhydrazone. *Biochim Biophys Acta* 1186: 27–34.

Reeves, P. (1993) Evolution of Salmonella O antigen variation by interspecific gene transfer on a large scale. *Trends Genet* 9: 17–22. Reeves, P. R., M. Hobbs, M. Valvano, M. Skurnik, C. Whitfield, D. Coplin, N. Kido, J. Klena, D. Maslcsll, C. Raetz, and P. Rick. 1996. Proposal for a new nomenclature for bacteirial surface polysaccharide genes. Trends Microbiol. 4: 495–503.

Rieder, B., Merrick, M. J., Castorph, H., Kleiner, D. (1994) Function of hisF and hisH gene products in histidine biosynthesis. *J Biol Chem* 269: 14386–14390.

Rivera, M., Bryan, L. E., Hancock, R. E. W. and McGroarty, E. J. 1988. Heterogeneity of lipopolysaccharides from *P. aeruginosa*: analysis of lipopolysaccharide chain leinth. *J Bacteriol* 170:512–521.

Rivera, M., T. R. Chivers, J. S. Lam, and E. J. McGroarty. 1992. Common antigen lipopolysaccharid, from *Pseudomonas aeruginosa* AK1401 as a receptor for bacteriophage A7. J. Bacteriol. 174:2407–2411.

Rossbach, S., D. A. Kulpa, U. Rossbach and F. J. de Bruijn (1994) Molecular and genetic char-acterization of the rhizopine catabolism (mocABRC) genes of *Rhizobium meliloti* L5-30. Mol Gen Genet 245: 11–24.

Ruvkun, G. B., and Ausulbel, F. M. 1981. A general method for site-directed mutagenesis in prok(iryotes. *Nature* (London) 289:85–88.

Schnaitman, C. A., and J. D. Klena. 1993. Genetics of lipopolysaccharide biosynthesis in enteric bacteria. Microbiol. Rev. 57: 655–682.

Schnier, J., M. Kimura, K. Foulaki, A. R. Subramanian, K. Isono, and B. Wittmann-Liebold. 1982. Primary structure of *Escherichia coli* ribosomal protein S1 and of its gene rpsA. Proc. Natl. Acad. Sci. U.S.A. 79:1008–1011.

Schweizer, H. P. 1993. Stall broad-host-range gentamycin resistance gene cassettes for site-specific insertion and deletion mutagenesis. *BioTechniques* 15:831–833.

Schweitzer, H. P., and T. T. Hoang. 1995. An improved system for gene replacement and xylE fusion analysis in *Pseudomonas aeruginosa*. Gene 158:15–22.

Segal G. and E. Z. Ron (1995) The dnaKJ operon of *Agrobacterium tumefaciens*: transcriptional analysis and evidence for a new heat shock promoter J Bacteriol 177: 5952–5958.

Simon, R., Priefer, U., and Pühler, A. 1983. A broad-host-range mobilization system for in vivo genetic engineering: transposon mutagenesis in gram negative bacteria. *Bio/Technology* 1:784–791.

Skurnik, M., Venho, R., Toivanen, P., and Alhendy, A. (1995). A novel locus of *Yersinia enterocolitica* serotype O:3 involved in lipopolysaccharide outer core biosynthesis. *Mol Microbiol* 17: 575–594.

Sokol, P. A., Luan, M. Z., Storey, D. G., and Thirukkumaran, P. (1994) Genetic rearrangement associated with in vivo mucoid conversion of *Pseudomonas aeruginosa* PAO is due to insertion elements. *J Bacteriol* 176: 553–562.

Soldo, B., Lazarevic, V., Margot, P., and Karamata, D. (1993) Sequencing and analysis of the divergon comprising gtaB, the structural gene of UDP-glucose pyrophosphorylase of *Bacillus subtilis* 168. *J Gen Microbiol* 139: 3185–3195.

Stutzman-Engwall, K. J., Otten, S. L., and Hutchinson, C. R. (1992) Regulation of secondary metabolism in Streptomyces spp. and overproduction of daunorubicin in *Streptomyces peucetius*. *J Bacteriol* 174: 144–154.

Sturm, S. and K. N. Timmis. 1986. Cloning of the rfb region of *Shigella dysenteriae* 1 and construction of an rfb-rfp gene cassette for the development of lipopolysaccharide-based live anti-dysentery vaccines. Microb. Pathog. 1:289–297.

Tabor, S., and C. C. Richardson. 1985. A bacteriophage T7 RNA polymerase/promoter system for controlled exclusive expression of specific genes. Proc. Nat. Acad. Sci. USA 82:1074–1078.

Takagi, M., Takada, H., and Imanaka, T. (1990) Nucleotide sequence and cloning in *Bacillus subtilis* of the *Bacillus stearothermophilus* pleiotropic regulatory gene degT. *J Bacteriol* 172: 411–418.

Tercero, J. A., Espinosa, J. C., Lacalle, R. A. and Jimenez, A. (1996) The biosynthetic pathway of the aminonucleoside antibiotic puromycin, as deduced from the molecular analysis of the pur cluster of *Streptomyces alboniger*. *J Biol Chem* 271: 1579–1590.

Thorson, J. S., Lo, S. F., Ploux, O., He, X., and Liu, H. -W. (1994) Studies of the biosynthesis of 3,6-dideoxyhexoses: molecular cloning and characterization of the asc (ascarylose) region from *Yersinia pseudotuberctilosis* serogroup VA. *J Bacteriol* 176: 5483–5493.

West, S. E. and Iglewski, B. H. (1988) Codon usage in *Pseudomonas aeruginosa*. Nucleic Acids Res 16: 9323–9335.

West, S. E. H., H. P. Schweizer, C. Dall, A. K. Sample, and L. J. Runyen-Janecky. 1994. Construction of improved *Escherichia-Pseudomonas* shuttle vectors derived from pUC18/19 and the sequence of the region required for their replication in *Pseudomonas aeruginosa*. Gene 128: 81–86.

West, S. E. H., Schweizer, H. P., Dall, C., Sample, A. K., and Runyen-Janecky, L. J. (1994) Construction of improved *Escherichia-P.* shuttle vectors derived from pUC18/19 and the sequence of the region required for their replication in *P. aeruginosa*. Gene 128:81–86.

Whitfield, C. 1995. Biosynthesis of lipopolysaccharide O-antigens. Trends Microbiol. 3:178–185.

Whitfield, C., and M. A. Valvano. 1993. Biosynthesis and expression of cell-surface polysaccharid es in gram-negative bacteria. Adv. Microb. Physiol. 35:135–246.

Wozniak, D. J. 1994. Integration host factor and sequences downstream of the *Pseudomonas aeruginosa* algD transcription start site are required for expression. J. Bacteriol. 176:5068–5076.

Wozniak, D. J., and D. E. Ohman. 1993. Involvement of the alginate algT gene and integration host factor in the regulation of the *Pseudomonas aeruginosa* algB gene. J Bacteriol 175: 4145–4153.

Wood, M. S., Byrne, A., and Lessie, T. G. (1991) IS406 and IS407, two gene-activating insertion sequences from *Pseudomonas cepacia*. Gene 105:101–105.

Xiao, Q. and Moore, C. H. (1993) The primary structure of phosphofructokinase from *Lactococcus lactis. Biochem Biophys Res Commun* 194: 65–71.

Yanisch-Perron, C., J. Vieira, and J. Messing. 1985. Improved M13 phage cloning vectors and host strains: nucleotide sequences of the M13mp18 and pUC19 vectors. Gene 33: 103–119

Detailed Figure Legends for FIGS. 22 to 29, 32, 33, and 43 to 47

FIG. 22. Silver-stained SDS-PAGE gel of LPS from PAO1, AK14O1, AK14O1(pFV100), and AK14O1(pFV.TK8) (Panel A) and Westernimmunoblots of this LPS reacted with O5-specific MAb MF15-4 (Panel B). Note that the two transconjugants strains, AK14O1(pFV100) and AK14O1 (pFV.TK8), produce levels of B-band LPS similar to the PAO1 wild-type strain.

FIG. 23. Restriction maps of the chromosomal inserts from pFV100 and several pFV subclones. Results of complementation studies of the SR mutants AK14O1 and rd7513 with the pFV subclones are also shown. The three Tn1000 insertions in the 1.5 kb XhoI fragment of pFV.TK6 that were found to interrupt O-antigen complementation in AK14O1 are indicated. This XhoI fragment was later purified and used as a probe in Southern blot analysis. Restriction sites: B, BamHI; X, XhoI; S, SpeI; Xb, XbaI; H, HindIII.

FIG. 24. Southern analysis the three rfc chromosomal mutants, OP5.2, OP5.3, and OP5.5, showing the insertion of an 875 bp $Gm^R$ cassette into the rfc gene. Restriction maps of the PAO1 wild-type (panel A) and mutant (panel B) rfc coding, regions are shown. Southern hybridizations of chromosomal DNA from PAO1 (lane 1) and mutants OP5.2, OP5.3, and OP5.5 (lanes 2–4, respectively) digested with XhoI were performed using an rfc probe (panel C). This DIG-labelled probe was generated from the 1.5 kb XhoI insert of pFV.TK7 (shown in panel A). The probe hybridized to a 1.5 kb fragment of PAO1 and a 2.4 kb fragment of thethree rfc mutants. The molecular size of the probe-reactive fragments are shown on the left (in kb).

Figure 25:
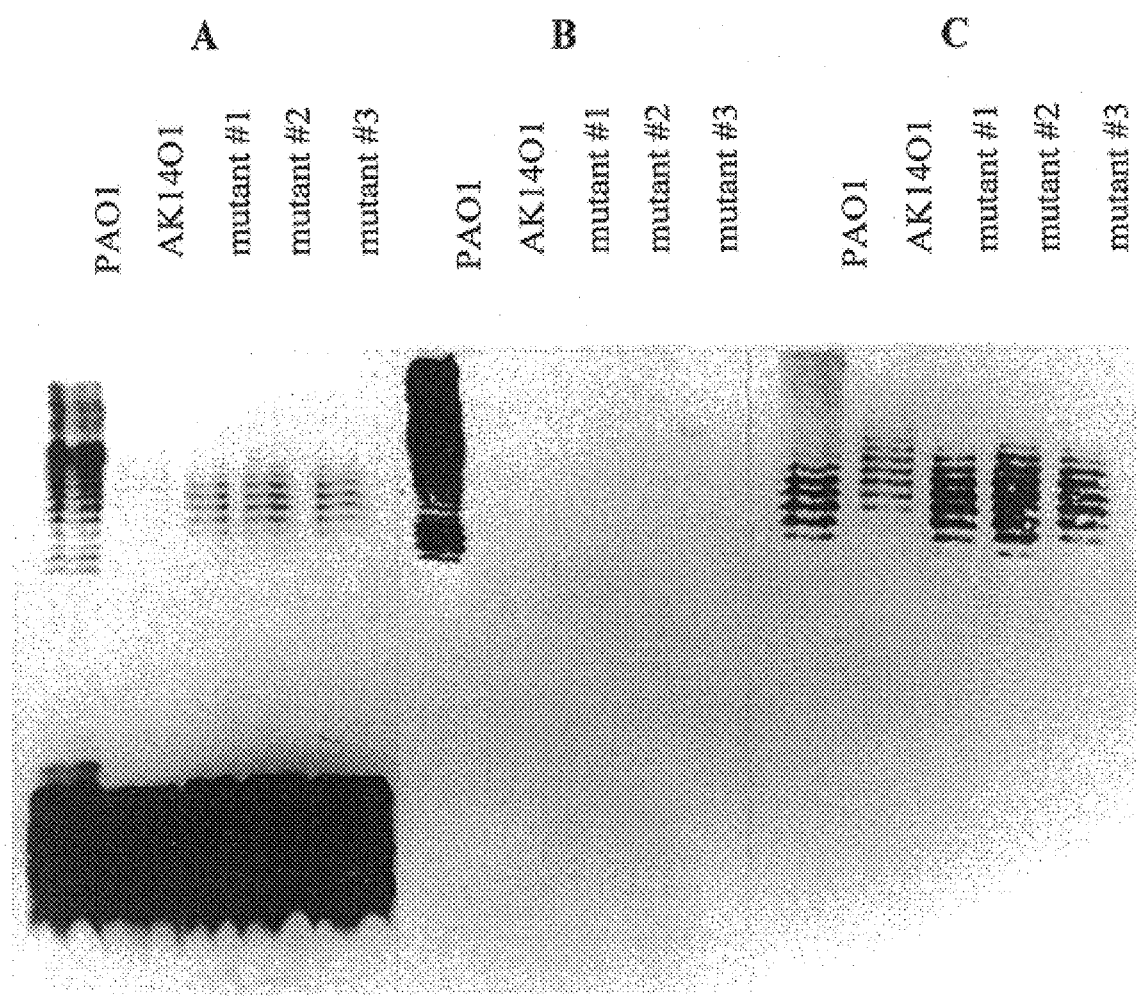
FIG. 25A shows a silver-strained SDS-PAGE gel LPS from PAO1, AK14O1 and the three rfc (wzy) chromosomal mutants, PO5.2, OP5.3, and OP5.5.
FIG. 25B shows a Western blot of LPS from PAO1, AK14O1 and the three rfc (wzy) chromosomal mutants PO5.2, OP5.3, and 0P5.5.
FIG. 25C shows a from PAO1 AK14O1 and the three rfc (wzy) chromosomal mutants PO5.2, OP5.3, and OP5.5.

FIG. 25. Silver-stained SDS-PAGE gel and Western blots of LPS from PAO1, AK14O1 and the three rfc chromosomal mutants, OP5.2, OP5.3, and OP5.5. Panel A: silver-stained SDS-PAGE gel; Panel B: Western blot reacted with O5-specific MAb MF15-4; Panel C: Western blot reacted with A-band specific MAb N1F10. Note that the chromosomal rfc mutants are not able to produce long-chain O-antigen; however, they are still expressing A-band LBS, like the SR mutant AK14O1.

FIG. 26. Restriction maps of recombinant plasmids pFV161, pFV401 and pFV402. Tihe shaded box represents the DIG-labeled probe generated from pFV161. Restriction sites: B, BamHI; H, HindIII; X, XhoI.

FIG. 27. Southern hybridizations of chromosomal DNA from PAO1 (lane 2) and rol mutants (lanes 3&4). Chromosomal DNA in Panel A was digested with PstI and SstI. DNA in Panel B was digested with HindIII. The samples in Panel A were probed with the $Gm^R$ cassette (Schweizer, 1993). The probe used in Panel B is the 2.3 kb HindIII insert from pFV401. Molecular weight markers, using λ DNA digested with HindIII, are indicated to the left of each panel.

FIG. 28. Characterization of LPS from PAO1 and PAO1 rol chromosomal mutants. The samples in each lane are as labeled. Panel A is a silver-stained SDS-PAGE gel. Panel B is the corresponding Western immunoblot reacted with an O5 (B-band)-specific mAb MF15-4.

FIG. 29. T7 protein expression of *P. aeruginosa* O5 Rol. This autoradiogram shows $^{35}$S-labeled proteins expressed by pFV401, which contains the ro! senie, and corresponding control plasmid vector pBluescript II SK in *E. coli* JM109DE3 by use of the T7 expression system. The arrow indicates the putative Rol protein. Molecular size markers are indicated to the left of the figure.

FIG. 32. Features of the initiation regions. Capital letters for bases indicate one of the following sites: potential ribosomal binding sites (RBS), the presumed start codon (also in bold and double underlined), the second codon where it is AAA (the preferred second codon), and components of the sequences TTAA and AAA from +10 to+13 and from −1 to −3 respectively (Gold and Stormo, 1987). The termination codon of the preceding gene is indicated by a bar above if it is in the region shown. The reference sequences involved are also shown above the set of sequences.

FIG. 33. NAD-binding domains of PsbA, PsbK and PsbM aligned with those of other bacterial proteins involved in polysaccharide biosynthesis. The consensus sequence for an NAD-binding domain (Macpherson et al., 1994) is shown at the bottom of the figure in bold underline. The first column contains the protein names; the second column indicates the location of the NAD-binding site within the protein; the third column shows the alignment of the NAD-binding domains with highly conserved residues indicated in bold type; and the fourth column gives the reference for the protein shown. Most of the proteins in this group of sugar biosynthesis enzymes function as dehydrogenases/dehydratases. Note that PsbM, BplL, and TrsG have two putative NAD-binding domains, instead of one. The presence of two domains supports the proposal that these large proteins arose from fusion of two smaller proteins.

FIG. 43. Physical map of the 5 end of the wbp cluster. The wzz gene ends approximately 800 bp upstream of wbpA, the first gene of the wbp cluster (8). The probe used to identify a HindIII fragment containing the intact wzz gene for clioining into pFV401 is shown as a black bar above the restriction map. The site of insertion of the gentamicin cassette used to create the wzz knockout mutants is indicated by a black triangle. Key: B, BamHI; H, HindIII; S, SstI; X, XhoI.

FIG. 44. Comparison of hydropathy plots of selected Wzz-like proteins. The hydropathy plots of selected Wzz-like proteins were calculated using PC/GENE SOAP. The X axis represents amino acid residues, while the Y axis represents relative hydropathy. Positive values indicate hydrophobicity; negative values indicate hydrophilicity. A, *P. aeruginosa* O5 Wzz, U50397; B, *E. coli* 0111 Wzz, Z17241; C, *E. coli* o349, M87049; D, *E. coli* FepE, P26266; E, *Y. enterocolitica* O8 Wzz, U43708; F, *Y. pseudotuberculosis* Wzz, ; G, *V. cholerae* O139 OtnB, X90547.

FIG. 45. Expression of *P. neruginosa* Wzz in vitro. The 40 kDa Wzz protein (indicated by black arrowhead) was expressed from the insert of pFV401 in both orientations. A 28 kDa protein was also expressed in both orientations and may represent either a breakdown product of the 40 kDa polypeptide, or initiation of translation from a secondary ribosome-binding site. There are several smaller ORFs encoded on the positive strand of the 2.3 kb insert of pFV401 which could correspond to the 10 kDa protein.

FIG. 46. Analysis of LPS from wzz knockout mutants. LPS from *P. aeruginosa* serotypes O5 and O16 and their corresponding wzz mutants was examined. FIG. 46A: Silver-stained 12.5% SDS-PAGE. FIG. 46B: Western immunoblot using MAb 18-19, specific for B-band LPS from the O5 serogroup (serotypes O2, O5, O16, O18, O20). FIG. 46C: Western immunoblot using MAb MF15-4, specific for serotype O5 B-band LPS. The plasmid pFV401-26 contains the O5 wzz gene cloned downstream of the lacZ promoter of shuttle vector pUCP26.

Figure 47:
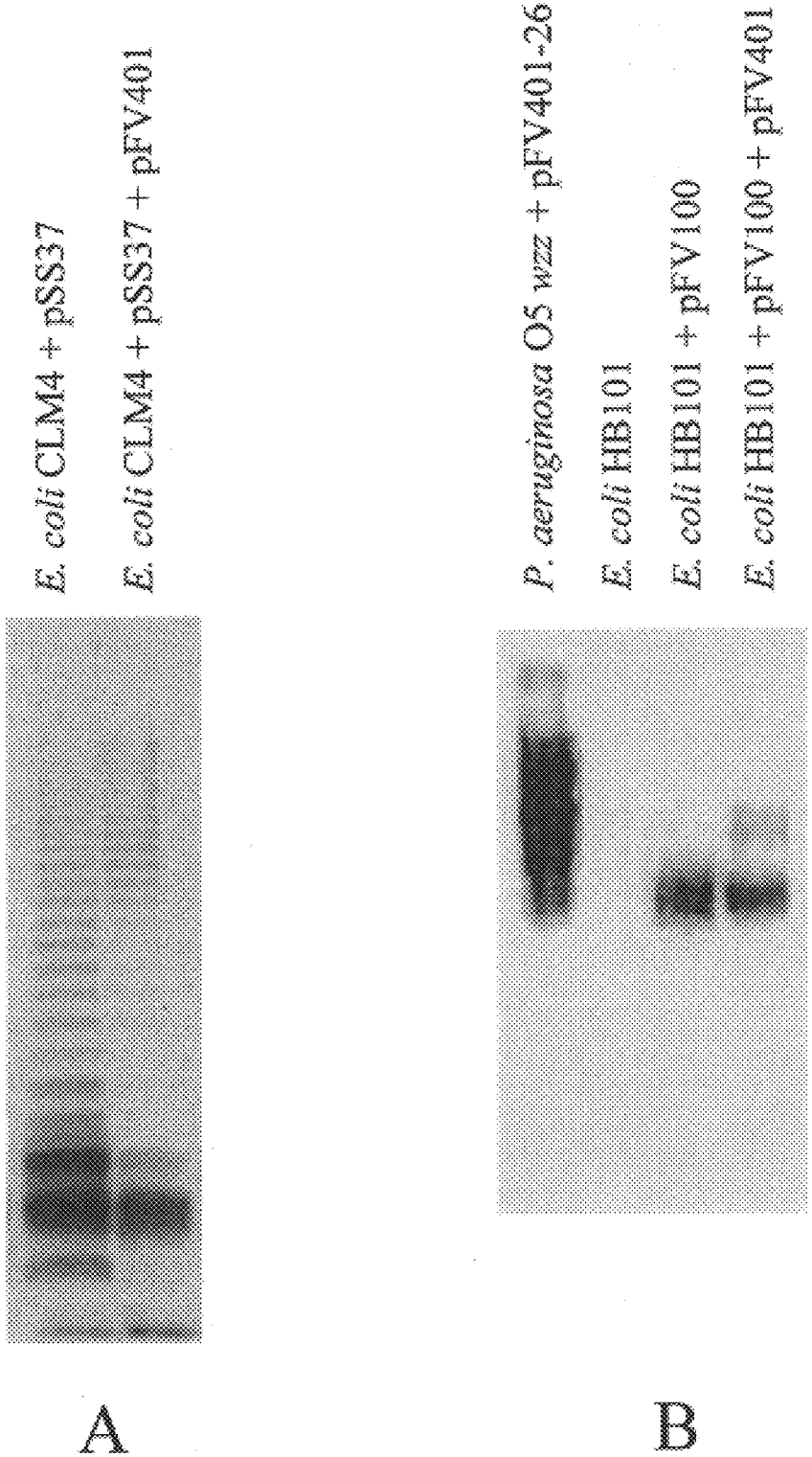
FIG. 47A shows a silver-stained SDS-PAGE gel of E. coli CLM4 which illustrates the ability of P. aeruginosa O5 Wzz to function in E. coli.
FIG. 47B shows a Western immunoblot of E. coli HB101 containing the P. aeruginosa O5 wbp cluster in pFV100, illustrating the ability of P. aeruginosa O5 Wzz to function in E. coli.

FIG. 47. Ability of P. aeruginosa O5 Wzz to function in E. coli.
Panel A. Silver-stained SDS-PAGE gel of E. coli CLM4 containing the Shigella dysenteriac rfb cluster on pSS37, with and without the P. aeruginosa wzz gene in pFV401.
Panel B. Western immunoblot of E. coli HB101 containing the P. aeruginosa O5 wbp cluster in pFV100, with and without the P. aeruginosa wzz gene in pFV401. The membrane was incubated with MAb MF15-4, specific for serotype O5 B-band LPS.

FIG. 48. Western immunoblot analysis of lipopolysaccharide (LPS) isolated using the hot water-phenol method of Westphal and Jann. Lanes O5 are LPS from the parent strain, while lanes F1 and F2 are LPS from two mutants containing a gentamicin cassette inserted at the SstI site within the open reading frame of wbpF. The monoclonal antibodies used are N1F10, specific for A-band LPS, and 18-19, specific for B-band LPS. Note that a knockout mutation of wbpF abrogates both A-band and B-band LPS expression.

We claim:

1. An isolated *P. aeruginosa* B-band gene cluster containing the following genes: wzz, wbpA, wbpB, wbpC, wbpD, wbpE, wzy, wbpF, wbpG, wbpH, wbpI, wbpJ, wbpK, wbpL, wbpM and wbpN involved in the synthesis, and assembly of lipopolysaccharide in *P. aeruginosa*.

2. An isolated *P. aeruginosa* B-band gene cluster as claimed in claim 1 wherein the genes are organized as shown in FIG. 1 (SEQ.ID.NO:1).

3. An isolated nucleic acid molecule encoding:
   (a) Wzz; (b) WbpA; (c) WbpB; (d) WbpC; (e) WbpD; (f) WbpE; (g) Wzy; (h) WbpF; (i) WbpG; (j) WbpI; (k) WbpJ; (l) WbpK; (m) WbpM; (n) WbpH; and (o) WbpN involved in *P. aeruginosa* O-antigen synthesis and assembly.

4. A recombinant molecule adapted for transformation of a host cell comprising a nucleic acid molecule as claimed in claim 3 and an expression control sequence operatively linked to the nucleic acid molecule.

5. A method for detecting the presence of a nucleic acid molecule as claimed in claim 3 in a sample, comprising contacting the sample with a nucleotide probe which hybridizes with the nucleic acid molecule under high stringency conditions, to form a hybridization product, under conditions which permit the formation of the hybridization product, and assaying for the hybridization product.

6. A method for detecting the presence of a nucleic acid molecule as claimed in claim 3, or a predetermined oligonucleotide fragment thereof in a sample, comprising treating the sample with primers which amplify the nucleic acid molecule or the predetermined oligonucleotide fragment thereof in a polymerase chain reaction to form amplified sequences under conditions which permit the formation of amplified sequences, and assaying for amplified sequences.

7. A kit for detecting the presence of a nucleic acid molecule as claimed in claim 3 in a sample comprising a nucleotide probe which hybridizes with the nucleic acid molecule under high stringency conditions, reagents required for hybridization of the nucleotide probe with the nucleic acid molecule, and directions for its use.

8. A transformant host cell including a recombinant molecule as claimed in claim 4.

9. An isolated nucleic acid molecule encoding *P. aeruginosa* WbpM.

10. A recombinant molecule adapted for transformation of a host cell comprising a nucleic acid molecule as claimed in claim 9, and an expression control sequence operatively linked to the nucleic acid molecule.

11. A transformed host cell including a recombinant molecule as claimed in claim 10.

12. An isolated nucleic acid molecule encoding *P. aeruginosa* WbpL.

13. A recombinant molecule adapted for transformation of a host cell comprising a nucleic acid molecule as claimed in claim 12, and an expression control sequence operatively linked to the nucleic acid molecule.

14. A transformed host cell including a recombinant molecule as claimed in claim 13.

* * * * *

SEQUENCE LISTING

<160> NUMBER OF SEQ ID NOS: 100

<210> SEQ ID NO 1
<211> LENGTH: 24417
<212> TYPE: DNA
<213> ORGANISM: Pseudomonas aeruginosa

<400> SEQUENCE: 1

```
ctcgagatat tgagcagcgc atacagaact tgcggagaga atgccaaggc agacgtgaag  60
atcgtattgt tcagctcaag gaggcgttga aggtcgcagg tgcgctgaaa ttggaggagc 120
ctccactgat cagtgggcaa tcctctgagg agctctcggc tatcatgaat ggaagtctga 180
tgtatatgcg tggcagtaag gcgattatgg ccgagattca gacattggag gcgcgtagct 240
ctgatgatcc ttttattccg gcgttgcgta ctcttcagga gcagcagtta ttgctgagta 300
gcttgcgtgt taattcggag cgggtttctg tttttcgaca agacggtccg atagaaacgc 360
cggactcacc agttcgtcca aggagagcga tgattttgat ttttgggttg ataattggtg 420
gtgtgcttgg tggtttttctg gcgttgtgcc ggattttttt gaagaagtat gctcgttagg 480
aaagagctag ttattgaagt ggtgatgcgt tgcacgtact ttggtcgagt aattttgtgg 540
agtaggtttt cgttgggtgg ctcgattgct gaggggtgag aacgtttcca tgccgtgttt 600
cctcagctct gtctcctgtg ccttggctcc ttgaacgcag aggttaacag ttgagctgtg 660
gttgtgggta tgtgacgtct gttgcggtgg tgtctggttc ctggtgtcgg gtgtgcgaga 720
agatgccaag ttgcctggca ggtcgttacg tgtcgtagcc gtattcgaag ctcggcaatc 780
gcggggtgat ttacaggact gtgcttaata cggcgcaggc ttggtcaggg tcgagtcggg 840
tcttcgggtg tcaactggat cgtgcgaaaa ccggtttcgt ggatgctgat aagctcggct 900
tgactggcag tccagggcgg ttaccaggtc tgtggaggcg caaaatgtat aggagcctgc 960
gtgagctggg caggctgaag gcctgctcga aagcgagtta gcattgtggt ccggaagggc 1020
atgggtggac cagagtgccg ttctgcacgg caaaagccaa cttgctcgga ggttccctag 1080
cgcctatgat tacgacgccc ttcattttg gccattgccg ccaggtgctg tggaaagcga 1140
cagtatccct tctttatcga tcttgtgaag atgtcgagag tggtcgcaga aaggattcac 1200
tcgactgacg aatgaatcgt ggaagattta agttcccgtt gtgcggtcgc aggcgcgggc 1260
aggtaaaatt gaggtgagtt ggaaaatgat agatgttaac acagtggtag agaagttcaa 1320
aagccgacag gccttgattg gtatcgtggg tctgggttat gtcggtttac cactgatgct 1380
gcgatacaac gccattggtt tcgatgtctt gggtatcgat atcgatgatg tcaaggttga 1440
caagcttaat gccgggcagt gctatatcga acatattccg caagccaaaa ttgctaaggc 1500
ccgtgcaagc ggtttcgagg ctacgaccga tttcagccgt gtcagtgaat gtgatgccct 1560
gatcctttgt gtgccgacgc cgctgaacaa gtatcgcgag ccggatatga gctttgtcat 1620
caataccacc gacgcactaa aaccgtatct gcgcgtaggg caggtggttt cgctggaaag 1680
taccacctat ccgggaacta ccgaggaaga gttgttgcca ccgcgtgcagg agggtggcct 1740
cgtggttggc cgggacatct acctggtcta ttctccggag cgtgaagatc cgggcaaccc 1800
gaacttcgag actcgtacca ttccgaaagt gatcggtggt cacactcctc agtgtctgga 1860
agtcggcatt gccctgtatg aacaggccat cgaccgggtc gtgccggtca gttccaccaa 1920
ggccgccgag atgaccaagc tgttggagaa cattcatcgc gcggtcaata tcggtctggt 1980
caacgaaatg aagatcgttg ctgatcgcat gggtatcgac atctttgaag tggttgatgc 2040
tgcggcgacc aagccgttcg gtttcactcc ttactaccca gggccgggac tgggcgggca 2100
ctgtatcccg atcgatccct tctacctgac ttggaaggct cgcgaatacg gactgcatac 2160
ccgcttcatc gaactgtctg gtgaggtcaa ccaggccatg cggtaatacg tactgggcaa 2220
actcatggat ggcctgaacg aggcaggcag ggccctcaag ggcagtcgtg tactggtatt 2280
gggtatcgct tataagaaga atgtcgacga catgcgcgag tcgccatccg tggaaatcat 2340
ggagctgatc gaagccaagg gtgggatggt cgcctatagc gatccgcatg tgccggtgtt 2400
cccgaagatg cgtgaacacc acttcgaact gacagtgag ccgctgactg ccgaaaacct 2460
ggctaggttc gacgctgtag tgcttgcgac cgaccatgac aagtttgact atgagctgat 2520
caaggccgaa gccaagctag ttgttgacag ccgtggcaag taccgctccc cggcggcaca 2580
catcatcaag gcttgatcac ccatcccagc atgtccatcc gctcgtgcca gaaggccggg 2640
cggatccgct catttccata ggacgaacca tgaaaaattt cgctctcatc ggtgctgccg 2700
gctacatcgc tcctcgccat atgcgcgcca tcaaagacac cggtaactgc ctggtttcgg 2760
cctatgacat caatgactcg gtcggtatta ttgatagcat ctctcccag agcgagtttt 2820
ttaccgagtt cgagttcttt cttgatcatg cgagcaacct caagcgcgac tctgctaccg 2880
cgctggacta cgtatcgatc tgctcgccca attacctgca ctaccccgcat atcgctgcag 2940
gtctgcgctt gggttgcgac gtaatctgcg aaaagccgct tgttccaacc ccagagatgc 3000
tcgatcagtt ggctgttatc gagcgcgaaa ccgataagcg cctctacaac attctgcaac 3060
tgcgtcatca ccaggcgatc atcgcattga aggacaaggt cgcccgcgaa aaaagtccgc 3120
ataagtacga ggtcgatctg acttacatta cttcccgcgg caactggtat ctgaaaagct 3180
ggaagggaga tccacgtaag tcgttcggcg tggctaccaa catcggtgtg cacttctacg 3240
acatgctgca cttcatcttt ggcaagctgc agcgtaatgt tgtgcacttc acttccgagt 3300
```

-continued

```
acaagacagc tggttatctg gagtacgagc aggcccgtgt gcgttggttt ctgtccgtgg 3360
atgctaacga cctgccggag tcggtcaagg gcaaaaagcc gacctatcgt tcgattaccg 3420
tcaacggtga ggaaatggag ttctctgaag gctttaccga tctacataca accagctacg 3480
aagaaattct cgctggtcgt ggttatggca tcgatgacgc tcgtcattgt gtggaaactg 3540
tcaataccat tcgcagcgcc gtcatcgtac cggcctctga taacgaaggg catccgttcg 3600
tcgcggcgct tgcgcgttga ggtagaaaag gagtggccgt cctcggtcac ctgtttacag 3660
caggtttccg caggatcatt catcagcatg tcatcagta gctctaaatt gctgaacggt 3720
atggtcgcgg taagttcagg cagaaacatt cggctggatg tccaggggct gcgggctgtt 3780
gcagttctgg ctgtgctagc ttaccacgcc aacagtgcct ggctcagggc tgggttgtc 3840
ggcgttgacg tgttcttcgt catttccggg tttatcatta ccgccttact ggtcgagcgc 3900
ggtgtaaaag ttgatctggt agagttttac gcgggccgta tcaaacgtat ttttccagcc 3960
tatttcgtca tgttggcgat tgtctgcatt gtctcgacaa ttctgtttct gcctgatgac 4020
tatgttttt ttgaaaaaag tctacagtca tctgtatttt tttccagtaa tcactatttc 4080
gctaattttg gtagttactt tgctccgaga gctgaagagc tgccgctgct gcatacttgt 4140
tcaatagcca acgagatgca gttttatctg ttctaccctg tactgttcat gtgcctgcca 4200
tgtcgatggc gcttgccggt gttcatccta ttagctattt tgctgttcat tgcgagtggc 4260
tattgcgtat tcagcggcag ccaagatgct cagtacttcg ccttgctagc tcgtgtacct 4320
gagttcatgt cgggagctgt tgtcgcatta tcattacgtg atcgtgagct acccgccagg 4380
cttgcgatac ttgcggggtt attgggggcg gcgttgctgg tctgctcctt cattatcatc 4440
gacaagcagc actttcccgg attctggctg ctcctgccat gcctgggagc cgctctgctc 4500
attgctgccc gacgtggccc tgccagcctg ctgctggcca gcaggcccat ggtctggata 4560
ggtggtatct cctattcgtt gtatctgtgg cactgtccaa ttctggcatt catccgttac 4620
tacaccggcc aatacgaatt gagcttcgtg gcgctgttgg catttctcac aggttcgttc 4680
ctgctggcct ggttctcata ccgctacatc gagacacctg ccagaaaggc tgtgggtctg 4740
cgccagcagg cgctgaagtg gatgttggcc gccagtgtgg tagctatagt ggttacgggg 4800
ggggcgcagt tcaatgtgtt ggttgtggcg ccggcgccaa ttcagttgac gcgctacgct 4860
gtaccagagt cgatctgcca tggtgttcag gtaggggagt gcaagcgagg cagcgtcaat 4920
gccgtacccc gtgtgctggt gatcggtgat agccatgcgc cgcacgttaa ctacttcttc 4980
gacgtggttg gcaacgagtc aggtgtggct taccgagtac tcaccggaag cagttgtgtg 5040
ccaatacctg ctttcgatct tgaacgtttg ccccgttggg cgcggaaacc ctgccaagcg 5100
cagattgatg cagttgccca atcaatgttg aactttgaca agatcattgt ggcgggcatg 5160
tggcagtatc agatgcagag tccggcattt gcccaggcta tgcgtgcctt ccttgtcgat 5220
accagctctg ccggcaagca ggtcgctcta ctcgggcaga taccgatgtt cgaatcaaac 5280
gtgcagcgtg tgcgtcgttt cagggagctg ggtttgtcag ctccgcttgt tagctccagc 5340
tggcaaggtg cgaaccagct gttgcgtgct ctagccgagg gtattccaaa cgtacggttc 5400
atggattttt cttccagcgc cttcttcgcc gatgctcctt atcaggacgg agagcttatt 5460
taccaggata gccatcacct taacgaggtg ggggctcgcc gctatggata tttcgcgagc 5520
cgtcaattgc agcggctgtt tgaacaacca caatcgagtg tgagtctcaa gccatgagtt 5580
attatcagca ccccagcgcg atcgtcgacg acggtgcgca gatcggtagc gactcccgag 5640
tttggcactt cgtgcacatc tgtgcaggtg cccggattgg cgcagggggtt tcgttgggtc 5700
agaacgtatt cgtcggcaac aagtcgtta ttggtgatca ctgcaagatc cagaacaacg 5760
tgtcggtata tgacaatgtc actctcgaag agggcgtgtt ctgcgggccg agcatggtat 5820
ttaccaacgt ttacaacccc cgctcgttga tcgagcgcaa ggatcagtac cgtaacacgt 5880
tggtaaaaaa aggtgccacg cttggtgcca actgcactat cgtctgtggc gtgactattg 5940
gtgaatatgc cttcctgggt gcgggtgcgg tcattaacaa gaatgttcca tcttatgccc 6000
tgatggtagg cgtgcccgct cgacagattg gttggatagc gaattcggtg agcagctgca 6060
gctgaacgag cagggcgaag ctgtctgctc acactccggt gcgcgctatg tactcaatgg 6120
aaagatcctg agcaaggtgg acgtgtgacc atgattgaat tcatcgacct gaagaaccag 6180
caagcgcgta tcaaggacaa gatcgatgcc ggtatccagc gcgtgctgag acacgggcag 6240
tacattcttg gcccggaagt cactgagctt gaggatcgcc tcgccgattt cgtcggcgct 6300
aagtactgca tcagttgcgc caacggtact gacgctctac agattgtgca gatgcgcttg 6360
ggtgttggcc caggtgacga agtaatcacc cctggtttta cttatgttgc gacagcggag 6420
accgtcgcgc tttttgggagc caagccggtt tacgtggata ttgatccacg cacctacaat 6480
cttgatccgc agttgctgga ggctgcgatc acaccgcgta cgaaggctat cattcctgtt 6540
tcgctgtatg gccagtgtgc agacttcgat gcaatcaacg ccattgcctc caaatatggt 6600
atccctgtca ttgaggatgc tgcacagagc ttcggtgctt cgtacaaggg taagcgttct 6660
tgtaatctga gtaccgttgc ctgcaccagc ttcttcccga gcaaaccgtt gggttgctat 6720
ggggatggtg gagcgatctt cactaacgac gatgaactgg ctactgctat tcgtcaaatt 6780
gcccgggcatg gtcaggaccg ccgctatcat cacattcgtg tggggggtgaa tagtcggttg 6840
gacacattgc aggctgcgat tcttctaccg aagcttgaaa ttttcgagga ggagattgcg 6900
ttgcgccaga aggtagccgc ggagtatgac ctatcactga aacaggtcgg tatcggcacg 6960
ccgtttattg gaagtggata acatcagtgt ttatgcccag tatacggtag gtatggataa 7020
tcgagagtct gttcaggctt ctttgaaagc tgccgggggtt ccaactgctg tgcattaccc 7080
tattccgctt aataagcagc ctgctgttgc ggatgagaaa gcgaaactac cagtgggtga 7140
caaggctgct actcaagtaa tgagcctacc catgcatccc tatctggata cggcatccat 7200
caaaatcatc tgtgctgcgt tgacgaattg acggatgtat atacttgctc gagtcgacag 7260
gtctattctg ctgaacacag tgttactgtt tgctttcttt tcagcgacag tgtgggtgaa 7320
taataattat atctatcatc tctatgatta tatgggggtct gcgaaaaaaa ctgtcgactt 7380
cggcttgtat ccgtacttga tggtcttggc gctcatctgt gccctgttgt gtggagggc 7440
aattcgcagg ccaggtgatc tgttagttac attattagtt gtaatacttg ttcctcattc 7500
attggttctt aatgagcta atcaatattc tccggatgcg caaccatggg ctggcgtgcc 7560
tctgcaatt gcttttggta ttttgatcat cggcattgtc aataagataa gattccatcc 7620
gctaggtgca ttgcagcgag aaaaccaagg aaggcgaatg ttagtgctac tgtcagtact 7680
caacatagta gtgcttgtgt ttattttctt taaaagcgct ggttattttc cctttgactt 7740
tgctgggcag tatgctcgcc gtgcacttgc tcgtgagggtt tttgctgcgg gttctgcaaa 7800
cggctacttg tcgtcaatcg gtacccaggc attcttttcct gtgttgtttg cctgggggt 7860
ctacagacga caatggttct acttggtcct gggtattgtc aatgcactag tgctgtgggg 7920
agcgtttgga cagaagtatc cttttgtcgt gttgttctta atttatggcc tgatggttta 7980
ttttcgacga ttcggtcagg tcagagtgtc ttggggttgtc tgcgcactat tgatgctttt 8040
gcttttaggg gcgttggaac atgaggtgtt tggctattca ttcttgaatg attattttct 8100
```

```
acgtcgtgct tttattgtgc cttccaccct gttgggggca gttgatcagt ttgtgtctca 8160
gttcggatcc aattattaca gggataccct gttgggcgcg ctcttgggtc agggtaggac 8220
tgagccgttg agctttcgtc tggggacgga aattttcaat aatcccgata tgaatgcgaa 8280
tgtaaacttc ttcgcgatag cctatatgca gttgggttat gtggggggtta tggctgagtc 8340
gatgttggtg ggcggtagtg tcgttctcat gaatttctta ttttcgaggt atggtgcatt 8400
catggccatt ccggttgctt tgttatttac tacaaagatt cttgagcagc ccctgctaac 8460
tgtaatgctt ggctctgtg ttttcttgat actgcttttc cttgcgctaa tttcttttcc 8520
actcaagatg tctttaggaa aaactctatg agtgcggctt ttatcaaccg tgtcgcacga 8580
gtattagtag gcaccttggg agcacagctc ataacgattg gtgtcactct gctactggtt 8640
cgtctgtatt ctcctgctga aatgggcgct ttcagtgttt ggctatcgtt cgctacgatt 8700
tttgcagttg tagttactgg gcgctatgag ttggctattt tttcgactcg agaagagggc 8760
gaactccagg caatcgtcaa gctgatactt cagttgacac tattgatttt cgttgccgtg 8820
gcgattgctg ttgttatagg tagacatctg attgagtcga tgccagttgt gatcggtgaa 8880
tactggttcg cattggcggt ggcttcgctg gggttgggga taaataagct agtcttgtcg 8940
ttacttacat ttcaacaatc ttttaatcgg ttgggagttg ctcgtgtaag cctggctgca 9000
tgtattgccg ttgcacaagt ttcagctgca tatttactg agggcgtatc agggctgatc 9060
tatggccagc tgtttggtgt cgtcgtagcc acggcgcttg cggccctttg ggtaggaaag 9120
tcgctgattt taaattgtat cgagacaccg tggcgtatgg tacgacaagt agcggtacag 9180
tacatcaatt tcccgaagtt ttctctgcct gcggatctgg tcaacacggt tgccagtcag 9240
gtgcctgtga ttttattggc ggcaaagttt ggtggagaca gtgcaggctg gtttgccctg 9300
actctgaaga taatgggagc tcccatttcc ttgttggctg cttcggtgct cgatgtgttc 9360
aaagaacaag ccgctcgtga ctaccgagag tttggtaatt gccgaggtat cttcctcaag 9420
actttcaggt tgcttgccgt cctcgcgcta cctcctttta ttatatttgg ttcattggcg 9480
agtgggcctt tgggttagtc tttggcgaag cgtgggctga gтcgggggcgt tatgctgtat 9540
tgatggttcc gттgтттттat atgcgtttcg tggtgagtcc gctcagctat acaatctata 9600
ttgcccagcg gcagagtatg gatttgttgt ggcagctagc cttgttgctc ctgacgttta 9660
тcтgтттттac cttgcctgac tctgtcgact cggtgttgtg gttttactcc atagcatatg 9720
ctgttatgta ttttgtctat ttctggatgt ccttccagtg tgccaaggga gatgccaagt 9780
gatcgttgtt атттgaттacg gtgtaggtaa сатттgсттca gtcttgaaca tgctgaagcg 9840
agttggtgcc aaagccaagg catccgatag ccgagaggat atcgagcagg cggagaaact 9900
gatttttgcct ggtgtcgtg cтттттgacgc cggaatgcaa acactacgca agagtgggct 9960
ggtggatgta ctgacagagc aggtcatgat caaacgaaag ccggtcatgg gggtgtgtct 10020
cgggagtcaa gatgctgggg cтgccgaтcтg aggagggagc ggaaccgggg cttgatgga 10080
tcgatatgga tagcgtccgt tt cgaaaggc gtgacgaccg aaaggttcca catatgggct 10140
ggaatcaagt gtccccgcaa tt ggagcatc ctatacttag cggtataaac gagcaaagcc 10200
gatt ctattt tgttcatagt tattatatgt ttccgaaaga cccagacgat atcctgttga 10260
gttgtaatta tggacaaaaa tt cactgcgg cggtggctcg ggaтaaтgттт tt cggatttc 10320
agтт tcatcc тgagaagaгт caaaaattcg gtatgcagtt att caaaaac tt cgtggagc 10380
ttgtctgatg gtccggaggc gcgttatccc atgcttgctg ctcaaggatc gcggtctagt 10440
gaaaaccgtg aagttcaagg agcccaagta cgttggagac ccgatcaacg caatacgcat 10500
ctt caatgag aaagaaggтcg acgaactgat ttttgctgat atagatgctt ccaggctcaa 10560
tcaagagcct aactatgagt tgatcgcgga agtggctggt gagtgtttta tgcctatttg 10620
ctatggggc ggtatcaaga catt ggagca tgcggaaaaa atctttt ccc taggtgtcga 10680
aaaagtttcg ataaataccg ccgctcttat ggatctttcg ttgatt cgaa gaatt gccga 10740
taagttttt gt tcgcaaagcg tagttggctc tatcgactgc cgcaagggtt тcтgggggagg 10800
acactccgtg ttctcagaga atgggacgcg cgacatgaaa cgctccccat tggagtgggc 10860
gcaagcgctc gaagaggctg gagtgggtga gatttt tcta aattctattg atcgagatgg 10920
agtgcagaaa ggcttcgaca acgctctagt ggaaaatatc gcttctaacg tccatgtgcc 10980
agtgatcgcc tgtggtgaga ctggctccat cgctgacctc atcgatcttt ttgagcgtac 11040
gtgtgtgtcg gcagtagcgg cgggaagcct attcgttttc catggcaagc atcgtgcggt 11100
acтgатт agt т atccggatg tcaacaagct cgacgtcggt таgагтgagс тgagттатттт 11160
atggcaagga cgcttgttgg caacgctata tgcgcttcaa gatt gtcgaa ct aaatttga 11220
gtt tgtcagt ggggcgtt cc атт aggcagg ccgaggtgag tgcttcggga ggttgttgtg 11280
atgaagatct gttcgcgctg tgttatggat acatctgacg ctgaaatcgt atttgatgag 11340
gcgggagtct gtaatcactg ccataaattt gacaatgttc agtcccggca gctgttttcc 11400
gatgctagtg gtgagcagcg ccttcaaaag ataattgggc agatcaagaa ggacgгттca 11460
ggtaaggatt atgactgcat cattggcctt agtggcggcg tagatagttc ctatcttgct 11520
gtaaaggtca aggatctttg cttgcgccca ctggttgtgc atgtggacgc cggctggaat 11580
agcgaacttg cagtcagtaa tattgaaaag att gtaaaat att gcggttt тgатттacат 11640
act catgtaa taaactggga ggaaatt cgt gatcttcagt tggcttatat gaaagctgct 11700
gtcgccaatc aggatgtgcc tcaagatcat gccttcttcg ctagtatgta tcactttgct 11760
gtgaagaata atattaagta cattctgagt ggтgгтaaтт tggccactga ggcagtatt c 11820
ccagatacat ggcacgтgcag cgctatggat gcaataaacc taaaggctat tcacaaaaaa 11880
тат ggtgagc гтccgcтaag ggactacaag actattagtt tt cttgagta ctatttctgg 11940
tat ccctttg tcaaggaat gagaacggtc cgtccgttga att т catggc ctatgataag 12000
gccaaggctg aaaccttcct tcaagaaacg ataggctatc gtt cttacgc gcgaaagcat 12060
ggagagtcga tt т tcaccaa gctt ttccag aactactatc taccgaccaa gtt tggctat 12120
gataaacgca aactgcacta ctccagcatg att т tgtctg ggcaaatgac gcgtgacgaa 12180
gctcaggcta aactggctga gccgctatat gatgcagatg aactgcagtt tgatatcgaa 12240
таттт cтgca agaagatt cg aat caccccag gctcaatttg aagagttgat gaatgcacct 12300
gttcatgact att cggagtt tgccaactgg gatt ct cgac agaggatt gc gaaaaaagtt 12360
caaatgattg tccagcgtgc gctgggtcgt cgcatcaatg tctactcgtg atgaccgggg 12420
ccgctcatga ctaaagttgc tcattt gaca tcgttcact cgcgttatga tattcgtata 12480
tttcgaaagc agtgtagaac actctctcaa tacggatacg atgtgtatct ggtt gtcgca 12540
gatggtaagg gtgatgaagt caaggatggt gtaaggatt g тт gatgtcgg agtactctca 12600
ggtcgcttga atcgtattct aaaaaccacc cgaaaatttt atgaacaggc tttggcgctt 12660
ggggctgatg tctatcattt tcatgatccc gaactgatac ctgttggtct tcgactgaaa 12720
aagcaaggta agcaggttat cttcgactcc catgaggatg tgccgaagca actgctgagt 12780
aaaccttaca tgcgaccgtt ttt acgccgt gtagtggctg tgtt att т tc ctgctatgag 12840
aaatatgcat gccctaagct ggatgcagtc cttacggcaa cgccgcatat tcgtgaaaaa 12900
```

```
tttaaaaata ttaatgggaa tgttctagat attaataact ttcccatgtt gggtgagttg    12960
gatgcgatgg ttccttgggc aagcaagaaa actgaagtct gctacgtcgg tggtatcact    13020
tccattcgtg gtgttcgtga agtcgttaag agtcttgagt gcttgaagtc ctcggcgcgc    13080
ttgaatttag tgggaaagtt ttcagagcca gagatagaaa aagaagtcag agcgctcaag    13140
ggatggaact ccgttaacga acatggtcag cttgatcgag aagatgttcg tcgtgtactc    13200
ggtgactctg ttgccgggtt ggtgacattt ctcccaatgc ctaatcatgt tgatgcacaa    13260
cctaataaga tgttcgagta tatgtcgtcg ggaatccctg tgatcgcttc caattttcct    13320
ctctggcggg aaattgttga aggtagcaat tgtggtatat gcgtagatcc tctaagtcct    13380
gctgccattg ctgaagcgat cgactatctg gtaagtaatc cgtgtgaggc ggcagcgctg    13440
ggacgtaatg gccagcgggc agtgaacgaa cgttataact gggatttgga agggcgcaaa    13500
ctagcgcgcgt tctattccga tctactgagt aagcgagatt ccatatgaaa attctgacca    13560
tcattggtgc gcgtccgcag tttattaaag cgagtgtggt ttcaaaggct atcattgagc    13620
agcagaccct ttcgaaaatc atcgttcata ctggtcagca tttttgatgcc aatatgtctg    13680
aaatatttttt cgaacagctg ggtattccaa agccggatta ccagttggat atccatggtg    13740
gtactcacgg ccaaatgacc gggcgtatgc taatggagat cgaggatgta attctcaagg    13800
agaaacctca tcgcgtattg gtatacgcg ataccaactc taccttggct ggagcgttgg    13860
ctgcctccaa gctgcatgtt cctatcgcac acatcgaagc cggcctgcga agtttcaata    13920
tgcggatgcc ggaggaaatt aaccgtattc ttactgatca ggttagtgat attctgtttt    13980
gccctactcg agttgcaatt gataatctca agaatgaagg tttcgaaaga aaggctgcga    14040
agatagtcaa cgtgggtgat gtgatgcagg atagcgctct attcttttcg cagcgtgcaa    14100
cctcgccaat tggacttgcg tcacaagatg ggtttattct cgcgaccctg catcgtgccg    14160
agaacaccga cgatccagtt cgcctgactt cgatagtcga ggctctgaat gaaatccaga    14220
ttaatgttgc acctgtggtg ctaccccctgc atccacgtac ccgcggtgtc atcgagcgcc    14280
tagggctcaa gctggaagtg caggttatcg atcctgtcga atatctggaa atgatctggc    14340
tgttgcaacg ctctggcctg gtgctcacgg acagcggcgg tgttcagaaa gaagcattct    14400
tcttcggcaa gccctgcgtg accatgcgtg accagaccga atgggtggag ctagtgacct    14460
gtggagccaa cgttcttgtg ggagcggccc gcgacatgat tgtcgaatct gcacggacta    14520
gcctgggaaa gaccattcaa gacgatggtc agctttacgg aggcggtcaa gcctctctcg    14580
gattgctgaa tatcttgcca agctgtgatg ctttgcgtgt cgagtttaaa taaaggattt    14640
atttagttcc atgaacgtct ggtatgtgca tccctatgct ggcggcccccg gagttggtcg    14700
ttattggcgg cccttattatt tctccaagtt ttggaatcag gctgggcatc ggtcggtcat    14760
aatctcggca ggctatcacc atctgctgga accggatgaa aagcgttcgg gcgtcacctg    14820
tgtaaatgga gccgaatacg catatgtacc tactttgccg tatttgggca atgcgtggg    14880
cagaatgcta tcgatgctca tatttaccat gatgttgctg ccattctgcc tgatcttggc    14940
cctgaagcgt ggaacgccgg atgcgattat ctactcatcg cctcacccgt ttggcgtcgt    15000
tagctgttgg ctggctgctc gcctgctagg tgcgaaattt gtatttgagg tgcgcgatat    15060
ctggcctttg agtctggtcg aactggggagg cttgaaagct gacaatcccc tggtgcgtgt    15120
taccggttgg atcgaaagat tctcctatgc gcgagctgat aagatcatca gtctgctgcc    15180
atgtgcggag ccgcacatgg ccgacaaagg acttcccgct ggaaagttcc tgtgggttcc    15240
gaatggcgtt gacagcagcg atatctctcc tgatagcgct gtgagttcaa gtgatttggt    15300
ccggcatgta caagttctca aggagcaggg tgtttttcgtt gtgatctatg ctggagcgca    15360
cggcgaaccc aatgctctgg agggattggt tcgctctgcc ggactgctgc gcgagcgtgg    15420
tgcaagtatc agaatcattc tggtgggcaa gggagagtgc aaagagcaac tcaaggcgat    15480
tgccgcacag gatgccagcg ggctagtgga gttttttcgat cagcagccca aagagactat    15540
catggctctg ctgaagcgt cgtcggcggg ctacatctcg ctcaagtcag aaccgatctt    15600
ccgctttggc gtgagcccca acaagctatg ggattacatg ctggttgggt tgccagtcat    15660
tttcgcctgc aaggcaggga acgaccgtt tagtgactac gattgcggtg tatctgccga    15720
cccagatgcc cctgaggata ttactgcagc catcttccgt ctgttgctgc tgagcgaaga    15780
cgagcgtcgc acaatgggc aaagagggcg tgatgcggtc gtggagcatt ataccttacga    15840
gagtctggct cttcaggtgt tgaacgccct tgctgatggg cgcgcagcat gaaagctgtc    15900
atggtgaccg gtgcatcagg attcgtcgga tcggccttgt gctgtgagct tgctcggaca    15960
gggtatgcgg tgattgcggt ggtacggcgg gttgttgaaa gaataccttc tgtgacgtac    16020
atcgaagctg atctgaccga tccagccacg tttgccggca agttcccgac ggtggattgc    16080
attattcatc tcgctggacg tgcccatata ctcactgcag aggttgcaga cccgctcgtc    16140
gcatttcgtg aagtcaaccg agatgcgact gtccggttgg ctacccgtgc gctcgaggct    16200
ggggtgaagc gtttcgtgtt tgtcagttca attggcgtta acggtaacag caccccggcaa    16260
caggctttca acgaagattc tccagccggc ccacatgcgc cctatgccat ctccaaatac    16320
gaggctgagc aggagctgga gactttgctc cggggtaaag gtatggagtt ggtggttgtc    16380
cgaccgcctt tgatctatgc caatgatgcg ccaggtaact tcggccgttt gctcaagctc    16440
gtcgctagtg gtctgccgct tccgcttgac ggtgtccgta atgcgcgcag cctggtttct    16500
aggagaaaca tcgtgggttt cctgagtctt tgtgccgaac accccgatgc tgcgggcgaa    16560
ctgttttctgg tggccgatgg cgaggatgtt tccattgcgg aaatgatcga ggccctgaat    16620
cggggaatgg gcaggcgtcc agctctttc acgttccag cggtgctgct gaagcttgta    16680
atgtgcttgc tgggtaaggc ttccatgcat gaacagctct gtggctcgtt acaggtcgat    16740
gcttccaagg cccgccggct gctcggctgg gttccgtcg agactattgg tgccggtctg    16800
caagcagcag gtcgagagta cattcttcgc cagagggagc gccgaaaatg gccgacacat    16860
ccaaacccct ggtcggcaat tacgctgaac tttaataagt tctctttcca atgatgatct    16920
ggatgatcgc cgtgtctagtt gtcttgctgt tttcatttgt cgctacctgg gggctgcgtc    16980
gctatgcatt agcgacgaaa ctgatggatg ttccgaatgc ccgtagctcc cacagtcaac    17040
cgacgcctag gggggaggt gttgcaatcg ttctggtctt cctttgcacg ttggtgtgaa    17100
tgctgagtgc aggcagtatc tccggcggct gggggggggc gatgctgggt gcaggttctg    17160
gcgtggcact gttagggttc ctggatgacc atgggcacat tgctgcgcgt tggcggctgc    17220
tcggccattt ctcagcagcg atatggatct tgctgtggac gggtggtttc ccgccgctgg    17280
atgtggttgg gcatgctgtc gacttaggat ggctgggcca cgtattgcga gtttttctatt    17340
tggtatgggt gctgaaccttt tataacttca tggatgggcat tgatgtggtatt gccagtgtcg    17400
aggccattgg tgtctgtgta ggagggggcc tgatctactg gcttacaggg catgtcgcga    17460
tggttggtat ccctctgttg ctggcgtgcg cggtcgccgg cttcctgatc tggaacttcc    17520
ctccagctcg aatcttcatg ggtgatgcgg ggagtggttt tcttggtatg gttattggtg    17580
cactagctat tcaggctgca tggaccgccc cctcgctgtt ctggtctgg ttgatattgc    17640
tgggagtgtt catcgttgat gcaacctata ctctgatccg ccggatcgcc agaggggaga    17700
```

```
aattctatga ggcgcatcgc agccacgctt atcagtttgc ctcgcgtcgt tatgctagcc 17760
atctgcgggt taccttgggt gttctggcta tcaacactct ttggttgttg cgttggcact 17820
gatggttgca ttgggttgga tcagcggctt catcggtatc ctggttgctt atgctcctct 17880
ttgcctcttg gcggtaggat acaaggcggg ttccttggaa aaatcctaag ccgtggattg 17940
acctgctccc cgatttcagt accacgccga acttagtaga gtctgttttc cgagcaggag 18000
acggcagtga aaaagcgttt tactgaagaa cagattctag actttctgaa gcaggcagaa 18060
gccggtgtgc cggtgaagga gctgtgtcgc cgacacagct tcagtgatgc cacgttctac 18120
acctagcggg ccaagttcgt cggcatgacc gtgccggatg ccaagcgcct gaaggatctc 18180
gaactggaaa acagccggct gaagaagttg ctcgccgagt ccctcctcga catcggggcg 18240
ctgaaagtgg tcacccgggg aaaggggag cccggcagcg gggcggggg caggagatt 18300
caggcgcaaa ccgacatctc cgagcgtcgt gccctgtcag ttgttcaggc tgtcccgctc 18360
tgtgttgtgc caccagccgc gaactagtgt gcaaaacacc gagctgcaag cccaactggt 18420
ggaactggca agggcttcgg cactttggct atcaccgcct gcacattctg ctgcggcgtg 18480
ctggtgtgca gatcaactac aagcggactt accggctata ctgagccgtc ggcttgatgg 18540
tgaagcggcg gaggcgccgc cacaggggcg cggtggcgtg cgaatgcctg agcctgccga 18600
gcgcaccgaa ctaggtcttg tcgatggatt tcgtcttcga ccgcgctcag actgggcgac 18660
ggatcaaatg cctgacggtg gtcgatgact tcaccaagga gtcggttggc atcctggttg 18720
agcacggtat cagccggtttt cgtgtcacac gggcgctgga cagatggcac ggttgcgcgg 18780
ttacccgaag gcgatccgca ccccgagtt caccggcaag gcgcttgatc agtgggccta 18840
tcggcgtgat attaagttga agctgactca gtccggcaag ccacgcaga acgccttcat 18900
cgtcattcca acggcaagtt ccgcaatgag cactgctgct cgctggtcga agccagaatc 18960
cgcatcgtgg cctggcggca cgattacaac gagcaccgac cgtccagcgc cattggcaat 19020
ctcacctcgc tagagtttgc tgcaagttgg cgaactcgcc agcagcaact gaagcaggaa 19080
aattgatgtc aaccccaggg cctactacct aggcagcgta ctaaaactgg gggcaggtca 19140
tctacgatcc ttgtgatagg tatcgacggt gctgtggcga tccgtcatg tggaactgat 19200
ctgggatttt ccctgcgtgt gtttcaggg gcctggcagt gattttttga gcattgccat 19260
gggggggcgg gttttttgcat cctgctcgga cgctgctga ttcccactcg acgtgctcgt 19320
gttcgatgtc acttttactt tgctgctgca tcgtttgtta tgaggcgata aaattcggca 19380
gagctatcga gtcacgcatg atggcacgtt ggtgtcgtgc tgaagtggca tttgccggtt 19440
atcctttgtg gctgtgatca gtttcttctg gttattaccc tagcattgct ggtagtacta 19500
agcattatcg acggagtact tggggggctta tcgcgtatgc tcctatggct tggatggcga 19560
cgagtcttgg gaggggatgt cctgagacgt agcgtgggcc ttgccatatt gttgccatgg 19620
ttatctgtct gatctgtctg gttggtatgg atgtattgaa cgggggctgat aaataggatg 19680
ttggataatt tgaggataaa gctcctggga ttgccgcgcc gctataagcg aatgctgcaa 19740
gtcgctgccg atgtgactct tgtgtggcta tccctctggc tggctttctt ggtcaggttg 19800
ggcacagaag acatgatcag cccgtttagc ggccatgcct ggctgttcat cgccgccccg 19860
ttggtggcca ttccctgtt catccgcttc ggcatgtacc gggcggtgat gcgctacctg 19920
ggcaacgacg cccctatcgc gatcgccaag gccgtcacca tttccgcgct ggtcctgtcg 19980
ttgctggtct actggtaccg ctccccgccg gcggtggtgc cgcgttccct ggtgttcaac 20040
tactggtggt tgagcatgct gctgatcggc ggcttgcgtc tggccatgcg ccagtatttc 20100
atgggagact ggtactctgc tgtgcagtcg gtaccatttc tcaaccgcca ggatggcctg 20160
cccagggtgg ctatctatgg cgcgggggcg gccgccaacc agttggttgc ggcattggcgt 20220
ctcggtcggg cgatgcgtcc ggtggcgttc atcgatgatg acaagcagat cgccaaccgg 20280
gtcatcgccg gtctgcgggt ctataccgcc aagcatatcc gccagatgat cgacgagacg 20340
ggcgcgcagg aggttctcct ggcgattcct tccgccactc ggccccggcg ccgagagatt 20400
ctcgagtccc tggagccgtt cccgctgcac gtgcgcagca tgcccggctt catggacctg 20460
accagcggcc gggtcaaggt ggacgacctg caggaggtgg acatcgctga cctgctgggg 20520
cgcgacagcg tcgcaccgcg caaggagctg ctggaacgtt gcatccgcgg tcaggtggtg 20580
atggtgaccg gggcgggcgg ctctatcggt tcggaactct gtcgcagat catgagttgt 20640
tcgcctagcg tgctgatcct gttcgagcac agcgaataca acctctatag catccatcag 20700
gaactggagc gtcggatcaa gcgcgagtcg ctttcggtga acctgttgcc gatcctcggt 20760
tcggtgcgca atcccgagcg cctggtggac gtgatgcgta cctggaaggt caataccgtc 20820
taccatgcgg cggcctacaa gcatgtgccg atcgtcgagc acaacatcgc cgagggcgtt 20880
ctcaacaacg tgataggcac cttgcatgcg gtgcaggccg cggtgcaggt cggcgtgcag 20940
aacttcgtgc tgatttccac cgacaaggcg gtgcgaccga ccaatgtgat gggcagcacc 21000
aagcgcctgg cggagatggt ccttcaggcg ctcagcaacg aatcggcacc gttgctgttc 21060
ggcgatcgga aggacgtgca tcacgtcaac aagacccgtt tcacaatggt ccgcttcggc 21120
aacgtcctcg gttcgtccgg ttcggtcatt ccgctgttcc gcgagcagat caagcgcggc 21180
ggcccggtga cggtcaccca cccgagcatc acccgttact tcatgaccat tcccgaggca 21240
gcgcagttgg tcatccaggc cggttcgatg gggcagggcg gagatgtatt cgtgctggac 21300
atgggggccgc cggtgaagat cctggagctc gccgagaaga tgatccacct gtccggcctg 21360
agcgtgcgtt ccgagcgttc gcccatggt gacatcgcca tcgagttcag tggcctgcgt 21420
cctggcgaga agctctacga agagctgctg atcggtgaca acgtgaatcc caccgaccat 21480
ccgatgatca tgcgggccaa cgaggaacac ctgagctggg aggccttcaa ggtcgtgctg 21540
gagcagttgc tggccgccgt ggagaaggac gactactcgc gggttcgcca gttgctgcgg 21600
gaaaccgtca gcggctatgc gcctgacggt gaaatcgtcg actgaatcta tcgccagagg 21660
cggcgagaac cctgagtcat cgttctccgg aaaaggccgc ctagcggcct ttttttgtttt 21720
ctccgtacga tgtttccggt gccggaccag gaagcgactg ctttgctggg gctgtcgatc 21780
caggtgcgtt ccacggcgat aaggtggttt cgtggatggg catgaagccc tctacgtggt 21840
cattcatctc tgaaggagtg cacccatgca cctaatcaaa tccgctctgc ttctcatcct 21900
gttcgcctgt cttccgtttt cggcttccgc cgcaccggtc gccgtcgcca agaatccgct 21960
ggccgcaacg acacctgcga cgaccgtgtc gccggggggag caggtcaata tcaatacggt 22020
cgacgaggcc gccctgatac gggggctcaa cggtgtcggc gaggccaagg ccagggcgat 22080
cctcgagtat cgtgccgggcc atggtccgtt cgtctccggtg gatcaactgc tggaagtgaa 22140
aggggtaggc ccggcgttgc tggagaagaa ccgggcgcgg atcgtcatcg agtgaggtgc 22200
gactgaaggg gcgaacttttc gtcccgataa cgaaaaagcc cccggcatgt gccgagggct 22260
ttgaatttgg ctccgcgacc tggactcgaa ccaggacccc aatgattaac agtcatttgc 22320
tctaccgact gagctatcgc ggaacagcga ggcgtatgtt actgattaaa aaggggaagc 22380
ctctcccgat gacttcccca ttttccctac aggacctgga cgatggcctt ggtgatggtc 22440
tccaggttcg atttgttcag cgcggcgacg cagatacggc cggtgctgac ggcgtagata 22500
```

-continued

```
ccgaactcgg tcttcaggcg ctcgacctgg tcggcggtca ggccggaata ggagaacatg 22560
ccacgttggc gaccgacgaa actgaagtcg cgcttggcgc cgtgggctgc cagttgctcg 22620
accatcgcca ggcgcatgtc gcggatgcgg tcgcgcatct cgcccagttc ctgctcccag 22680
agggcccgca gttccgggct gttgagcacg gaggagacga cgctggcgcc gtgggtcggt 22740
gggttcgaat agttggtgcg gatcacccgc ttcacctggg acagcacgcg ggccgattca 22800
tcgcggcttt cggtcacgat cgagagggcg ccgacgcgtt cgccatagag cgagaaggat 22860
ttggagaacg agctggaaac gaagaagctc aggcccgact gggcgaacag gcgcaccgcg 22920
gcggcgtctt cctcgatgcc gttgccgaag ccctggtagg cgatgtcgag gaacggcacg 22980
tggcccttgg ccttgagcac gtccagcacc tgtttccagt cgtccagctc gagatcgacg 23040
ccggtcggat tatggcagca ggcgtgcaga accacgatcg agcgggccgg cagggcattc 23100
aggtcttcca gcaggccggc gcggttcacg ccattgctgg cggcgtcgta atagcggtag 23160
ttctgcaccg ggaagccggc ggcttcgaac agtgcgcggt ggttttccca gctcgggtcg 23220
ctgatggcca cggtggcgtc gggcagcagg cgcttgagga agtcggcgcc gagcttgagc 23280
gcgccggtgc cgccgacggc ctgggtcgtg accacacggc cggcggccag cagctcggac 23340
tcgttaccga acagcagttt ctgtacgccc tggtcgtagg cggcgatccc ttcgatcggc 23400
aggtagccgc gcggcgcgtg ggcctcgatg cgggccttct cgcagcgctg cacggcacgc 23460
aacagcggaa tgcgcccctc ctcgttgtag tacacgccca cgcccaggtt gatcttgccc 23520
ggacgggtat cggcgttgaa ggcttcgttc aggccaagga tgggatcacg cggtgccatt 23580
tcgacggcag aaaacagact cattttgcgg ctgctcggag tgtgaagaga ggagggcaac 23640
gcaacccgtt atgcggggcg gcaaagggtt gcgcaaacgg gggtttatta tagacacccc 23700
ttgatgcatg cggcgacatt taggtgcatg ctttcagcta tttctgacgc cggattttcc 23760
ttggcgtcac agctccctgc gaggttttc atggatacgt tccaactcga ctcgcgcttc 23820
aagcccgccg gcgaccagcc ggaagccatc cggcaaatgg tcgaggggct ggaggcgggg 23880
cttcgcacc agaccctgct ggggtgacg ggctctggca agactttcag catcgccaac 23940
gtgattgccc aggtgcagcg cccgaccctg gtcctggcgc cgaacaagac cctggcggcc 24000
cagctctacg gggagttcaa gacgttcttc ccgcacaatt ccgtggagta cttcgtttcc 24060
tactacgact actaccagcc ggaggcctac gtcccgtctt ccgatacccta tatcgagaag 24120
gactcctcga tcaacgacca tatcgagcag atgcgcctgt cggcgaccaa ggcgctgatc 24180
gagcgtccgg atgcgatcat cgtcgccacc gtgtcgtcca tctacggcct cggtgatccc 24240
gcgtcctacc tgaagatggt cctgcacctg gaccgcggcg accgcatcga ccagcgcgaa 24300
ctgctgcggc gactgaccag cctgcagtac acccgcaacg acatggattt cgcccgtgcg 24360
actttccgtg tgcgtggcga tgtgatcgac atcttcccgg ccgaatccga tctcgag    24417
```

<210> SEQ ID NO 2
<211> LENGTH: 158
<212> TYPE: PRT
<213> ORGANISM: Pseudomonas aeruginosa

<400> SEQUENCE: 2

```
Arg Asp Ile Glu Gln Arg Ile Gln Asn Leu Arg Arg Glu Cys Gln Gly
  1               5                  10                  15
Arg Arg Glu Asp Arg Ile Val Gln Leu Lys Glu Ala Leu Lys Val Ala
             20                  25                  30
Gly Ala Leu Lys Leu Glu Glu Pro Pro Leu Ile Ser Gly Gln Ser Ser
         35                  40                  45
Glu Glu Leu Ser Ala Ile Met Asn Gly Ser Leu Met Tyr Met Arg Gly
     50                  55                  60
Ser Lys Ala Ile Met Ala Glu Ile Gln Thr Leu Glu Ala Arg Ser Ser
 65                  70                  75                  80
Asp Asp Pro Phe Ile Pro Ala Leu Arg Thr Leu Gln Glu Gln Gln Leu
                 85                  90                  95
Leu Leu Ser Ser Leu Arg Val Asn Ser Glu Arg Val Ser Val Phe Arg
            100                 105                 110
Gln Asp Gly Pro Ile Glu Thr Pro Asp Ser Pro Val Arg Pro Arg Arg
        115                 120                 125
Ala Met Ile Leu Ile Phe Gly Leu Ile Ile Gly Gly Val Leu Gly Gly
    130                 135                 140
Phe Leu Ala Leu Cys Arg Ile Phe Leu Lys Lys Tyr Ala Arg
145                 150                 155
```

<210> SEQ ID NO 3
<211> LENGTH: 436
<212> TYPE: PRT
<213> ORGANISM: Pseudomonas aeruginosa

<400> SEQUENCE: 3

```
Met Ile Asp Val Asn Thr Val Val Glu Lys Phe Lys Ser Arg Gln Ala
  1               5                  10                  15
Leu Ile Gly Ile Val Gly Leu Gly Tyr Val Gly Leu Pro Leu Met Leu
             20                  25                  30
Arg Tyr Asn Ala Ile Gly Phe Asp Val Leu Gly Ile Asp Ile Asp Asp
         35                  40                  45
Val Lys Val Asp Lys Leu Asn Ala Gly Gln Cys Tyr Ile Glu His Ile
     50                  55                  60
Pro Gln Ala Lys Ile Ala Lys Ala Arg Ala Ser Gly Phe Glu Ala Thr
 65                  70                  75                  80
```

```
    Thr Asp Phe Ser Arg Val Ser Glu Cys Asp Ala Leu Ile Leu Cys Val
                     85                  90                  95
    Pro Thr Pro Leu Asn Lys Tyr Arg Glu Pro Asp Met Ser Phe Val Ile
                100                 105                 110
    Asn Thr Thr Asp Ala Leu Lys Pro Tyr Leu Arg Val Gly Gln Val Val
            115                 120                 125
    Ser Leu Glu Ser Thr Thr Tyr Pro Gly Thr Thr Glu Glu Leu Leu
        130                 135                 140
    Pro Arg Val Gln Glu Gly Gly Leu Val Gly Arg Asp Ile Tyr Leu
    145                 150                 155                 160
    Val Tyr Ser Pro Glu Arg Glu Asp Pro Gly Asn Pro Asn Phe Glu Thr
                    165                 170                 175
    Arg Thr Ile Pro Lys Val Ile Gly His Thr Pro Gln Cys Leu Glu
                180                 185                 190
    Val Gly Ile Ala Leu Tyr Glu Gln Ala Ile Asp Arg Val Val Pro Val
                195                 200                 205
    Ser Ser Thr Lys Ala Ala Glu Met Thr Lys Leu Leu Glu Asn Ile His
        210                 215                 220
    Arg Ala Val Asn Ile Gly Leu Val Asn Glu Met Lys Ile Val Ala Asp
    225                 230                 235                 240
    Arg Met Gly Ile Asp Ile Phe Glu Val Val Asp Ala Ala Thr Lys
                    245                 250                 255
    Pro Phe Gly Phe Thr Pro Tyr Tyr Pro Gly Pro Gly Leu Gly Gly His
                260                 265                 270
    Cys Ile Pro Ile Asp Pro Phe Tyr Leu Thr Trp Lys Ala Arg Glu Tyr
                275                 280                 285
    Gly Leu His Thr Arg Phe Ile Glu Leu Ser Gly Glu Val Asn Gln Ala
        290                 295                 300
    Met Pro Glu Tyr Val Leu Gly Lys Leu Met Asp Gly Leu Asn Glu Ala
    305                 310                 315                 320
    Gly Arg Ala Leu Lys Gly Ser Arg Val Leu Val Leu Gly Ile Ala Tyr
                    325                 330                 335
    Lys Lys Asn Val Asp Asp Met Arg Glu Ser Pro Ser Val Glu Ile Met
                340                 345                 350
    Glu Leu Ile Glu Ala Lys Gly Gly Met Val Ala Tyr Ser Asp Pro His
            355                 360                 365
    Val Pro Val Phe Pro Lys Met Arg Glu His His Phe Glu Leu Ser Ser
        370                 375                 380
    Glu Pro Leu Thr Ala Glu Asn Leu Ala Arg Phe Asp Ala Val Val Leu
    385                 390                 395                 400
    Ala Thr Asp His Asp Lys Phe Asp Tyr Glu Leu Ile Lys Ala Glu Ala
                    405                 410                 415
    Lys Leu Val Val Asp Ser Arg Gly Lys Tyr Arg Ser Pro Ala Ala His
                420                 425                 430
    Ile Ile Lys Ala
                435

<210> SEQ ID NO 4
<211> LENGTH: 316
<212> TYPE: PRT
<213> ORGANISM: Pseudomonas aeruginosa

<400> SEQUENCE: 4

Met Lys Asn Phe Ala Leu Ile Gly Ala Ala Gly Tyr Ile Ala Pro Arg
    1               5                   10                  15
    His Met Arg Ala Ile Lys Asp Thr Gly Asn Cys Leu Val Ser Ala Tyr
                20                  25                  30
    Asp Ile Asn Asp Ser Val Gly Ile Ile Asp Ser Ile Ser Pro Gln Ser
                35                  40                  45
    Glu Phe Phe Thr Glu Phe Glu Phe Leu Asp His Ala Ser Asn Leu
        50                  55                  60
    Lys Arg Asp Ser Ala Thr Ala Leu Asp Tyr Val Ser Ile Cys Ser Pro
    65                  70                  75                  80
    Asn Tyr Leu His Tyr Pro His Ile Ala Ala Gly Leu Arg Leu Gly Cys
                    85                  90                  95
    Asp Val Ile Cys Glu Lys Pro Leu Val Pro Thr Pro Glu Met Leu Asp
                100                 105                 110
    Gln Leu Ala Val Ile Glu Arg Glu Thr Asp Lys Arg Leu Tyr Asn Ile
            115                 120                 125
    Leu Gln Leu Arg His His Gln Ala Ile Ile Ala Leu Lys Asp Lys Val
        130                 135                 140
    Ala Arg Glu Lys Ser Pro His Lys Tyr Glu Val Asp Leu Thr Tyr Ile
    145                 150                 155                 160
    Thr Ser Arg Gly Asn Trp Tyr Leu Lys Ser Trp Lys Gly Asp Pro Arg
                    165                 170                 175
    Lys Ser Phe Gly Val Ala Thr Asn Ile Gly Val His Phe Tyr Asp Met
                180                 185                 190
    Leu His Phe Ile Phe Gly Lys Leu Gln Arg Asn Val Val His Phe Thr
```

```
            195                 200                 205
Ser Glu Tyr Lys Thr Ala Gly Tyr Leu Glu Tyr Glu Gln Ala Arg Val
    210                 215                 220
Arg Trp Phe Leu Ser Val Asp Ala Asn Asp Leu Pro Glu Ser Val Lys
225                 230                 235                 240
Gly Lys Lys Pro Thr Tyr Arg Ser Ile Thr Val Asn Gly Glu Glu Met
                245                 250                 255
Glu Phe Ser Glu Gly Phe Thr Asp Leu His Thr Thr Ser Tyr Glu Glu
            260                 265                 270
Ile Leu Ala Gly Arg Gly Tyr Gly Ile Asp Asp Ala Arg His Cys Val
        275                 280                 285
Glu Thr Val Asn Thr Ile Arg Ser Ala Val Ile Val Pro Ala Ser Asp
    290                 295                 300
Asn Glu Gly His Pro Phe Val Ala Ala Leu Ala Arg
305                 310                 315
```

<210> SEQ ID NO 5
<211> LENGTH: 766
<212> TYPE: PRT
<213> ORGANISM: Pseudomonas aeruginosa

<400> SEQUENCE: 5

```
Met Leu Cys Thr Ser Leu Pro Ser Thr Arg Gln Leu Val Ile Trp Ser
  1               5                  10                  15
Thr Ser Arg Pro Val Cys Val Gly Phe Cys Pro Trp Met Leu Thr Thr
                 20                  25                  30
Cys Arg Ser Ser Arg Ala Lys Ser Arg Pro Ile Val Arg Leu Pro
             35                  40                  45
Ser Thr Val Arg Lys Trp Ser Ser Leu Lys Ala Leu Pro Ile Tyr Ile
         50                  55                  60
Gln Pro Ala Thr Lys Lys Phe Ser Leu Val Val Val Met Ala Ser Met
 65                  70                  75                  80
Thr Leu Val Ile Val Trp Lys Leu Ser Ile Pro Phe Ala Ala Pro Ser
                     85                  90                  95
Ser Tyr Arg Pro Leu Ile Thr Lys Gly Ile Arg Ser Ser Arg Arg Leu
                100                 105                 110
Arg Val Glu Val Glu Lys Glu Trp Pro Ser Ser Val Thr Cys Leu Gln
            115                 120                 125
Gln Val Ser Ala Gly Ser Phe Ile Ser Met Ser Ser Ser Ser Ser Lys
        130                 135                 140
Leu Leu Asn Gly Met Val Ala Val Ser Ser Gly Arg Asn Ile Arg Leu
145                 150                 155                 160
Asp Val Gln Gly Leu Arg Ala Val Ala Leu Ala Val Leu Ala Tyr
                165                 170                 175
His Ala Asn Ser Ala Trp Leu Arg Ala Gly Phe Val Gly Val Asp Val
                180                 185                 190
Phe Phe Val Ile Ser Gly Phe Ile Ile Thr Ala Leu Leu Val Glu Arg
            195                 200                 205
Gly Val Lys Val Asp Leu Val Glu Phe Tyr Ala Gly Arg Ile Lys Arg
        210                 215                 220
Ile Phe Pro Ala Tyr Phe Val Met Leu Ala Ile Val Cys Ile Val Ser
225                 230                 235                 240
Thr Ile Leu Phe Leu Pro Asp Asp Tyr Val Phe Phe Glu Lys Ser Leu
                245                 250                 255
Gln Ser Ser Val Phe Phe Ser Ser Asn His Tyr Phe Ala Asn Phe Gly
                260                 265                 270
Ser Tyr Phe Ala Pro Arg Ala Glu Glu Leu Pro Leu Leu His Thr Cys
            275                 280                 285
Ser Ile Ala Asn Glu Met Gln Phe Tyr Leu Tyr Pro Val Leu Phe
        290                 295                 300
Met Cys Leu Pro Cys Arg Trp Arg Leu Pro Val Phe Ile Leu Leu Ala
305                 310                 315                 320
Ile Leu Leu Phe Ile Trp Ser Gly Tyr Cys Val Phe Ser Gly Ser Gln
                325                 330                 335
Asp Ala Gln Tyr Phe Ala Leu Leu Ala Arg Val Pro Glu Phe Met Ser
                340                 345                 350
Gly Ala Val Val Ala Leu Ser Leu Arg Asp Arg Glu Leu Pro Ala Arg
            355                 360                 365
Leu Ala Ile Leu Ala Gly Leu Leu Gly Ala Ala Leu Leu Val Cys Ser
        370                 375                 380
Phe Ile Ile Ile Asp Lys Gln His Phe Pro Gly Phe Trp Ser Leu Leu
385                 390                 395                 400
Pro Cys Leu Gly Ala Ala Leu Leu Ile Ala Ala Arg Arg Gly Pro Ala
                405                 410                 415
Ser Leu Leu Leu Ala Ser Arg Pro Met Val Trp Ile Gly Gly Ile Ser
                420                 425                 430
Tyr Ser Leu Tyr Leu Trp His Trp Pro Ile Leu Ala Phe Ile Arg Tyr
            435                 440                 445
```

```
        Tyr Thr Gly Gln Tyr Glu Leu Ser Phe Val Ala Leu Leu Ala Phe Leu
                450                 455                 460
        Thr Gly Ser Phe Leu Leu Ala Trp Phe Ser Tyr Arg Tyr Ile Glu Thr
        465                 470                 475                 480
        Pro Ala Arg Lys Ala Val Gly Leu Arg Gln Gln Ala Leu Lys Trp Met
                        485                 490                 495
        Leu Ala Ala Ser Val Val Ala Ile Val Val Thr Gly Gly Ala Gln Phe
                        500                 505                 510
        Asn Val Leu Val Val Ala Pro Ala Pro Ile Gln Leu Thr Arg Tyr Ala
                        515                 520                 525
        Val Pro Glu Ser Ile Cys His Gly Val Gln Val Gly Glu Cys Lys Arg
                        530                 535                 540
        Gly Ser Val Asn Ala Val Pro Arg Val Leu Val Ile Gly Asp Ser His
        545                 550                 555                 560
        Ala Ala Gln Leu Asn Tyr Phe Phe Asp Val Val Gly Asn Glu Ser Gly
                        565                 570                 575
        Val Ala Tyr Arg Val Leu Thr Gly Ser Ser Cys Val Pro Ile Pro Ala
                        580                 585                 590
        Phe Asp Leu Glu Arg Leu Pro Arg Trp Ala Arg Lys Pro Cys Gln Ala
                        595                 600                 605
        Gln Ile Asp Ala Val Ala Gln Ser Met Leu Asn Phe Asp Lys Ile Ile
                        610                 615                 620
        Val Ala Gly Met Trp Gln Tyr Gln Met Gln Ser Pro Ala Phe Ala Gln
        625                 630                 635                 640
        Ala Met Arg Ala Phe Leu Val Asp Thr Ser Tyr Ala Gly Lys Gln Val
                        645                 650                 655
        Ala Leu Leu Gly Gln Ile Pro Met Phe Glu Ser Asn Val Gln Arg Val
                        660                 665                 670
        Arg Arg Phe Arg Glu Leu Gly Leu Ser Ala Pro Leu Val Ser Ser Ser
                        675                 680                 685
        Trp Gln Gly Ala Asn Gln Leu Leu Arg Ala Leu Ala Glu Gly Ile Pro
        690                 695                 700
        Asn Val Arg Phe Met Asp Phe Ser Ser Ser Ala Phe Phe Ala Asp Ala
        705                 710                 715                 720
        Pro Tyr Gln Asp Gly Glu Leu Ile Tyr Gln Asp Ser His His Leu Asn
                        725                 730                 735
        Glu Val Gly Ala Arg Arg Tyr Gly Tyr Phe Ala Ser Arg Gln Leu Gln
                        740                 745                 750
        Arg Leu Phe Glu Gln Pro Gln Ser Ser Val Ser Leu Lys Pro
        755                 760                 765

<210> SEQ ID NO 6
<211> LENGTH: 160
<212> TYPE: PRT
<213> ORGANISM: Pseudomonas aeruginosa

<400> SEQUENCE: 6

Met Ser Tyr Tyr Gln His Pro Ser Ala Ile Val Asp Asp Gly Ala Gln
        1               5                   10                  15
        Ile Gly Ser Asp Ser Arg Val Trp His Phe Val His Ile Cys Ala Gly
                        20                  25                  30
        Ala Arg Ile Gly Ala Gly Val Ser Leu Gly Gln Asn Val Phe Val Gly
                        35                  40                  45
        Asn Lys Val Val Ile Gly Asp Arg Cys Lys Ile Gln Asn Asn Val Ser
                        50                  55                  60
        Val Tyr Asp Asn Val Thr Leu Glu Glu Val Phe Cys Gly Pro Ser
        65                  70                  75                  80
        Met Val Phe Thr Asn Val Tyr Asn Pro Arg Ser Leu Ile Glu Arg Lys
                        85                  90                  95
        Asp Gln Tyr Arg Asn Thr Leu Val Lys Lys Gly Ala Thr Leu Gly Ala
                        100                 105                 110
        Asn Cys Thr Ile Val Cys Gly Val Thr Ile Gly Glu Tyr Ala Phe Leu
                        115                 120                 125
        Gly Ala Gly Ala Val Ile Asn Lys Asn Val Pro Ser Tyr Ala Leu Met
                        130                 135                 140
        Val Gly Val Pro Ala Arg Gln Ile Gly Trp Ile Ala Asn Ser Val Ser
        145                 150                 155                 160

<210> SEQ ID NO 7
<211> LENGTH: 276
<212> TYPE: PRT
<213> ORGANISM: Pseudomonas aeruginosa

<400> SEQUENCE: 7

Met Ile Glu Phe Ile Asp Leu Lys Asn Gln Gln Ala Arg Ile Lys Asp
        1               5                   10                  15
```

```
Lys Ile Asp Ala Gly Ile Gln Arg Val Leu Arg His Gly Gln Tyr Ile
             20                  25                  30
Leu Gly Pro Glu Val Thr Glu Leu Glu Asp Arg Leu Ala Asp Phe Val
         35                  40                  45
Gly Ala Lys Tyr Cys Ile Ser Cys Ala Asn Gly Thr Asp Ala Leu Gln
 50                  55                  60
Ile Val Gln Met Ala Leu Gly Val Gly Pro Gly Asp Glu Val Ile Thr
 65                  70                  75                  80
Pro Gly Phe Thr Tyr Val Ala Thr Ala Glu Thr Val Ala Leu Leu Gly
                 85                  90                  95
Ala Lys Pro Val Tyr Val Asp Ile Asp Pro Arg Thr Tyr Asn Leu Asp
             100                 105                 110
Pro Gln Leu Leu Glu Ala Ala Ile Thr Pro Arg Thr Lys Ala Ile Ile
         115                 120                 125
Pro Val Ser Leu Tyr Gly Gln Cys Ala Asp Phe Asp Ala Ile Asn Ala
 130                 135                 140
Ile Ala Ser Lys Tyr Gly Ile Pro Val Ile Glu Asp Ala Ala Gln Ser
 145                 150                 155                 160
Phe Gly Ala Ser Tyr Lys Gly Lys Arg Ser Cys Asn Leu Ser Thr Val
                 165                 170                 175
Ala Cys Thr Ser Phe Phe Pro Ser Lys Pro Leu Gly Cys Tyr Gly Asp
             180                 185                 190
Gly Gly Ala Ile Phe Thr Asn Asp Asp Glu Leu Ala Thr Ala Ile Arg
         195                 200                 205
Gln Ile Ala Arg His Gly Gln Asp Arg Arg Tyr His His Ile Arg Val
 210                 215                 220
Gly Val Asn Ser Arg Leu Asp Thr Leu Gln Ala Ala Ile Leu Leu Pro
 225                 230                 235                 240
Lys Leu Glu Ile Phe Glu Glu Glu Ile Ala Leu Arg Gln Lys Val Ala
                 245                 250                 255
Ala Glu Tyr Asp Leu Ser Leu Lys Gln Val Gly Ile Gly Thr Pro Phe
             260                 265                 270
Ile Gly Ser Gly
         275
```

<210> SEQ ID NO 8
<211> LENGTH: 438
<212> TYPE: PRT
<213> ORGANISM: Pseudomonas aeruginosa

<400> SEQUENCE: 8

```
Met Tyr Ile Leu Ala Arg Val Asp Arg Ser Ile Leu Leu Asn Thr Val
 1               5                  10                  15
Leu Leu Phe Ala Phe Phe Ser Ala Thr Val Trp Val Asn Asn Asn Tyr
             20                  25                  30
Ile Tyr His Leu Tyr Asp Tyr Met Gly Ser Ala Lys Lys Thr Val Asp
         35                  40                  45
Phe Gly Leu Tyr Pro Tyr Leu Met Val Leu Ala Leu Ile Cys Ala Leu
 50                  55                  60
Leu Cys Gly Gly Ala Ile Arg Arg Pro Gly Asp Leu Leu Val Thr Leu
 65                  70                  75                  80
Leu Val Val Ile Leu Val Pro His Ser Leu Val Leu Asn Gly Ala Asn
                 85                  90                  95
Gln Tyr Ser Pro Asp Ala Gln Pro Trp Ala Gly Val Pro Leu Ala Ile
             100                 105                 110
Ala Phe Gly Ile Leu Ile Ile Gly Ile Val Asn Lys Ile Arg Phe His
         115                 120                 125
Pro Leu Gly Ala Leu Gln Arg Glu Asn Gln Gly Arg Arg Met Leu Val
 130                 135                 140
Leu Leu Ser Val Leu Asn Ile Val Leu Val Phe Ile Phe Lys
 145                 150                 155                 160
Ser Ala Gly Tyr Phe Ser Phe Asp Phe Ala Gly Gln Tyr Ala Arg Arg
                 165                 170                 175
Ala Leu Ala Arg Glu Val Phe Ala Ala Gly Ser Ala Asn Gly Tyr Leu
             180                 185                 190
Ser Ser Ile Gly Thr Gln Ala Phe Phe Pro Val Leu Phe Ala Trp Gly
         195                 200                 205
Val Tyr Arg Arg Gln Trp Phe Tyr Leu Val Leu Gly Ile Val Asn Ala
 210                 215                 220
Leu Val Leu Trp Gly Ala Phe Gly Gln Lys Tyr Pro Phe Val Val Leu
 225                 230                 235                 240
Phe Leu Ile Tyr Gly Leu Met Val Tyr Phe Arg Arg Phe Gly Gln Val
                 245                 250                 255
Arg Val Ser Trp Val Val Cys Ala Leu Leu Met Leu Leu Leu Leu Gly
             260                 265                 270
Ala Leu Glu His Glu Val Phe Gly Tyr Ser Phe Leu Asn Asp Tyr Phe
         275                 280                 285
Leu Arg Arg Ala Phe Ile Val Pro Ser Thr Leu Leu Gly Ala Val Asp
```

```
        290                 295                 300
Gln Phe Val Ser Gln Phe Gly Ser Asn Tyr Tyr Arg Asp Thr Leu Leu
305                 310                 315                 320
Gly Ala Leu Leu Gly Gln Gly Arg Thr Glu Pro Leu Ser Phe Arg Leu
                325                 330                 335
Gly Thr Glu Ile Phe Asn Asn Pro Asp Met Asn Ala Asn Val Asn Phe
            340                 345                 350
Phe Ala Ile Ala Tyr Met Gln Leu Gly Tyr Val Gly Val Met Ala Glu
            355                 360                 365
Ser Met Leu Val Gly Gly Ser Val Val Leu Met Asn Phe Leu Phe Ser
        370                 375                 380
Arg Tyr Gly Ala Phe Met Ala Ile Pro Val Ala Leu Leu Phe Thr Thr
385                 390                 395                 400
Lys Ile Leu Glu Gln Pro Leu Leu Thr Val Met Leu Gly Ser Gly Val
                405                 410                 415
Phe Leu Ile Leu Leu Phe Leu Ala Leu Ile Ser Phe Pro Leu Lys Met
                420                 425                 430
Ser Leu Gly Lys Thr Leu
            435
```

<210> SEQ ID NO 9
<211> LENGTH: 316
<212> TYPE: PRT
<213> ORGANISM: Pseudomonas aeruginosa

<400> SEQUENCE: 9

```
    Met Ser Ala Ala Phe Ile Asn Arg Val Ala Arg Val Leu Val Gly Thr
    1               5                   10                  15
    Leu Gly Ala Gln Leu Ile Thr Ile Gly Val Thr Leu Leu Leu Val Arg
                    20                  25                  30
    Leu Tyr Ser Pro Ala Glu Met Gly Ala Phe Ser Val Trp Leu Ser Phe
                35                  40                  45
    Ala Thr Ile Phe Ala Val Val Val Thr Gly Arg Tyr Glu Leu Ala Ile
            50                  55                  60
    Phe Ser Thr Arg Glu Glu Gly Leu Gln Ala Ile Val Lys Leu Ile
    65                  70                  75                  80
    Leu Gln Leu Thr Leu Leu Ile Phe Val Ala Val Ile Ala Val Val
                    85                  90                  95
    Ile Gly Arg His Leu Ile Glu Ser Met Pro Val Val Ile Gly Glu Tyr
                    100                 105                 110
    Trp Phe Ala Leu Ala Val Ala Ser Leu Gly Leu Gly Ile Asn Lys Leu
                115                 120                 125
    Val Leu Ser Leu Leu Thr Phe Gln Gln Ser Phe Asn Arg Leu Gly Val
            130                 135                 140
    Ala Arg Val Ser Leu Ala Ala Cys Ile Ala Val Ala Gln Val Ser Ala
    145                 150                 155                 160
    Ala Tyr Leu Leu Glu Gly Val Ser Gly Leu Ile Tyr Gly Gln Leu Phe
                    165                 170                 175
    Gly Val Val Ala Thr Ala Leu Ala Ala Leu Trp Val Gly Lys Ser
                    180                 185                 190
    Leu Ile Leu Asn Cys Ile Glu Thr Pro Trp Arg Met Val Arg Gln Val
                195                 200                 205
    Ala Val Gln Tyr Ile Asn Phe Pro Lys Phe Ser Leu Pro Ala Asp Leu
            210                 215                 220
    Val Asn Thr Val Ala Ser Gln Val Pro Val Ile Leu Leu Ala Ala Lys
    225                 230                 235                 240
    Phe Gly Gly Asp Ser Ala Gly Trp Phe Ala Leu Thr Leu Lys Ile Met
                    245                 250                 255
    Gly Ala Pro Ile Ser Leu Leu Ala Ala Ser Val Leu Asp Val Phe Lys
                    260                 265                 270
    Glu Gln Ala Ala Arg Asp Tyr Arg Glu Phe Gly Asn Cys Arg Gly Ile
                275                 280                 285
    Phe Leu Lys Thr Phe Arg Leu Leu Ala Val Leu Ala Leu Pro Pro Phe
            290                 295                 300
    Ile Ile Phe Gly Ser Leu Ala Ser Gly Pro Leu Gly
    305                 310                 315
```

<210> SEQ ID NO 10
<211> LENGTH: 118
<212> TYPE: PRT
<213> ORGANISM: Pseudomonas aeruginosa

<400> SEQUENCE: 10

```
    Met Leu Gly Leu Arg Ser Glu Glu Gly Ala Glu Pro Gly Leu Gly Trp
    1               5                   10                  15
    Ile Asp Met Asp Ser Val Arg Phe Glu Arg Arg Asp Asp Arg Lys Val
```

```
                    20                  25                  30
        Pro His Met Gly Trp Asn Gln Val Ser Pro Gln Leu Glu His Pro Ile
                35                  40                  45
        Leu Ser Gly Ile Asn Glu Gln Ser Arg Phe Tyr Phe Val His Ser Tyr
                50                  55                  60
        Tyr Met Val Pro Lys Asp Pro Asp Ile Leu Leu Ser Cys Asn Tyr
        65                  70                  75                  80
        Gly Gln Lys Phe Thr Ala Ala Val Ala Arg Asp Asn Val Phe Gly Phe
                        85                  90                  95
        Gln Phe His Pro Glu Lys Ser His Lys Phe Gly Met Gln Leu Phe Lys
                        100                 105                 110
        Asn Phe Val Glu Leu Val
                        115

<210> SEQ ID NO 11
<211> LENGTH: 251
<212> TYPE: PRT
<213> ORGANISM: Pseudomonas aeruginosa

<400> SEQUENCE: 11

Met Val Arg Arg Val Ile Pro Cys Leu Leu Lys Asp Arg Gly
        1               5                   10                  15
        Leu Val Lys Thr Val Lys Phe Lys Glu Pro Lys Tyr Val Gly Asp Pro
                        20                  25                  30
        Ile Asn Ala Ile Arg Ile Phe Asn Glu Lys Glu Val Asp Glu Leu Ile
                        35                  40                  45
        Leu Leu Asp Ile Asp Ala Ser Arg Leu Asn Gln Glu Pro Asn Tyr Glu
                        50                  55                  60
        Leu Ile Ala Glu Val Ala Gly Glu Cys Phe Met Pro Ile Cys Tyr Gly
        65                  70                  75                  80
        Gly Gly Ile Lys Thr Leu Glu His Ala Glu Lys Ile Phe Ser Leu Gly
                        85                  90                  95
        Val Glu Lys Val Ser Ile Asn Thr Ala Ala Leu Met Asp Leu Ser Leu
                        100                 105                 110
        Ile Arg Arg Ile Ala Asp Lys Phe Gly Ser Gln Ser Val Val Gly Ser
                        115                 120                 125
        Ile Asp Cys Arg Lys Gly Phe Trp Gly Gly His Ser Val Phe Ser Glu
                        130                 135                 140
        Asn Gly Thr Arg Asp Met Lys Arg Ser Pro Leu Glu Trp Ala Gln Ala
        145                 150                 155                 160
        Leu Glu Glu Ala Gly Val Gly Glu Ile Phe Leu Asn Ser Ile Asp Arg
                        165                 170                 175
        Asp Gly Val Gln Lys Gly Phe Asp Asn Ala Leu Val Glu Asn Ile Ala
                        180                 185                 190
        Ser Asn Val His Val Pro Val Ile Ala Cys Gly Gly Ala Gly Ser Ile
                        195                 200                 205
        Ala Asp Leu Ile Asp Leu Phe Glu Arg Thr Cys Val Ser Ala Val Ala
                        210                 215                 220
        Ala Gly Ser Leu Phe Val Phe His Gly Lys His Arg Ala Val Leu Ile
        225                 230                 235                 240
        Ser Tyr Pro Asp Val Asn Lys Leu Asp Val Gly
                        245                 250

<210> SEQ ID NO 12
<211> LENGTH: 376
<212> TYPE: PRT
<213> ORGANISM: Pseudomonas aeruginosa

<400> SEQUENCE: 12

Met Lys Ile Cys Ser Arg Cys Val Met Asp Thr Ser Asp Ala Glu Ile
        1               5                   10                  15
        Val Phe Asp Glu Ala Gly Val Cys Asn His Cys His Lys Phe Asp Asn
                        20                  25                  30
        Val Gln Ser Arg Gln Leu Phe Ser Asp Ala Ser Gly Glu Gln Arg Leu
                        35                  40                  45
        Gln Lys Ile Ile Gly Gln Ile Lys Lys Asp Gly Ser Gly Lys Asp Tyr
                        50                  55                  60
        Asp Cys Ile Ile Gly Leu Ser Gly Gly Val Asp Ser Ser Tyr Leu Ala
        65                  70                  75                  80
        Val Lys Val Lys Asp Leu Gly Leu Arg Pro Leu Val Val His Val Asp
                        85                  90                  95
        Ala Gly Trp Asn Ser Glu Leu Ala Val Ser Asn Ile Glu Lys Ile Val
                        100                 105                 110
        Lys Tyr Cys Gly Phe Asp Leu His Thr His Val Ile Asn Trp Glu Glu
                        115                 120                 125
        Ile Arg Asp Leu Gln Leu Ala Tyr Met Lys Ala Ala Val Ala Asn Gln
```

```
            130                 135                 140
Asp Val Pro Gln Asp His Ala Phe Phe Ala Ser Met Tyr His Phe Ala
145                 150                 155                 160
Val Lys Asn Asn Ile Lys Tyr Ile Leu Ser Gly Gly Asn Leu Ala Thr
                165                 170                 175
Glu Ala Val Phe Pro Asp Thr Trp His Gly Ser Ala Met Asp Ala Ile
            180                 185                 190
Asn Leu Lys Ala Ile His Lys Lys Tyr Gly Glu Arg Pro Leu Arg Asp
        195                 200                 205
Tyr Lys Thr Ile Ser Phe Leu Glu Tyr Tyr Phe Trp Tyr Pro Phe Val
210                 215                 220
Lys Gly Met Arg Thr Val Arg Pro Leu Asn Phe Met Ala Tyr Asp Lys
225                 230                 235                 240
Ala Lys Ala Glu Thr Phe Leu Gln Glu Thr Ile Gly Tyr Arg Ser Tyr
                245                 250                 255
Ala Arg Lys His Gly Glu Ser Ile Phe Thr Lys Leu Phe Gln Asn Tyr
            260                 265                 270
Tyr Leu Pro Thr Lys Phe Gly Tyr Asp Lys Arg Lys Leu His Tyr Ser
        275                 280                 285
Ser Met Ile Leu Ser Gly Gln Met Thr Arg Asp Glu Ala Gln Ala Lys
        290                 295                 300
Leu Ala Glu Pro Leu Tyr Asp Ala Asp Glu Leu Gln Phe Asp Ile Glu
305                 310                 315                 320
Tyr Phe Cys Lys Lys Met Arg Ile Thr Gln Ala Gln Phe Glu Glu Leu
                325                 330                 335
Met Asn Ala Pro Val His Asp Tyr Ser Glu Phe Ala Asn Trp Asp Ser
            340                 345                 350
Arg Gln Arg Ile Ala Lys Lys Val Gln Met Ile Val Gln Arg Ala Leu
        355                 360                 365
Gly Arg Arg Ile Asn Val Tyr Ser
370                 375

<210> SEQ ID NO 13
<211> LENGTH: 373
<212> TYPE: PRT
<213> ORGANISM: Pseudomonas aeruginosa

<400> SEQUENCE: 13

Met Thr Lys Val Ala His Leu Thr Ser Val His Ser Arg Tyr Asp Ile
1               5                   10                  15
Arg Ile Phe Arg Lys Gln Cys Arg Thr Leu Ser Gln Tyr Gly Tyr Asp
            20                  25                  30
Val Tyr Leu Val Val Ala Asp Gly Lys Gly Asp Glu Val Lys Asp Gly
        35                  40                  45
Val Arg Ile Val Asp Val Gly Val Leu Ser Gly Arg Leu Asn Arg Ile
    50                  55                  60
Leu Lys Thr Thr Arg Lys Ile Tyr Glu Gln Ala Leu Ala Leu Gly Ala
65                  70                  75                  80
Asp Val Tyr His Phe His Asp Pro Glu Leu Ile Pro Val Gly Leu Arg
                85                  90                  95
Leu Lys Lys Gln Gly Lys Gln Val Ile Phe Asp Ser His Glu Asp Val
            100                 105                 110
Pro Lys Gln Leu Leu Ser Lys Pro Tyr Met Arg Pro Phe Leu Arg Arg
        115                 120                 125
Val Val Ala Val Leu Phe Ser Cys Tyr Glu Lys Tyr Ala Cys Pro Lys
    130                 135                 140
Leu Asp Ala Val Leu Thr Ala Thr Pro His Ile Arg Glu Lys Phe Lys
145                 150                 155                 160
Asn Ile Asn Gly Asn Val Leu Asp Ile Asn Asn Phe Pro Met Leu Gly
                165                 170                 175
Glu Leu Asp Ala Met Val Pro Trp Ala Ser Lys Lys Thr Glu Val Cys
            180                 185                 190
Tyr Val Gly Gly Ile Thr Ser Ile Arg Gly Val Arg Glu Val Val Lys
        195                 200                 205
Ser Leu Glu Cys Leu Lys Ser Ser Ala Arg Leu Asn Leu Val Gly Lys
    210                 215                 220
Phe Ser Glu Pro Glu Ile Glu Lys Glu Val Arg Ala Leu Lys Gly Trp
225                 230                 235                 240
Asn Ser Val Asn Glu His Gly Gln Leu Asp Arg Glu Asp Val Arg Arg
                245                 250                 255
Val Leu Gly Asp Ser Val Ala Gly Leu Val Thr Phe Leu Pro Met Pro
            260                 265                 270
Asn His Val Asp Ala Gln Pro Asn Lys Met Phe Glu Tyr Met Ser Ser
        275                 280                 285
Gly Ile Pro Val Ile Ala Ser Asn Phe Pro Leu Trp Arg Glu Ile Val
    290                 295                 300
Glu Gly Ser Asn Cys Gly Ile Cys Val Asp Pro Leu Ser Pro Ala Ala
305                 310                 315                 320
```

```
        Ile Ala Glu Ala Ile Asp Tyr Leu Val Ser Asn Pro Cys Glu Ala Ala
                        325                 330                 335
        Ala Leu Gly Arg Asn Gly Gln Arg Ala Val Asn Glu Arg Tyr Asn Trp
                        340                 345                 350
        Asp Leu Glu Gly Arg Lys Leu Ala Arg Phe Tyr Ser Asp Leu Leu Ser
                        355                 360                 365
        Lys Arg Asp Ser Ile
                        370

<210> SEQ ID NO 14
<211> LENGTH: 362
<212> TYPE: PRT
<213> ORGANISM: Pseudomonas aeruginosa

<400> SEQUENCE: 14

Met Lys Ile Leu Thr Ile Ile Gly Ala Arg Pro Gln Phe Ile Lys Ala
         1               5                  10                  15
        Ser Val Val Ser Lys Ala Ile Glu Gln Thr Leu Ser Glu Ile
                        20                  25                  30
        Ile Val His Thr Gly Gln His Phe Asp Ala Asn Met Ser Glu Ile Phe
                        35                  40                  45
        Phe Glu Gln Leu Gly Ile Pro Lys Pro Asp Tyr Gln Leu Asp Ile His
                50                  55                  60
        Gly Gly Thr His Gly Gln Met Thr Gly Arg Met Leu Met Glu Ile Glu
         65                  70                  75                  80
        Asp Val Ile Leu Lys Glu Lys Pro His Arg Val Leu Val Tyr Gly Asp
                            85                  90                  95
        Thr Asn Ser Thr Leu Ala Gly Ala Leu Ala Ala Ser Lys Leu His Val
                        100                 105                 110
        Pro Ile Ala His Ile Glu Ala Gly Leu Arg Ser Phe Asn Met Arg Met
                        115                 120                 125
        Pro Glu Glu Ile Asn Arg Ile Leu Thr Asp Gln Val Ser Asp Ile Leu
                130                 135                 140
        Phe Cys Pro Thr Arg Val Ala Ile Asp Asn Leu Lys Asn Glu Gly Phe
        145                 150                 155                 160
        Glu Arg Lys Ala Ala Lys Ile Val Asn Val Gly Asp Val Met Gln Asp
                        165                 170                 175
        Ser Ala Leu Phe Phe Ala Gln Arg Ala Thr Ser Pro Ile Gly Leu Ala
                        180                 185                 190
        Ser Gln Asp Gly Phe Ile Leu Ala Thr Leu His Arg Ala Glu Asn Thr
                        195                 200                 205
        Asp Asp Pro Val Arg Leu Thr Ser Ile Val Glu Ala Leu Asn Glu Ile
                210                 215                 220
        Gln Ile Asn Val Ala Pro Val Val Leu Pro Leu His Pro Arg Thr Arg
        225                 230                 235                 240
        Gly Val Ile Glu Arg Leu Gly Leu Lys Leu Glu Val Gln Val Ile Asp
                        245                 250                 255
        Pro Val Gly Tyr Leu Glu Met Ile Trp Leu Leu Gln Arg Ser Gly Leu
                        260                 265                 270
        Val Leu Thr Asp Ser Gly Gly Val Gln Lys Glu Ala Phe Phe Phe Gly
                        275                 280                 285
        Lys Pro Cys Val Thr Met Arg Asp Gln Thr Glu Trp Val Glu Leu Val
                290                 295                 300
        Thr Cys Gly Ala Asn Val Leu Val Gly Ala Ala Arg Asp Met Ile Val
        305                 310                 315                 320
        Glu Ser Ala Arg Thr Ser Leu Gly Lys Thr Ile Gln Asp Asp Gly Gln
                        325                 330                 335
        Leu Tyr Gly Gly Gly Gln Ala Ser Leu Gly Leu Leu Asn Ile Leu Pro
                        340                 345                 350
        Ser Cys Asp Ala Leu Arg Val Glu Phe Lys
                        355                 360

<210> SEQ ID NO 15
<211> LENGTH: 413
<212> TYPE: PRT
<213> ORGANISM: Pseudomonas aeruginosa

<400> SEQUENCE: 15

Met Asn Val Trp Tyr Val His Pro Tyr Ala Gly Gly Pro Gly Val Gly
         1               5                  10                  15
        Arg Tyr Trp Arg Pro Tyr Tyr Phe Ser Lys Phe Trp Asn Gln Ala Gly
                        20                  25                  30
        His Arg Ser Val Ile Ile Ser Ala Gly Tyr His His Leu Leu Glu Pro
                        35                  40                  45
        Asp Glu Lys Arg Ser Gly Val Thr Cys Val Asn Gly Ala Glu Tyr Ala
                50                  55                  60
```

```
    Tyr Val Pro Thr Leu Arg Tyr Leu Gly Asn Gly Val Gly Arg Met Leu
     65                  70                  75                  80
    Ser Met Leu Ile Phe Thr Met Met Leu Leu Pro Phe Cys Leu Ile Leu
                     85                  90                  95
    Ala Leu Lys Arg Gly Thr Pro Asp Ala Ile Ile Tyr Ser Ser Pro His
                100                 105                 110
    Pro Phe Gly Val Val Ser Cys Trp Leu Ala Arg Leu Leu Gly Ala
            115                 120                 125
    Lys Phe Val Phe Glu Val Arg Asp Ile Trp Pro Leu Ser Leu Val Glu
        130                 135                 140
    Leu Gly Gly Leu Lys Ala Asp Asn Pro Leu Val Arg Val Thr Gly Trp
    145                 150                 155                 160
    Ile Glu Arg Phe Ser Tyr Ala Arg Ala Asp Lys Ile Ile Ser Leu Leu
                    165                 170                 175
    Pro Cys Ala Glu Pro His Met Ala Asp Lys Gly Leu Pro Ala Gly Lys
                180                 185                 190
    Phe Leu Trp Val Pro Asn Gly Val Asp Ser Ser Asp Ile Ser Pro Asp
            195                 200                 205
    Ser Ala Val Ser Ser Asp Leu Val Arg His Val Gln Val Leu Lys
    210                 215                 220
    Glu Gln Gly Val Phe Val Val Ile Tyr Ala Gly Ala His Gly Glu Pro
    225                 230                 235                 240
    Asn Ala Leu Glu Gly Leu Val Arg Ser Ala Gly Leu Leu Arg Glu Arg
                    245                 250                 255
    Gly Ala Ser Ile Arg Ile Ile Leu Val Gly Lys Gly Glu Cys Lys Glu
                260                 265                 270
    Gln Leu Lys Ala Ile Ala Ala Gln Asp Ala Ser Gly Leu Val Glu Phe
            275                 280                 285
    Phe Asp Gln Gln Pro Lys Glu Thr Ile Met Ala Val Leu Lys Leu Ala
    290                 295                 300
    Ser Ala Gly Tyr Ile Ser Leu Lys Ser Glu Pro Ile Phe Arg Phe Gly
    305                 310                 315                 320
    Val Ser Pro Asn Lys Leu Trp Asp Tyr Met Leu Val Gly Leu Pro Val
                    325                 330                 335
    Ile Phe Ala Cys Lys Ala Gly Asn Asp Pro Val Ser Asp Tyr Asp Cys
                340                 345                 350
    Gly Val Ser Ala Asp Pro Asp Ala Pro Glu Asp Ile Thr Ala Ala Ile
            355                 360                 365
    Phe Arg Leu Leu Leu Ser Glu Asp Glu Arg Arg Thr Met Gly Gln
    370                 375                 380
    Arg Gly Arg Asp Ala Val Leu Glu His Tyr Thr Tyr Glu Ser Leu Ala
    385                 390                 395                 400
    Leu Gln Val Leu Asn Ala Leu Ala Asp Gly Arg Ala Ala
                    405                 410

<210> SEQ ID NO 16
<211> LENGTH: 320
<212> TYPE: PRT
<213> ORGANISM: Pseudomonas aeruginosa

<400> SEQUENCE: 16

Met Lys Ala Val Met Val Thr Gly Ala Ser Gly Phe Val Gly Ser Ala
      1               5                  10                  15
    Leu Cys Cys Glu Leu Ala Arg Thr Gly Tyr Ala Val Ile Ala Val Val
                     20                  25                  30
    Arg Arg Val Glu Arg Ile Pro Ser Val Thr Tyr Ile Glu Ala Asp
                 35                  40                  45
    Leu Thr Asp Pro Ala Thr Phe Ala Gly Glu Phe Pro Thr Val Asp Cys
         50                  55                  60
    Ile Ile His Leu Ala Gly Arg Ala His Ile Leu Thr Asp Lys Val Ala
     65                  70                  75                  80
    Asp Pro Leu Ala Ala Phe Arg Glu Val Asn Arg Asp Ala Thr Val Arg
                     85                  90                  95
    Leu Ala Thr Arg Ala Leu Glu Ala Gly Val Lys Arg Phe Val Phe Val
                100                 105                 110
    Ser Ser Ile Gly Val Asn Gly Asn Ser Thr Arg Gln Gln Ala Phe Asn
                115                 120                 125
    Glu Asp Ser Pro Ala Gly Pro His Ala Pro Tyr Ala Ile Ser Lys Tyr
        130                 135                 140
    Glu Ala Glu Gln Glu Leu Gly Thr Leu Leu Arg Gly Lys Gly Met Glu
    145                 150                 155                 160
    Leu Val Val Val Arg Pro Pro Leu Ile Tyr Ala Asn Asp Ala Pro Gly
                    165                 170                 175
    Asn Phe Gly Arg Leu Leu Lys Leu Val Ala Ser Gly Leu Pro Leu Pro
                180                 185                 190
    Leu Asp Gly Val Arg Asn Ala Arg Ser Leu Val Ser Arg Arg Asn Ile
        195                 200                 205
    Val Gly Phe Leu Ser Leu Cys Ala Glu His Pro Asp Ala Ala Gly Glu
```

```
            210                 215                 220
    Leu Phe Leu Val Ala Asp Gly Glu Asp Val Ser Ile Ala Gln Met Ile
    225                 230                 235                 240
    Glu Ala Leu Ser Arg Gly Met Gly Arg Arg Pro Ala Leu Phe Thr Phe
                        245                 250                 255
    Pro Ala Val Leu Leu Lys Leu Val Met Cys Leu Leu Gly Lys Ala Ser
                260                 265                 270
    Met His Glu Gln Leu Cys Gly Ser Leu Gln Val Asp Ala Ser Lys Ala
            275                 280                 285
    Arg Arg Leu Leu Gly Trp Val Pro Val Glu Thr Ile Gly Ala Gly Leu
    290                 295                 300
    Gln Ala Ala Gly Arg Glu Tyr Ile Leu Arg Gln Arg Glu Arg Arg Lys
    305                 310                 315                 320
```

<210> SEQ ID NO 17
<211> LENGTH: 665
<212> TYPE: PRT
<213> ORGANISM: Pseudomonas aeruginosa

<400> SEQUENCE: 17

```
    Met Leu Asp Asn Leu Arg Ile Lys Leu Leu Gly Leu Pro Arg Arg Tyr
    1               5                   10                  15
    Lys Arg Met Leu Gln Val Ala Ala Asp Val Thr Leu Val Trp Leu Ser
                    20                  25                  30
    Leu Trp Leu Ala Phe Leu Val Arg Leu Gly Thr Glu Asp Met Ile Ser
                35                  40                  45
    Pro Phe Ser Gly His Ala Trp Leu Phe Ile Ala Ala Pro Leu Val Ala
                50                  55                  60
    Ile Pro Leu Phe Ile Arg Phe Gly Met Tyr Arg Ala Val Met Arg Tyr
    65                  70                  75                  80
    Leu Gly Asn Asp Ala Leu Ala Ile Ala Lys Ala Val Thr Ile Ser
                        85                  90                  95
    Ala Leu Val Leu Ser Leu Leu Val Tyr Trp Tyr Arg Ser Pro Pro Ala
                    100                 105                 110
    Val Val Pro Arg Ser Leu Val Phe Asn Tyr Trp Leu Ser Met Leu
                    115                 120                 125
    Leu Ile Gly Gly Leu Arg Leu Ala Met Arg Gln Tyr Phe Met Gly Asp
                130                 135                 140
    Trp Tyr Ser Ala Val Gln Ser Val Pro Phe Leu Asn Arg Gln Asp Gly
    145                 150                 155                 160
    Leu Pro Arg Val Ala Ile Tyr Gly Ala Gly Ala Ala Asn Gln Leu
                        165                 170                 175
    Val Ala Ala Leu Arg Leu Gly Arg Ala Met Arg Pro Val Ala Phe Ile
                    180                 185                 190
    Asp Asp Asp Lys Gln Ile Ala Asn Arg Val Ile Ala Gly Leu Arg Val
                    195                 200                 205
    Tyr Thr Ala Lys His Ile Arg Gln Met Ile Asp Glu Thr Gly Ala Gln
                210                 215                 220
    Glu Val Leu Leu Ala Ile Pro Ser Ala Thr Arg Ala Arg Arg Glu
    225                 230                 235                 240
    Ile Leu Glu Ser Leu Glu Pro Phe Pro Leu His Val Arg Ser Met Pro
                        245                 250                 255
    Gly Phe Met Asp Leu Thr Ser Gly Arg Val Lys Val Asp Asp Leu Gln
                    260                 265                 270
    Glu Val Asp Ile Ala Asp Leu Leu Gly Arg Asp Ser Val Ala Pro Arg
                    275                 280                 285
    Lys Glu Leu Leu Glu Arg Cys Ile Arg Gly Gln Val Val Met Val Thr
                290                 295                 300
    Gly Ala Gly Gly Ser Ile Gly Ser Glu Leu Cys Arg Gln Ile Met Ser
    305                 310                 315                 320
    Cys Ser Pro Ser Val Leu Ile Leu Phe Glu His Ser Glu Tyr Asn Leu
                        325                 330                 335
    Tyr Ser Ile His Gln Glu Leu Glu Arg Arg Ile Lys Arg Glu Ser Leu
                    340                 345                 350
    Ser Val Asn Leu Leu Pro Ile Leu Gly Ser Val Arg Asn Pro Glu Arg
                    355                 360                 365
    Leu Val Asp Val Met Arg Thr Trp Lys Val Asn Thr Val Tyr His Ala
                370                 375                 380
    Ala Ala Tyr Lys His Val Pro Ile Val Glu His Asn Ile Ala Glu Gly
    385                 390                 395                 400
    Val Leu Asn Asn Val Ile Gly Thr Leu His Ala Val Gln Ala Ala Val
                        405                 410                 415
    Gln Val Gly Val Gln Asn Phe Val Leu Ile Ser Thr Asp Lys Ala Val
                    420                 425                 430
    Arg Pro Thr Asn Val Met Gly Ser Thr Lys Arg Leu Ala Glu Met Val
                    435                 440                 445
    Leu Gln Ala Leu Ser Asn Glu Ser Ala Pro Leu Leu Phe Gly Asp Arg
                450                 455                 460
```

```
      Lys Asp Val His His Val Asn Lys Thr Arg Phe Thr Met Val Arg Phe
      465                 470                 475                 480
      Gly Asn Val Leu Gly Ser Ser Gly Ser Val Ile Pro Leu Phe Arg Glu
                      485                 490                 495
      Gln Ile Lys Arg Gly Gly Pro Val Thr Val Thr His Pro Ser Ile Thr
                  500                 505                 510
      Arg Tyr Phe Met Thr Ile Pro Glu Ala Ala Gln Leu Val Ile Gln Ala
              515                 520                 525
      Gly Ser Met Gly Gln Gly Gly Asp Val Phe Val Leu Asp Met Gly Pro
          530                 535                 540
      Pro Val Lys Ile Leu Glu Leu Ala Glu Lys Met Ile His Leu Ser Gly
      545                 550                 555                 560
      Leu Ser Val Arg Ser Glu Arg Ser Pro His Gly Asp Ile Ala Ile Glu
                      565                 570                 575
      Phe Ser Gly Leu Arg Pro Gly Glu Lys Leu Tyr Glu Glu Leu Leu Ile
                  580                 585                 590
      Gly Asp Asn Val Asn Pro Thr Asp His Pro Met Ile Met Arg Ala Asn
                  595                 600                 605
      Glu Glu His Leu Ser Trp Glu Ala Phe Lys Val Val Leu Glu Gln Leu
              610                 615                 620
      Leu Ala Ala Val Glu Lys Asp Asp Tyr Ser Arg Val Arg Gln Leu Leu
      625                 630                 635                 640
      Arg Glu Thr Val Ser Gly Tyr Ala Pro Asp Gly Glu Ile Val Asp Trp
                      645                 650                 655
      Ile Tyr Arg Gln Arg Arg Arg Glu Pro
                      660                 665

<210> SEQ ID NO 18
<211> LENGTH: 463
<212> TYPE: PRT
<213> ORGANISM: Pseudomonas aeruginosa

<400> SEQUENCE: 18

Met Ile Asn Ser His Leu Leu Tyr Arg Leu Ser Tyr Arg Gly Thr Ala
      1               5                   10                  15
      Arg Arg Met Leu Leu Ile Lys Lys Gly Lys Pro Leu Pro Met Thr Ser
                      20                  25                  30
      Pro Phe Ser Leu Gln Asp Leu Asp Asp Gly Leu Gly Asp Gly Leu Gln
                  35                  40                  45
      Val Arg Phe Val Gln Arg Gly Asp Ala Asp Thr Ala Gly Ala Asp Gly
          50                  55                  60
      Val Asp Thr Glu Leu Gly Leu Gln Ala Leu Asp Leu Val Gly Gly Gln
      65                  70                  75                  80
      Ala Gly Ile Gly Glu His Ala Thr Leu Ala Thr Asp Glu Thr Glu Val
                      85                  90                  95
      Ala Leu Gly Ala Val Gly Cys Gln Leu Leu Asp His Arg Gln Ala His
                  100                 105                 110
      Val Ala Asp Ala Val Ala His Leu Ala Gln Phe Leu Leu Pro Glu Gly
                  115                 120                 125
      Pro Gln Phe Arg Ala Val Glu His Gly Gly Asp Asp Ala Gly Ala Val
                  130                 135                 140
      Gly Arg Trp Val Arg Ile Val Gly Ala Asp His Pro Leu His Leu Gly
      145                 150                 155                 160
      Gln His Ala Gly Arg Phe Ile Ala Ala Phe Gly His Asp Arg Glu Gly
                      165                 170                 175
      Ala Asp Ala Phe Ala Ile Glu Arg Glu Gly Phe Gly Glu Arg Ala Gly
                  180                 185                 190
      Asn Glu Glu Ala Gln Ala Arg Leu Gly Glu Gln Ala His Arg Gly Gly
                  195                 200                 205
      Val Phe Leu Asp Ala Val Ala Glu Ala Leu Val Gly Asp Val Glu Glu
                  210                 215                 220
      Arg His Val Ala Leu Gly Leu Glu His Val Gln His Leu Phe Pro Val
      225                 230                 235                 240
      Val Gln Leu Glu Ile Asp Ala Gly Arg Ile Met Ala Ala Gly Val Gln
                      245                 250                 255
      Asn His Asp Arg Ala Gly Arg Gln Gly Ile Gln Val Phe Gln Gln Ala
                  260                 265                 270
      Gly Ala Val His Ala Ile Ala Gly Val Val Ile Ala Val Val Leu
                  275                 280                 285
      His Arg Glu Ala Gly Gly Phe Glu Gln Cys Ala Val Val Phe Pro Ala
      290                 295                 300
      Arg Val Ala Asp Gly His Gly Gly Val Gly Gln Ala Leu Glu Glu
      305                 310                 315                 320
      Val Gly Ala Glu Leu Glu Arg Ala Gly Ala Ala Asp Gly Leu Gly Arg
                      325                 330                 335
      Asp His Thr Ala Gly Gly Gln Gln Leu Gly Leu Val Thr Glu Gln Gln
                  340                 345                 350
      Phe Leu Tyr Ala Leu Val Val Gly Gly Asp Pro Phe Asp Arg Gln Val
```

```
            355                 360                 365
    Ala Ala Arg Arg Val Gly Leu Asp Ala Gly Leu Leu Gly Ser Leu His
        370                 375                 380
    Gly Thr Gln Gln Arg Asn Ala Pro Leu Leu Val Val Val His Ala His
    385                 390                 395                 400
    Ala Gln Val Asp Leu Ala Arg Thr Gly Ile Gly Val Glu Gly Phe Val
                    405                 410                 415
    Gln Ala Lys Asp Gly Ile Thr Arg Cys His Phe Asp Gly Arg Lys Gln
                420                 425                 430
    Thr His Phe Ala Ala Arg Ser Val Lys Arg Gly Gly Gln Arg Asn
            435                 440                 445
    Pro Leu Cys Gly Gly Ala Lys Gly Cys Ala Asn Gly Gly Leu Leu
        450                 455                 460

<210> SEQ ID NO 19
<211> LENGTH: 238
<212> TYPE: PRT
<213> ORGANISM: Pseudomonas aeruginosa

<400> SEQUENCE: 19

Met His Ala Ala Thr Phe Arg Cys Met Leu Ser Ala Ile Ser Asp Ala
    1               5                   10                  15
    Gly Phe Ser Leu Ala Ser Gln Leu Pro Ala Arg Phe Phe Met Asp Thr
                    20                  25                  30
    Phe Gln Leu Asp Ser Arg Phe Lys Pro Ala Gly Asp Gln Pro Glu Ala
                35                  40                  45
    Ile Arg Gln Met Val Glu Gly Leu Glu Ala Gly Leu Ser His Gln Thr
            50                  55                  60
    Leu Leu Gly Val Thr Gly Ser Gly Lys Thr Phe Ser Ile Ala Asn Val
    65                  70                  75                  80
    Ile Ala Gln Val Gln Arg Pro Thr Leu Val Leu Ala Pro Asn Lys Thr
                    85                  90                  95
    Leu Ala Ala Gln Leu Tyr Gly Glu Phe Lys Thr Phe Phe Pro His Asn
                    100                 105                 110
    Ser Val Glu Tyr Phe Val Ser Tyr Tyr Asp Tyr Tyr Gln Pro Glu Ala
                115                 120                 125
    Tyr Val Pro Ser Ser Asp Thr Tyr Ile Glu Lys Asp Ser Ser Ile Asn
            130                 135                 140
    Asp His Ile Glu Gln Met Arg Leu Ser Ala Thr Lys Ala Leu Leu Glu
    145                 150                 155                 160
    Arg Pro Asp Ala Ile Ile Val Ala Thr Val Ser Ser Ile Tyr Gly Leu
                    165                 170                 175
    Gly Asp Pro Ala Ser Tyr Leu Lys Met Val Leu His Leu Asp Arg Gly
                    180                 185                 190
    Asp Arg Ile Asp Gln Arg Glu Leu Leu Arg Arg Leu Thr Ser Leu Gln
                195                 200                 205
    Tyr Thr Arg Asn Asp Met Asp Phe Ala Arg Ala Thr Phe Arg Val Arg
            210                 215                 220
    Gly Asp Val Ile Asp Ile Phe Pro Ala Glu Ser Asp Leu Glu
    225                 230                 235

<210> SEQ ID NO 20
<211> LENGTH: 303
<212> TYPE: PRT
<213> ORGANISM: Pseudomonas aeruginosa

<400> SEQUENCE: 20

Met Met Ile Trp Met Ile Ala Cys Leu Val Val Leu Leu Phe Ser Phe
    1               5                   10                  15
    Val Ala Thr Trp Gly Leu Arg Arg Tyr Ala Leu Ala Thr Lys Leu Met
                    20                  25                  30
    Asp Val Pro Asn Ala Arg Ser Ser His Ser Gln Pro Thr Pro Arg Gly
                35                  40                  45
    Gly Gly Val Ala Ile Val Leu Val Phe Leu Ala Ala Leu Val Trp Met
            50                  55                  60
    Leu Ser Ala Gly Ser Ile Ser Gly Gly Trp Gly Gly Ala Met Leu Gly
    65                  70                  75                  80
    Ala Gly Ser Gly Val Ala Leu Leu Gly Phe Leu Asp Asp His Gly His
                    85                  90                  95
    Ile Ala Ala Arg Trp Arg Leu Leu Gly His Phe Ser Ala Ala Ile Trp
                    100                 105                 110
    Ile Leu Leu Trp Thr Gly Gly Phe Pro Pro Leu Val Val Gly His
                115                 120                 125
    Ala Val Asp Leu Gly Trp Leu Gly His Val Leu Ala Val Phe Tyr Leu
            130                 135                 140
    Val Trp Val Leu Asn Leu Tyr Asn Phe Met Asp Gly Ile Asp Gly Ile
```

```
                145                 150                 155                 160
        Ala Ser Val Glu Ala Ile Gly Val Cys Val Gly Gly Ala Leu Ile Tyr
                        165                 170                 175
        Trp Leu Thr Gly His Val Ala Met Val Gly Ile Pro Leu Leu Leu Ala
                        180                 185                 190
        Cys Ala Val Ala Gly Phe Leu Ile Trp Asn Phe Pro Pro Ala Arg Ile
                        195                 200                 205
        Phe Met Gly Asp Ala Gly Ser Gly Phe Leu Gly Met Val Ile Gly Ala
                210                 215                 220
        Leu Ala Ile Gln Ala Ala Trp Thr Ala Pro Ser Leu Phe Trp Cys Trp
        225                 230                 235                 240
        Leu Ile Leu Leu Gly Val Phe Ile Val Asp Ala Thr Tyr Thr Leu Ile
                        245                 250                 255
        Arg Arg Ile Ala Arg Gly Glu Lys Phe Tyr Glu Ala His Arg Ser His
                        260                 265                 270
        Ala Tyr Gln Phe Ala Ser Arg Arg Tyr Ala Ser His Leu Arg Val Thr
                275                 280                 285
        Leu Gly Val Leu Ala Ile Asn Thr Leu Trp Leu Leu Arg Trp His
                290                 295                 300
```

<210> SEQ ID NO 21
<211> LENGTH: 19
<212> TYPE: DNA
<213> ORGANISM: Pseudomonas aeruginosa

<400> SEQUENCE: 21
catttgacat ggtataatg                                              19

<210> SEQ ID NO 22
<211> LENGTH: 19
<212> TYPE: DNA
<213> ORGANISM: Pseudomonas aeruginosa

<400> SEQUENCE: 22
cttttgtgaa cgcagaaag                                              19

<210> SEQ ID NO 23
<211> LENGTH: 19
<212> TYPE: DNA
<213> ORGANISM: Pseudomonas aeruginosa

<400> SEQUENCE: 23
tatttgcccc gctttgttg                                              19

<210> SEQ ID NO 24
<211> LENGTH: 19
<212> TYPE: DNA
<213> ORGANISM: Pseudomonas aeruginosa

<400> SEQUENCE: 24
cacttggcag tcaagattg                                              19

<210> SEQ ID NO 25
<211> LENGTH: 19
<212> TYPE: DNA
<213> ORGANISM: Pseudomonas aeruginosa

<400> SEQUENCE: 25
ctgttggcac agtttgctg                                              19

<210> SEQ ID NO 26
<211> LENGTH: 19
<212> TYPE: DNA
<213> ORGANISM: Pseudomonas aeruginosa

<400> SEQUENCE: 26
gttttggcgc actaagcag                                              19

```
<210> SEQ ID NO 27
<211> LENGTH: 19
<212> TYPE: DNA
<213> ORGANISM: Pseudomonas aeruginosa

<400> SEQUENCE: 27
tagttgatga actacctag                                                  19

<210> SEQ ID NO 28
<211> LENGTH: 19
<212> TYPE: DNA
<213> ORGANISM: Pseudomonas aeruginosa

<400> SEQUENCE: 28
tgcttgctga cggatcgtc                                                  19

<210> SEQ ID NO 29
<211> LENGTH: 34
<212> TYPE: DNA
<213> ORGANISM: Pseudomonas aeruginosa

<400> SEQUENCE: 29
aaattgaggt gagttggaaa atgatagatg ttaa                                 34

<210> SEQ ID NO 30
<211> LENGTH: 34
<212> TYPE: DNA
<213> ORGANISM: Pseudomonas aeruginosa

<400> SEQUENCE: 30
tcatttccat aggacgaacc atgaaaaatt tcgc                                 34

<210> SEQ ID NO 31
<211> LENGTH: 34
<212> TYPE: DNA
<213> ORGANISM: Pseudomonas aeruginosa

<400> SEQUENCE: 31
ctttggcaag ctgcagcgta atgttgtgca cttc                                 34

<210> SEQ ID NO 32
<211> LENGTH: 34
<212> TYPE: DNA
<213> ORGANISM: Pseudomonas aeruginosa

<400> SEQUENCE: 32
tcgagtgtga gtctcaagcc atgagttatt atca                                 34

<210> SEQ ID NO 33
<211> LENGTH: 34
<212> TYPE: DNA
<213> ORGANISM: Pseudomonas aeruginosa

<400> SEQUENCE: 33
agcaaggtgg acgtgtgacc atgattgaat tcat                                 34

<210> SEQ ID NO 34
<211> LENGTH: 34
<212> TYPE: DNA
<213> ORGANISM: Pseudomonas aeruginosa

<400> SEQUENCE: 34
ctgcgttgac gaattgacgg atgtatatat actt                                 34
```

<210> SEQ ID NO 35
<211> LENGTH: 34
<212> TYPE: DNA
<213> ORGANISM: Pseudomonas aeruginosa

<400> SEQUENCE: 35
atgtctttag gaaaaactct atgagtgcgg cttt                        34

<210> SEQ ID NO 36
<211> LENGTH: 34
<212> TYPE: DNA
<213> ORGANISM: Pseudomonas aeruginosa

<400> SEQUENCE: 36
tgtgccaagg gagatgccaa gtgatcgttg ttat                        34

<210> SEQ ID NO 37
<211> LENGTH: 34
<212> TYPE: DNA
<213> ORGANISM: Pseudomonas aeruginosa

<400> SEQUENCE: 37
aacttcgtgg agcttgtctg atggtccgga ggcg                        34

<210> SEQ ID NO 38
<211> LENGTH: 34
<212> TYPE: DNA
<213> ORGANISM: Pseudomonas aeruginosa

<400> SEQUENCE: 38
tgcttcggga ggttgttgtg atgaaagatc tgtt                        34

<210> SEQ ID NO 39
<211> LENGTH: 34
<212> TYPE: DNA
<213> ORGANISM: Pseudomonas aeruginosa

<400> SEQUENCE: 39
cgtgatgacc ggggccgctc atgactaaag ttgc                        34

<210> SEQ ID NO 40
<211> LENGTH: 34
<212> TYPE: DNA
<213> ORGANISM: Pseudomonas aeruginosa

<400> SEQUENCE: 40
ctgagtaagc gagattccat atgaaaattc tgac                        34

<210> SEQ ID NO 41
<211> LENGTH: 34
<212> TYPE: DNA
<213> ORGANISM: Pseudomonas aeruginosa

<400> SEQUENCE: 41
taaaggattt atttagttcc atgaacgtct ggta                        34

<210> SEQ ID NO 42
<211> LENGTH: 34
<212> TYPE: DNA
<213> ORGANISM: Pseudomonas aeruginosa

<400> SEQUENCE: 42
cttgctgatg ggcgcgcagc atgaaagctg tcat                        34

<210> SEQ ID NO 43
<211> LENGTH: 34
<212> TYPE: DNA
<213> ORGANISM: Pseudomonas aeruginosa

<400> SEQUENCE: 43
gaacggggct gataaatagg atgttggata attt                          34

<210> SEQ ID NO 44
<211> LENGTH: 34
<212> TYPE: DNA
<213> ORGANISM: Pseudomonas aeruginosa

<400> SEQUENCE: 44
ggactcgaac cagggaccca atgattaaca gtca                          34

<210> SEQ ID NO 45
<211> LENGTH: 29
<212> TYPE: PRT
<213> ORGANISM: Pseudomonas aeruginosa

<400> SEQUENCE: 45

Leu Ile Gly Ile Val Gly Leu Gly Tyr Val Gly Leu Pro Leu Met Leu
 1               5                  10                  15
Arg Tyr Asn Ala Ile Gly Gly Asp Val Leu Gly Ile Asp
            20                  25

<210> SEQ ID NO 46
<211> LENGTH: 35
<212> TYPE: PRT
<213> ORGANISM: Pseudomonas aeruginosa

<400> SEQUENCE: 46

Ala Val Met Val Thr Gly Ala Ser Gly Phe Val Gly Ser Ala Leu Cys
 1               5                  10                  15
Cys Glu Leu Ala Arg Thr Gly Tyr Ala Val Ile Ala Val Arg Arg
            20                  25                  30
Val Val Glu
        35

<210> SEQ ID NO 47
<211> LENGTH: 31
<212> TYPE: PRT
<213> ORGANISM: Pseudomonas aeruginosa

<400> SEQUENCE: 47

Val Val Met Val Thr Gly Ala Gly Gly Ser Ile Gly Ser Glu Leu Cys
 1               5                  10                  15
Arg Gln Ile Met Ser Cys Ser Pro Ser Val Leu Ile Leu Phe Glu
            20                  25                  30

<210> SEQ ID NO 48
<211> LENGTH: 30
<212> TYPE: PRT
<213> ORGANISM: Pseudomonas aeruginosa

<400> SEQUENCE: 48

Leu Val Ile Gln Ala Gly Ser Met Gly Gln Gly Gly Asp Val Phe Val
 1               5                  10                  15
Leu Asp Met Gly Pro Pro Val Lys Ile Leu Glu Leu Ala Glu
            20                  25                  30

<210> SEQ ID NO 49
<211> LENGTH: 29
<212> TYPE: PRT
<213> ORGANISM: Pseudomonas aeruginosa

```
<400> SEQUENCE: 49

Arg Ile Ser Ile Phe Gly Leu Gly Tyr Val Gly Ala Val Cys Ala Gly
    1               5                   10                  15
    Cys Leu Ser Ala Arg Gly Gly Glu Val Ile Gly Val Asp
                20                  25

<210> SEQ ID NO 50
<211> LENGTH: 31
<212> TYPE: PRT
<213> ORGANISM: Pseudomonas aeruginosa

<400> SEQUENCE: 50

Val Val Met Val Thr Gly Ala Gly Gly Ser Ile Gly Ser Glu Leu Cys
    1               5                   10                  15
    Arg Gln Ile Leu Ala Leu Arg Pro Arg Lys Leu Val Leu Phe Glu
                20                  25                  30

<210> SEQ ID NO 51
<211> LENGTH: 30
<212> TYPE: PRT
<213> ORGANISM: Pseudomonas aeruginosa

<400> SEQUENCE: 51

Leu Val Leu Gln Ala Gly Ala Met Gly Glu Ser Gly Ser Val Phe Val
    1               5                   10                  15
    Leu Asp Met Gly Glu Pro Val Leu Ile Arg Glu Leu Ala Glu
                20                  25                  30

<210> SEQ ID NO 52
<211> LENGTH: 34
<212> TYPE: PRT
<213> ORGANISM: Pseudomonas aeruginosa

<400> SEQUENCE: 52

Thr Ile Leu Val Thr Gly Ala Gly Gly Ser Ile Gly Ser Glu Ile Cys
    1               5                   10                  15
    Arg Gln Val Ser Lys Phe Asp Pro Gln Lys Ile Ile Leu Leu Gly His
                20                  25                  30
    Gly Glu

<210> SEQ ID NO 53
<211> LENGTH: 30
<212> TYPE: PRT
<213> ORGANISM: Pseudomonas aeruginosa

<400> SEQUENCE: 53

Lys Ile Leu Ile Thr Gly Thr Ala Gly Phe Ile Gly Ser His Leu Ala
    1               5                   10                  15
    Lys Lys Leu Ile Lys Gln Gly Gly Tyr Val Ile Gly Val Asp
                20                  25                  30

<210> SEQ ID NO 54
<211> LENGTH: 28
<212> TYPE: PRT
<213> ORGANISM: Pseudomonas aeruginosa

<400> SEQUENCE: 54

Asn Ile Ala Val Val Gly Leu Gly Tyr Val Gly Leu Pro Val Ala Val
    1               5                   10                  15
    Thr Phe Gly Asn Lys His Lys Val Ile Gly Phe Asp
                20                  25

<210> SEQ ID NO 55
<211> LENGTH: 30
<212> TYPE: PRT
<213> ORGANISM: Pseudomonas aeruginosa

<400> SEQUENCE: 55
```

```
        Cys Val Leu Val Thr Gly Gly Ser Gly Phe Val Gly Ala Asn Leu Val
        1               5                   10                  15
        Thr Glu Leu Leu Asp Arg Gly Tyr Ala Val Arg Ser Phe Asp
                        20                  25                  30
```

<210> SEQ ID NO 56
<211> LENGTH: 29
<212> TYPE: PRT
<213> ORGANISM: Pseudomonas aeruginosa

<400> SEQUENCE: 56

```
        Thr Ile Ser Val Val Gly Leu Gly Tyr Ile Gly Leu Pro Thr Ala Thr
        1               5                   10                  15
        Val Leu Ala Ser Arg Gln Arg Glu Leu Ile Gly Val Asp
                        20                  25
```

<210> SEQ ID NO 57
<211> LENGTH: 30
<212> TYPE: PRT
<213> ORGANISM: Pseudomonas aeruginosa

<400> SEQUENCE: 57

```
        Asn Ile Leu Val Val Gly Gly Ala Gly Tyr Ile Gly Ser His Thr Cys
        1               5                   10                  15
        Leu Gln Leu Ala Ala Asp Gly Tyr Gln Pro Val Val Tyr Asp
                        20                  25                  30
```

<210> SEQ ID NO 58
<211> LENGTH: 30
<212> TYPE: PRT
<213> ORGANISM: Pseudomonas aeruginosa

<400> SEQUENCE: 58

```
        Arg Val Leu Val Thr Gly Gly Ser Gly Val Ile Gly Ser Lys Thr Cys
        1               5                   10                  15
        Val Gln Leu Leu Gln Asn Gly His Asp Val Ile Ile Leu Asp
                        20                  25                  30
```

<210> SEQ ID NO 59
<211> LENGTH: 36
<212> TYPE: PRT
<213> ORGANISM: Pseudomonas aeruginosa

<400> SEQUENCE: 59

```
        Arg Leu Leu Val Thr Gly Ala Ala Gly Phe Ile Gly Ser His Tyr Val
        1               5                   10                  15
        Arg Glu Ile Leu Ala Gly Ser Tyr Pro Glu Ser Asp Asp Val His Val
                        20                  25                  30
        Thr Val Val Asp
                35
```

<210> SEQ ID NO 60
<211> LENGTH: 31
<212> TYPE: PRT
<213> ORGANISM: Pseudomonas aeruginosa

<400> SEQUENCE: 60

```
        Lys Ile Leu Ile Thr Gly Gly Ala Gly Phe Ile Gly Ser Ala Leu Val
        1               5                   10                  15
        Arg Tyr Ile Ile Asn Glu Thr Ser Asp Ala Val Val Val Val Asp
                        20                  25                  30
```

<210> SEQ ID NO 61
<211> LENGTH: 28
<212> TYPE: PRT
<213> ORGANISM: Pseudomonas aeruginosa

<400> SEQUENCE: 61

```
      Lys Ile Gly Ile Ile Gly Leu Gly Tyr Val Gly Leu Pro Leu Ala Val
      1               5                   10                  15
      Glu Phe Gly Lys Lys Val Thr Thr Ile Gly Phe Asp
                  20                  25
```

<210> SEQ ID NO 62
<211> LENGTH: 28
<212> TYPE: PRT
<213> ORGANISM: Pseudomonas aeruginosa

<400> SEQUENCE: 62

```
      Lys Ile Ala Ile Ile Gly Leu Gly Tyr Val Gly Leu Pro Leu Ala Ala
      1               5                   10                  15
      Glu Phe Gly Lys Ile Arg Gln Val Val Gly Phe Asp
                  20                  25
```

<210> SEQ ID NO 63
<211> LENGTH: 35
<212> TYPE: PRT
<213> ORGANISM: Pseudomonas aeruginosa

<400> SEQUENCE: 63

```
      Val Tyr Leu Ile Tyr Gly Ala Gly Ser Ala Gly Arg Gln Leu Ala Ile
      1               5                   10                  15
      Ala Leu Arg Asn Ser Glu Asn Tyr Lys Glu Val Ile Met Gly Met Gln
                  20                  25                  30
      Val His Asp
                  35
```

<210> SEQ ID NO 64
<211> LENGTH: 31
<212> TYPE: PRT
<213> ORGANISM: Pseudomonas aeruginosa

<400> SEQUENCE: 64

```
      Lys Ile Leu Val Thr Gly Gly Ala Gly Phe Ile Gly Ser Ala Val Val
      1               5                   10                  15
      Arg His Ile Ile Asn Asn Thr Gln Asp Ser Val Val Asn Val Asp
                  20                  25                  30
```

<210> SEQ ID NO 65
<211> LENGTH: 29
<212> TYPE: PRT
<213> ORGANISM: Pseudomonas aeruginosa

<400> SEQUENCE: 65

```
      Thr Ile Ser Val Ile Gly Leu Gly Tyr Ile Gly Leu Pro Thr Ala Ala
      1               5                   10                  15
      Ala Phe Ala Ser Arg Gln Lys Gln Val Ile Gly Val Asp
                  20                  25
```

<210> SEQ ID NO 66
<211> LENGTH: 30
<212> TYPE: PRT
<213> ORGANISM: Pseudomonas aeruginosa

<400> SEQUENCE: 66

```
      Arg Ile Leu Leu Thr Gly His Gln Gly Tyr Leu Gly Thr Val Met Ala
      1               5                   10                  15
      Pro Val Leu Thr Ala Ala Gly His Gln Val Thr Gly Leu Asp
                  20                  25                  30
```

<210> SEQ ID NO 67
<211> LENGTH: 31
<212> TYPE: PRT
<213> ORGANISM: Pseudomonas aeruginosa

<400> SEQUENCE: 67

```
        Val Val Met Val Thr Gly Ala Gly Gly Ser Ile Gly Ser Glu Leu Cys
        1               5                   10                  15
        Arg Gln Ile Ile Val Glu Lys Pro Ser Leu Leu Ile Leu Phe Asp
                    20                  25                  30
```

<210> SEQ ID NO 68
<211> LENGTH: 27
<212> TYPE: PRT
<213> ORGANISM: Pseudomonas aeruginosa

<400> SEQUENCE: 68

```
        Leu Val Ile Gln Ala Gly Ala Met Gly Gln Gly Gly Asp Val Phe Val
        1               5                   10                  15
        Leu Asp Met Gly Asp Pro Val Lys Ile Ile Asp
                    20                  25
```

<210> SEQ ID NO 69
<211> LENGTH: 29
<212> TYPE: PRT
<213> ORGANISM: Pseudomonas aeruginosa

<400> SEQUENCE: 69

```
        Arg Val Ala Ile Phe Gly Thr Gly Tyr Val Gly Leu Val Thr Gly Thr
        1               5                   10                  15
        Cys Leu Ala Glu Val Gly His His Val Ile Cys Val Asp
                    20                  25
```

<210> SEQ ID NO 70
<211> LENGTH: 28
<212> TYPE: PRT
<213> ORGANISM: Pseudomonas aeruginosa

<400> SEQUENCE: 70

```
        Lys Ile Ala Ile Ile Gly Leu Gly Tyr Val Gly Leu Pro Leu Ala Val
        1               5                   10                  15
        Glu Phe Gly Lys Ser Arg Gln Val Val Gly Phe Asp
                    20                  25
```

<210> SEQ ID NO 71
<211> LENGTH: 30
<212> TYPE: PRT
<213> ORGANISM: Pseudomonas aeruginosa

<400> SEQUENCE: 71

```
        Arg Trp Leu Ile Thr Gly Val Ala Gly Phe Ile Gly Ser Gly Leu Leu
        1               5                   10                  15
        Glu Glu Leu Leu Phe Leu Asn Gln Thr Val Ile Gly Leu Asp
                    20                  25                  30
```

<210> SEQ ID NO 72
<211> LENGTH: 436
<212> TYPE: PRT
<213> ORGANISM: Pseudomonas aeruginosa

<400> SEQUENCE: 72

```
        Met Ile Asp Val Asn Thr Val Val Glu Lys Phe Lys Ser Arg Gln Ala
        1               5                   10                  15
        Leu Ile Gly Ile Val Gly Leu Gly Tyr Val Gly Leu Pro Leu Met Leu
                    20                  25                  30
        Arg Tyr Asn Ala Ile Gly Phe Asp Val Leu Gly Ile Asp Ile Asp Asp
                35                  40                  45
        Val Lys Val Asp Lys Leu Asn Ala Gly Gln Cys Tyr Ile Glu His Ile
        50                  55                  60
        Pro Gln Ala Lys Ile Ala Lys Ala Arg Ala Ser Gly Phe Glu Ala Thr
        65                  70                  75                  80
        Thr Asp Phe Ser Arg Val Ser Glu Cys Asp Ala Leu Ile Leu Cys Val
                        85                  90                  95
        Pro Thr Pro Leu Asn Lys Tyr Arg Glu Pro Asp Met Ser Phe Val Ile
                    100                 105                 110
```

```
    Asn Thr Thr Asp Ala Leu Lys Pro Tyr Leu Arg Val Gly Gln Val Val
                115                 120                 125
    Ser Leu Glu Ser Thr Thr Tyr Pro Gly Thr Thr Glu Glu Leu Leu
        130                 135                 140
    Pro Arg Val Gln Glu Gly Gly Leu Val Val Gly Arg Asp Ile Tyr Leu
    145                 150                 155                 160
    Val Tyr Ser Pro Glu Arg Glu Asp Pro Gly Asn Pro Asn Phe Glu Thr
                    165                 170                 175
    Arg Thr Ile Pro Lys Val Ile Gly His Thr Pro Gln Cys Leu Glu
                180                 185                 190
    Val Gly Ile Ala Leu Tyr Glu Gln Ala Ile Asp Arg Val Val Pro Val
            195                 200                 205
    Ser Ser Thr Lys Ala Ala Glu Met Thr Lys Leu Leu Glu Asn Ile His
            210                 215                 220
    Arg Ala Val Asn Ile Gly Leu Val Asn Glu Met Lys Ile Val Ala Asp
    225                 230                 235                 240
    Arg Met Gly Ile Asp Ile Phe Glu Val Val Asp Ala Ala Thr Lys
                    245                 250                 255
    Pro Phe Gly Phe Thr Pro Tyr Tyr Pro Gly Pro Gly Leu Gly Gly His
                260                 265                 270
    Cys Ile Pro Ile Asp Pro Phe Tyr Leu Thr Trp Lys Ala Arg Glu Tyr
            275                 280                 285
    Gly Leu His Thr Arg Phe Ile Glu Leu Ser Gly Glu Val Asn Gln Ala
            290                 295                 300
    Met Pro Glu Tyr Val Leu Gly Lys Leu Met Asp Gly Leu Asn Glu Ala
    305                 310                 315                 320
    Gly Arg Ala Leu Lys Gly Ser Arg Val Leu Val Leu Gly Ile Ala Tyr
                    325                 330                 335
    Lys Lys Asn Val Asp Asp Met Arg Glu Ser Pro Ser Val Glu Ile Met
                340                 345                 350
    Glu Leu Ile Glu Ala Lys Gly Gly Met Val Ala Tyr Ser Asp Pro His
            355                 360                 365
    Val Pro Val Phe Pro Lys Met Arg Glu His His Phe Glu Leu Ser Ser
    370                 375                 380
    Glu Pro Leu Thr Ala Glu Asn Leu Ala Arg Phe Asp Ala Val Val Leu
    385                 390                 395                 400
    Ala Thr Asp His Asp Lys Phe Asp Tyr Glu Leu Ile Lys Ala Glu Ala
                    405                 410                 415
    Lys Leu Val Val Asp Ser Arg Gly Lys Tyr Arg Ser Pro Ala Ala His
                420                 425                 430
    Ile Ile Lys Ala
            435

<210> SEQ ID NO 73
<211> LENGTH: 420
<212> TYPE: PRT
<213> ORGANISM: Pseudomonas aeruginosa

<400> SEQUENCE: 73

Met Ser Phe Ala Thr Ile Ser Val Ile Gly Leu Gly Tyr Ile Gly Leu
    1               5                   10                  15
    Pro Thr Ala Ala Ala Phe Ala Ser Arg Gln Lys Gln Val Ile Gly Val
                    20                  25                  30
    Asp Ile Asn Gln His Ala Val Asp Thr Ile Asn Arg Gly Glu Ile His
                35                  40                  45
    Ile Val Glu Pro Asp Leu Ala Ser Val Val Lys Thr Ala Val Glu Gly
            50                  55                  60
    Gly Phe Leu Arg Ala Ser Thr Thr Pro Val Glu Ala Asp Ala Trp Leu
    65                  70                  75                  80
    Ile Ala Val Pro Thr Pro Phe Lys Gly Asp His Glu Pro Asp Met Thr
                    85                  90                  95
    Tyr Val Glu Ser Ala Ala Arg Ser Ile Ala Pro Val Leu Lys Lys Gly
                    100                 105                 110
    Ala Leu Val Ile Leu Glu Ser Thr Ser Pro Val Gly Ser Thr Glu Lys
            115                 120                 125
    Met Ala Glu Trp Leu Ala Glu Met Arg Pro Asp Leu Thr Phe Pro Gln
        130                 135                 140
    Gln Val Gly Glu Gln Ala Asp Val Asn Ile Ala Tyr Cys Pro Glu Arg
    145                 150                 155                 160
    Val Leu Pro Gly Gln Val Met Val Glu Leu Ile Lys Asn Asp Arg Val
                    165                 170                 175
    Ile Gly Gly Met Thr Pro Val Cys Ser Ala Arg Ala Ser Glu Leu Tyr
                    180                 185                 190
    Lys Ile Phe Leu Glu Gly Glu Cys Val Val Thr Asn Ser Arg Thr Ala
            195                 200                 205
    Glu Met Cys Lys Leu Thr Glu Asn Ser Phe Arg Asp Val Asn Ile Ala
        210                 215                 220
    Phe Ala Asn Glu Leu Ser Leu Ile Cys Ala Asp Gln Gly Ile Asn Val
```

```
            225                 230                 235                 240
        Trp Glu Leu Ile Arg Leu Ala Asn Arg His Pro Arg Val Asn Ile Leu
                        245                 250                 255
        Gln Pro Gly Pro Gly Val Gly His Cys Ile Ala Val Asp Pro Trp
                    260                 265                 270
        Phe Ile Val Ala Gln Asn Pro Gln Gln Ala Arg Leu Ile Arg Thr Ala
                275                 280                 285
        Arg Glu Val Asn Asp His Lys Pro Phe Trp Val Ile Asp Gln Val Lys
        290                 295                 300
        Ala Ala Val Ala Asp Cys Leu Ala Thr Asp Lys Arg Ala Ser Glu
        305                 310                 315                 320
        Leu Lys Ile Ala Cys Phe Gly Leu Ala Phe Lys Pro Asn Ile Asp Asp
                        325                 330                 335
        Leu Arg Glu Ser Pro Ala Met Glu Ile Ala Glu Leu Ile Ala Gln Trp
                    340                 345                 350
        His Ser Gly Glu Thr Leu Val Val Glu Pro Asn Ile His Gln Leu Pro
                355                 360                 365
        Lys Lys Leu Thr Gly Leu Cys Thr Leu Ala Gln Leu Asp Glu Ala Leu
        370                 375                 380
        Ala Thr Ala Asp Val Leu Val Met Leu Val Asp His Ser Gln Phe Lys
        385                 390                 395                 400
        Val Ile Asn Gly Asp Asn Val His Gln Gln Tyr Val Val Asp Ala Lys
                        405                 410                 415
        Gly Val Trp Arg
                    420

<210> SEQ ID NO 74
<211> LENGTH: 423
<212> TYPE: PRT
<213> ORGANISM: Pseudomonas aeruginosa

<400> SEQUENCE: 74

Met Asp Arg Ala Ile Glu Ile Asp Phe Arg Thr Ile Ser Val Val Gly
        1               5                   10                  15
        Leu Gly Tyr Ile Gly Leu Pro Thr Ala Thr Val Leu Ala Ser Arg Gln
                        20                  25                  30
        Arg Glu Leu Ile Gly Val Asp Ile Asn Gln His Ala Val Asp Thr Ile
                    35                  40                  45
        Asn Gln Ala Arg Ile His Ile Val Glu Pro Asp Leu Asp Met Leu Val
                50                  55                  60
        Arg Ala Ala Val Ser Gln Gly Tyr Leu Arg Ala Thr Thr Glu Pro Glu
        65                  70                  75                  80
        Pro Ala Asp Ala Phe Leu Ile Ala Val Pro Thr Pro Phe Leu Glu Asp
                        85                  90                  95
        Lys Gln Pro Asp Leu Thr Tyr Ile Glu Ala Ala Lys Ala Ile Ala
                    100                 105                 110
        Pro Val Leu Lys Arg Gly Asp Leu Val Val Leu Glu Ser Thr Ser Pro
                    115                 120                 125
        Val Gly Ala Thr Glu Gln Leu Ser Ala Trp Leu Ser Glu Gln Arg Ser
                    130                 135                 140
        Asp Leu Ser Phe Pro His Gln Leu Gly Glu Gly Ser Asp Ile Arg Val
        145                 150                 155                 160
        Ala His Cys Pro Glu Arg Val Leu Pro Gly His Val Leu Arg Glu Leu
                        165                 170                 175
        Val Glu Asn Asp Arg Ile Ile Gly Gly Met Thr Pro Arg Cys Ser Gln
                    180                 185                 190
        Ala Ala Gln Arg Leu Tyr Glu Leu Phe Val Arg Gly Arg Cys Ile Val
                    195                 200                 205
        Thr Asp Ala Arg Thr Ala Glu Met Cys Lys Leu Thr Glu Asn Ala Phe
        210                 215                 220
        Arg Asp Val Asn Ile Ala Phe Ala Asn Glu Leu Ser Met Ile Cys Asp
        225                 230                 235                 240
        Glu Ile Gly Val Asn Val Trp Glu Leu Ile Ser Val Ala Asn Arg His
                        245                 250                 255
        Pro Arg Val Asn Ile Leu Gln Pro Gly Pro Gly Val Gly His Cys
                    260                 265                 270
        Ile Ala Val Asp Pro Trp Phe Ile Val Asp Ala Ala Pro Glu Ser Ala
                275                 280                 285
        Arg Leu Ile Arg Thr Ala Arg Glu Val Asn Asp Ala Lys Pro His Tyr
                290                 295                 300
        Val Leu Asp Arg Val Lys Gln Ala Ala Arg Phe Lys Glu Pro Val
        305                 310                 315                 320
        Ile Ala Cys Phe Gly Leu Ser Phe Lys Ala Asn Ile Asp Asp Leu Arg
                        325                 330                 335
        Glu Ser Pro Ala Ile Glu Ile Arg Thr Met Val Gln Gln Gln Leu
                    340                 345                 350
        Gly Thr Val Leu Val Val Glu Pro His Ile Lys Val Leu Pro Ala Ser
                355                 360                 365
```

```
        Leu Glu Gly Val Glu Leu Leu Asn Ala Glu Pro Ala Leu Ser Arg Ala
            370                 375                 380
        Asp Ile Val Val Leu Val Asp His Gln Lys Phe Arg Lys Leu Asp
        385                 390                 395                 400
        Thr Asp Arg Leu Gln Ser Arg Val Val Ile Asp Thr Arg Gly Met Trp
                        405                 410                 415
        Ser Ala Lys Arg Leu Ala Ala
                        420

<210> SEQ ID NO 75
<211> LENGTH: 163
<212> TYPE: PRT
<213> ORGANISM: Pseudomonas aeruginosa

<400> SEQUENCE: 75

Met Ser Tyr Tyr Gln His Pro Ser Ala Ile Val Asp Asp Gly Ala Gln
        1               5                   10                  15
        Ile Gly Ser Asp Ser Arg Val Trp His Phe Val His Ile Cys Ala Gly
                        20                  25                  30
        Ala Arg Ile Gly Ala Gly Val Ser Leu Gly Gln Asn Val Phe Val Gly
                        35                  40                  45
        Asn Lys Val Val Ile Gly Asp Arg Cys Lys Ile Gln Asn Asn Val Ser
                50                  55                  60
        Val Tyr Asp Asn Val Thr Leu Glu Glu Gly Val Phe Cys Gly Pro Ser
        65                  70                  75                  80
        Met Val Phe Thr Asn Val Tyr Asn Pro Arg Ser Leu Ile Glu Arg Lys
                        85                  90                  95
        Asp Gln Tyr Arg Asn Thr Leu Val Lys Lys Gly Ala Thr Leu Gly Ala
                        100                 105                 110
        Asn Cys Thr Ile Val Cys Gly Val Thr Ile Gly Glu Tyr Ala Phe Leu
                        115                 120                 125
        Gly Ala Gly Ala Val Ile Asn Lys Asn Val Pro Ser Tyr Ala Leu Met
                        130                 135                 140
        Val Gly Val Pro Ala Arg Gln Ile Gly Trp Ile Ala Asn Ser Val Ser
        145                 150                 155                 160
        Ser Cys Ser

<210> SEQ ID NO 76
<211> LENGTH: 191
<212> TYPE: PRT
<213> ORGANISM: Pseudomonas aeruginosa

<400> SEQUENCE: 76

Met Thr Thr Ile His Pro Thr Ala Ile Val Asp Glu Gly Ala Arg Ile
        1               5                   10                  15
        Gly Ala Asn Ser Arg Ile Trp His Trp Val His Ile Cys Gly Gly Ala
                        20                  25                  30
        Glu Ile Gly Ala Gly Cys Ser Leu Gly Gln Asn Val Phe Val Gly Asn
                        35                  40                  45
        Arg Val Arg Ile Gly Asp Arg Val Lys Ile Gln Asn Asn Val Ser Val
                50                  55                  60
        Tyr Asp Asn Val Phe Leu Glu Asp Asp Val Phe Cys Gly Pro Ser Met
        65                  70                  75                  80
        Val Phe Thr Asn Val Tyr Asn Pro Arg Ala Ala Ile Glu Arg Lys Asn
                        85                  90                  95
        Glu Tyr Arg Asp Thr Leu Val Arg Gln Gly Ala Thr Leu Gly Ala Asn
                        100                 105                 110
        Cys Thr Ile Val Cys Gly Ala Thr Val Gly Arg Tyr Ala Phe Val Gly
                        115                 120                 125
        Ala Gly Ala Val Val Asn Lys Asp Val Pro Asp Phe Ala Leu Val Val
                        130                 135                 140
        Gly Val Pro Ala Arg Gln Ile Gly Trp Met Ser Arg His Gly Glu Gln
        145                 150                 155                 160
        Leu Asp Leu Pro Leu Ala Gly Asn Gly Gln Ala Arg Cys Pro His Thr
                        165                 170                 175
        Gly Asp Leu Tyr Ile Leu Glu Asn Gly Val Cys Arg Leu Gly Glu
                        180                 185                 190

<210> SEQ ID NO 77
<211> LENGTH: 276
<212> TYPE: PRT
<213> ORGANISM: Pseudomonas aeruginosa

<400> SEQUENCE: 77
```

```
Met Ile Glu Phe Ile Asp Leu Lys Asn Gln Gln Ala Arg Ile Lys Asp
 1               5                  10                  15
Lys Ile Asp Ala Gly Ile Gln Arg Val Leu Arg His Gly Gln Tyr Ile
                20                  25                  30
Leu Gly Pro Glu Val Thr Glu Leu Glu Asp Arg Leu Ala Asp Phe Val
            35                  40                  45
Gly Ala Lys Tyr Cys Ile Ser Cys Ala Asn Gly Thr Asp Ala Leu Gln
        50                  55                  60
Ile Val Gln Met Ala Leu Gly Val Gly Pro Gly Asp Glu Val Ile Thr
65                  70                  75                  80
Pro Gly Phe Thr Tyr Val Ala Thr Ala Glu Thr Val Ala Leu Leu Gly
                85                  90                  95
Ala Lys Pro Val Tyr Val Asp Ile Asp Pro Arg Thr Tyr Asn Leu Asp
            100                 105                 110
Pro Gln Leu Leu Glu Ala Ala Ile Thr Pro Arg Thr Lys Ala Ile Ile
        115                 120                 125
Pro Val Ser Leu Tyr Gly Gln Cys Ala Asp Phe Asp Ala Ile Asn Ala
130                 135                 140
Ile Ala Ser Lys Tyr Gly Ile Pro Val Ile Glu Asp Ala Ala Gln Ser
145                 150                 155                 160
Phe Gly Ala Ser Tyr Lys Gly Lys Arg Ser Cys Asn Leu Ser Thr Val
                165                 170                 175
Ala Cys Thr Ser Phe Phe Pro Ser Lys Pro Leu Gly Cys Tyr Gly Asp
            180                 185                 190
Gly Gly Ala Ile Phe Thr Asn Asp Asp Glu Leu Ala Thr Ala Ile Arg
        195                 200                 205
Gln Ile Ala Arg His Gly Gln Asp Arg Arg Tyr His His Ile Arg Val
210                 215                 220
Gly Val Asn Ser Arg Leu Asp Thr Leu Gln Ala Ala Ile Leu Leu Pro
225                 230                 235                 240
Lys Leu Glu Ile Phe Glu Glu Ile Ala Leu Arg Gln Lys Val Ala
                245                 250                 255
Ala Glu Tyr Asp Leu Ser Leu Lys Gln Val Gly Ile Gly Thr Pro Phe
            260                 265                 270
Ile Gly Ser Gly
            275
```

<210> SEQ ID NO 78
<211> LENGTH: 366
<212> TYPE: PRT
<213> ORGANISM: Pseudomonas aeruginosa

<400> SEQUENCE: 78

```
Met Gln Phe Ile Asp Leu Lys Thr Gln Tyr Gln Ala Leu Arg Asp Thr
 1               5                  10                  15
Ile Asn Pro Arg Ile Gln Ala Val Leu Asp His Gly Gln Phe Ile Met
                20                  25                  30
Gly Pro Glu Val Lys Glu Leu Glu Ala Ala Leu Cys Ala Tyr Thr Gly
            35                  40                  45
Ala Lys His Cys Ile Thr Val Ala Ser Gly Thr Glu Ala Leu Leu Ile
        50                  55                  60
Ser Leu Met Ala Leu Gly Val Lys Ala Gly Asp Glu Val Ile Thr Thr
65                  70                  75                  80
Ser Phe Thr Phe Val Ala Thr Ala Glu Val Ile Ala Leu Leu Gly Ala
                85                  90                  95
Lys Pro Val Phe Val Asp Val Glu Pro Asp Thr Cys Asn Ile Lys Val
            100                 105                 110
Ser Glu Ile Glu Ala Lys Ile Thr Pro Arg Thr Lys Ala Ile Ile Pro
        115                 120                 125
Val Ser Leu Tyr Gly Gln Cys Gly Asp Met Asp Glu Val Asn Ala Val
130                 135                 140
Ala Ala Arg His Gly Leu Pro Val Ile Glu Asp Ala Ala Gln Ser Phe
145                 150                 155                 160
Gly Ala Thr Tyr Lys Gly Arg Lys Ser Cys Asn Leu Ser Thr Ile Gly
                165                 170                 175
Cys Thr Ser Phe Phe Pro Ser Lys Pro Leu Gly Cys Tyr Gly Asp Gly
            180                 185                 190
Gly Ala Leu Phe Thr Asn Asp Asp Glu Leu Ala Gln Ala Met Arg Glu
        195                 200                 205
Ile Arg Val His Gly Gln Ser Gly Arg Tyr Tyr His Ala Arg Ile Gly
210                 215                 220
Val Gly Gly Arg Met Asp Thr Leu Gln Cys Ala Val Val Leu Gly Lys
225                 230                 235                 240
Leu Glu Arg Phe Asp Trp Glu Ile Ala Gln Arg Ile Lys Ile Gly Ala
                245                 250                 255
Arg Tyr Gln Gln Leu Leu Ala Asp Leu Pro Gly Gly Ala Cys Thr Val
            260                 265                 270
Thr Val Arg Pro Asp Arg Asp Ser Val Trp Ala Gln Phe Thr Val Met
```

-continued

```
                    275                 280                 285
        Val Pro Asn Arg Glu Ala Val Ile Ala Gln Leu Lys Glu Ala Gly Ile
                290                 295                 300
        Pro Thr Ala Val His Tyr Pro Arg Pro Ile His Ala Gln Pro Ala Tyr
        305                 310                 315                 320
        Glu Gln Tyr Ala Glu Gly Ala Gly Ala Thr Pro Val Ser Asp Asp Leu
                        325                 330                 335
        Ala Ala Arg Val Met Ser Leu Pro Met His Pro Asp Leu Asp Glu Ala
                        340                 345                 350
        Thr Gln Asp Lys Ile Val Ala Ala Leu Arg Gln Ala Leu Asn
                        355                 360                 365

<210> SEQ ID NO 79
<211> LENGTH: 372
<212> TYPE: PRT
<213> ORGANISM: Pseudomonas aeruginosa

<400> SEQUENCE: 79

Met Asn Val Pro Met Leu Asp Leu Ser Glu Gln Tyr Glu Gln Leu Lys
        1               5                   10                  15
        Pro Glu Ile Met Arg Val Leu Asp Glu Val Met Arg Ser Ser Arg Phe
                        20                  25                  30
        Ile Leu Gly Asp Tyr Val Lys Lys Leu Glu Ala Asp Ile Ala Ala Tyr
                        35                  40                  45
        Ser Arg Ala Lys His Gly Ile Gly Cys Gly Asn Gly Ser Asp Ala Ile
                50                  55                  60
        His Ile Ala Leu Gln Ala Ala Gly Val Gly Pro Gly Asp Glu Val Ile
        65                  70                  75                  80
        Thr Thr Ala Phe Thr Phe Phe Ala Thr Ala Gly Ser Ile Ala Arg Ala
                        85                  90                  95
        Gly Ala Lys Pro Val Phe Val Asp Ile Asp Pro Val Thr Phe Asn Ile
                        100                 105                 110
        Asp Pro Ala Gln Val Glu Ala Val Thr Glu Lys Thr Lys Ala Ile
                        115                 120                 125
        Ile Pro Val His Leu Tyr Gly Gln Met Ala Asp Met Glu Ala Ile Ala
                        130                 135                 140
        Ala Ile Ala Lys Arg His Gly Leu Val Val Ile Glu Asp Ala Ala Gln
        145                 150                 155                 160
        Ala Ile Gly Ala Lys Tyr Asn Gly Lys Cys Val Gly Glu Leu Gly Thr
                        165                 170                 175
        Ala Ala Thr Tyr Ser Phe Phe Pro Thr Lys Asn Leu Gly Ala Tyr Gly
                        180                 185                 190
        Asp Gly Gly Met Ile Ile Thr Asn Asp Asp Glu Leu Ala Glu Lys Cys
                        195                 200                 205
        Arg Val Ile Arg Val His Gly Ser Lys Pro Lys Tyr Tyr His His Val
                        210                 215                 220
        Leu Gly Tyr Asn Ser Arg Leu Asp Glu Met Gln Ala Ala Ile Leu Ser
        225                 230                 235                 240
        Val Lys Phe Pro His Leu Asp Arg Trp Thr Glu Gln Arg Arg Lys His
                        245                 250                 255
        Ala Ala Thr Tyr Thr Arg Leu Leu Glu Ala Val Gly Asp Leu Val
                        260                 265                 270
        Val Thr Pro Lys Glu Val Asp Gly Arg Tyr His Val Phe His Gln Tyr
                        275                 280                 285
        Thr Ile Arg Ala Pro Lys Arg Asp Glu Leu Gln Ala Phe Leu Lys Glu
                        290                 295                 300
        Gln Gly Ile Ala Thr Met Val Tyr Pro Leu Pro Leu His Leu Gln
        305                 310                 315                 320
        Pro Val Phe Ala Ser Leu Gly Tyr Lys Glu Gly Gln Leu Pro Glu Ala
                        325                 330                 335
        Glu Lys Ala Ala Lys Glu Ala Leu Ser Leu Pro Met Phe Pro Glu Leu
                        340                 345                 350
        Lys Glu Glu Gln Gln Gln Tyr Val Val Glu Lys Ile Ala Glu Phe Tyr
                        355                 360                 365
        Arg His Phe Ala
                370

<210> SEQ ID NO 80
<211> LENGTH: 365
<212> TYPE: PRT
<213> ORGANISM: Pseudomonas aeruginosa

<400> SEQUENCE: 80

Met Asp Val Pro Phe Leu Asp Leu Gln Ala Ala Tyr Leu Glu Leu Arg
        1               5                   10                  15
        Ser Asp Ile Asp Gln Ala Cys Arg Arg Val Leu Gly Ser Gly Trp Tyr
```

```
            20                  25                  30
Leu His Gly Pro Glu Asn Glu Ala Phe Glu Ala Phe Ala Ala Tyr
         35                  40                  45
Cys Glu Asn Ala His Cys Val Thr Val Gly Ser Gly Cys Asp Ala Leu
 50                  55                  60
Glu Leu Ser Leu Val Ala Leu Gly Val Gly Gln Gly Asp Glu Val Ile
 65                  70                  75                  80
Val Pro Ser His Thr Phe Ile Ala Thr Trp Leu Gly Val Pro Val Gly
                 85                  90                  95
Ala Val Pro Val Pro Val Glu Pro Gly Val Ser His Thr Leu Asp
            100                 105                 110
Pro Ala Leu Val Glu Gln Ala Ile Thr Pro Arg Thr Ala Ala Ile Leu
            115                 120                 125
Pro Val His Leu Tyr Gly His Pro Ala Asp Leu Asp Ala Leu Arg Ala
            130                 135                 140
Ile Ala Asp Arg His Gly Leu Ala Leu Val Glu Asp Val Ala Gln Ala
145                 150                 155                 160
Val Gly Ala Arg His Arg Gly His Arg Val Gly Ala Gly Ser Asn Ala
                165                 170                 175
Ala Ala Phe Ser Phe Tyr Pro Gly Lys Asn Leu Gly Ala Leu Gly Asp
            180                 185                 190
Gly Gly Ala Val Val Thr Thr Asp Pro Ala Leu Ala Glu Arg Ile Arg
            195                 200                 205
Leu Leu Arg Asn Tyr Gly Ser Lys Gln Lys Tyr Val His Glu Val Arg
            210                 215                 220
Gly Thr Asn Ala Arg Leu Asp Glu Leu Gln Ala Ala Val Leu Arg Val
225                 230                 235                 240
Lys Leu Arg His Leu Asp Asp Trp Asn Ala Arg Arg Thr Thr Leu Ala
                245                 250                 255
Gln His Tyr Gln Thr Glu Leu Lys Asp Val Pro Gly Ile Thr Leu Pro
            260                 265                 270
Glu Thr His Pro Trp Ala Asp Ser Ala Trp His Leu Phe Val Leu Arg
            275                 280                 285
Cys Glu Asn Arg Asp His Leu Gln Arg His Leu Thr Asp Ala Gly Val
290                 295                 300
Gln Thr Leu Ile His Tyr Pro Thr Pro Val His Leu Ser Pro Ala Tyr
305                 310                 315                 320
Ala Asp Leu Gly Leu Pro Pro Gly Ser Phe Pro Val Ala Glu Ser Leu
                325                 330                 335
Ala Gly Glu Val Leu Ser Leu Pro Ile Gly Pro His Leu Ser Arg Glu
            340                 345                 350
Ala Ala Asp His Val Ile Ala Thr Leu Lys Ala Gly Ala
            355                 360                 365

<210> SEQ ID NO 81
<211> LENGTH: 370
<212> TYPE: PRT
<213> ORGANISM: Pseudomonas aeruginosa

<400> SEQUENCE: 81

Met Ser Thr Tyr Val Trp Gln Tyr Leu Asn Glu Tyr Arg Glu Glu Arg
 1               5                  10                  15
Ala Asp Ile Leu Asp Ala Val Glu Thr Val Phe Glu Ser Gly Gln Leu
            20                  25                  30
Ile Leu Gly Thr Ser Val Arg Ser Phe Glu Glu Phe Ala Ala Tyr
         35                  40                  45
His Gly Leu Pro Tyr Cys Thr Gly Val Asp Asn Gly Thr Asn Ala Leu
 50                  55                  60
Val Leu Gly Leu Arg Ala Leu Gly Ile Gly Pro Gly Asp Glu Val Val
 65                  70                  75                  80
Thr Val Ser Asn Thr Ala Ala Pro Thr Val Val Ala Ile Asp Ala Val
                 85                  90                  95
Gly Ala Thr Pro Val Phe Val Asp Val His Glu Glu Asn Tyr Leu Met
            100                 105                 110
Asp Thr Gly Arg Leu Arg Ser Val Ile Gly Pro Arg Thr Arg Cys Leu
            115                 120                 125
Leu Pro Val His Leu Tyr Gly Gln Ser Val Asp Met Thr Pro Val Leu
            130                 135                 140
Glu Leu Ala Ala Glu His Asp Leu Lys Val Leu Glu Asp Cys Ala Gln
145                 150                 155                 160
Ala His Gly Ala Arg Arg His Gly Arg Leu Val Gly Thr Gln Gly His
                165                 170                 175
Ala Ala Ala Phe Ser Phe Tyr Pro Thr Lys Val Leu Gly Ala Tyr Gly
            180                 185                 190
Asp Gly Gly Ala Val Val Thr Pro Asp Ala Glu Val Asp Arg Arg Leu
            195                 200                 205
Arg Arg Leu Arg Tyr Tyr Gly Met Gly Glu Arg Tyr Tyr Val Val Asp
            210                 215                 220
```

```
    Thr Pro Gly His Asn Ser Arg Leu Asp Glu Val Gln Ala Glu Ile Leu
    225                 230                 235                 240
    Arg Arg Lys Leu Arg Arg Leu Asp Ala Tyr Val Glu Gly Arg Arg Ala
                        245                 250                 255
    Val Ala Arg Arg Tyr Glu Glu Gly Leu Gly Asp Leu Asp Gly Leu Val
                260                 265                 270
    Leu Pro Thr Ile Ala Glu Gly Asn Asp His Val Tyr Tyr Val Tyr Val
                    275                 280                 285
    Val Arg His Pro Glu Arg Asp Arg Ile Leu Glu Ala Leu Thr Ala Tyr
                290                 295                 300
    Asp Ile His Leu Asn Ile Ser Tyr Pro Trp Pro Val His Thr Met Ser
    305                 310                 315                 320
    Gly Phe Ala His Leu Gly Tyr Gly Pro Gly Asp Leu Pro Val Thr Glu
                        325                 330                 335
    Arg Leu Ala Gly Glu Ile Phe Ser Leu Pro Met Tyr Pro Ser Leu Arg
                340                 345                 350
    Pro Asp Ala Gln Glu Lys Val Ile Asp Ala Val Arg Glu Val Val Gly
                    355                 360                 365
    Ser Leu
    370

<210> SEQ ID NO 82
<211> LENGTH: 389
<212> TYPE: PRT
<213> ORGANISM: Pseudomonas aeruginosa

<400> SEQUENCE: 82

Met Val Gln Lys Arg Asn His Phe Leu Pro Tyr Ser Leu Pro Leu Ile
    1               5                   10                  15
    Gly Lys Glu Glu Ile Gln Glu Val Thr Glu Thr Leu Glu Ser Gly Trp
                    20                  25                  30
    Leu Ser Lys Gly Pro Lys Val Gln Gln Phe Glu Lys Glu Phe Ala Ala
                35                  40                  45
    Phe Val Gly Ala Lys His Ala Val Ala Val Asn Ser Cys Thr Ala Ala
    50                  55                  60
    Leu Phe Leu Ala Leu Lys Ala Lys Gly Ile Gly Pro Gly Asp Glu Val
    65                  70                  75                  80
    Ile Thr Ser Pro Leu Thr Phe Ser Ser Thr Ala Asn Thr Ile Ile His
                    85                  90                  95
    Thr Gly Ala Thr Pro Val Phe Ala Asp Ile Asp Glu Asn Thr Leu Asn
                    100                 105                 110
    Ile Asp Pro Val Lys Leu Glu Ala Ala Val Thr Pro Arg Thr Lys Ala
                115                 120                 125
    Val Val Pro Val His Phe Gly Gly Gln Ser Cys Asp Met Asp Ala Ile
                130                 135                 140
    Leu Ala Val Ala Gln Asn His Gly Leu Phe Val Leu Glu Asp Ala Ala
    145                 150                 155                 160
    His Ala Val Tyr Thr Thr Tyr Lys Gln Arg Met Ile Gly Ser Ile Gly
                        165                 170                 175
    Asp Ala Thr Ala Phe Ser Phe Tyr Ala Thr Lys Asn Leu Ala Thr Gly
                    180                 185                 190
    Glu Gly Gly Met Leu Thr Thr Asp Asp Glu Leu Ala Asp Lys Ile
                195                 200                 205
    Arg Val Leu Ser Leu His Gly Met Ser Lys Ala Ala Trp Asn Arg Tyr
                210                 215                 220
    Ser Ser Asn Gly Ser Trp Tyr Tyr Glu Val Glu Ser Pro Gly Tyr Lys
    225                 230                 235                 240
    Met Asn Met Phe Asp Leu Gln Ala Ala Leu Gly Leu His Gln Leu Lys
                        245                 250                 255
    Arg Leu Asp Asp Met Gln Lys Arg Arg Glu Ile Ala Gly Arg Tyr
                260                 265                 270
    Gln Thr Ala Phe Gln Gln Ile Pro Gly Leu Ile Thr Pro Phe Val His
                    275                 280                 285
    Asp Asp Gly Arg His Ala Trp His Leu Tyr Val Leu Gln Val Asp Glu
                290                 295                 300
    Lys Lys Ala Gly Val Thr Arg Ser Glu Met Ile Thr Ala Leu Lys Asp
    305                 310                 315                 320
    Glu Tyr Asn Ile Gly Thr Ser Val His Phe Ile Pro Val His Ile His
                        325                 330                 335
    Pro Tyr Tyr Gln Lys Gln Phe Gly Tyr Lys Glu Ala Asp Phe Pro Asn
                    340                 345                 350
    Ala Met Asn Tyr Tyr Lys Arg Thr Leu Ser Leu Pro Leu Tyr Pro Ser
                    355                 360                 365
    Met Ser Asp Asp Val Asp Val Ile Glu Ala Val Arg Asp Ile
    370                 375                 380
    Val Lys Gly Ala Asp
    385
```

```
<210> SEQ ID NO 83
<211> LENGTH: 362
<212> TYPE: PRT
<213> ORGANISM: Pseudomonas aeruginosa

<400> SEQUENCE: 83

Met Lys Ile Leu Thr Ile Ile Gly Ala Arg Pro Gln Phe Ile Lys Ala
    1               5                   10                  15
    Ser Val Val Ser Lys Ala Ile Glu Gln Gln Thr Leu Ser Glu Ile
                20                  25                  30
    Ile Val His Thr Gly Gln His Phe Asp Ala Asn Met Ser Glu Ile Phe
            35                  40                  45
    Phe Glu Gln Leu Gly Ile Pro Lys Pro Asp Tyr Gln Leu Asp Ile His
        50                  55                  60
    Gly Gly Thr His Gly Gln Met Thr Gly Arg Met Leu Met Glu Ile Glu
    65                  70                  75                  80
    Asp Val Ile Leu Lys Glu Lys Pro His Arg Val Leu Val Tyr Gly Asp
                    85                  90                  95
    Thr Asn Ser Thr Leu Ala Gly Ala Leu Ala Ala Ser Lys Leu His Val
                100                 105                 110
    Pro Ile Ala His Ile Glu Ala Gly Leu Arg Ser Phe Asn Met Arg Met
                115                 120                 125
    Pro Glu Glu Ile Asn Arg Ile Leu Thr Asp Gln Val Ser Asp Ile Leu
            130                 135                 140
    Phe Cys Pro Thr Arg Val Ala Ile Asp Asn Leu Lys Asn Glu Gly Phe
    145                 150                 155                 160
    Glu Arg Lys Ala Ala Lys Ile Val Asn Val Gly Asp Val Met Gln Asp
                    165                 170                 175
    Ser Ala Leu Phe Phe Ala Gln Arg Ala Thr Ser Pro Ile Gly Leu Ala
                180                 185                 190
    Ser Gln Asp Gly Phe Ile Leu Ala Thr Leu His Arg Ala Glu Asn Thr
                195                 200                 205
    Asp Asp Pro Val Arg Leu Thr Ser Ile Val Glu Ala Leu Asn Glu Ile
            210                 215                 220
    Gln Ile Asn Val Ala Pro Val Val Leu Pro Leu His Pro Arg Thr Arg
    225                 230                 235                 240
    Gly Val Ile Glu Arg Leu Gly Leu Lys Leu Glu Val Gln Val Ile Asp
                    245                 250                 255
    Pro Val Gly Tyr Leu Glu Met Ile Trp Leu Leu Gln Arg Ser Gly Leu
                260                 265                 270
    Val Leu Thr Asp Ser Gly Gly Val Gln Lys Glu Ala Phe Phe Gly
                275                 280                 285
    Lys Pro Cys Val Thr Met Arg Asp Gln Thr Glu Trp Val Glu Leu Val
        290                 295                 300
    Thr Cys Gly Ala Asn Val Leu Val Gly Ala Ala Arg Asp Met Ile Val
    305                 310                 315                 320
    Glu Ser Ala Arg Thr Ser Leu Gly Lys Thr Ile Gln Asp Asp Gly Gln
                    325                 330                 335
    Leu Tyr Gly Gly Gln Ala Ser Leu Gly Leu Leu Asn Ile Leu Pro
                340                 345                 350
    Ser Cys Asp Ala Leu Arg Val Glu Phe Lys
            355                 360

<210> SEQ ID NO 84
<211> LENGTH: 362
<212> TYPE: PRT
<213> ORGANISM: Pseudomonas aeruginosa

<400> SEQUENCE: 84

Met Pro Lys Lys Ile Leu Thr Val Leu Gly Ala Arg Pro Gln Phe Ile
    1               5                   10                  15
    Lys Ala Ser Val Val Ser Ala Ala Ile Ala Gln His Pro Glu Leu Thr
                20                  25                  30
    Glu Val Val His Thr Gly Gln His Phe Asp Ala Asn Met Ser Asp
            35                  40                  45
    Val Phe Phe Asp Glu Leu Gly Met Gln Thr Pro Ala His Gln Leu Asp
        50                  55                  60
    Ile His Gly Gly His Gly Asp Met Thr Gly Arg Met Leu Val Ala
    65                  70                  75                  80
    Leu Glu Gln Val Met Gln Ala Glu Lys Pro Asp Val Val Leu Val Tyr
                    85                  90                  95
    Gly Asp Thr Asn Ser Thr Leu Ala Gly Ala Leu Ala Ala Val Lys Leu
                100                 105                 110
    His Ile Pro Val Ala His Val Glu Ala Gly Leu Arg Ser Phe Asn Leu
                115                 120                 125
    Arg Met Pro Glu Glu Val Asn Arg Ile Leu Thr Asp Arg Ile Ser Arg
```

```
            130                 135                 140
    Trp Leu Phe Thr Pro Thr Asp Ser Ala Thr Arg His Leu Ala Ala Glu
    145                 150                 155                 160
    Gly Gln Ser Gly Glu Lys Val Val Gln Val Gly Asp Val Met Tyr Asp
                    165                 170                 175
    Val Ala Leu His His Gly Ala Arg Val Thr Ala Glu Gly Arg Ala Leu
                180                 185                 190
    Ala Ala His Gly Leu Lys Pro Gly Gly Tyr Val Leu Ala Thr Ile His
                195                 200                 205
    Arg Ala Glu Asn Thr Asp Asp Ala Gln Arg Leu Thr Thr Ile Val Arg
    210                 215                 220
    Ala Leu Gln Ala Leu Ala Glu Arg Gln Val Val Trp Pro Leu His
    225                 230                 235                 240
    Pro Arg Thr Trp Gly Ile Leu Ala Arg Leu Gly Leu Leu Asp Glu Leu
                    245                 250                 255
    Ala Ser Thr Val Thr Leu Leu Glu Pro Val Gly Tyr Leu Asp Met Val
                    260                 265                 270
    Gln Leu Glu Lys Tyr Ala Ala Leu Ile Ala Thr Asp Ser Gly Gly Val
                275                 280                 285
    Gln Lys Glu Ala Phe Phe His Arg Ile Pro Cys Val Thr Leu Arg Asp
                290                 295                 300
    Glu Thr Glu Trp Thr Glu Leu Val Asp Ala Gly Trp Asn Arg Leu Ala
    305                 310                 315                 320
    Pro Pro Val Ser Ser Ala Val Val Ala Gln Ala Val Gln Asp Ala Leu
                    325                 330                 335
    Arg Glu Gln Pro Arg Asp Val Gln Pro Tyr Gly Asp Gly Gln Ala Ala
                    340                 345                 350
    Arg Arg Ile Val Asp Ala Leu Ala Ala His
                    355                 360

<210> SEQ ID NO 85
<211> LENGTH: 376
<212> TYPE: PRT
<213> ORGANISM: Pseudomonas aeruginosa

<400> SEQUENCE: 85

Met Lys Val Leu Thr Val Phe Gly Thr Arg Pro Glu Ala Ile Lys Met
    1               5                   10                  15
    Ala Pro Leu Val His Ala Leu Ala Lys Asp Pro Phe Phe Glu Ala Lys
                    20                  25                  30
    Val Cys Val Thr Ala Gln His Arg Glu Met Leu Asp Gln Val Leu Lys
                35                  40                  45
    Leu Phe Ser Ile Val Pro Asp Tyr Asp Leu Asn Ile Met Gln Pro Gly
                50                  55                  60
    Gln Gly Leu Thr Glu Ile Thr Cys Arg Ile Leu Glu Gly Leu Lys Pro
    65                  70                  75                  80
    Ile Leu Ala Glu Phe Lys Pro Asp Val Val Leu Val His Gly Asp Thr
                    85                  90                  95
    Thr Thr Thr Leu Ala Thr Ser Leu Ala Ala Phe Tyr Gln Arg Ile Pro
                    100                 105                 110
    Val Gly His Val Glu Ala Gly Leu Arg Thr Gly Asp Leu Tyr Ser Pro
                115                 120                 125
    Trp Pro Glu Glu Ala Asn Arg Thr Leu Thr Gly His Leu Ala Met Tyr
                130                 135                 140
    His Phe Ser Pro Thr Glu Thr Ser Arg Gln Asn Leu Leu Arg Glu Asn
    145                 150                 155                 160
    Val Ala Asp Ser Arg Ile Phe Ile Thr Gly Asn Thr Val Ile Asp Ala
                    165                 170                 175
    Leu Leu Trp Val Arg Asp Gln Val Met Ser Ser Asp Lys Leu Arg Ser
                    180                 185                 190
    Glu Leu Ala Ala Asn Tyr Pro Phe Ile Asp Pro Asp Lys Lys Met Ile
                195                 200                 205
    Leu Val Thr Gly His Arg Arg Glu Ser Phe Gly Arg Gly Phe Glu Glu
    210                 215                 220
    Ile Cys His Ala Leu Ala Asp Ile Ala Thr His Gln Asp Ile Gln
    225                 230                 235                 240
    Ile Val Tyr Pro Val His Leu Asn Pro Asn Val Arg Glu Pro Val Asn
                    245                 250                 255
    Arg Ile Leu Gly His Val Lys Asn Val Ile Leu Ile Asp Pro Gln Glu
                    260                 265                 270
    Tyr Leu Pro Phe Val Trp Leu Met Asn His Ala Trp Leu Ile Leu Thr
                275                 280                 285
    Asp Ser Gly Gly Ile Gln Glu Glu Ala Pro Ser Leu Gly Lys Pro Val
                290                 295                 300
    Leu Val Met Arg Asp Thr Thr Glu Arg Pro Glu Ala Val Thr Ala Gly
    305                 310                 315                 320
    Thr Val Arg Leu Val Gly Thr Asp Lys Gln Arg Ile Val Glu Glu Val
                    325                 330                 335
```

```
        Thr Arg Leu Leu Lys Asp Glu Asn Glu Tyr Gln Ala Met Ser Arg Ala
                        340                 345                 350
        His Asn Pro Tyr Gly Asp Gly Gln Ala Cys Ser Arg Ile Leu Glu Ala
                    355                 360                 365
        Leu Lys Asn Asn Arg Ile Ser Leu
                    370                 375
```

<210> SEQ ID NO 86
<211> LENGTH: 380
<212> TYPE: PRT
<213> ORGANISM: Pseudomonas aeruginosa

<400> SEQUENCE: 86

```
        Met Lys Lys Leu Lys Val Met Thr Val Phe Gly Thr Arg Pro Glu Ala
         1               5                  10                  15
        Ile Lys Met Ala Pro Leu Val Leu Glu Leu Lys Lys Tyr Pro Glu Ile
                        20                  25                  30
        Asp Ser Tyr Val Thr Val Thr Ala Gln His Arg Gln Met Leu Asp Gln
                    35                  40                  45
        Val Leu Asp Ala Phe His Ile Lys Pro Asp Phe Asp Leu Asn Ile Met
                50                  55                  60
        Lys Glu Arg Gln Thr Leu Ala Glu Ile Thr Ser Asn Ala Leu Val Arg
         65                  70                  75                  80
        Leu Asp Glu Leu Phe Lys Asp Ile Lys Pro Asp Ile Val Leu Val His
                        85                  90                  95
        Gly Asp Thr Thr Thr Thr Phe Ala Gly Ser Leu Ala Ala Phe Tyr His
                        100                 105                 110
        Gln Ile Ala Val Gly His Val Glu Ala Gly Leu Arg Thr Gly Asn Lys
                    115                 120                 125
        Tyr Ser Pro Phe Pro Glu Glu Leu Asn Arg Gln Met Thr Gly Ala Ile
                130                 135                 140
        Ala Asp Leu His Phe Ala Pro Thr Gly Gln Ala Lys Asp Asn Leu Leu
        145                 150                 155                 160
        Lys Glu Asn Lys Lys Ala Asp Ser Ile Phe Val Thr Gly Asn Thr Ala
                        165                 170                 175
        Ile Asp Ala Leu Asn Thr Thr Val Arg Asp Gly Tyr Ser His Pro Val
                    180                 185                 190
        Leu Asp Gln Val Gly Glu Asp Lys Met Ile Leu Leu Thr Ala His Arg
                195                 200                 205
        Arg Glu Asn Leu Gly Glu Pro Met Glu Asn Met Phe Lys Ala Ile Arg
            210                 215                 220
        Arg Ile Val Gly Glu Phe Glu Asp Val Gln Val Val Tyr Pro Val His
        225                 230                 235                 240
        Leu Asn Pro Val Val Arg Glu Ala Ala His Lys His Phe Gly Asp Ser
                        245                 250                 255
        Asp Arg Val His Leu Ile Glu Pro Leu Glu Val Ile Asp Phe His Asn
                    260                 265                 270
        Phe Ala Ala Lys Ser His Phe Ile Leu Thr Asp Ser Gly Gly Val Gln
                275                 280                 285
        Glu Glu Ala Pro Ser Leu Gly Lys Pro Val Leu Val Leu Arg Asp Thr
            290                 295                 300
        Thr Glu Arg Pro Glu Gly Val Ala Gly Thr Leu Lys Leu Ala Gly
        305                 310                 315                 320
        Thr Asp Glu Gly Asn Ile Tyr Gln Leu Ala Lys Gln Leu Leu Thr Asp
                        325                 330                 335
        Pro Asp Glu Tyr Lys Lys Met Ser Gln Ala Ser Asn Pro Tyr Gly Asp
                    340                 345                 350
        Gly Glu Ala Ser Arg Arg Ile Val Glu Glu Leu Leu Phe His Tyr Gly
                355                 360                 365
        Tyr Arg Lys Glu Gln Pro Asp Ser Phe Thr Gly Lys
            370                 375                 380
```

<210> SEQ ID NO 87
<211> LENGTH: 378
<212> TYPE: PRT
<213> ORGANISM: Pseudomonas aeruginosa

<400> SEQUENCE: 87

```
        Met Ser Lys Val Leu Phe Val Phe Gly Thr Arg Pro Glu Ala Ile Lys
         1               5                  10                  15
        Met Ala Pro Leu Val Ile Glu Phe Lys Asn Asn Pro Ala Ile Glu Val
                        20                  25                  30
        Lys Val Cys Val Thr Gly Gln His Arg Glu Met Leu Asp Gln Val Leu
                    35                  40                  45
        Asp Phe Phe Glu Ile Glu Pro Asp Tyr Asp Leu Asn Ile Met Lys Gln
                50                  55                  60
```

```
       Lys Gln Ser Leu Gly Ser Ile Thr Cys Ser Ile Leu Thr Arg Leu Asp
        65                  70                  75                  80
       Glu Ile Leu Ala Ser Phe Met Pro Ala His Ile Phe Val His Gly Asp
                       85                  90                  95
       Thr Thr Thr Thr Phe Ala Ala Ser Leu Ala Ala Phe Tyr Gln Asn Ile
                   100                 105                 110
       Lys Val Trp His Ile Glu Ala Gly Leu Arg Thr Trp Asn Met Asn Ser
                   115                 120                 125
       Pro Phe Pro Glu Glu Gly Asn Arg Gln Leu Thr Ser Lys Leu Ala Phe
       130                 135                 140
       Phe His Ala Ala Pro Thr Leu Gln Ala Lys Asp Asn Leu Leu Arg Glu
       145                 150                 155                 160
       Ser Val Lys Glu Lys Asn Ile Ile Val Thr Gly Asn Thr Val Ile Asp
                       165                 170                 175
       Ala Leu Leu Ile Gly Ile Lys Lys Ile Thr Gly Ser Thr Gly Asp Val
                   180                 185                 190
       Arg Glu Ile Ile Ser Leu Lys Asn Lys Leu Asn Leu Asp Lys Lys Ile
                   195                 200                 205
       Ile Leu Val Thr Leu His Arg Arg Glu Asn Gln Gly Glu Leu Leu Arg
       210                 215                 220
       Thr Ile Cys Asp Asp Ile Lys Gln Leu Ala Leu Glu His Asp Asp Ile
       225                 230                 235                 240
       Glu Ile Val Phe Pro Val His Met Ser Pro Arg Ile Arg Glu Val Val
                       245                 250                 255
       Asn Glu Lys Leu Ser Gly Val Val Asn Ile Lys Leu Val Glu Pro Leu
                   260                 265                 270
       Ala Tyr Pro Gly Phe Ile Trp Leu Met Asn Asn Ala His Phe Ile Leu
                   275                 280                 285
       Ser Asp Ser Gly Gly Val Gln Glu Glu Ala Pro Ser Leu Gln Lys Pro
       290                 295                 300
       Val Leu Val Ala Arg Asp Thr Thr Glu Arg Pro Glu Val Ile Glu Asn
       305                 310                 315                 320
       Gly Ala Ala Met Leu Val Asp Pro Arg Ile Pro Asn Asn Ile Tyr Ser
                       325                 330                 335
       Ser Cys Lys Lys Leu Leu Ser Asp Glu Arg Leu Tyr Glu Lys Met Ser
                   340                 345                 350
       Gln Ala Gly Asn Pro Phe Gly Asp Gly Lys Ala Ser Lys Ile Leu
                   355                 360                 365
       Asp Tyr Phe Val Ser Leu Glu Asp Ile Lys
       370                 375
```

<210> SEQ ID NO 88
<211> LENGTH: 413
<212> TYPE: PRT
<213> ORGANISM: Pseudomonas aeruginosa

<400> SEQUENCE: 88

```
       Met Asn Val Trp Tyr Val His Pro Tyr Ala Gly Pro Gly Val Gly
        1               5                   10                  15
       Arg Tyr Trp Arg Pro Tyr Tyr Phe Ser Lys Phe Trp Asn Gln Ala Gly
                       20                  25                  30
       His Arg Ser Val Ile Ile Ser Ala Gly Tyr His His Leu Leu Glu Pro
                   35                  40                  45
       Asp Glu Lys Arg Ser Gly Val Thr Cys Val Asn Gly Ala Glu Tyr Ala
       50                  55                  60
       Tyr Val Pro Thr Leu Arg Tyr Leu Gly Asn Gly Val Gly Arg Met Leu
        65                  70                  75                  80
       Ser Met Leu Ile Phe Thr Met Met Leu Leu Pro Phe Cys Leu Ile Leu
                       85                  90                  95
       Ala Leu Lys Arg Gly Thr Pro Asp Ala Ile Tyr Ser Ser Pro His
                   100                 105                 110
       Pro Phe Gly Val Val Ser Cys Trp Leu Ala Ala Arg Leu Leu Gly Ala
                   115                 120                 125
       Lys Phe Val Phe Glu Val Arg Asp Ile Trp Pro Leu Ser Leu Val Glu
       130                 135                 140
       Leu Gly Gly Leu Lys Ala Asp Asn Pro Leu Val Arg Val Thr Gly Trp
       145                 150                 155                 160
       Ile Glu Arg Phe Ser Tyr Ala Arg Ala Asp Lys Ile Ile Ser Leu Leu
                       165                 170                 175
       Pro Cys Ala Glu Pro His Met Ala Asp Lys Gly Leu Pro Ala Gly Lys
                   180                 185                 190
       Phe Leu Trp Val Pro Asn Gly Val Asp Ser Ser Asp Ile Ser Pro Asp
                   195                 200                 205
       Ser Ala Val Ser Ser Ser Asp Leu Val Arg His Val Gln Val Leu Lys
       210                 215                 220
       Glu Gln Gly Val Phe Val Val Ile Tyr Ala Gly Ala His Gly Glu Pro
       225                 230                 235                 240
       Asn Ala Leu Glu Gly Leu Val Arg Ser Ala Gly Leu Leu Arg Glu Arg
```

```
            245                 250                 255
Gly Ala Ser Ile Arg Ile Ile Leu Val Gly Lys Gly Glu Cys Lys Glu
            260                 265                 270
Gln Leu Lys Ala Ile Ala Ala Gln Asp Ala Ser Gly Leu Val Glu Phe
            275                 280                 285
Phe Asp Gln Gln Pro Lys Glu Thr Ile Met Ala Val Leu Lys Leu Ala
            290                 295                 300
Ser Ala Gly Tyr Ile Ser Leu Lys Ser Glu Pro Ile Phe Arg Phe Gly
305                 310                 315                 320
Val Ser Pro Asn Lys Leu Trp Asp Tyr Met Leu Val Gly Leu Pro Val
            325                 330                 335
Ile Phe Ala Cys Lys Ala Gly Asn Asp Pro Val Ser Asp Tyr Asp Cys
            340                 345                 350
Gly Val Ser Ala Asp Pro Asp Ala Pro Glu Asp Ile Thr Ala Ala Ile
            355                 360                 365
Phe Arg Leu Leu Leu Ser Glu Asp Glu Arg Arg Thr Met Gly Gln
            370                 375                 380
Arg Gly Arg Asp Ala Val Leu Glu His Tyr Thr Tyr Glu Ser Leu Ala
385                 390                 395                 400
Leu Gln Val Leu Asn Ala Leu Ala Asp Gly Arg Ala Ala
            405                 410

<210> SEQ ID NO 89
<211> LENGTH: 403
<212> TYPE: PRT
<213> ORGANISM: Pseudomonas aeruginosa

<400> SEQUENCE: 89

Met Glu Phe Arg Pro Tyr Tyr Phe Gly Arg Glu Trp Ile Gly His Gly
1               5                   10                  15
His Gln Val Lys Val Ala Ala Ser Thr Ile Ser His Ile Arg Ala Arg
            20                  25                  30
Ala Pro Gln Ala Gly Gly Arg Leu Thr Arg Glu Asn Val Asp Gly Ile
            35                  40                  45
Glu Tyr Leu Trp Tyr Ala Thr Leu Pro Tyr Gln Gly Asn Gly Ala Arg
        50                  55                  60
Arg Leu Leu Asn Met Leu Gln Phe Ser Ala Arg Leu Tyr Gly Leu Arg
65                  70                  75                  80
Arg Asp Leu Gly Gly Trp Arg Pro Asp Ile Val Ile Ala Ser Ser Thr
                85                  90                  95
His Pro Tyr Asp Val Leu Pro Ala Ala Arg Leu Ala Arg Gln Thr Gly
            100                 105                 110
Ala Arg Leu Val Phe Glu Val His Asp Leu Trp Pro Leu Thr Pro Arg
            115                 120                 125
Leu Leu Gly Gly Phe Lys Ala Trp His Pro Met Ile Ala Ser Met Gln
        130                 135                 140
Tyr Ala Glu Asp Tyr Ala Tyr Arg His Ala Asp Leu Thr Val Ser Met
145                 150                 155                 160
Leu Pro Cys Ala Leu Pro Tyr Met Arg Glu Arg Gly Leu Asp Pro Arg
                165                 170                 175
Arg Tyr Ala His Val Pro Asn Gly Val Pro Val Thr Glu Tyr Ser Ser
            180                 185                 190
Pro Asp Phe Asp Asn Pro Asp Tyr Leu Arg Val Arg Ala Gln Ile Arg
            195                 200                 205
Gln Leu Arg Glu Gln Cys Asp Phe Val Leu Ala Tyr Ala Gly Thr His
        210                 215                 220
Gly His Ala Asn Ala Leu Asp Met Leu Leu Gln Ala Met Ala Arg Leu
225                 230                 235                 240
Arg Asp Gln Pro Ile Gly Leu Leu Leu Leu Gly Asp Gly Pro Asp Lys
                245                 250                 255
Pro Glu Leu Lys Arg Leu Ala Gly Gln Leu Gly Leu Arg His Ile Ala
            260                 265                 270
Phe Ala Asp Pro Val Pro Arg Pro Ala Val Gln Ala Val Met Ala Asp
            275                 280                 285
Ile Asp Ala Ala Tyr Ile Gly Leu Arg Arg Ser Pro Leu Phe Gln Phe
        290                 295                 300
Gly Val Ser Pro Asn Lys Leu Phe Asp Tyr Met Leu Ser Ala Cys Pro
305                 310                 315                 320
Val Val Gln Ser Ile Glu Ser Gly Asn Asp Ile Val Ala Asp Ala Arg
                325                 330                 335
Cys Gly Leu Ser Val Pro Ala Glu Asp Pro Ala Ala Leu Ala Ala Ala
            340                 345                 350
Leu His Gly Leu Arg Thr Leu Pro Ala Ala Glu Arg Gln Ala Met Gly
        355                 360                 365
Arg Arg Gly Arg Asp Tyr Val Leu Ala Arg His Asp Tyr Pro Val Leu
        370                 375                 380
Ala Gln Gln Phe Leu Asp Ala Val Gln Ser Val Thr Pro Arg Arg Ala
385                 390                 395                 400
```

```
              Ala Ser Arg

<210> SEQ ID NO 90
<211> LENGTH: 344
<212> TYPE: PRT
<213> ORGANISM: Pseudomonas aeruginosa

<400> SEQUENCE: 90

Met Tyr Glu Ala Gly His Asn Val Met Ile Ile Ser Leu Thr Gly Glu
      1               5                   10                  15
      Thr Leu Val Arg Pro Asn Asp Gly Ile Gln Leu Asn Glu Leu Lys Leu
                  20                  25                  30
      Asp Lys Ala Pro Phe Ser Leu Phe Lys Gly Leu Phe Glu Val Lys Lys
                35                  40                  45
      Ile Ile Lys Lys Phe Lys Pro Asp Ile Val His Ser His Met Phe His
      50                  55                  60
      Ala Asn Leu Phe Ala Arg Ile Leu Arg Val Phe Thr Lys Ile Pro Ala
      65                  70                  75                  80
      Leu Ile Cys Thr Ala His Asn Thr Asn Glu Gly Ser Ser Leu Arg Met
                      85                  90                  95
      Leu Ala Tyr Lys Tyr Thr Asp Lys Leu Ala Ser Leu Ser Thr Asn Val
                  100                 105                 110
      Ser Gln Asp Ala Val Asp Ser Phe Ile His Lys Gly Ala Ser Ser Thr
                  115                 120                 125
      Gly Arg Met Ile Ala Val Ser Asn Gly Ile Asp Ala Ser Gln Phe Asp
                  130                 135                 140
      Phe Ser Met Asp Glu Arg Lys Val Lys Arg Ser Glu Leu Gly Ile Phe
      145                 150                 155                 160
      Asn Asp Thr Pro Ile Ile Leu Ser Val Gly Arg Leu Thr Glu Ala Lys
                      165                 170                 175
      Asp Tyr Pro Asn Leu Leu Thr Ala Phe Ser Leu Leu Ile Lys Asp Asn
                  180                 185                 190
      Ser Leu Gln Ser Phe Pro Gln Leu Phe Ile Val Gly Thr Gly His Leu
                  195                 200                 205
      Asp Gly Tyr Leu Lys Asn Met Ser Lys Glu Phe Gly Ile Asp Lys Tyr
                  210                 215                 220
      Val Thr Leu Phe Gly Gln Arg Asp Asp Ile Leu Gln Leu Met Cys Ala
      225                 230                 235                 240
      Ala Asp Ile Phe Val Leu Ser Ser Glu Trp Glu Gly Phe Pro Leu Val
                      245                 250                 255
      Ile Thr Glu Ala Met Ala Cys Lys Lys Ile Ile Val Ala Thr Asp Ala
                  260                 265                 270
      Gly Gly Ile Thr Glu Ala Leu Gly Asp Cys Gly Ser Ile Val Pro Ile
                  275                 280                 285
      Lys Asp Pro Asn Ser Leu Ser Gln Ala Ile Asn Lys Met Ile Lys Leu
                  290                 295                 300
      Ser Asp Asn Glu Lys Glu Ile Leu Gly Asn Lys Ala Arg Glu Arg Ile
      305                 310                 315                 320
      Ile Gln Thr Asn Ser Ile Glu Lys Ile Ile Glu Leu Gly Cys Leu Phe
                      325                 330                 335
      Ile Leu Asn Leu Lys Asn Asn Cys
                  340

<210> SEQ ID NO 91
<211> LENGTH: 303
<212> TYPE: PRT
<213> ORGANISM: Pseudomonas aeruginosa

<400> SEQUENCE: 91

Met Met Ile Trp Met Ile Ala Cys Leu Val Val Leu Leu Phe Ser Phe
      1               5                   10                  15
      Val Ala Thr Trp Gly Leu Arg Arg Tyr Ala Leu Ala Thr Lys Leu Met
                  20                  25                  30
      Asp Val Pro Asn Ala Arg Ser Ser His Ser Gln Pro Thr Pro Arg Gly
                35                  40                  45
      Gly Gly Val Ala Ile Val Leu Val Phe Leu Ala Ala Leu Val Trp Met
            50                  55                  60
      Leu Ser Ala Gly Ser Ile Ser Gly Gly Trp Gly Gly Ala Met Leu Gly
      65                  70                  75                  80
      Ala Gly Ser Gly Val Ala Leu Leu Gly Leu Asp Asp His Gly His
                      85                  90                  95
      Ile Ala Ala Arg Trp Arg Leu Leu Gly His Phe Ser Ala Ala Ile Trp
                  100                 105                 110
      Ile Leu Leu Trp Thr Gly Gly Phe Pro Pro Leu Asp Val Val Gly His
                  115                 120                 125
      Ala Val Asp Leu Gly Trp Leu Gly His Val Leu Ala Val Phe Tyr Leu
```

```
            130                 135                 140
    Val Trp Val Leu Asn Leu Tyr Asn Phe Met Asp Gly Ile Asp Gly Ile
    145                 150                 155                 160
    Ala Ser Val Glu Ala Ile Gly Val Cys Val Gly Gly Ala Leu Ile Tyr
                    165                 170                 175
    Trp Leu Thr Gly His Val Ala Met Val Gly Ile Pro Leu Leu Leu Ala
                180                 185                 190
    Cys Ala Val Ala Gly Phe Leu Ile Trp Asn Phe Pro Pro Ala Arg Ile
            195                 200                 205
    Phe Met Gly Asp Ala Gly Ser Gly Phe Leu Gly Met Val Ile Gly Ala
        210                 215                 220
    Leu Ala Ile Gln Ala Ala Trp Thr Ala Pro Ser Leu Phe Trp Cys Trp
    225                 230                 235                 240
    Leu Ile Leu Leu Gly Val Phe Ile Val Asp Ala Thr Tyr Thr Leu Ile
                    245                 250                 255
    Arg Arg Ile Ala Arg Gly Glu Lys Phe Tyr Glu Ala His Arg Ser His
                260                 265                 270
    Ala Tyr Gln Phe Ala Ser Arg Arg Tyr Ala Ser His Leu Arg Val Thr
            275                 280                 285
    Leu Gly Val Leu Ala Ile Asn Thr Leu Trp Leu Leu Arg Trp His
        290                 295                 300
```

<210> SEQ ID NO 92
<211> LENGTH: 341
<212> TYPE: PRT
<213> ORGANISM: Pseudomonas aeruginosa

<400> SEQUENCE: 92

```
    Met Pro Thr Phe Phe Phe Leu Leu Thr Ile Phe Phe Leu Leu Ser Val
    1               5                   10                  15
    Gly Leu Thr Tyr Leu Leu Arg Leu Tyr Ala Leu Lys Asn Asn Ile Ile
                    20                  25                  30
    Asp Thr Pro Asn Ser Arg Ser Ser His Val Thr Pro Thr Pro Arg Gly
                35                  40                  45
    Gly Gly Val Ala Ile Val Ile Ser Phe Leu Ile Gly Ile Ile Leu Phe
            50                  55                  60
    Tyr Phe Leu Gly Tyr Leu Pro Ile Leu Ser Val Val Gly Leu Ile Val
    65                  70                  75                  80
    Ser Gly Gly Val Ile Ala Leu Val Gly Phe Trp Asp Asp His Gly His
                    85                  90                  95
    Ile Ala Ala Arg Trp Arg Leu Leu Ala His Phe Ser Ala Ala Ala Phe
                    100                 105                 110
    Leu Leu Phe Cys Phe Gly Gly Phe Pro Val Leu Asn Val Ser Gly Phe
                115                 120                 125
    Ile Ile Glu Leu Gly Ile Phe Gly Ser Leu Phe Gly Leu Leu Phe Leu
            130                 135                 140
    Val Trp Met Leu Asn Leu Tyr Asn Phe Met Asp Gly Ile Asp Gly Leu
    145                 150                 155                 160
    Ala Ser Ala Glu Ala Val Thr Ala Cys Ile Gly Met Ile Ala Ile Tyr
                    165                 170                 175
    Tyr Ile Ser Gly Asp His Ile Glu Leu Asn Ser Phe Leu Val Leu Trp
                180                 185                 190
    Leu Leu Ala Cys Thr Val Leu Gly Phe Leu Leu Trp Asn Phe Pro Pro
            195                 200                 205
    Ala Lys Ile Phe Met Gly Asp Ala Gly Ser Gly Phe Leu Gly Leu Met
        210                 215                 220
    Ile Gly Ser Leu Ala Ile Ser Ala Gly Trp Ile Asp Thr Arg Phe Phe
    225                 230                 235                 240
    Phe Cys Trp Leu Ile Leu Leu Gly Leu Phe Ile Val Asp Ala Thr Trp
                    245                 250                 255
    Thr Leu Val Arg Arg Val Leu Gly Gly Phe Lys Val Tyr Glu Ala His
                260                 265                 270
    Arg Ser His Gly Tyr Gln Ile Ala Ser Arg Arg Phe Lys Arg His Leu
            275                 280                 285
    Pro Val Thr Leu Ser Ala Ile Ala Ile Asn Ile Ile Trp Leu Phe Pro
        290                 295                 300
    Ile Ala Leu Leu Ala Gly Leu Asn Ile Val Asn Pro Ile Ile Ala Leu
    305                 310                 315                 320
    Ile Ile Ser Tyr Ile Pro Leu Leu Tyr Ile Asp Tyr Lys Leu Asn Ala
                    325                 330                 335
    Gly Val Asn Asn Asp
                340
```

<210> SEQ ID NO 93
<211> LENGTH: 355
<212> TYPE: PRT
<213> ORGANISM: Pseudomonas aeruginosa

<400> SEQUENCE: 93

```
Met Leu Ser Ile Phe Val Thr Phe Leu Gly Ala Phe Leu Thr Leu Ile
 1               5                  10                  15
Val Met Arg Pro Leu Ala Asn Trp Ile Gly Leu Val Asp Lys Pro Asn
             20                  25                  30
Tyr Arg Lys Arg His Gln Gly Thr Ile Pro Leu Ile Gly Gly Ala Ser
         35                  40                  45
Leu Phe Val Gly Asn Leu Cys Tyr Tyr Leu Met Glu Trp Asp Gln Leu
     50                  55                  60
Arg Leu Pro Tyr Leu Tyr Leu Phe Ser Ile Phe Val Leu Leu Ala Ile
 65                  70                  75                  80
Gly Ile Leu Asp Asp Arg Phe Asp Ile Ser Pro Phe Leu Arg Ala Gly
                 85                  90                  95
Ile Gln Ala Ile Leu Ala Ile Leu Met Ile Asp Leu Gly Asn Ile Tyr
            100                 105                 110
Leu Asp His Leu Gly Gln Ile Leu Gly Pro Phe Gln Leu Thr Leu Gly
        115                 120                 125
Ser Ile Gly Leu Ile Ile Thr Val Phe Ala Thr Ile Ala Ile Ile Asn
    130                 135                 140
Ala Phe Asn Met Ile Asp Gly Ile Asp Gly Leu Leu Gly Gly Leu Ser
145                 150                 155                 160
Cys Val Ser Phe Ala Ala Ile Gly Ile Leu Met Tyr Arg Asp Gly Gln
                165                 170                 175
Met Asp Met Ala His Trp Ser Phe Ala Leu Ile Val Ser Ile Leu Pro
            180                 185                 190
Tyr Leu Met Leu Asn Leu Gly Ile Pro Phe Gly Pro Lys Tyr Lys Val
        195                 200                 205
Phe Met Gly Asp Ala Gly Ser Thr Leu Ile Gly Phe Thr Ile Ile Trp
    210                 215                 220
Ile Leu Leu Leu Ser Thr Gln Gly Lys Gly His Pro Met Asn Pro Val
225                 230                 235                 240
Thr Ala Leu Trp Ile Ile Ala Ile Pro Leu Ile Asp Met Val Ala Ile
                245                 250                 255
Ile Tyr Arg Arg Val Arg Lys Gly Lys Ser Pro Phe Arg Pro Asp Arg
            260                 265                 270
Leu His Val His His Leu Met Val Arg Ala Gly Leu Thr Ser Arg Gln
        275                 280                 285
Ala Phe Leu Leu Ile Thr Phe Val Ser Ala Val Cys Ala Thr Ile Gly
    290                 295                 300
Ile Leu Gly Glu Val Tyr Tyr Val Asn Glu Trp Ala Met Phe Val Gly
305                 310                 315                 320
Phe Phe Ile Leu Phe Phe Leu Tyr Val Tyr Ser Ile Thr His Ala Trp
                325                 330                 335
Arg Ile Thr Arg Trp Val Arg Arg Met Lys Arg Ala Lys Arg Leu
            340                 345                 350
Lys Lys Ala
        355
```

<210> SEQ ID NO 94
<211> LENGTH: 665
<212> TYPE: PRT
<213> ORGANISM: Pseudomonas aeruginosa

<400> SEQUENCE: 94

```
Met Leu Asp Asn Leu Arg Ile Lys Leu Leu Gly Leu Pro Arg Arg Tyr
 1               5                  10                  15
Lys Arg Met Leu Gln Val Ala Ala Asp Val Thr Leu Val Trp Leu Ser
             20                  25                  30
Leu Trp Leu Ala Phe Leu Val Arg Leu Gly Thr Glu Asp Met Ile Ser
         35                  40                  45
Pro Phe Ser Gly His Ala Trp Leu Phe Ile Ala Ala Pro Leu Val Ala
     50                  55                  60
Ile Pro Leu Phe Ile Arg Phe Gly Met Tyr Arg Ala Val Met Arg Tyr
 65                  70                  75                  80
Leu Gly Asn Asp Ala Leu Ile Ala Ile Ala Lys Ala Val Thr Ile Ser
                 85                  90                  95
Ala Leu Val Leu Ser Leu Val Tyr Trp Tyr Arg Ser Pro Pro Ala
            100                 105                 110
Val Val Pro Arg Ser Leu Val Phe Asn Tyr Trp Leu Ser Met Leu
        115                 120                 125
Leu Ile Gly Gly Leu Arg Leu Ala Met Arg Gln Tyr Phe Met Gly Asp
    130                 135                 140
Trp Tyr Ser Ala Val Gln Ser Val Pro Phe Leu Asn Arg Gln Asp Gly
145                 150                 155                 160
Leu Pro Arg Val Ala Ile Tyr Gly Ala Gly Ala Ala Asn Gln Leu
                165                 170                 175
```

```
    Val Ala Ala Leu Arg Leu Gly Arg Ala Met Arg Pro Val Ala Phe Ile
                180                 185                 190
    Asp Asp Asp Lys Gln Ile Ala Asn Arg Val Ile Ala Gly Leu Arg Val
                195                 200                 205
    Tyr Thr Ala Lys His Ile Arg Gln Met Ile Asp Glu Thr Gly Ala Gln
                210                 215                 220
    Glu Val Leu Leu Ala Ile Pro Ser Ala Thr Arg Ala Arg Arg Arg Glu
    225                 230                 235                 240
    Ile Leu Glu Ser Leu Glu Pro Phe Pro Leu His Val Arg Ser Met Pro
                245                 250                 255
    Gly Phe Met Asp Leu Thr Ser Gly Arg Val Lys Val Asp Asp Leu Gln
                260                 265                 270
    Glu Val Asp Ile Ala Asp Leu Leu Gly Arg Asp Ser Val Ala Pro Arg
                275                 280                 285
    Lys Glu Leu Leu Glu Arg Cys Ile Arg Gly Gln Val Val Met Val Thr
                290                 295                 300
    Gly Ala Gly Gly Ser Ile Gly Ser Glu Leu Cys Arg Gln Ile Met Ser
    305                 310                 315                 320
    Cys Ser Pro Ser Val Leu Ile Leu Phe Glu His Ser Glu Tyr Asn Leu
                325                 330                 335
    Tyr Ser Ile His Gln Glu Leu Glu Arg Arg Ile Lys Arg Glu Ser Leu
                340                 345                 350
    Ser Val Asn Leu Leu Pro Ile Leu Gly Ser Val Arg Asn Pro Glu Arg
                355                 360                 365
    Leu Val Asp Val Met Arg Thr Trp Lys Val Asn Thr Val Tyr His Ala
                370                 375                 380
    Ala Ala Tyr Lys His Val Pro Ile Val Glu His Asn Ile Ala Glu Gly
    385                 390                 395                 400
    Val Leu Asn Asn Val Ile Gly Thr Leu His Ala Val Gln Ala Ala Val
                405                 410                 415
    Gln Val Gly Val Gln Asn Phe Val Leu Ile Ser Thr Asp Lys Ala Val
                420                 425                 430
    Arg Pro Thr Asn Val Met Gly Ser Thr Lys Arg Leu Ala Glu Met Val
                435                 440                 445
    Leu Gln Ala Leu Ser Asn Glu Ser Ala Pro Leu Leu Phe Gly Asp Arg
    450                 455                 460
    Lys Asp Val His His Val Asn Lys Thr Arg Phe Thr Met Val Arg Phe
    465                 470                 475                 480
    Gly Asn Val Leu Gly Ser Ser Gly Ser Val Ile Pro Leu Phe Arg Glu
                485                 490                 495
    Gln Ile Lys Arg Gly Gly Pro Val Thr Val Thr His Pro Ser Ile Thr
                500                 505                 510
    Arg Tyr Phe Met Thr Ile Pro Glu Ala Ala Gln Leu Val Ile Gln Ala
                515                 520                 525
    Gly Ser Met Gly Gln Gly Gly Asp Val Phe Val Leu Asp Met Gly Pro
                530                 535                 540
    Pro Val Lys Ile Leu Glu Leu Ala Glu Lys Met Ile His Leu Ser Gly
    545                 550                 555                 560
    Leu Ser Val Arg Ser Glu Arg Ser Pro His Gly Asp Ile Ala Ile Glu
                565                 570                 575
    Phe Ser Gly Leu Arg Pro Gly Glu Lys Leu Tyr Glu Glu Leu Leu Ile
                580                 585                 590
    Gly Asp Asn Val Asn Pro Thr Asp His Pro Met Ile Met Arg Ala Asn
                595                 600                 605
    Glu Glu His Leu Ser Trp Glu Ala Phe Lys Val Val Leu Glu Gln Leu
                610                 615                 620
    Leu Ala Ala Val Glu Lys Asp Asp Tyr Ser Arg Val Arg Gln Leu Leu
    625                 630                 635                 640
    Arg Glu Thr Val Ser Gly Tyr Ala Pro Asp Gly Glu Ile Val Asp Trp
                645                 650                 655
    Ile Tyr Arg Gln Arg Arg Glu Pro
                660                 665
```

<210> SEQ ID NO 95
<211> LENGTH: 638
<212> TYPE: PRT
<213> ORGANISM: Pseudomonas aeruginosa

<400> SEQUENCE: 95

```
    Met Phe Leu Val Phe Leu Leu Ser Leu Pro Arg Pro Val Lys Arg Thr
    1               5                   10                  15
    Ile Met Leu Leu Leu Asp Thr Ile Leu Ile Ala Leu Ala Tyr Trp Gly
                20                  25                  30
    Ala Phe Trp Val Arg Leu Asp Val Asp Ser Pro Phe Thr Ser Ile Glu
                35                  40                  45
    Gln Trp Val Ala Leu Ala Ala Ile Ile Pro Pro Thr Leu Phe Ala Tyr
                50                  55                  60
    Ile Lys Leu Gly Leu Tyr Arg Thr Val Leu Arg Tyr Val Ser Ala Lys
```

```
               65                  70                  75                  80
      Ile Val Ser Ile Val Leu Val Gly Val Leu Ser Ser Gly Leu Leu
                          85                  90                  95
      Val Leu Gly Ser Tyr Phe Leu Gly Val Tyr Leu Pro Arg Thr Val Ser
                         100                 105                 110
      Val Met Phe Phe Ile Phe Ser Leu Val Leu Ile Cys Gly Ser Arg Leu
                         115                 120                 125
      Phe Phe Arg Met Leu Leu Asn Tyr Gly Val Arg Gly Gln Ile Pro Val
                         130                 135                 140
      Val Ile Tyr Gly Ala Gly Ala Ser Gly Arg Gln Leu Leu Pro Ala Leu
      145                 150                 155                 160
      Met Gln Ala Ser Glu Tyr Phe Pro Ile Ala Phe Val Asp Asp Asn Pro
                         165                 170                 175
      Lys Leu His Lys Ala Val Ile His Gly Val Thr Val Tyr Pro Ser Glu
                         180                 185                 190
      Lys Leu Glu Tyr Leu Ile Gly Arg Tyr Gly Ile Lys Lys Val Leu Leu
                         195                 200                 205
      Ala Met Pro Ser Val Ser Gln Ser Gln Arg Arg Ala Val Val Asn Lys
                         210                 215                 220
      Leu Glu Asn Leu Ser Cys Glu Val Leu Ser Ile Pro Gly Met Ser Asp
      225                 230                 235                 240
      Leu Val Glu Gly Arg Ala Gln Ile Ser Ser Leu Lys Lys Val Ser Ile
                         245                 250                 255
      Glu Glu Leu Leu Gly Arg Asp Pro Val Val Pro Asp Glu Lys Leu Leu
                         260                 265                 270
      Ala Lys Asn Ile Thr Gly Lys Val Val Met Val Thr Gly Ala Gly Gly
                         275                 280                 285
      Ser Ile Gly Ser Glu Leu Cys Arg Gln Ile Ile Val Glu Lys Pro Ser
                         290                 295                 300
      Leu Leu Ile Leu Phe Asp Ile Ser Glu Phe Ser Leu Tyr Ser Ile Glu
      305                 310                 315                 320
      Asn Glu Met Ala Ala Ile Cys Lys Lys Asn Lys Ile Glu Thr Glu Phe
                         325                 330                 335
      Val Ala Leu Leu Gly Ser Val Gln Ser Glu Lys Arg Leu Val Gln Ile
                         340                 345                 350
      Met Ser Asn Phe His Val Asn Thr Val Tyr His Ala Ala Tyr Lys
                         355                 360                 365
      His Val Pro Leu Val Glu Asn Asn Val Ile Glu Gly Val Arg Asn Asn
                         370                 375                 380
      Ile Phe Gly Thr Leu Tyr Cys Ala Lys Ala Ala Ile Lys Ser Gly Val
      385                 390                 395                 400
      Glu Lys Phe Val Leu Ile Ser Thr Asp Lys Ala Val Arg Pro Thr Asn
                         405                 410                 415
      Thr Met Gly Ala Thr Lys Arg Met Ala Glu Leu Val Leu Gln Ala Leu
                         420                 425                 430
      Ser Thr Glu Gln Asn Lys Thr Lys Phe Cys Met Val Arg Phe Gly Asn
                         435                 440                 445
      Val Leu Gly Ser Ser Gly Ser Val Val Pro Leu Phe Lys Lys Gln Ile
                         450                 455                 460
      Ala Glu Gly Gly Pro Ile Thr Leu Thr His Lys Asp Ile Ile Arg Tyr
      465                 470                 475                 480
      Phe Met Thr Ile Pro Glu Ala Ala Gln Leu Val Ile Gln Ala Gly Ala
                         485                 490                 495
      Met Gly Gln Gly Gly Asp Val Phe Val Leu Asp Met Gly Asp Pro Val
                         500                 505                 510
      Lys Ile Ile Asp Leu Ala Lys Arg Met Ile Asn Leu Ser Gly Leu Ser
                         515                 520                 525
      Ile Lys Ser Glu Glu Asn Leu Asp Gly Asp Ile Ala Ile Glu Ile Ser
                         530                 535                 540
      Gly Leu Arg Pro Gly Glu Lys Leu Tyr Glu Glu Leu Leu Ile Gly Asp
      545                 550                 555                 560
      Ser Val Gln His Thr Tyr His Pro Arg Ile Met Thr Ala Thr Glu Ile
                         565                 570                 575
      Met Leu Glu Trp Asp Asp Leu Asn Ile Leu Leu Asn Lys Ile Glu Thr
                         580                 585                 590
      Ala Cys Asn Asp Phe Asn Tyr Glu Cys Ile Arg Ser Leu Leu Leu Glu
                         595                 600                 605
      Ala Pro Thr Gly Phe Gln Pro Thr Asp Gly Ile Cys Asp Val Val Trp
                         610                 615                 620
      Gln Lys Thr His Ser Glu Asn Ala Lys Asn Val Ile Val His
      625                 630                 635
```

<210> SEQ ID NO 96
<211> LENGTH: 624
<212> TYPE: PRT
<213> ORGANISM: Pseudomonas aeruginosa

<400> SEQUENCE: 96

```
Met Thr Leu Pro Tyr Ala Ile Arg Arg Leu Phe Val Asp Leu Pro Arg
 1               5                  10                  15
Pro Phe Lys Gln Met Leu Ala Ile Val Leu Asp Ala Val Ile Leu Leu
             20                  25                  30
Gly Ala Phe His Leu Ala Leu Trp Leu Arg Phe Glu Leu Phe Phe Leu
         35                  40                  45
Thr Asp Gln Tyr Leu Phe Leu Ser Leu Leu Ala Cys Ala Gly Gly Ile
 50                  55                  60
Ala Ala Leu Ala Ala Phe Gly Val Tyr Leu Tyr Ile Leu Arg Tyr Met
 65                  70                  75                  80
Ser Glu Arg Val Leu Ala Ala Ile Leu Gly Gly Ile Val Ser Val
                 85                  90                  95
Met Val Val Thr Ala Gly Asn Thr Phe Leu Gln Leu Ala Thr Ile Ser
            100                 105                 110
Arg Gly Val Leu Val Leu Tyr Ala Ala Leu Ala Leu Val Gly Leu Ile
            115                 120                 125
Gly Val Arg Leu Ile Ala Arg Lys Leu Leu Phe Pro Ala Asp His His
            130                 135                 140
Met Ala Asp Pro Arg Thr Pro Val Leu Ile Tyr Gly Ala Gly Gly Ala
145                 150                 155                 160
Gly Ser Gln Leu Ala Met Ala Leu Arg Thr Gly Pro His Tyr Arg Pro
            165                 170                 175
Val Ala Met Leu Asp Asp Asp Lys Arg Lys His Arg Leu Val Val Asn
            180                 185                 190
Gly Leu Arg Val Tyr Pro Pro Glu Gln Leu Pro Lys Leu Ile Asp Arg
            195                 200                 205
His Asn Ile Arg Gln Leu Leu Ile Ala Met Pro Ser Ala Pro Pro Lys
            210                 215                 220
Gln Ile Arg Ser Ile Val Glu Ala Ala Glu Pro Tyr Arg Leu Arg Ile
225                 230                 235                 240
Arg Leu Val Pro Ser Met Arg Glu Leu Ile Asp Pro Thr Asn Gly Val
                245                 250                 255
Arg Leu Arg Asp Val Gln Val Glu Asp Leu Leu Gly Arg Asp Pro Val
            260                 265                 270
Ala Pro Ile Asp Thr Leu Leu Gly Arg Cys Val Thr Asp Arg Val Val
            275                 280                 285
Met Val Thr Gly Ala Gly Gly Ser Ile Gly Ser Glu Leu Cys Arg Gln
            290                 295                 300
Ile Leu Ala Leu Arg Pro Arg Lys Leu Val Leu Phe Glu Ile Ala Glu
305                 310                 315                 320
Pro Ala Leu Tyr Ala Ile Glu Gln Asp Leu Arg Gln Arg Ile Gly Glu
                325                 330                 335
Arg Asn Ile Glu Ile Ala Gly Val Leu Gly Ser Val Arg Asp Ala Ala
            340                 345                 350
His Cys Leu Ala Gln Leu Gln His Gly Val Gln Thr Ile Tyr His
            355                 360                 365
Ala Ala Ala Tyr Lys His Val Pro Ile Val Glu His Asn Val Ser Glu
370                 375                 380
Gly Ile Arg Thr Asn Ala Phe Gly Thr Leu Asn Met Ala Glu Thr Ala
385                 390                 395                 400
Ile Gln Ala Gly Val Leu Asp Phe Val Leu Ile Ser Thr Asp Lys Ala
                405                 410                 415
Val Arg Pro Thr Asn Val Met Gly Ala Ser Lys Arg Leu Ala Glu Leu
                420                 425                 430
Ile Leu Gln Ala His Ala Gln Ile Gln Asp Lys Thr Arg Phe Ser Met
            435                 440                 445
Val Arg Phe Gly Asn Val Leu Gly Ser Ser Gly Ser Val Val Pro Leu
            450                 455                 460
Phe Arg Arg Gln Ile Leu Glu Gly Gly Pro Ile Thr Leu Thr His Pro
465                 470                 475                 480
Glu Ile Thr Arg Tyr Phe Met Thr Ile Pro Glu Ala Ala Gln Leu Val
                485                 490                 495
Leu Gln Ala Gly Ala Met Gly Glu Ser Gly Ser Val Phe Val Leu Asp
            500                 505                 510
Met Gly Glu Pro Val Leu Ile Arg Glu Leu Ala Glu Arg Met Val Arg
            515                 520                 525
Leu Tyr Gly Leu Thr Val Lys Asn Ser Asp Gln Pro Asp Gly Asp Ile
            530                 535                 540
Glu Ile Arg Ile Thr Gly Leu Arg Pro Gly Glu Lys Leu Tyr Glu Glu
545                 550                 555                 560
Leu Leu Ile Gly Glu Asp Ser Arg Glu Thr Leu His Pro Arg Ile Met
                565                 570                 575
Arg Ala Thr Glu Tyr Ser Leu Pro Tyr Glu Thr Leu Met Gly Gln Leu
            580                 585                 590
Arg Met Leu Asp Arg Ser Leu Gln Met Cys Ser Pro Arg Gln Ala Ala
            595                 600                 605
Glu Leu Leu Gly Gln Ile Val Arg Glu Tyr Ala Ser Val Thr Tyr Ala
            610                 615                 620
```

-continued

```
<210> SEQ ID NO 97
<211> LENGTH: 599
<212> TYPE: PRT
<213> ORGANISM: Pseudomonas aeruginosa

<400> SEQUENCE: 97

Met Thr Ser Ile Ser Ala Lys Leu Arg Phe Leu Ile Leu Ile Ile Ile
 1               5                  10                  15
Asp Ser Phe Ile Val Thr Phe Ser Val Phe Leu Gly Tyr Ala Ile Leu
             20                  25                  30
Glu Pro Tyr Phe Lys Gly Tyr Ser Ile Asp Leu Leu Val Leu Ser Ser
         35                  40                  45
Val Ile Leu Leu Val Ser His His Ile Phe Ala Tyr Val Phe Asn Leu
     50                  55                  60
Tyr His Arg Ala Trp Glu Tyr Ala Ser Val Ser Glu Leu Met Ser Val
 65                  70                  75                  80
Leu Lys Ala Val Thr Ser Ser Ile Val Val Thr Leu Leu Val Ser
                 85                  90                  95
Leu Leu Ile Ser Glu Ser Pro Phe Leu Arg Leu Tyr Phe Ile Thr Trp
                100                 105                 110
Met Met His Leu Leu Leu Ile Gly Gly Ser Arg Leu Phe Trp Arg Val
            115                 120                 125
Tyr Arg Arg Tyr Phe Ile Asp Asn Ala Val Glu Lys Ala Thr Leu
        130                 135                 140
Val Val Gly Ala Gly Gln Gly Gly Ser Val Leu Ile Arg Glu Met Leu
145                 150                 155                 160
Arg Ser Gln Asp Met Arg Met Gln Pro Val Leu Ala Val Asp Asp Asp
                165                 170                 175
Lys Asn Lys Gln Lys Met Thr Ile Thr Glu Arg Val Lys Val Gln Gly
            180                 185                 190
Tyr Val Glu Asp Ile Pro Glu Leu Val Lys Lys Phe Arg Ile Lys Lys
        195                 200                 205
Ile Ile Ile Ala Ile Pro Thr Leu Ser Gln Lys Arg Leu Asn Glu Ile
    210                 215                 220
Asn Lys Ile Cys Asn Ile Glu Gly Val Glu Leu Phe Lys Met Pro Asn
225                 230                 235                 240
Ile Glu Asp Val Leu Ser Gly Glu Leu Glu Val Asn Asn Leu Lys Lys
                245                 250                 255
Val Glu Val Glu Asp Leu Leu Gly Arg Asp Pro Val Glu Leu Asp Met
            260                 265                 270
Ala Leu Ile Ser Arg Glu Leu Thr Asn Lys Thr Ile Leu Val Thr Gly
        275                 280                 285
Ala Gly Gly Ser Ile Gly Ser Glu Ile Cys Arg Gln Val Ser Lys Phe
    290                 295                 300
Asp Pro Gln Lys Ile Ile Leu Leu Gly His Gly Glu Asn Ser Ile Tyr
305                 310                 315                 320
Ser Ile His Gln Glu Leu Ser Lys Thr Tyr Gly Asn Arg Ile Glu Phe
                325                 330                 335
Val Pro Val Ile Ala Asp Val Gln Asn Lys Thr Arg Ile Leu Glu Val
            340                 345                 350
Met Asn Glu Phe Lys Pro Tyr Ala Val Tyr His Ala Ala His Lys
        355                 360                 365
His Val Pro Leu Met Glu Tyr Asn Pro His Glu Ala Ile Arg Asn Asn
    370                 375                 380
Ile Leu Gly Thr Lys Asn Val Ala Glu Ser Ala Lys Glu Gly Glu Val
385                 390                 395                 400
Ser Lys Phe Val Met Ile Ser Thr Asp Lys Ala Val Asn Pro Ser Asn
                405                 410                 415
Val Met Gly Ala Thr Lys Arg Ile Ala Glu Met Val Ile Gln Ser Leu
            420                 425                 430
Asn Glu Asp Asn Ser Lys Thr Ser Phe Val Ala Val Arg Phe Gly Asn
        435                 440                 445
Val Leu Gly Ser Arg Gly Ser Val Ile Pro Leu Phe Lys Asn Gln Ile
    450                 455                 460
Glu Ser Gly Gly Pro Val Thr Val Thr His Pro Glu Met Thr Arg Tyr
465                 470                 475                 480
Phe Met Thr Ile Pro Glu Ala Ser Arg Leu Val Leu Gln Ala Gly Ala
                485                 490                 495
Leu Ala Gln Gly Gly Glu Val Phe Val Leu Asp Met Gly Lys Pro Val
            500                 505                 510
Lys Ile Val Asp Leu Ala Lys Asn Leu Ile Arg Leu Ser Gly Lys Lys
        515                 520                 525
Glu Glu Asp Ile Gly Ile Glu Ile Phe Ser Gly Ile Arg Pro Gly Glu Lys
    530                 535                 540
Leu Tyr Glu Glu Leu Leu Asn Lys Asn Glu Ile His Pro Gln Gln Val
545                 550                 555                 560
Tyr Glu Lys Ile Tyr Arg Gly Lys Val Asp His Tyr Ile Lys Thr Glu
                565                 570                 575
Val Asp Leu Ile Val Glu Asp Leu Ile Asn Asn Phe Ser Lys Glu Lys
```

|                  | 580             | 585             | 590             |
|------------------|-----------------|-----------------|-----------------|
| Leu Leu Lys Ile Ala Asn Arg |  |  |  |
| 595              |                 |                 |                 |

<210> SEQ ID NO 98
<211> LENGTH: 1047
<212> TYPE: DNA
<213> ORGANISM: Pseudomonas aeruginosa

<400> SEQUENCE: 98

```
atgactgacg aaatacaaaa gcacggcggt gtagctggcg atatcgatct ggttgagctg   60
gttcgaggat tatgggagga gaagtggata gttcttatat tttcttttgct aggtattttg  120
tttgcagcta tctacgcttt tctcagtact cctgtctatg aggcccgcat agcgattttg  180
cctccgtcgt tgagtgatgt ggcaggtttc aatcagggac gtaccaggga aaccgggctt  240
ggtcccttca aggtccagga tgtgtactct gttttttgttc gcaacctgca ggctgatgga  300
actcgtcatc gttttttcaa tgagacctat ttgccttctt ggatgaaga gcttcgttcg  360
gtttcgcgtg atgcgctcta taaaaggttc actgatcaga taagtattag tttgccgggg  420
aaagactttc cgggtcgtta tcttgttgcg attgaacagg aggatccgga gcgtgcggcg  480
agttgggttc gtcggtatat agctgatgcg gccgagattt ctattcagga aatgttgaac  540
aatgcgcatc gcgagattga ggtcaaggct cgagatattg agcagcgcat acagaacttg  600
cggagagaat gccaaggcag acgtgaagat cgtattgttc agctcaagga ggcgttgaag  660
gtcgcaggtg cgctgaaatt ggaggagcct ccactgatca gtgggcaatc tctctgaggag  720
ctctcggcta tcatgaatgg aagtctgatg tatatgcgtg gcagtaaggc gattatgggcc  780
gagattcaga cattggaggc gcgtagctct gatgatcctt ttattccggc gttgcgtact  840
cttcaggagc agcagttatt gctgagtagc ttgcgtgtta attcggagcg ggtttctgtt  900
tttcgacaag acgtccgat agaaacgccg gactcaccag ttcgtccaag agagcgatg   960
atttttgattt tgggttgat aattggtggt gtgcttggtg gttttctggc gttgtgccgg 1020
attttttttga agaagtatgc tcgttag                                    1047
```

<210> SEQ ID NO 99
<211> LENGTH: 920
<212> TYPE: DNA
<213> ORGANISM: Pseudomonas aeruginosa

<400> SEQUENCE: 99

```
gagctcgagt tcaaggtcat caagctcgac cagaagcgca acaacgttgt cgtttcccgc   60
cgcagcgtcc ggaagccgag aacagcgccg agcgtgaagc tctgctggaa tcgctgcagg  120
aaggccagca ggtcaaaggt tcgtcaagaa cctcaccgac tacggcgcat tcgtggacct  180
gggcggcgta gacggcctgc tacacatcac gacatggcct ggaagcgcat caagcatccg  240
tccgagatcg tcaacgttgg cgacgagatc gacgtcaagg cctgaagttc gaccgcgagc  300
gcaaccgtgt atccctgggc gtgaagcaac tgggcgaaga cccgtgggtt ccatcaaggc  360
gcgttacccg gaagtaccgc gtcatggccg cgtcaccaac ctcaccgact acggctgctt  420
gccgaactgg aagaggcgtg aagctggta cacgtctccg aaatggactg gaccaacaag  480
aacatccatc gtcgaaagtc gtccaggttg gcgatgaagt ggaagttcag gttctggaca  540
tcgacgaaga gcgtcgtcgt tctccctggg tatcaagcag tgcaaatcca acccgtgaga  600
agacttctcc agccagttca acaagggtga cgtatctccg gtaccatcaa gtcgatcacc  660
gacttcggta tcttcatcgg tctggacggc ggcatcgacg cctggtccac ctgtccgaca  720
tctcctggaa cgaagtcggc gaagaagccg tacgtcgctt caagaagggc acgagctgga  780
aaccgtcatc ctgtcggtcg atccggagcg cgagcgcatc tccctgggca tcaagcagct  840
gaagacgatc cgttctccaa ctacgcgtcc tgcacgagaa agcagcatcg tccgcggtac  900
cgtgaaggaa tcaacgccca                                             920
```

<210> SEQ ID NO 100
<211> LENGTH: 1217
<212> TYPE: DNA
<213> ORGANISM: Pseudomonas aeruginosa

<400> SEQUENCE: 100

```
aaaaatcgaa gtatcctgaa ggcttccgaa atcagccgtg accgcgtcga agacgcgcgc   60
aagtcctgaa gaaggggagg aagtcgaagc caagattatc agcatcgacc gcaagagcgg  120
gtcatcagct tttccgtcaa tccaaggacg tcgacgacga gaaggacgca atgaaagaac  180
tgcgtaagca ggaagtagaa agcgctggtc gaccaccatc ggtgatctga tccgtgctca  240
gatggagaat cagggctaag tctctgatcc atcatgaaaa gggcggccta ggccgccctt  300
tttcgttttc ccttcttgg acctgttcaa agactgatgc gcatgctaaa gagacctgag  360
ctgatctagc cgcttgaaaa agaaggggaaa accatgacca agtcggagtt gatcgaacgg  420
tcgttaccca tcaggggcaa ctgtccgcga aggatgtcga gttggcaatc aagaccatgc  480
tggagcaaat tcccaggccc tggcgaccgg gaccggatcg agatccgtgg cttcggcagc  540
ttttccttgc attaccgcgc ccgcgcgtcg ttcgcaaccc caagaccggg gagtcggtac  600
gcttcgacgg caagttcgtg ccgcacttca gccggggcaag gagttgcgtg atcgggtcaa  660
cgagccggag tgatttctgc cttgttcaga tgttgagtt ccatgctttg ggtcaagcgt  720
acgttaatgg cggtgggggct gttagttgtc gccctttttca tgattgtggt gctttggaga  780
accggcaaag cgtcagcttt gaactcttg tcttgccac gccagattta cctgtggtcc  840
ttatgttgcg ttagcatta ttgctgcgcg tattattggt atgttgatca gcgtgcctct  900
tctggctcgt ccaaagtgcg tctcagatct gcaagatctg atctgtttcg tactcgaaaa  960
```

-continued

```
gaactcgcag tatctcagtc accgccctgc ggtgaggtct gctcgagtcc ctgcctgttc 1020
tttgtgggct cgagtgctat tcgcatctag tgacaacaca atgcttggaa ggtcgggtgg 1080
gatgggtgtc ctgttagagg gggtgctgag ttaccatgtc tactggtttg gctggagtct 1140
gtagatggag tctgtagatg gaggcttggt tcatggcatc gtgtcgctcc ggttggtctt 1200
cgccaaaggt caagctt                                               1217
```